(12) United States Patent
Colucci et al.

(10) Patent No.: US 6,991,794 B1
(45) Date of Patent: Jan. 31, 2006

(54) PROGENITOR CELL PRESERVATION FACTORS AND METHODS FOR AND PRODUCTS OF THEIR USE

(75) Inventors: M. Gabriella Colucci, La Jolla, CA (US); Maarten J. Chrispeels, La Jolla, CA (US); Jeffrey G. Moore, Kennebunkport, ME (US)

(73) Assignees: ImClone Systems Incorporated, New York, NY (US); The Regents of the University of California, La Jolla, CA (US)

(*) Notice: Subject to any disclaimer, the term of this patent is extended or adjusted under 35 U.S.C. 154(b) by 0 days.

(21) Appl. No.: 09/476,485

(22) Filed: Dec. 30, 1999

Related U.S. Application Data

(63) Continuation-in-part of application No. 08/881,189, filed on Jun. 24, 1997, now Pat. No. 6,310,195.

(51) Int. Cl.
*A61K 39/00* (2006.01)
*A61K 39/38* (2006.01)
*A61K 38/00* (2006.01)
*C07K 14/00* (2006.01)

(52) U.S. Cl. ............................. 424/185.1; 424/184.1; 424/192.1; 530/300; 530/350

(58) Field of Classification Search ................ 530/300, 530/350; 424/184.1, 192.1, 185.1
See application file for complete search history.

(56) References Cited

U.S. PATENT DOCUMENTS

| 4,808,611 A | | 2/1989 | Cosman |
| 5,186,931 A | | 2/1993 | Kishimoto et al. |
| 5,472,867 A | | 12/1995 | Kanz et al. |
| 5,545,820 A | | 8/1996 | Gatehouse et al. |
| 6,084,060 A | * | 7/2000 | Moore |
| 6,110,891 A | | 8/2000 | Pusztai et al. ................ 514/8 |

FOREIGN PATENT DOCUMENTS

| EP | 1009418 | 3/2002 |
| EP | 0942741 | 12/2002 |
| WO | WO 95 00554 | 1/1995 |
| WO | WO9741224 | 6/1997 |
| WO | WO 97 41224 | 11/1997 |
| WO | WO 98 25457 | 6/1998 |
| WO | WO 98 59038 | 12/1998 |

OTHER PUBLICATIONS

Mikayama et al. PNAS, 1993. 90: 10056–10060.*
Ngo et al, in The Protein Folding Problem and Tertiary Structure Prediction, 1994. (ed.), Birkhauser, Boston, MA, pp. 433 and 492–495.*

Altabella, T., et al., "Tobacco Plants Transformed with the Bean αai Gene Express an Inhibitor of Insect α–Amylase in Their Seeds", Plant Physiol. 93:805–810, 1990.

An, G., et al., "Binary Vectors", Plant Molecular Biology Manual A3:1–19, 1998.

Arar, C., et al., "ERGIC–53, A Membrane Protein of the Endoplasmic Reticulum–Golgi Intermediate Compartment, is Identical to MR60, an Intracellular Mannose–Specific Lectin of Myelomonocytic Cells", J. Biol. Chem. 270(8):3551–3553, 1995.

Barondes, S.H., et al., "Bifunctional Properties of Lectins: Lectins Redefined", Trends in Biochemical Sciences 13:480–482, 1988.

Berardi, A.C., et al., "Functional Isolation and Characterization of Human Hematopoietic Stem Cells", Science 267:104–108, 1995.

Borge, O.J., et al., "Thrombopoietin, But Not Erythropoietin Promotes Viability and inhibits Apoptosis of Multipotent Murine Hematopoietic Progenitor Cells In Vitro", Blood 88(8):2859–2870, 1996.

Colucci, G., et al., "cDNA cloning of FRIL, a lectin from *Dolichos lablab*, that preserves hematopoietic progenitors in suspension culture", Proc. Natl. Acad. Sci. 96:646–650, 1999.

Dexter, et al., "The Structure of the Hemopoietic System", Cell Biol. 3:423–441, 1987.

Dosil, M., et al, "Mitogenic Signalling and Substrate Specificity of the Flk2/Flt3 Receptor Tyrosine Kinase in Fibroblasts and Interleukin 3–Dependent Hematopoietic Cells", Molecular and Cellular Biolog. 13(10):6572–6586, 1993.

Dwek, R.A., "Glycobiology: More Functions for Oligosaccharides", Science 269:1234–1235, 1995.

Gabius, H.J. "Non–Carbohydrate Binding Partners/Domains of Animal Lectins", Int. J. Biochem. 26(4):469–477, 1994.

Gowda, L.R., et al., "The Complete Primary Structure of a Unique Mannose/Glucose–Specific Lectin from Field Bean", The Journal of Biological Chemistry 269(29):18789–18793, 1994.

Hao, Q.L., et al., "Extended Long–Term Culture Reveals a Highly Quiescent and Primitive Human Hematopoietic Progenitor Population", Blood 88(9):3306–3313, 1996.

(Continued)

*Primary Examiner*—Christina Chan
*Assistant Examiner*—Michail A Belyavskyi
(74) *Attorney, Agent, or Firm*—Wilmer Cutler Pickering Hale and Dorr

(57) ABSTRACT

Disclosed are the FRIL family of progenitor cell preservation factors and nucleic acids encoding the same. FRIL family members preserve progenitor cells both in vivo and ex vivo. FRIL family members find use as therapeutics for alleviating and/or reducing the hematopoietic progenitor cell-depleting activity of many cancer therapeutics. FRIL family members are also useful for isolating rare, primitive progenitor cells.

13 Claims, 42 Drawing Sheets

OTHER PUBLICATIONS

Higgins, T.J.V., et al., "The Sequence of Pea Vicilin Gene and its Expression in Transgenic Tobacco Plants", Plant Molecular Biology 11:683–695, 1988.

Hoffman, L.M., et al., "Molecular Cloning of *Phaseolus Vulgaris* Lectin mRNA and Use of cDNA as a Probe to Estimate Lectin Transcript Levels in Various Tissues", Nucleic Acids Research 10(23):7820–7829, 1982.

Kuby, J. *Immunology*, W.H. Freeman & Co. NY, p. 95, 1992.

Kuriyama, M., et al., "Identification of AF–6 and Canoe as Putative Targets for Ras", The Journal of Biological Chemistry 271(2):607–610, 1996.

Lenfant, M., et al., "Inhibitor of Hematopoletic Pluripotent Stem Cell Proliferation: Purification and Determination of Its Structure", National Academy of Science 86:779–782, 1989.

Marfatia, S.M., et al., "Identification of the Protein 4.1 Binding Interface on Glycophorin C and p55, a Hmologue of the *Drosophila discs–large* Tumor Suppressor Protein", The Journal of Biological Chemistry 270(2):715–719, 1995.

Moore, J.G., et al., "Presevation of hematopoietic progenitors for prolonged periods in suspension cultures by Flk2/flt3 receptor–interacting lectin (FRIL), a new lectin identified in red kidney beans", Blood 90:P 428A, 1997 (39$^{th}$ annual meeting of the American Society of Hematology: San Diego, California, Dec. 5–9, 1997).

Moreno, J., et al., "A Lectin Gene Encodes the α–amylase Inhibitor of the Common Bean", Proc. Natl. Acad. Sci 86:7885–7889, 1986.

Mosmann, T., "Rapid Colorimetric Assay for Cellular Growth and Survival: Application to Proliferation and Cytotoxicity Assays", Journal of Immunological Methods 65:55–63, 1983.

Opdenakker, C., et al., "Cells Regulate the Activities of Cytokines by Glycosylation", The FASEB Journal 9:453–457, 1995.

Pueyo, J.J., et al., "Degradation of Transport–Competent Destabilized Phaseolin with a Signal for Retention in the Endoplasmic Reticulum Occurs in the Vacuole", Planta 196:586–596, 1995.

Shah, A.J., et al., "Flt3 Ligand Induces Proliferation of Quiescent Human Bone Marrow CD34$^+$CD38 Cells and Maintains Progenitor Cells in Vitro", Blood 87(9):3563–3570, 1996.

Sharon, N., et al., "Lectins as Cell Recognition Molecules", Science 246:227–234, 1989.

Small, D., et al., STK–1, the Human Hmolog of Flk–2/Flt–3, is Selectively Expressed in CD34$^+$ Human Bone Marrow Cells and is Involved in the Proliferation of Early Progenitor/Stem Cells Proc. Natl. ACad. Sci. 91:459–463, 1994.

Stubbs, M.E., et al., "Production of Pea Lectin in *Escherichia coli*", J. Biol. Chem. 261(14):6141–6144, 1986.

Tessler, S., et al., "Heparin Modulates the Interaction of VEGF$_{165}$ with Solubel and Cell Associated *flk*–1 Receptors", The Journal of Biological Chemistry 269(17):12456–12461, 1994.

Turhan, A.G., et al., "Clonal Hematopoiesis Demonstrated by X–Linked DNA Polymorphisms After Allogeneic Bone Marrow Transplantation", The New England Journal of Medicine 320(25):1655–1661, 1989.

Van Damme, E.J., et al, Molecular Cloning of the Bark and Seed Lectins from the Japanese Pagoda Tree (*Sophora Japonica*) Plant Mol Biol. Feb.;33(3):523–36. 1997.

van Eijsden, R.R., et al., "Mutational Analysis of Pea Lectin. Substitution of Asn125 for Asp in the Monosaccharide–Binding Site Eliminatesmannose/glucose–binding Activity". Plant Mol Biol. Dec.;20(6):1049–58, 1992.

Young, J.C., et al., "Retention of Quiescent Hematopoietic Cells with High Proliferative Potential During Ex Vivo Stem Cell Culture", Blood 87(2):545–556, 1996.

Zipori, D., "Regulation of Hemopoiesis by Cytokines that Restrict Options for Growth and Differentiation", Cancer Cells 2(7):205–211, 1990.

Zipori, D., "The Renewal and Differentiation of Hemopoietic Stem Cells", The FASEB Journal 6:2691–2697.

Moore, J. G. et al., "Preservation of Hematopoietic progenitors for Prolonged Periods in Suspension Cultures By Flk2/Flt3 Receptor–Interacting Lectin (FRIL), A New Lectin Identified in Red Kidney Beans." Blood 90: 428A, 1997 (39$^{th}$ Annual Meeting Of the American Society of Hematology: San Diego, California, Dec. 5–9, 1997).

Lenfant M., "Inhibitor of Hematopoietic Pluripotent Stem Cell Proliferation: Purification and Determination of its Structure." Proc. Natl. Acad. Sci. U S A. 86(3): 779–782, 1989.

Sharon N and Lis H, "Lectins as Cell Recognition Molecules", Science 246:227–234 (1989).

Small D, Levenstein M, Kim E, Carow C, Amin S, Rockwell P. Witte L, Burrow C, Ratajczak MZ, Gewirtz AM and Civin CI, "STK–1, the Human Hmolog of Flk–2/Flt–3, is Selectively Expressed in CD34$^+$ Human Bone Marrow Cells and is Involved in the Proliferation of Early Progenitor/Stem Cells", Proc. Natl. Acad. Sci. USA 91:459–463 (1994).

Tessler S, Rockwell P, Hicklin D, Cohen T, Levi B–Z, Witte L, Lemischka IR, Neufeld G, "Heparin Modulates the Interaction of VEGF$_{165}$ with Soluble and Cell Associated *flk*–1 Receptors", The Journal of Biological Chemistry 269 (17):12456–12461 (1994).

Turhan AG, Humphries K, Phillips GL, Eaves AC and Eaves CJ, "Clonal Hematopoiesis Demonstrated by X–Linked DNA Polymorphisms After Allogeneic Bone Marrow Transplantation", The New England Journal of Medicine 320(25):1655–1661 (1989).

Young JC, Varma A, DiGiusto D and Backer MP, "Retention of Quiescent Hematopoietic Cells with High Proliferative Potential During Ex Vivo Stem Cell Culture", Blood 87(2):545–556 (1996).

Zipori D, "Regulation of Hemopoiesis by Cytokines that Restrict Options for Growth and Differentiation", Cancer Cells 2(7):205–211 (1990).

Zipori D, "The Renewal and Differentiation of Hemopoietic Stem Cells", The FASEB Journal 6:2691–2697.

\* cited by examiner

β-Subunit

```
Gowda    1   AQSLSFSFTKFDPNQEDLIFQGTATS..........KLDSAGNPVSSSAGRV   42
             ||||||||||||||||||||||||||          ||||||||||||||||||
FRIL     1   AQSLSFSFTKFDPNQEDLIFQGHATSTNNVLQVTKLDSAGNPVSSSSAGRV   50

Gowda    43  LYSAPLRLWEDSAVLTSFDPTIY..IFTNYTSRIADGLA.FIAPPDSVIS   89
             |||||||||||||||||||| ||  |||||||||||||| |||||||||
FRIL     51  LYSAPLRLWEDSAVLTSFDTIINFEISTPYTSRIADGLAFFIAPPDSVIS  100

Gowda    90  YHGGFLGLFPNAAESG........  105
             |||||||||||| |
FRIL     101 YHGGFLGLFPNANTLNNSSTSEN   123
```

α-Subunit

```
Gowda    1   ......IAESNVVAVEFDTDYLNPDYGDPNYIHIGIDVNSIRSKVTASWDW    45
                   ||||||||||||| ||||||||||||||||||||||||||| ||
FRIL     1   QTTTKAASSNVVAVEFDT.YLNPDYGDPNYIHIGIDVNSIRSKVTAKWDW    49

Gowda    46  QNGKIATAH

FIG. 24B

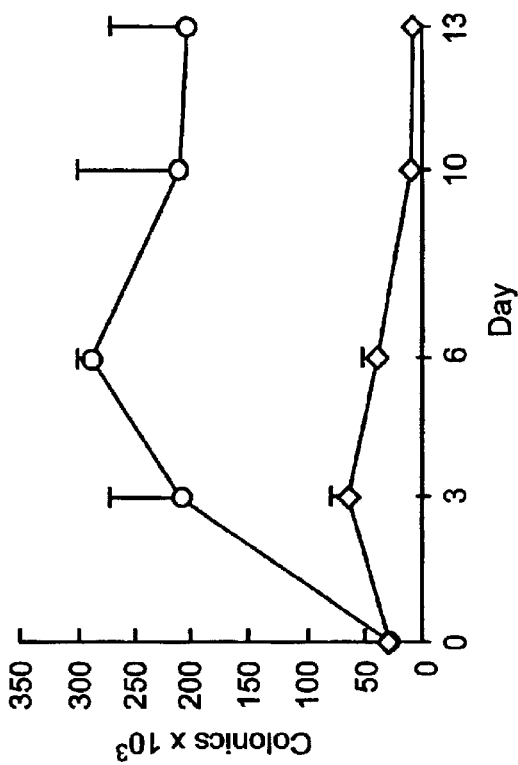
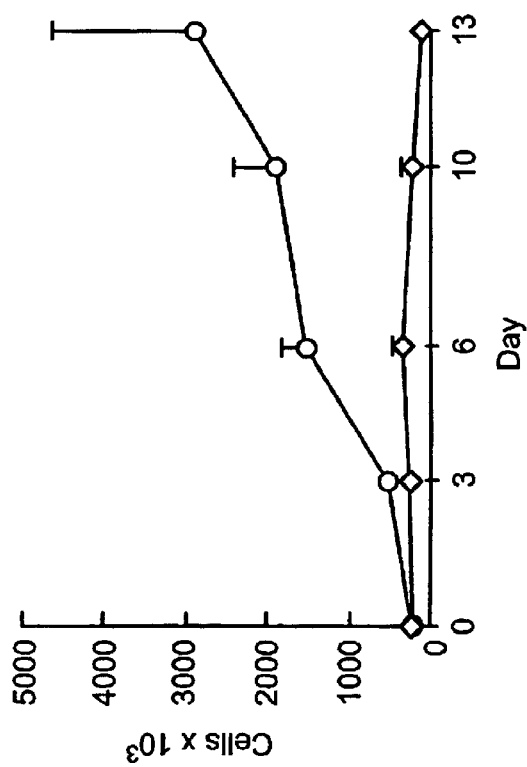
FIG. 27B
FIG. 27A

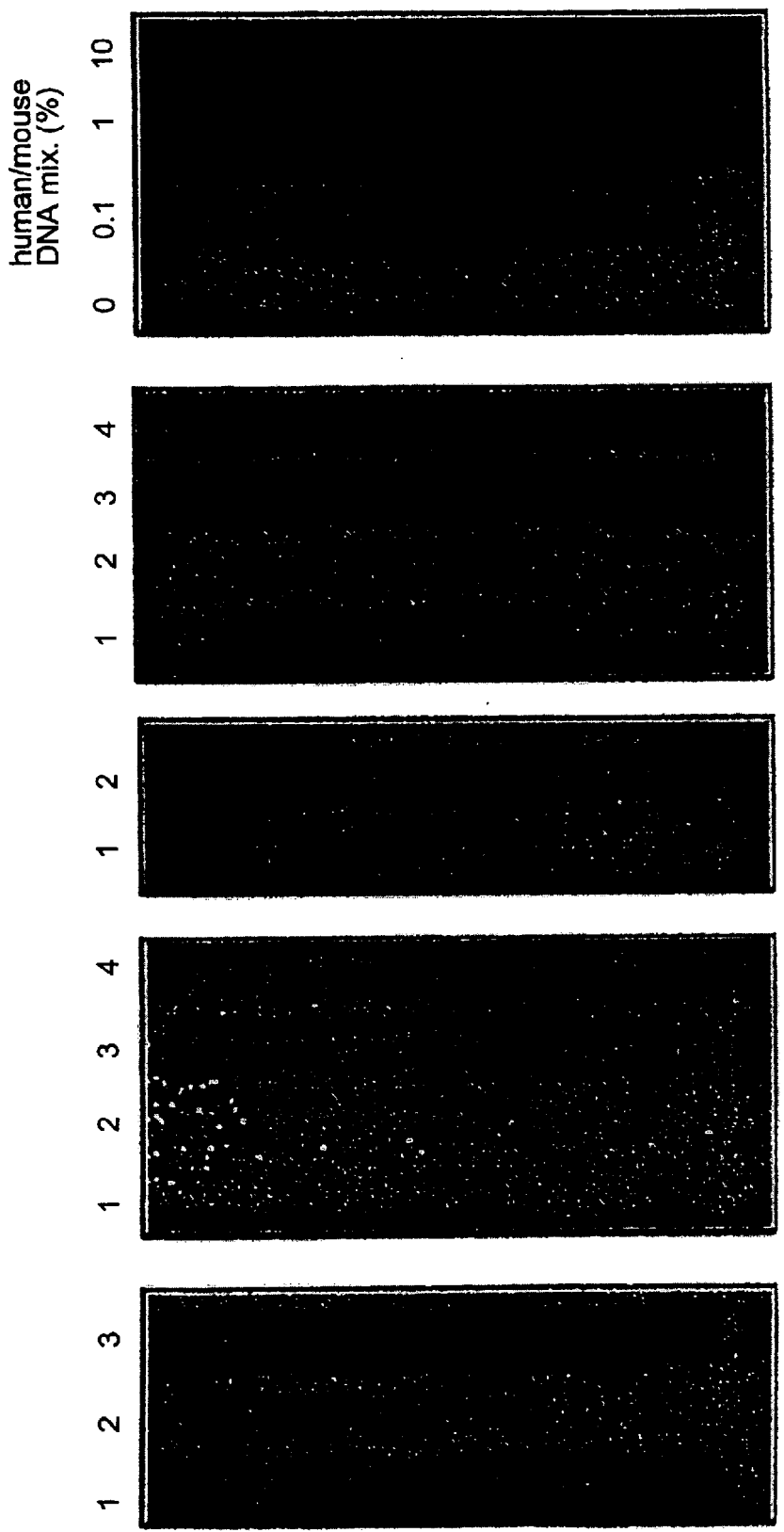

| Band 5 | DSSTS EXQTT TKAAS SNVVA |
| Band 4 | DSSTS EXQTT TKA |
| Band 3 | DSSTS EXQTT TKAAS SNVVA |
| Band 2 | TT TKAAS SNVVA VEFKT YLN |

Band 1   AQSLSF FSFTK FDPNQ EDLIF QHATS TNNV

FIG. 1. Fractionation of purified hyacinth bean FRIL by SDS/PAGE and amino-terminal amino acid sequences of the constituent polypeptides.

PROGENITOR CELL PRESERVATION FACTORS AND METHODS FOR AND PRODUCTS OF THEIR USE

This application is a continuation in part of U.S. Ser. No. 08/881,189, filed Jun. 24, 1997, now U.S. Pat. No. 6,310,195, the entire contents of which are hereby incorporated by reference.

BACKGROUND OF THE INVENTION

1. Field of the Invention

The invention relates to the preservation of progenitor cells. More specifically, the invention relates to the in vivo or ex vivo preservation of progenitor cells, such as hematopoietic progenitor cells.

2. Summary of the Related Art

The wide variety of functionally and phenotypically different types of cells in a multi-cellular eukaryotic organism results in part from the proliferation and differentiation of rare and mostly quiescent populations of progenitor cells. For example, hematopoiesis involves the process of producing a balanced supply of different blood cells from such progenitor cells found in the adult bone marrow. The development of other cell types also depends upon production of the differentiated cells from such progenitor cells.

Progenitor cells are activated by signals, such as cell-cell contact or soluble regulators, to generate daughter cells that are identical to the parent (i.e., self-renewal of the parent) and/or to generate daughter cells that are more differentiated than the parent, thus beginning an irreversible process that ends with the production of differentiated, functional cells. In the process of hematopoiesis, differentiation is coupled to proliferation as a progenitor cell gives rise to more differentiated daughter cells that progressively become committed to producing only one blood cell type. The enormous activation of hematopoietic progenitor cells needed to meet the body's daily requirement for hundreds of billions of new mature blood cells is directed by potent soluble regulators (e.g., colony stimulating factors and cytokines) acting upon the hematopoietic progenitor cells themselves, and their more differentiated daughter cells.

Although progenitor cells eventually produce so many of the mature cells of the body, they occur only rarely. Moreover, typically the more primitive (i.e., undifferentiated) the progenitor cell, the more rare the progenitor cell. For example, the currently believed most primitive of the hematopoietic progenitor cells, which are called hematopoietic stem cells, occur at a frequency of only from about 1 in 10,000 to about 1 in 100,000 of the cells in the bone marrow. Hematopoietic stem cells have the capacity to generate more than $10^{13}$ mature blood cells of all lineages, including other progenitor cells which, although more differentiated than hematopoietic stem cells, are themselves capable of giving rise to several different types of mature blood cells.

Hematopoietic stem cells are responsible for sustaining blood cell production over the life of an animal. The small population of hematopoietic stem cells is sufficient to produce all the mature blood cells in a healthy individual; however, some unhealthy individuals suffer from a lack of a sufficient number of progenitor cells and/or mature blood cells. For example, cancer patients receiving chemotherapeutic or radiotherapy treatments designed to kill the rapidly dividing cancer cells also suffer from the depletion of white blood cells and platelets, thus exposing these patients to life-threatening opportunistic infections and bleeding episodes. Indeed, this hematopoietic progenitor cell-depleting activity is the dose-limiting factor for most of these chemotherapeutic and radiotherapeutic agents.

Many cancer patients are routinely treated with cytokines, including G-CSF, GM-CSF, SCF, Erythropoietin, and IL-11, to accelerate restoration of hematopoiesis following chemotherapy (Moore, M. A., Blood 78: 1–19, 1991). However, these cytokines lead to the irreversible differentiation of hematopoietic progenitor cells, including hematopoietic stem cells, into more differentiated daughter cells. Thus, better protection of hematopoietic progenitor cells is needed during chemotherapy.

Workers in the field have attempted to use cytokines in mice to protect progenitors from the toxicity of chemotherapy (Neta et al., J. Immunol. 136: 2483–2485, 1986; Neta et al., J. Immunol. 140: 108–111, 1988; Neta et al., J. Exp. Med. 173: 1177–1182, 1991; de Haan et al., Blood 87: 4581–4588, 1996; Lyman and Jacobsen, Blood 91: 1101–1134, 1998; Dalmau et al., Bone Marrow Transplant. 12: 551–563, 1993; Grzegorzewski et al., J. Exp. Med. 180: 1046–1057, 1994; Grzegorzewski et al., Blood 94:1066a (Abstr.)1999). Marshall et al. (Euro. J. Cancer 34: 1023–1029, 1998) and Gilmore et al. (Exp. Hematol. 27: 195–202, 1999) describe the use in clinical trials of a chemokine that allegedly inhibits progenitor cell proliferation, MIP1-α, as a chemoprotectant. Marshall (Marshall, A., Nat. Biotechnol. 16: 129, 1999) describes the use of MPIF-1, a chemokine that allegedly inhibits progenitor cell proliferation, in clinical trials as a chemoprotectant.

There are several drawbacks to using chemokines, cytokines, and other immmunoregulators as chemoprotectants during the chemotherapeutic or radiotherapeutic treatment of cancer patients. These drawbacks include the cost of production and toxicity to the patient.

Therefore, there is a need for improved reagents that are non-toxic and inexpensive to produce for use in preserving progenitor cells.

BRIEF SUMMARY OF THE INVENTION

The invention provides a family of factors that preserve progenitor cells. Members of this family, the FRIL family, are non-toxic, inexpensively produced reagents that preserve progenitor cells. The invention provides compositions comprising at least one member of the FRIL family, as well as methods for using members of the FRIL family to preserve progenitor cells both in vivo and ex vivo.

Accordingly, in a first aspect, the invention provides an essentially pure composition of one or more members of the FRIL family of progenitor cell preservation factors.

In certain embodiments of the first aspect of the invention, the FRIL family member is from a legume. In some embodiments, the legume is Dolichos lab lab. In some embodiments, the legume is Phaseolus vulgaris. In some embodiments, the legume is Sphenostylis stenocarpa.

In certain embodiments of the first aspect of the invention, the FRIL family member is a mutant derived from a second member of the FRIL family, wherein the mutant is selected from the group consisting of a substitution mutant, a deletion mutant, an addition mutant, or a combination thereof.

In certain embodiments of the first aspect of the invention, the FRIL family member is a fusion protein comprising a first portion and a second portion, wherein the first portion is derived from a second member of the FRIL family.

In a second aspect, the invention provides a recombinant nucleic acid molecule encoding a composition of a member of the FRIL family of progenitor cell preservation factors.

In a third aspect, the invention provides a pharmaceutical formulation comprising an essentially pure composition of one or more members of the FRIL family of progenitor cell preservation factors and a pharmaceutically acceptable carrier.

In certain embodiments of the third aspect of the invention, administration of a therapeutically effective amount of the formulation to a patient suffering from a condition whereby the patient's hematopoietic progenitor cells are depleted alleviates and/or reduces the condition in the patient.

In certain embodiments of the third aspect of the invention, administration of a therapeutically effective amount of the formulation to a patient prior to treatment of the patient with a therapeutic treatment having a hematopoietic progenitor cell-depleting activity alleviates and/or reduces the hematopoietic progenitor cell-depleting activity of the therapeutic treatment in the patient. In certain embodiments, the patient is a human or is a domesticated mammal. In some embodiments, the patient has cancer. In some embodiments, the therapeutic treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In a fourth aspect, the invention provides a method for alleviating or reducing the hematopoietic progenitor cell-depleting activity of a therapeutic treatment in a patient, comprising administering to the animal a therapeutically effective amount of a composition of a FRIL family member prior to administration of the therapeutic treatment to the patient.

In certain embodiments of the fourth aspect, the patient is a human or is a domesticated mammal. In some embodiments, the patient has cancer. In some embodiments, the therapeutic treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In a fifth aspect, the invention provides a method for isolating a population of progenitor cells, comprising contacting a population of cells with a plurality of FRIL family member molecules, and separating the unbound cells, wherein the cells bound to the FRIL family member molecules are an isolated population of progenitor cells. Preferably, the isolated population of progenitor cells is from a human.

In certain embodiments of the fifth aspect of the invention, the FRIL family member molecules are detectably labeled. In certain embodiments, the detectably labeled FRIL family member molecules are labeled with a chromophore. In certain embodiments, the unbound cells are separated by using a flow cytometry cell sorter to sort the population of cells contacted with the FRIL family member molecules detectably labeled with a chromophore.

In certain embodiments of the fifth aspect, the FRIL family member molecules is immobilized on a solid support. In some embodiments, the solid support is a bead, such as a magnetic bead. In some embodiments, the unbound cells are separated by applying a magnet to the population of cells contacted with the FRIL family member molecules immobilized on the magnetic bead. In further embodiments, the population of cells bound to the FRIL family member molecules immobilized on a magnetic bead is rinsed with a physiologically acceptable solution while the magnet is applied.

In certain embodiments of the fifth aspect, the solid support is the bottom of a tissue culture plate. In some embodiments, the unbound cells are separated by rinsing the population of cells contacted with the FRIL family member immobilized on the bottom of a tissue culture plate with a physiologically acceptable solution.

In preferred embodiments of the fifth aspect of the invention, the isolated population of progenitor cells is a population of hematopoietic progenitor cells. In various embodiments, the population of cells is whole blood, umbilical cord blood, bone marrow cells, or fetal liver cells.

In certain embodiments of the fifth aspect of the invention, the population of cells is a sorted population of cells, wherein a cell of the sorted population does not express a cell surface molecule selected from the group consisting of CD11b, CD11c, and CD38. In certain embodiments, the sorted population of cells is sorted by flow cytometry or by magnetic bead selection.

In a sixth aspect, the invention provides an isolated population of progenitor cells isolated by a method comprising contacting a population of cells with a plurality of FRIL family member molecules, and separating the unbound cells, wherein the cells bound to the FRIL family member molecules are an isolated population of progenitor cell. Preferably, the progenitor cell is from a human.

In certain embodiments of the sixth aspect, the cells of the isolated population do not express CD34. In certain embodiments, the cells of the isolated population express a receptor tyrosine kinase selected from the group consisting of FLK1, FLT1, FLT3, FLT4, and Kit. In some embodiments, the cells of the isolated population express a cell surface molecule selected from the group consisting of CD11b and CD11c. In preferred embodiments, the cells of the isolated population express FLT3.

In various embodiments of the sixth aspect of the invention, the cells of the isolated population are hemangioblasts, mesenchymal stem cells, bone progenitor cells, hepatic progenitor cells, endothelial progenitor cells, hematopoietic progenitor cells, embryonal stem cells, brain progenitor cells, or dendritic progenitor cells. Preferably, the cells of the isolated population are hematopoietic progenitor cells.

In certain embodiments of the sixth aspect of the invention, where the cells of the isolated population are hematopoietic progenitor cells, transplantation of the isolated population into an animal lacking a population of hematopoietic progenitor cells sufficient to enable survival of the animal reconstitutes the animal, wherein the transplanted animal survives. In certain embodiments, the hematopoietic progenitor cells are from a human or a mouse and wherein the animal is a mouse. In some embodiments, the mouse is a SCID mouse or the mouse is sublethally irradiated or the mouse is treated with a sublethal dose of a chemotherapeutic. In certain embodiments, the hematopoietic progenitor cells are from a human and the animal is a human. In some embodiments, the human is a cancer patient receiving a treatment that depletes the patient's hematopoietic progenitor cells. In some embodiments, the treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In a seventh aspect, the invention provides a method for preserving progenitor cells ex vivo comprising contacting a population of cells comprising at least one progenitor cell with an effective amount of a composition of a FRIL family member for an effective period of time, wherein the progenitor cells in the population are rendered quiescent.

In certain embodiments of the seventh aspect, the progenitor cells are from a human. In certain embodiments, the population of cells is bone marrow cells. In some embodiments, the non-progenitor cells in the population of cells differentiate or die.

In certain embodiments of the seventh aspect, the population of cells is removed from a cancer patient prior to treatment of the cancer patient with a therapeutic treatment having a hematopoietic progenitor cell-depleting activity. In some embodiments, the therapeutic treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In an eighth aspect, the invention provides a method for preserving progenitor cells in vivo, comprising administering to a patient an effective amount of a composition of a FRIL family member for an effective period of time, wherein the progenitor cells in the patient are rendered quiescent. Preferably, the patient is a human or a domesticated animal.

In certain embodiments of the eighth aspect of the invention, the patient is a (cancer patient. In some embodiments, the effective amount of the composition of a FRIL family member is administered prior to the treatment of the patient with a therapeutic treatment having a hematopoietic progenitor cell-depleting activity. In some embodiments, the therapeutic treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In a ninth aspect, the invention provides a method for identifying a progenitor cell, comprising contacting a candidate cell with a FRIL family member molecule, wherein binding of the candidate cell to the FRIL family member molecule identifies the candidate cell as a progenitor cell.

In certain embodiments of the ninth aspect, the candidate cell is in a population of cells. In certain embodiments, the candidate cell is from a human.

In a tenth aspect, the invention provides a progenitor cell identified by a method comprising contacting a candidate cell with a FRIL family member molecule, wherein binding of the candidate cell to the FRIL family member identifies the candidate cell as a progenitor cell.

In an eleventh aspect, the invention provides a method for identifying a composition of a member of the FRIL family of progenitor cell preservation factors, comprising contacting a candidate compound with a glycosylated extracellular domain of an FLT3 receptor, wherein the glycosylation pattern of the extracellular domain of the FLT3 receptor is the same as the glycosylation pattern of an extracellular domain of a normally glycosylated FLT3 receptor, wherein a candidate compound that binds the glycosylated extracellular domain of the FLT3 receptor is identified as a composition of a FRIL family member.

In certain embodiments of the eleventh aspect, the candidate compound is a lectin. In certain embodiments, the lectin is synthetic. In certain embodiments, the lectin is from a legume.

In a twelfth aspect, the invention provides an essentially pure composition of a FRIL family member identified by the method comprising contacting a candidate compound with a glycosylated extracellular domain of an FLT3 receptor, wherein the glycosylation pattern of the extracellular domain of the FLT3 receptor is the same as the glycosylation pattern of an extracellular domain of a normally glycosylated FLT3 receptor, wherein a candidate compound that binds the glycosylated extracellular domain of the FLT3 receptor is identified as a member of the FRIL family.

According to the invention, compositions of a FRIL family member may be used as therapeutic agents to preserve progenitor cells in patients, such as cancer patients receiving chemotherapy, who suffer from a condition that diminishes their progenitor cells. For example, compositions of a FRIL family member may be administered with a pharmaceutically-acceptable carrier (e.g., physiological sterile saline solution) via any route of administration to a cancer patient receiving chemotherapy in an attempt to reduce the progenitor cell-depleting effects of the chemotherapeutic so that the patient can receive a higher dose of the chemotherapeutic and, preferably, recover from cancer. Pharmaceutically-acceptable carriers and their formulations are well-known and generally described in, for example, Remington's Pharmaceutical Sciences (18th Edition, ed. A. Gennaro, Mack Publishing Co., Easton, Pa., 1990).

BRIEF DESCRIPTION OF THE DRAWINGS

FIG. 2 shows a direct amino acid sequence comparison of the mannose lectin described by Gowda et al. (*J. Biol Chem* 269:18789–18793, 1994: SEQ ID NO:49 and SEQ ID NO:51) and the derived amino acid sequence of Dl-FRIL, a representative, non-limiting FRIL family member of the invention (SEQ ID NO:50 and SEQ ID NO:52), encoded by a representative, non-limiting nucleic acid of the invention.

FIG. 19A shows that rhM-CSF specifically stimulated Fms 3T3 (solid circles) but neither mFlt3/Fms 3T3 (open circles) nor parent 3T3 cells (solid squares) in biological screening assay in a dose-dependent manner. FIG. 19B shows that PHA-LCM (reciprocal dilution) stimulated mFlt3/Fms 3T3 (solid circles) and Stk 3T3 (open circles) but not parent untransfected 3T3 cells (solid squares).

FIG. 20A shows the number of viable cells cord blood cells observed microscopically. FIG. 20B shows the stimulation of mFlt3/Fms 3T3 cells by anion exchange column fractions. FIG. 20C shows the stimulation of Stk 3T3 cells by anion exchange column fractions. FIG. 20D shows the stimulation of Fms 3T3 cells by anion exchange column fractions.

FIG. 21A shows that the plateau stimulation of Flt3 3T3 cells decreased during purification from crude, 10-fold concentrated PHA-LCM (solid circles) to partially purified (open circles), and highly purified (solid squares). Medium control is shown is open squares. FIG. 21B shows that the decreased plateau stimulation of Flt3 3T3 cells (solid circles) was restored by addition of sub-optimal concentrations (1:200) of crude PHA-LCM (solid squares). Corresponding medium controls are shown in open symbols.

FIG. 24B shows a direct amino acid sequence comparison of Pv-FRIL(SEQ ID NO:56), a representative, non-limiting FRIL family member of the invention, with DLL (SEQ ID NO:55), the mannose binding lectin of Gowda et al., and the PHA lectin, PHA-E (SEQ ID NO:57).

FIGS. 27A–27B are representations of line graphs showing the total cell numbers and progenitor levels in the presence of Dl-FRIL, a representative, non-limiting FRIL family member of the invention, or cytokines. Enriched CB CD34$^+$ cells were cultured for 3, 6, 10, or 13 days in the presence of Dl-FRIL (solid symbols) or cytokines (open symbols). Colonies were scored on day 14 and progenitor levels were calculated based on total cell numbers. Values shown represent the mean±SEM of data from up to 10 experiments. FIG. 27A shows the total cell numbers over time. FIG. 27B shows the progenitor levels in cultures over time.

FIG. 28A shows the total numbers of cells cultured with Dl-FRIL for the entire 10 days (solid symbols) or for 6 days followed by 4 days of cytokine stimulation (open symbols). FIG. 28B shows the progenitor levels in cells cultured with Dl-FRIL for the entire 10 days (solid symbols) or for 6 days followed by 4 days of cytokine stimulation (open symbols). FIG. 28C shows the total numbers of cells cultured with Dl-FRIL for 13 days (solid symbols) or for 10 days followed by 3 days of cytokine stimulation (open symbols). FIG. 28D shows the progenitor levels in cells cultured with Dl-FRIL for 13 days (solid symbols) or for 10 days followed by 3 days of cytokine stimulation (open symbols).

FIGS. 29A–29D are representations of representative Southern blot analyses showing the quantitative analysis of SRC after ex vivo cultures with Dl-FRIL, a representative, non-limiting FRIL family member of the invention, or cytokines and after transplantation into mice. FIG. 29A is a representation of a representative Southern blot showing human DNA in the marrow of mice transplanted with cells that were cultured with Dl-FRIL for 6 days (lane 1), Dl-FRIL for 10 days (lane 2), or with Dl-FRIL for 6 days followed by 4 days with cytokine stimulation (lane 3). FIG. 29B is a representation of a representative Southern blot showing human DNA in the marrow of mice transplanted with cells cultured with Dl-FRIL for 10 days (lanes 1–2), or with Dl-FRIL for 6 days followed by 4 days with cytokine stimulation (lanes 3–4). FIG. 29C is a representation of a representative Southern blot showing human DNA in the marrow of mice transplanted with the original cells prior to seeding (lane 1), or with cells cultured with Dl-FRIL for 13 days (lane 2). FIG. 29D is a representation of a representative Southern blot showing human DNA in the marrow of mice transplanted with cells cultured with FRIL for 10 days (lane 1), Dl-FRIL for 6 days followed by 4 days of cytokine stimulation (lane 2), Dl-FRIL for 13 days (lane 3), or with Dl-FRIL for 10 days followed by 3 days of cytokine stimulation (lane 4).

FIG. 29E is a representation of a Southern blot analysis showing the detection of a 0%, 0.1%, 1%, and 10% human DNA per murine DNA.

FIG. 33A shows the number of colonies per $2\times10^5$ cells, where the cells treated as indicated prior to transplantation into mice were recovered from the murine BM, and seeded into semisolid media selective for human colonies. Progenitor levels were calculated based on the total human cell numbers ($2\times10^5$ cells) in the marrow of transplanted mice. Values shown represent the mean±SEM of data from 3 experiments, 9 mice/treatment. FIG. 33B shows a representative flow cytometry analysis showing nonspecific labeling where mouse IgG was used as isotype control. FIGS. 33C and 33D show representative flow cytometry analyses of BM cells from mice that were transplanted with $CD34^+$ cells (FIG. 33C) or $CD34^+CD38^{-/low}$ cells (FIG. 33D) precultured with Dl-FRIL for 10 days, where the harvested BM cells were stained with anti human CD45 and anti-human CD19. FIGS. 33E and 33F show representative flow cytometry analyses of BM cells from mice that were engrafted by $CD34^+$ cells (FIG. 33E) or $CD34^+CD38^{-/low}$ cells (FIG. 33F) precultured with Dl-FRIL for 10 days, where the harvested BM cells were subsequently cultured with SCF+IL-15 for 10 days, and then stained with human specific monoclonal anti-CD45 and anti-CD56.

FIG. 34A shows the total cell numbers. FIG. 34B shows the percentage of CFU-GEMM out of total colonies. Values shown are per $2\times10^5$ seeded cells and represent the mean±SEM of data from 5 experiments.

FIG. 36A shows the dose response to Ara-C; FIG. 36B shows the dose response to doxorubicin; and FIG. 36C shows the dose response to 5-FU.

DETAILED DESCRIPTION OF THE PREFERRED EMBODIMENTS

Figure 1:
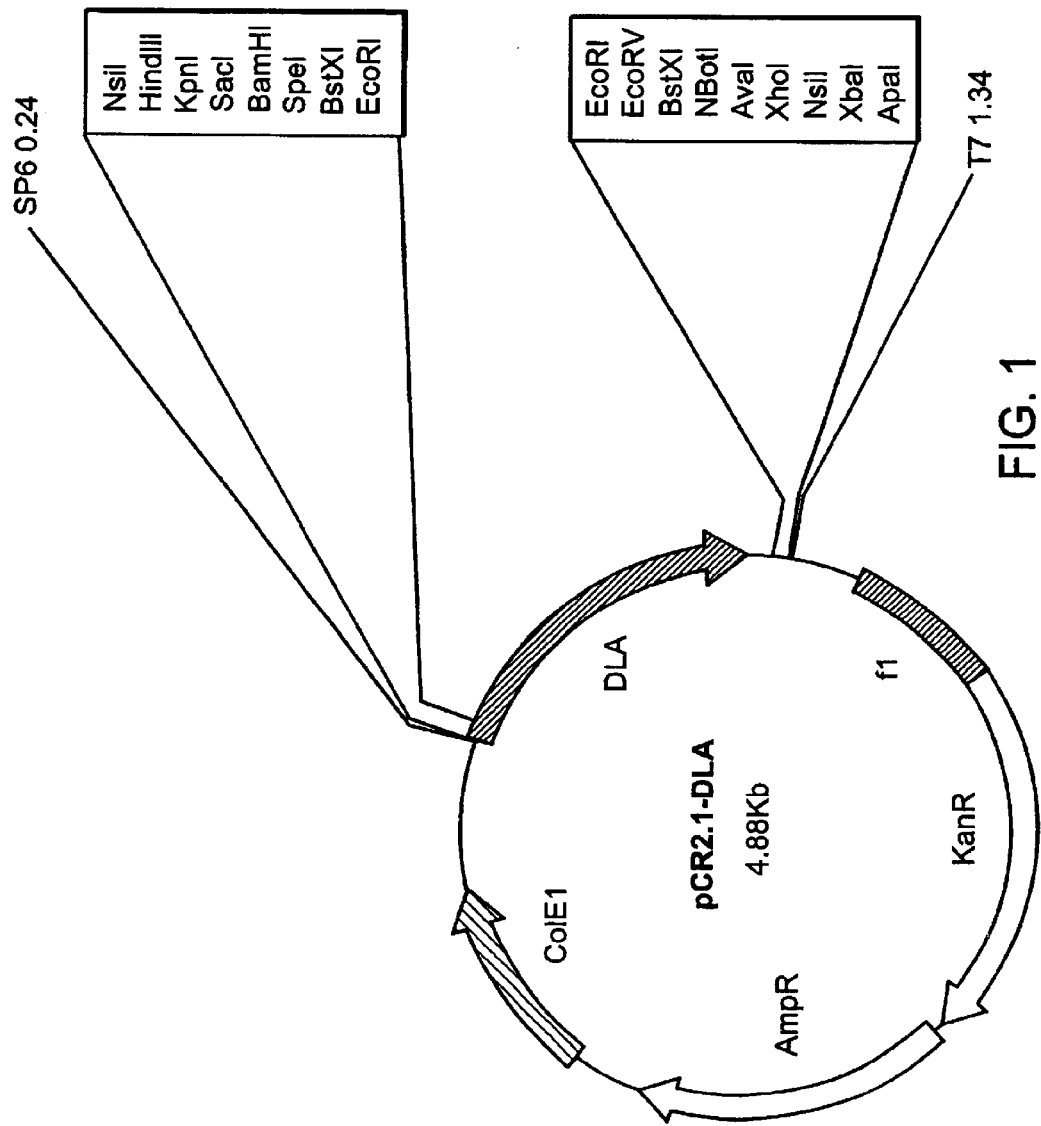
FIG. 1 is a map of a cloning vector pCR2.1-DLA manufactured by ligating a cDNA according to the invention in the EcoRI site of the cloning vector pCR2.1.

The invention relates the preservation of progenitor cells by members of the FRIL family of progenitor cell preservation factors. More specifically, the invention relates to the in vivo or ex vivo preservation of progenitor cells, such as hematopoietic progenitor cells, using members of the FRIL family of progenitor cell preservation factors.

The invention provides a family of factors that preserve progenitor cells. Members of this family, the FRIL family, are non-toxic, inexpensively produced reagents that preserve progenitor cells. The invention provides compositions comprising at least one member of the FRIL family, as well as methods for using members of the FRIL family to preserve progenitor cells both in vivo and ex vivo.

All of the patents and publications cited herein reflect the knowledge in the art and are hereby incorporated by reference in entirety to the same extent as if each were specifically stated to be incorporated by reference. Any inconsistency between these patents and publications and the present disclosure shall be resolved in favor of the present disclosure.

In a first aspect, the invention provides an essentially pure composition of a member of the FRIL family of progenitor cell preservation factors. The term, "FRIL family of progenitor cell preservation factors" is used to mean a family of lectins, wherein each FRIL family member molecule binds to a normally glycosylated FLT3 receptor, wherein each FRIL family member molecule preserves progenitor cells, and wherein one FRIL family member molecule that is isolated from a hyacinth bean (i.e., *Dolichos lab lab*) has an amino acid sequence which comprises the following eight amino acid sequence: TNNVLQXT (SEQ ID NO: 24). By "FRIL family member" or "FRIL family member molecule" is meant one or more molecules of the FRIL family of progenitor cell preservation factors.

In accordance with the first aspect of the invention, a composition of a FRIL family member, which includes a mutant of another FRIL family member molecule or a fusion protein comprising a portion derived from a FRIL family member molecule or mutant thereof, wherein each FRIL family member molecule that binds to a normally glycosylated FLT3 receptor has at least about 45% amino acid sequence identity with another amino acid sequence of another member of the FRIL family, preferably at least about 50% identity, even more preferably at least about 55% identity, still more preferably at least about 60% identity, and still more preferably at least about 65% identity with the sequence of the second protein. In the case of proteins having high sequence identity, the amino acid sequence of the first protein shares at least about 75% sequence identity, preferably at least about 85% identity, and more preferably at least about 95% identity, with the amino acid sequence of another member of the FRIL family.

Both amino acid sequence identity and nucleic acid sequence identity between two proteins or two nucleic acid molecules can be measured according to standard methods. For example, in order to compare a first amino acid sequence to a second amino acid sequence or a first nucleic acid sequence to a second nucleic acid sequence for the purpose of determining percentage identity between the two sequences, the sequences are aligned so as to maximize the number of identical amino acid or nucleic acid residues. The sequences of proteins sharing at least 50% amino acid sequence identity or the sequences of nucleic acids sharing at least 45% nucleic acid sequence identity can usually be aligned by visual inspection. If visual inspection is insufficient, the proteins or nucleic acids may be aligned in accordance with the FASTA method in accordance with Pearson and Lipman (*Proc. Natl. Acad. Sci. USA* 85:2444–2448, 1988), or, preferably, any of the methods described by George, D. G. et al., in *Macromolecular Sequencing and Synthesis, Selected Methods and Applications*, pages 127–149, Alan R. Liss, Inc. (1988), such as formula 4 at page 137 using a match score of 1, a mismatch score of 0, and a gap penalty of −1. From this method, percentage of sequence identity between the first and second amino acid sequences or between the first and second nucleic acid can be determined.

Other methods for determining amino acid or nucleic acid sequence identity are described in Feng and Doolittle (*Journal of Molecular Evolution* 25: 351–360, 1987) and Higgins and Sharp (*CABIOS* 5: 151–153, 1989).

Another method for determining amino acid or nucleic acid sequence identity between two proteins or nucleic acids is by using sequence analysis software with the default parameters specified therein. Various software packages exist including Sequence Analysis Software Package of the Genetics Computer Group (University of Wisconsin Biotechnology Center, Madison, Wis.), and the various BLAST programs of the National Center for Biotechnology (National Library of Medicine, Bethesda, Md.).

Unless otherwise specified, percentage of amino acid sequence identity or percentage of nucleic acid sequence identity is determined using the basic BLAST program of the National Center for Biotechnology (National Library of Medicine, Bethesda, Md.), using the default settings defined therein.

Another test for percentage identity of two nucleic acid sequences is whether they hybridize under normal hybridization conditions, preferably under stringent hybridization conditions. Thus, also included in the invention are proteins that are encoded by nucleic acid molecules that hybridize under high stringent conditions to a sequence complementary to SEQ ID NO: 1, SEQ ID NO: 3, SEQ ID NO: 5, and/or SEQ ID NO: 7. The term "stringent conditions," as used herein, is equivalent to "high stringent conditions" and "high stringency." These terms are used interchangeably in the art.

Stringent conditions are defined in a number of ways. In one definition, stringent conditions are selected to be about 50° C. lower than the thermal melting point ($T_m$) for a specific sequence at a defined ionic strength and pH. The $T_m$ is the temperature (under defined ionic strength and pH) at which 50% of the target sequence hybridizes to a perfectly matched sequence. Typical stringent conditions are those in which the salt concentration is at least about 0.02 M at pH 7 and the temperature is at least about 60° C. "Stringent conditions," in referring to percentage identity (e.g., homology) or substantial similarity in the hybridization context, can be combined conditions of salt, temperature, organic solvents or other parameters that are typically known to control hybridization reactions. The combination of parameters is more important than the measure of any single parameter. If incompletely complementary sequences recognize each other under high stringency conditions, then these sequences hybridize under conditions of high stringency (see U.S. Pat. No. 5,786,210; Wetmur and Davidson, *J. Mol. Biol.* 31, 349–370, 1968). Control of hybridization conditions, and the relationships between hybridization conditions and degree of homology are understood by those skilled in the art. See, e.g., Sambrook et al., *Molecular Cloning. A Laboratory Manual*, 2ed., Cold Spring Harbor Laboratory, Cold Spring Harbor, 1989. Further examples of stringent conditions can be found in Goeddel et al., U.S. Pat. No. 5,789,550.

In a non-limiting example, "stringent conditions" can be provided in a variety of ways such as overnight incubation at 42° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA. Alternatively, the stringent conditions are characterized by a hybridization buffer comprising 30% formamide in 5×SSPE (0.18 M NaCl, 0.01 M NaPO$_4$, pH 7.7, 0.0001 M EDTA) buffer at a temperature of 42° C., and subsequent washing at 42° C. with 0.2×SSPE. Preferably, stringent conditions involve the use of a hybridization buffer comprising 50% formamide in 5×SSPE at a temperature of 42° C. and washing at the same temperature with 0.2×SSPE.

As used herein, by "preserves progenitor cells" is meant an ability of a FRIL family member molecule (or mutant thereof or fusion protein comprising a FRIL family member molecule or mutant thereof) to retain (i.e., preserve) progenitor cells in an undifferentiated state, which can be determined using the assays described below (e.g., the SCID mouse reconstituting cell assay and the methylcellulose or other semi-solid medium based hematopoietic progenitor cell assay). In accordance with the invention, "progenitor cell" refers to any normal somatic cell that has the capacity to generate fully differentiated, functional progeny by differentiation and proliferation. Progenitor cells include progenitors from any tissue or organ system, including, but not limited to, blood, mesenchymal, embryonic, nerve, muscle, skin, gut, bone, kidney, liver, pancreas, thymus, brain and the like. Progenitor cells are distinguished from "differentiated cells," the latter being defined as those cells that may or may not have the capacity to proliferate, i.e., self-replicate, but that are unable to undergo further differentiation to a different cell type under normal physiological conditions. Moreover, progenitor cells are further distinguished from abnormal cells such as neoplastic cells, as defined herein. For example, leukemia cells proliferate (self-replicate), but generally do not further differentiate, despite appearing to be immature or undifferentiated.

Progenitor cells include all the cells in a lineage of differentiation and proliferation prior to the most differentiated or the fully mature cell. Thus, for example, progenitors include the skin progenitor in the mature individual. The skin progenitor is capable of differentiation to only one type of cell, but is itself not fully mature or fully differentiated.

By "hematopoiesis" is meant the development of mature, functional blood cells. The progenitor cells that give rise to mature, functional blood cells are called hematopoietic progenitor cells. The most primitive, undifferentiated hematopoietic progenitor cell is called a hematopoietic stem cell. Hematopoietic stem cells typically reside in the bone marrow primarily in a quiescent state, and may form identical daughter cells through a process called "self-renewal."

Production of some mature, functional blood cells results from proliferation and differentiation of "unipotential progenitors," i.e., those progenitors that have the capacity to make only one type of blood cell. For red blood cell (erythrocyte) production, a unipotential progenitor called a "CFU-E" (colony forming unit-erythroid) has the capacity to generate two to 32 mature progeny cells. Various other hematopoietic progenitors have been characterized. For example, hematopoietic progenitor cells include those cells that are capable of successive cycles of differentiating and proliferating to yield up to eight different mature hematopoietic cell lineages.

Uncommitted progenitor cells, such as hematopoietic stem cells, can be described as being "totipotent," i.e., both necessary and sufficient for generating all types of mature cells. Progenitor cells that retain a capacity to generate all cell lineages, but that cannot self-renew, are termed "pluripotent." Cells that can produce some but not all blood lineages and cannot self-renew are termed "multipotent."

Progenitor cells can be defined by mRNA levels of genes that either specifically regulate progenitors or serve as markers of lineage commitment. For example, genes induced in primitive human hematopoietic progenitor cells include those encoding the shared beta subunits of the IL3, IL5, and/or granulocyte-macrophage colony-stimulating factor (GM-CSF) receptors, termed the beta common chain (McClanahan et al., *Blood* 81:3903–2915, 1993); CD34 genes; and/or the receptors for Kit (Turner et al., *Blood* 88:3383–3390, 1996), FLT1, FLT4 (Galland et al., *Oncogene* 8:3233–1240, 1993), FLK1 (Broxmeyer et al., *Int. J. Hematol.* 62:303–215, 1995), and FLT3 (Lyman and Jacobsen, *Blood* 91:3101–1134., 1998). Those genes for intermediate progenitors include the c-Fms, G-CSF receptor, and/or CD34 genes; and the IL-7 receptor gene, a gene induced for B lymphopoiesis.

Murine primitive progenitor populations include receptors for interleukin-1 alpha (IL-1α), IL-3, IL-6, granulocyte colony-stimulating factor (G-CSF), and/or FLK1-1 (the murine homologue of human KDR which binds VEGF) (Broxmeyer, supra), but lack receptors for macrophage colony-stimulating factor (M-CSF), granulocyte-macrophage colony stimulating factor (GM-CSF), and leukemia inhibitory factor (LIF). Cells within the intermediate progenitor cell population include receptors for GM-CSF, G-CSF, IL-6, and/or IL-1α.

In accordance with the first aspect of the invention, the terms "bind," "binds," or "bound" are used interchangeably to mean that a FRIL family member molecule of the invention binds to a normally glycosylated FLT3 receptor with an affinity higher than the affinity with which the FLT3-Ligand binds the FLT3 receptor. Preferably, a FRIL family member molecule binds to a normally glycosylated FLT3 receptor with an affinity that is at least as high as the affinity with which an antibody binds its specific ligand. Even more preferably, a FRIL family member molecule of the invention binds to a normally glycosylated FLT3 receptor with an affinity that is higher than the affinity with which an antibody binds its specific ligand. Still more preferably, a FRIL family member molecule of the invention binds to a normally glycosylated FLT3 receptor with a dissociation constant ($K_D$) of at least $10^{-7}$ M, more preferably $10^{-8}$ M, even more preferably $10^{-9}$ M, still more preferably, at least $10^{-10}$ M, and most preferably, a FRIL family member molecule of the invention binds to a normally glycosylated FLT3 receptor with a dissociation constant ($K_D$) of at least $10^{-11}$ M. Standard methods for determining binding and binding affinity are known.

In accordance with the invention, by "normally glycosylated FLT3 receptor" is meant an FLT3 receptor that has a glycosylation pattern of an FLT3 cell glycosylated by a normal cell. By "normal cell," as used herein in accordance with all aspects of the present invention, is meant a cell that is not neoplastic. As used herein, by "neoplastic cell" is meant a cell that shows aberrant proliferation, particularly increased proliferation, that is not regulated by such factors as cell-cell contact inhibition and soluble regulators (e.g., cytokines or hormones), and that abnormally glycosylates the FLT3 receptor such that the glycosylation pattern on the FLT3 receptor on the neoplastic cells is abnormal and such that the FLT3 receptor on the neoplastic cell is not bound by a FRIL family member molecule.

In accordance with the first aspect of the invention, by "essentially pure" means a molecule, such as a nucleic acid or protein (e.g., a FRIL family member molecule), or composition of a molecule that is more free from other organic molecules (e.g., carbohydrates, nucleic acids, proteins, and lipids) that naturally occur with an impure molecule, and is substantially free as well of materials used during the purification process. For example, a protein or nucleic acid molecule is considered to be essentially pure if it is at least approximately 60%, preferably at least approximately 75%, more preferably approximately at least 85%, most preferably approximately at least 90%, and optimally approximately at least 95% pure, ie., free from other organic molecules with which it naturally occurs and free from materials used during the purification process. Methods for purifying proteins are known in the art and include, without limitation, HPLC, SDS-PAGE, immunoprecipitation, recombinant protein production, affinity chromatography using specific antibodies, ion-exchange, size-exclusion, and hydrophobic interaction chromatography, or a combination of any of these methods. These and other suitable methods are described, e.g., in Marston, "The purification of eukaryotic proteins expressed in *E. coli*," in *DNA Cloning*, Glover D. M., ed., Volume III, IRL Press Ltd., Oxford, 1987; Marston and Hartley, "Solubilization of protein aggregates," pp. 266–267 in *Guide to Protein Purification*, Deutscher M P, ed., Academic Press, San Diego, 1990; Laemmli, U. K., *Nature* 227:680–685, 1970. A FRIL family member can also be purified by binding to a mannose, which may be coupled on a solid support (e.g., a sepharose bead).

Methods for purifying nucleic acids are known in the art and include, without limitation, Guanidine-HCl extraction, polymerase chain reaction, CsCl gradient fractionation, phenol: chloroform extraction, ethanol precipitation, and standard recombinant DNA methodologies. Standard methods for purifying both proteins and nucleic acid molecules are provided in, e.g., Ausubel et al., *Current Protocols in Molecular Biology*, John Wiley & Sons, New York, N.Y., 1994; Sambrook et al., supra.

In accordance with the first aspect of the invention, a FRIL family member molecule may be purified from a natural source by methods well known in the art. For example, the purification of Dl-FRIL from *Dolichos lab lab* is described below in Example 1. The purification of Pv-FRIL from *Phaseolus vulgaris* as described below in Example 5. The purification of YamFRIL from *Sphenostylis stenocarpa* is described below in Example 22. Such methods also include, for example, those described by Moore in PCT application PCT/US97/22486 and by Gowda et al., supra. A suitable natural source from which to purify a FRIL family member molecule includes plants, especially legume plants. Legumes, such as the garden pea or the common bean, are plants ("leguminous plants") from a family (Leguminosae) of dicotyledonous herbs, shrubs, and trees bearing (nitrogen-fixing bacteria) nodules on their roots. These plants are commonly associated with their seeds (e.g., the garden pea or the common bean)

More specifically, a FRIL family member molecule according to the first aspect of the invention can be purified from members of the tribe *Phaseoleae*. For example, a FRIL family member molecule can be purified from *Dolichos lab lab* (e.g., hyacinth beans, which is also known by other common names throughout the world). Alternatively, a FRIL family member molecule can be purified from varieties of the common bean (*Phaseolus vulgaris*) (e.g., red kidney beans and white kidney beans), from the yam bean (*Sphenostylis stenocarpa*) or from *Vigna sinensis*, commonly known as the black-eyed pea.

As demonstrated in the examples below, purification of a FRIL family member molecule from a legume is rapid and inexpensive, and results in a large amount of essentially pure lectin. A native FRIL family member molecule can be easily purified from legumes, such as hyacinth beans (pesticide-free), by mannose-affinity chromatography or ovalbumin affinity chromatography, and is more than 100 times cheaper to produce than recombinant cytokines. In accordance with the first aspect of the invention, by "lectin" is meant a protein that binds sugar residues with high affinity. Most preferably, a FRIL family member molecule is a mannose/glucose-specific legume lectin.

As demonstrated in the examples below, FRIL family member molecules, and compositions of FRIL family member molecules, have many attributes as reagents to either alleviate the progenitor cell-depleting activity of a therapeutic (e.g., a chemotherapeutic) or to alleviate the symptoms of a condition where the patient's progenitor cells are depleted. For example, FRIL family members have unique properties and are the first soluble regulators reported to preserve hematopoietic stem cells and progenitors in a dormant state for extended periods, even in the presence of potent stimulators of proliferation and differentiation. Moreover, because mice tolerate very high levels of compositions of FRIL family members, this may permit more effective protection of stem cells and progenitors by preventing their recruitment during aggressive dose intensification regimens aimed at increasing frequency and dosage levels of chemotherapy. While the biological activity of Dl-FRIL is similar to cytokines (ng/ml range), as demonstrated in the examples below, mice tolerated up to a 1,000-fold more Dl-FRIL than cytokines.

In addition, by preserving hematopoietic stem cells and other progenitor cells in a dormant state, one or more members of the FRIL family allows for the administration of a broad range of cell cycle active chemotherapy drugs with greater frequency and higher dose. Thus, administration of a composition of one or more FRIL family members may permit more aggressive dose-intensification chemotherapy regimens for a broad range of chemotherapy drugs. Administration of a composition of a FRIL family member also provides for a larger reservoir of progenitor cells which could rapidly respond to stimulatory signals after completing chemotherapy.

In certain embodiment of the first aspect of the invention, the FRIL family member of the invention is from a legume (e.g., a bean plant).

In some embodiments, the FRIL family member molecule of the invention is from a hyacinth bean (i.e., *Dolichos lab lab*), and has an amino acid sequence comprising the sequence of SEQ ID NO: 24. Preferably, the FRIL family member molecule of the invention isolated from a hyacinth bean has the amino acid sequence of SEQ ID NO: 2 or comprises a signal sequence having the amino acid sequence of SEQ ID NO: 4, and, even more preferably, is encoded by a nucleic acid having the nucleic acid sequence of SEQ ID NO: 1 or the nucleic acid sequence of SEQ ID NO: 3.

In some embodiments, the FRIL family member molecule of the invention is from a red kidney bean (i.e., *Phaseolus vulgans*). Preferably, the FRIL family member of the invention isolated from a red kidney bean has the amino acid sequence of SEQ ID NO: 6, and, even more preferably, is encoded by a nucleic acid having the nucleic acid sequence of SEQ ID NO: 5.

In some embodiments, the FRIL family member of the invention is from a yam bean (i.e., *Sphenostylis stenocarpa*). Preferably, the FRIL family member of the invention isolated from a yam bean has the amino acid sequence comprising the amino acid sequence of SEQ ID NO: 8, more preferably has a β subunit having an amino acid sequence which comprises the amino acid sequence of SEQ ID NO: 9, even more preferably has an α subunit having an amino acid sequence which comprises the amino add sequence of SEQ ID NO: 10, and, even more preferably, is encoded by a nucleic acid having a nucleic acid sequence which comprises the nucleic acid sequence of SEQ ID NO: 7.

In certain embodiments of the first aspect of the invention, the FRIL family member molecule is a mutant derived from a second member of the FRIL family, wherein the mutant is selected from the group consisting of a substitution mutant, a deletion mutant, an addition mutant, or a combination thereof (e.g., a mutant of Dl-FRIL or Pv-FRIL described below). For example, it is preferred to substitute amino acids in a sequence with equivalent amino acids. Groups of amino acids known normally to be equivalent are: (1) Ala(A), Ser(S), Thr(T), Pro(P), and Gly(G); (2) Asn(N), Asp(D), Glu(E), Gln(Q); (3) His(H), Arg(R), Lys(K); (4) Met(M), Leu(L), Ile(I), Val(V); and (5) Phe(F), Tyr(Y), Trp(W). Substitutions, additions, and/or deletions in an amino acid sequence can be made as long as the mutant FRIL family member molecule continues to satisfy the functional criteria described herein. An amino acid sequence that is substantially the same as another sequence, but that differs from the other sequence by means of one or more substitutions, additions, and/or deletions, is considered to be an equivalent sequence. Preferably, less than 50%, more preferably less than 25%, and still more preferably less than 10%, of the number of amino acid residues in a sequence are substituted for, added to, or deleted from the FRIL family member molecule upon which the mutant FRIL family member was derived.

In certain embodiments of the first aspect of the invention, the FRIL family member molecule is a fusion protein comprising a first portion and a second portion, wherein the first portion is derived from a second member of the FRIL family. By "fusion protein" is meant a molecule comprising at least two proteins or polypeptide fragments thereof joined together, wherein the proteins or polypeptide fragments thereof are not joined together in the naturally-occurring organism from which the proteins or polypeptide fragments thereof were derived. The two proteins or polypeptide fragments thereof of a fusion protein may be joined by any means, including, without limitation, a chemical linker, a peptide bond, or a non-covalent bond, such as an ionic bond. By "protein" or "polypeptide" is meant a chain of two or more amino acid residues joined with a peptide bond regardless of length or post-translational modification such as acetylation, glycosylation, lipidation, or phosphorylation.

A FRIL family member molecule that is a fusion protein may comprise a first portion derived from a FRIL family member and a second portion derived from a protein or other molecule not related to the FRIL family (e.g., the heavy chain of an antibody).

An additional FRIL family member molecule that is a fusion protein is FRIL family member comprising the α subunit from a first FRIL family member and β subunit from a second FRIL family member. Such a fusion protein may be generated, for example, by joining a nucleic acid sequence encoding the α subunit of the first FRIL family member in frame with a nucleic acid sequence encoding the β subunit of the second FRIL family member. The nucleic acid encoding such a fusion protein can be engineered to encode an enzyme-specific cleavage site between the portion encoding the α subunit of the first FRIL family member and the portion encoding the β subunit of the second FRIL family member.

Where a FRIL family member is a fusion protein, identity of the fusion protein as a FRIL family member is determined by the sequence identity between the FRIL family member-derived portion of the fusion protein and a second FRIL family member, where the FRIL family member-derived portion of the fusion protein and the second FRIL family member share at least about 45% amino acid sequence identity, even more preferably at least about 50% identity, even more preferably at least about 55% identity, still more preferably at least about 60% identity, still more preferably at least about 65% identity yet more preferably at least about 75% sequence identity, still more preferably at least about 85% identity, and most preferably at least about 95% identity, with the amino acid sequence of a second member of the FRIL family.

A FRIL family member in accordance with the first aspect of the invention can also be a recombinant protein made by expressing a recombinant nucleic acid that encodes FRIL in a suitable host. Thus, in a second aspect, the invention features an essentially pure nucleic acid molecule encoding a member of the FRIL family of progenitor cell preservation factors. Exemplary purifications of the nucleic acid molecules of the invention from *Dolichos lab lab* and *Phaseolus vulgaris* are described below. As is well known, if an amino acid sequence (primary structure) is known, a family of nucleic acids can then be constructed, each having a sequence that differs from the others by at least one nucleotide, but where each different nucleic acid still encodes the same protein. For example, if a protein has been sequenced but its corresponding gene has not been identified, the gene can be acquired through amplification of genomic DNA using a set of degenerate primers that specify all possible sequences encoding the protein. Thus, a nucleic acid in accordance to this aspect of the invention need not have a naturally occurring sequence, but need only encode a FRIL family member according to the first aspect of the invention.

In accordance with the second aspect of the invention, a "member of the FRIL family of progenitor cell preservation factors" is as described above in the first aspect of the invention. "Essentially pure" is used as described for the first aspect of the invention.

By a "recombinant nucleic acid" is meant a nucleic acid which encodes a FRIL family member molecule, or a portion encoding at least 15 contiguous amino acids thereof, or a mutant thereof, or a fusion protein comprising the molecule, portion thereof, or mutant thereof, or is capable of expressing an antisense molecule specifically complementary thereto, or a sense molecule that shares nucleic acid sequence identity thereto wherein the recombinant nucleic acid may be in the form of linear DNA or RNA, covalently closed circular DNA or RNA, or as part of a chromosome, provided however that it cannot be the native chromosomal locus for a FRIL family member molecule. Preferred recombinant nucleic acids of the invention are vectors, which may include an origin of replication and are thus capable of replication in one or more cell type. Certain preferred recombinant nucleic acids are expression vectors, and further comprise at least a promoter and passive terminator, thereby allowing transcription of the recombinant nucleic acid in a bacterial, fungal, plant, insect or mammalian cell. By "nucleic acid" or "nucleic acid molecule" as used herein, means any deoxyribonucleic acid (DNA) or ribonucleic acid (RNA), including, without limitation, complementary DNA (cDNA), genomic DNA, RNA, hnRNA, messenger RNA (mRNA), DNA/RNA hybrids, or synthetic nucleic acids (e.g., an oligonucleotide) comprising ribonucleic and/or deoxyribonucleic acids or synthetic variants thereof. The nucleic acid of the invention includes, without limitation, an oligonucleotide or a polynucleotide. The nucleic acid can be single stranded, or partially or completely double stranded (duplex). Duplex nucleic acids can be homoduplex or heteroduplex.

In accordance with the second aspect of the invention, a nucleic acid encoding a FRIL family member has at least about 50% nucleic acid sequence identity with a nucleic acid encoding another member of the FRIL family, preferably at least about 55% nucleic acid sequence identity, more preferably at least about 60% nucleic acid sequence identity, more preferably at least about 65% nucleic acid sequence identity, still more preferably at least about 75% nucleic acid sequence identity, still more preferably at least about 85% nucleic acid sequence identity, and most preferably at least about 95% nucleic acid sequence identity with a nucleic acid encoding another member of the FRIL family. Percentage nucleic acid sequence identity can be determined as described for the first aspect of the invention.

A recombinant nucleic acid according to the second aspect of the invention can also be chemically synthesized by methods known in the art. For example, recombinant DNA can be synthesized chemically from the four nucleotides in whole or in part by methods known in the art. Such methods include those described in Caruthers, M. H., *Science* 230(4723):281–285, 1985. DNA can also be synthesized by preparing overlapping double-stranded oligonucleotides, filling in the gaps, and ligating the ends together. See, generally, Sambrook et al., supra, and Glover and Hames, eds., *DNA Cloning*, 2d ed., Vols. 1–4, IRL Press, Oxford, 1995.

A recombinant nucleic acid molecule of the invention encoding a mutant FRIL family member can be prepared from wild-type DNA by site-directed mutagenesis (see, for example, Zoller and Smith, *Nucleic. Acids. Res.* 10:6487–6500, 1982; Zoller, M. J., *Methods Enzymol.* 100:468–500, 1983; Zoller, M. J., *DNA* 3(6):479–488, 1984; and McPherson, M. J., ed., *Directed Mutagenesis: A Practical Approach*, IRL Press, Oxford, 1991.

A recombinant nucleic acid of the second aspect of the invention can be amplified by methods known in the art One suitable method is the polymerase chain reaction (PCR) method described in Saiki et al., *Science* 239:487, 1988, Mullis et al., U.S. Pat. No. 4,683,195, and Sambrook et al., supra. It is convenient to amplify the clones in the lambda-gt10 or lambda-gt11 vectors using lambda-gt10- or lambda-gt11-specific oligomers as the amplimers (available from Clontech, Palo Alto, Calif.). Larger synthetic nucleic acid structures can also be manufactured having specific and recognizable utilities according to the invention. For example, vectors (e.g., recombinant expression vectors) are known which permit the incorporation of recombinant nucleic acids of interest for cloning and transformation of other cells. Thus, the invention further includes vectors (e.g., plasmids, phages, and cosmids) which incorporate a nucleotide sequence of the invention, especially vectors which include the recombinant nucleic acid molecule of the invention for expression of a FRIL family member.

A recombinant nucleic acid of the invention can be replicated and used to express a FRIL family member following insertion into a wide variety of host cells in a wide variety of cloning and expression vectors. The host can be prokaryotic or eukaryotic. The nucleic acid can be obtained from natural sources and, optionally, modified. The genes can also be synthesized in whole or in part.

Cloning vectors can comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as M13fd, and other filamentous single-stranded DNA phages.

Vectors for expressing proteins in bacteria, especially *E. coli*, are also known. Such vectors include the pK233 (or any of the tac family of plasmids), T7, and lambda $P_L$. Examples of vectors that express fusion proteins are PATH vectors described in Dieckmann and Tzagoloff (*J. Biol. Chem.* 260(3):1513–1520, 1985). These vectors contain DNA sequences that encode anthranilate synthetase (TrpE) followed by a polylinker at the carboxy terminus. Other expression vector systems are based on beta-galactosidase (pEX); maltose binding protein (pMAL); glutathione S-transferase (pGST) (see, e.g., Smith, D. B., *Gene* 67:31–40, 1988 and Abath, F. G., *Peptide Research* 3(4):167–168, 1990). Vectors useful for cloning and expression in yeast are also available. A suitable example is the $2\mu$ circle plasmid.

Suitable cloning/expression vectors for use in mammalian cells are also known. Such vectors include well-known derivatives of SV-40, adenovirus, and cytomegalovirus (CMV) retrovirus-derived DNA sequences. Any such vectors, when coupled with vectors derived from a combination of plasmids and phage DNA, i.e., shuttle vectors, allow for the isolation and identification of protein coding sequences in prokaryotes.

Further eukaryotic expression vectors are known in the art (e.g., Southern and Berg, *J. Mol. Appl. Genet.* 1:327–341, 1982; Subramani et al., *Mol. Cell. Biol.* 1:854–864, 1981; Kaufmann and Sharp, *J. Mol. Biol.* 159:601–621, 1982; Kaufmann and Sharp, *Mol. Cell. Biol.* 159:601–664, 1982; Scahill et al., *Proc. Natl. Acad. Sci. USA* 80:4654–4659, 1983; Urlaub and Chasin, *Proc. Natl. Acad. Sci. USA* 77:4216–4220, 1980).

The expression vectors useful in the present invention contain at least one expression control sequence that is operatively linked to the recombinant nucleic acid molecule or fragment thereof to be expressed. The control sequence is inserted in the vector in order to control and to regulate the expression of the recombinant nucleic acid of the invention. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts for expressing the recombinant nucleic acids of the invention include well-known prokaryotic and eukaryotic cells. Some suitable prokaryotic hosts include, for example, E. coli, such as E. coli SG-936, E. coli HB101, E. coli W3110, E. coli X1776, E. coli X2282, E. coli DHI, and E. coli MRCl, Pseudomonas, Bacillus, such as B. subtilis, and Streptomyces. Suitable eukaryotic cells include yeasts and other fungi, insect, animal cells, such as COS cells and CHO cells, human cells and plant cells in tissue culture.

Given the recombinant nucleic acid sequences disclosed herein, the artisan can further design recombinant nucleic acids having particular functions in various types of applications. For example, the artisan can construct oligonucleotides or polynucleotides for use as primers in nucleic acid amplification procedures, such as the polymerase chain reaction (PCR), ligase chain reaction (LCR), Repair Chain Reaction (RCR), PCR oligonucleotide ligation assay (PCR-OLA), and the like. Oligonucleotides useful as probes in hybridization studies, such as in situ hybridization, can be constructed. Numerous methods for labeling such probes with radioisotopes, fluorescent tags, enzymes, binding moieties (e.g., biotin), and the like are known, so that the probes of the invention can be adapted for easy detectability.

Oligonucleotides can also be designed and manufactured for other purposes. For example, the invention enables the artisan to design antisense oligonucleotides, and triplex-forming oligonucleotides, and the like, for use in the study of structure/function relationships. Homologous recombination can be implemented by adaptation of the nucleic acid of the invention for use as targeting means.

Recombinant nucleic acids of the invention produced as described above can further be modified to alter biophysical or biological properties by means of techniques known in the art. For example, the recombinant nucleic acid can be modified to increase its stability against nucleases (e.g., "end-capping"), or to modify its lipophilicity, solubility, or binding affinity to complementary sequences. Methods for modifying nucleic acids to achieve specific purposes are disclosed in the art, for example, in Sambrook et al., supra. Moreover, the recombinant nucleic acid of the invention can include one or more portions of nucleotide sequence that are non-coding for a FRIL family member.

In a third aspect, the invention provides a pharmaceutical formulation comprising an essentially pure composition of one or more members of the FRIL family of progenitor cell preservation factors and a pharmaceutically acceptable carrier. By "pharmaceutically acceptable carrier" is meant any inert carrier that is non-toxic to the animal to which it is administered and that retains the therapeutic properties of the compound with which it is administered (i.e., the FRIL family member). Pharmaceutically acceptable carriers and their formulations are well-known and generally described in, for example, Remington's Pharmaceutical Sciences (18th Edition, ed. A. Gennaro, Mack Publishing Co., Easton, Pa., 1990). One exemplary pharmaceutically acceptable carrier is physiological saline. Pharmaceutical formulations of the invention may employ any pharmaceutically acceptable carrier, depending upon the route of administration of the composition.

Compositions of FRIL family members may be used safely and efficaciously as a therapeutic. The gastrointestinal tracts of animals come in constant contact with lectins, such as FRIL family members, in raw and/or cooked vegetables and fruits. Many lectins pass through the gastrointestinal tract biologically intact (Pusztai, A., Eur. J. Clin. Nutr. 47: 691–699, 1993). Some lectins interact with the gut and are transported into the peripheral blood circulation. For example, a recent study found peanut agglutinin (PNA) in the blood of humans at levels of 1–5 µg/ml an hour after ingesting 200 g of raw peanuts (Wang et al., Lancet 352: 1831–1832, 1998). Antibodies to dietary lectins are commonly found in people at levels of ~1 µg/ml (Tchernychev and Wilchek, FEBS Lett. 397: 139–142, 1996). These circulating antibodies do not block carbohydrate binding of the lectins.

In certain embodiments of the third aspect of the invention, administration of a therapeutically effective amount of the pharmaceutical formulation to a patient suffering from a condition whereby the patient's hematopoietic progenitor cells are depleted alleviates and/or reduces the condition in the patient.

In accordance with the third aspect of the invention, by "therapeutically effective amount" is meant a dosage of a composition of a FRIL family member or pharmaceutical formulation comprising a composition of a FRIL family member that is effective to alleviate and/or reduce either a condition whereby the patient's hematopoietic progenitor cells are depleted or a hematopoietic progenitor cell-depleting activity of a therapeutic (e.g., a chemotherapeutic). Preferably, such administration is systemic (e.g., by intravenous injection). When administered systemically, a therapeutically effective amount is an amount of between about 500 ng of the FRIL family member/kg total body weight and about 5 mg/kg total body weight per day. Preferably, a therapeutically effective amount is between about 500 ng/kg and 500 µg/kg total body weight of the FRIL family member per day. Still more preferably, a therapeutically effective amount is between about 5 µg/kg and 50 µg/kg total body weight of the FRIL family member per day. Most preferably, a therapeutically effective amount is an amount that delivers about 50 µg/kg total body weight of the FRIL family member per day.

A composition of a FRIL family member of the invention and pharmaceutical formulation comprising a composition of a FRIL family member of the invention may be administered to patients having, or predisposed to developing, a condition whereby the patient's hematopoietic progenitor cells are depleted. Such a condition may be congenital. For example, the patient may have severe combined immunodeficiency or aplastic anemia.

The condition may also be induced by a drug. Thus, in certain embodiments of the third aspect of the invention, administration of a therapeutically effective amount of the pharmaceutical formulation to a patient prior to treatment of the patient with a therapeutic treatment having a hematopoietic progenitor cell-depleting activity alleviates the hematopoietic progenitor cell-depleting activity of the therapeutic in the patient. For example, cancer patients are often treated with radiotherapeutics or chemotherapeutics that have hematopoietic progenitor cell-depleting activity. By "hematopoietic progenitor cell-depleting activity" is meant an activity of a therapeutic treatment whereby the hematopoietic progenitor cells in the patient being treated with the therapeutic treatment are depleted, either by killing the progenitor cells or by inducing the progenitor cells to undergo irreversible differentiation. Non-limiting examples of therapeutic treatments having hematopoietic progenitor cell-depleting activity are the chemotherapeutic agents cytarabine (Ara-C), doxorubicin (Dox), daunorubicin, and 5-fluorouracil (5-FU).

In certain embodiments, administration of the pharmaceutical formulation of the invention to a patient prior to the treatment of the patient with a therapeutic treatment having a hematopoietic progenitor cell-depleting activity enables treatment of the patient with a higher dosage of the therapeutic treatment. The higher dosage of the therapeutic treatment may be accomplished by either an increased dose of the therapeutic treatment and/or an increased duration of treatment with the therapeutic treatment. For example, a child diagnosed with childhood Acute Myelogenous Leukemia (AML) is typically initially treated for the first seven days with daunorubicin at 45 mg/m$^2$ on Days 1–3 plus Ara-C at 100 mg/m$^2$ for 7 days plus GTG at 100 mg/m$^2$ for 7 days. The same child pretreated with a composition in accordance with this aspect of the invention may be able to tolerate a higher dosage (i.e., higher dose and/or prolonged treatment period) of any or all of these chemotherapeutics. Such an increase in dosage tolerance of a therapeutic treatment (e.g., a chemotherapeutic) having a hematopoietic progenitor cell-depleting activity in a cancer patient is desirable since a higher dosage may result in the destruction of more cancerous cells.

The pharmaceutical formulations and/or compositions of the invention may be administered by any appropriate means. For example, the pharmaceutical formulations and/or compositions of the invention may be administered to a mammal within a pharmaceutically acceptable diluent, carrier, or excipient, in unit dosage form according to conventional pharmaceutical practice. Administration may begin before the mammal is symptomatic for a condition whereby the patient's hematopoietic progenitor cells are depleted. For example, administration of the pharmaceutical formulations of the third aspect of the invention to a cancer patient may begin before the patient receives radiotherapy and/or chemotherapy treatment.

Any appropriate route of administration of a pharmaceutical formulation and/or composition of the invention may be employed, including, without limitation, parenteral intravenous, intra-arterial, subcutaneous, sublingual, transdermal, topical, intrapulmonary, intramuscular, intraperitoneal, by inhalation, intranasal, aerosol, intrarectal, intravaginal, or by oral administration. Pharmaceutical formulations and/or compositions of the invention may be in the form of liquid solutions or suspensions; for oral administration, formulations may be in the form of tablets or capsules; and for intranasal formulations, in the form of powders, nasal drops, or aerosols. The pharmaceutical formulations and/or compositions may be administered locally to the area affected by a condition whereby the patient's hematopoietic progenitor cells are depleted. For example, the pharmaceutical formulations and/or compositions of the invention may be administered directly into the patient's bone marrow. The pharmaceutical formulations and/or compositions of the invention may be administered systemically.

In certain embodiments of the third aspect of the invention, the patient is human or a domesticated animal. By "domesticated animal" is meant an animal domesticated by humans, including, without limitation, a cat, a dog, an elephant, a horse, a sheep, a cow, a pig, and a goat. In some embodiments, the patient has cancer.

In some embodiments of the third aspect, the treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In a fourth aspect, the invention provides a method for alleviating and/or reducing the hematopoietic progenitor cell-depleting activity of a therapeutic treatment in a patient, comprising administering to the animal a therapeutically effective amount of a composition of a FRIL family member prior to administration of the therapeutic treatment to the patient. "Hematopoietic progenitor cell-depleting activity" is as described for the third aspect of the invention. Routes of administration of a composition of a FRIL family member of this aspect of the invention are as described for the administration of the pharmaceutical formulation of the third aspect of the invention. "Therapeutically effective amount" is as described for the third aspect of the invention.

In certain embodiments of the fourth aspect, the patient is a human or a domesticated animal. "Domesticated animal" is as described for the third aspect of the invention. In certain embodiments, the patient has cancer. In some embodiments, the therapeutic treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In a fifth aspect, the invention provides a method for isolating a population of progenitor cells, comprising contacting a population of cells with a plurality of FRIL family member molecules, and separating the unbound cells, wherein the cells bound to the FRIL family member molecules are an isolated population of progenitor cells. "FRIL family member molecule" and "progenitor cell" are as described for the first aspect of the invention. By "unbound cell" is meant a cell that does not bind to a FRIL family member. "Bind" is as described for the first aspect of the invention.

By "isolated" is meant a population of progenitor cells that is separated from a larger population of cells, wherein the percentage of progenitor cells in the isolated population is at least two fold greater than the percentage of progenitor cells in the larger population. Preferably, the percentage of progenitor cells in the isolated population is at least four fold greater than the percentage of progenitor cells in the larger population. A non-limiting example of the increased percentage of progenitor cells in an isolated population of progenitor cells of the invention is shown below in Table 11. Preferably, the isolated population of progenitor cells of the invention is at most 2% of the total population of umbilical cord blood mononuclear cells (CB mnc). Preferably, the population of progenitor cells of the invention is at most 1% of the total population of umbilical cord blood mononuclear cells (CB mnc). Preferably, an isolated population of progenitor cells binds to a normally glycosylated FLT3 receptor. "Normally glycosylated FLT3 receptor" is as defined above.

In preferred embodiments, the isolated population of progenitor cells is from a human or a domesticated animal.

In certain embodiments of the fifth aspect of the invention, the FRIL family member molecules are detectably labeled. By "detectably labeled" is meant that the FRIL family member is attached to a label that is detectable visually or instrumentally. Detectable labels such as enzymes and chromophoric molecules can be conjugated to the FRIL family member molecules by means of coupling agents, such as dialdehydes, carbodiimides, and dimaleimides. Numerous methods of labeling proteins are known in the art The label can also be directly attached through a functional group on the FRIL family member. Such a functional group may be present on the FRIL family member molecule to be detectably labeled; alternatively, the FRIL family member molecules can be modified using standard techniques to contain a functional group. Some examples of suitable functional groups include, without limitation, amino, carboxyl, sulfhydryl, maleimide, isocyanate, and isothiocyanate.

In certain embodiments, the detectable label is radioactive or non-radioactive. Some examples of useful radioactive labels include $^{32}$P, $^{125}$I, $^{131}$I, and $^{3}$H. Use of radioactive labels have been described in U.K. patent document 2,034,323, and U.S. Pat. Nos. 4,358,535, and 4,302,204. Some examples of non-radioactive labels include enzymes, chromophores, atoms and molecules detectable by electron microscopy, and metal ions detectable by their magnetic properties.

In certain embodiments of the fifth aspect of the invention, the detectable label is an enzymatic label. Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, and EP 63,879, each incorporated herein by reference, and by Rotman, *Proc. Natl. Acad. Sci. USA* 47:1981–1991, 1961.

In certain embodiments of this aspect of the invention, the detectably labeled FRIL family member molecules are labeled by being specifically bound by an antibody that is detectably labeled.

In certain embodiments of this aspect of the invention, the FRIL family member molecules are conjugated to a receptor (or ligand) and is detectably labeled by binding the receptor (or ligand) with the ligand (or receptor), wherein the ligand (or receptor) is detectably labeled. Any of the known ligand-receptor combinations is suitable. Some suitable ligand-receptor pairs include, for example, biotin-avidin or -streptavidin, and antibody-antigen. In certain embodiments, biotin-avidin combination is preferred.

In certain embodiments, the detectable label is a chromophore. Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

In certain embodiments of this aspect of the invention, where the FRIL family member molecules are detectably labeled to a chromophore, the unbound cells are separated by using a flow cytometry cell sorter to sort the population of cells contacted with the FRIL family member molecules detectably labeled with a fluorescent marker.

In certain embodiments of the fifth aspect of the invention, the FRIL family member molecules are immobilized on a solid support. "Solid support" includes any surface, including, without limitation, the surface of a sepharose bead, a gel, a matrix, a magnetic bead, and a plastic surface (e.g., the bottom of a tissue culture dish or flask).

In some embodiments, the solid support is a bead, for example, a magnetic bead. In some embodiments, where the solid support is a magnetic bead, the unbound cells are separated by applying a magnet to the population of cells contacted with the FRIL family member molecules immobilized on the magnetic bead. In further embodiments, the population of cells bound to the FRIL family member molecules immobilized on a magnetic bead is rinsed with a physiologically acceptable solution while the magnet is applied. By "physiologically acceptable solution" is meant an inert solution, such as sterile saline solution or tissue culture medium, which is non-toxic to the cells.

Methods for isolating cells that bind FRIL family member molecule-coated magnetic beads are described below in Example 16. Magnetic beads are commerically available (e.g., from Dynabeads Tosylactivated, Lake Success, N.Y.; or from Miltenyi Biotec, Auburn, Calif.). Since the FRIL family member is protein, it can be conjugated to a magnetic bead via amino- or sulfhydryl-groups of the protein. A FRIL family member molecule can also be immobilized on magnetic beads by a biotin-strepavidin interaction.

Preferred magnetic beads are the MACS superparamagnetic MicroBeads (from Miltenyi Biotec) which are extremely small, approximately 50 nm in diameter (MACS beads are about one million times smaller in volume than eukaryotic cells). Because MACS beads react like magnetic antibodies, magnetic labeling is achieved within minutes. MACS MicroBeads form a stable colloidal suspension and do not precipitate or aggregate in magnetic fields. Because of their size and composition (iron oxide and polysaccharide) MACS beads are biodegradable, so labeled cells retain their physiological function. This property of MACS beads is particularly useful for bead-sorted FRIL family member-binding cells, which bind the FRIL family member with such high affinity that it is difficult to remove the beads.

In certain embodiments of the fifth aspect, the solid support is the bottom of a tissue culture plate. In some embodiments, the unbound cells are separated by rinsing the population of cells contacted with the FRIL family member molecules immobilized on the bottom of a tissue culture plate with a physiologically acceptable solution.

FRIL family member molecules may be directly or indirectly attached to the bottom of a tissue culture plate. Following a standard "panning" protocol (see, e.g., Stengelin et al., *EMBO J.* 7(4):1053–1059, 1988; Aruffo and Seed, *Proc. Natl. Acad. Sci. USA* 84(23): 8573–8577, 1987), a population of cells suspected of containing FRIL family member-binding progenitor cells is incubated on the plate. The plate is then gently rinsed with a physiologically acceptable solution, thereby removing the unbound cells while leaving the FRIL family member-binding population of cells attached to the FRIL family member-coated plate.

In preferred embodiments of the fifth aspect of the invention, the isolated population of progenitor cells is a population of hematopoietic progenitor cells. In various embodiments, the population of cells is whole blood, umbilical cord blood, bone marrow cells, or fetal liver cells.

In certain embodiments of the fifth aspect of the invention, the population of cells is a sorted population of cells, wherein a cell of the sorted population does not express CD11b, CD11c, or CD38. Because more primitive progenitor cells typically express few cell surface molecules, prior to isolating a population of progenitor cells that binds to a FRIL family member, the population of cells is preferably sorted to first remove cells that express one or more of the following cell surface molecules: CD11b, CD11c, and CD38. Following this negative sort (i.e., a sort, wherein the cells retained do not express CD11b, CD11c, and/or CD38), the sorted population is positively sorted for an ability to bind a FRIL family member.

In certain embodiments, the sorted population of cells is sorted by flow cytometry or by magnetic bead selection. Thus, a population of cells (e.g., human umbilical cord blood cells) may be first contacted with chromophore-labeled antibodies (or other molecule such as a ligand) which specifically bind CD11b, CD11c, and/or CD38. Following binding, the population of cells is then negatively sorted by flow cytometry, where the cells which are not bound by the antibodies (and so do not express CD11b, CD11c, and/or CD38) are retained and further sorted for an ability to bind a FRIL family member, wherein the population of cells that binds a FRIL family member is an isolated population of progenitor cells according to the invention.

A population of cells may also be contacted with a molecule, such as an antibody, which specifically binds CD11b, CD11c, and/or CD38, wherein the molecule is attached to a solid support, such as a magnetic bead. The population is then negatively sorted by applying a magnet to the beads, and retaining the cells that do not bind the beads and so are not attracted to the magnet. These sorted cells are then further sorted for an ability to bind a FRIL family member, wherein the population of cells that binds a FRIL family member is an isolated population of progenitor cells according to the invention.

In a sixth aspect, invention provides an isolated population of progenitor cells isolated by a method comprising contacting a population of cells with a plurality of FRIL family member molecules, and separating the unbound cells, wherein the cells bound to the FRIL family member are an isolated population of progenitor cells. "FRIL family member molecule," "progenitor cell," "unbound cell," and "bind" are as described above.

In preferred embodiments, the isolated population of progenitor cells is from a human or a domesticated animal.

In certain embodiments of the sixth aspect, the cells of the isolated population do not express CD34 on their cell surface. In certain embodiments, the cells of the isolated population express the FLK1, FLT1, FLT3, FLT4, or Kit receptor tyrosine kinases. In some embodiments, the cells of the isolated population express the CD11b or CD11c cell surface molecules. In preferred embodiments, the cells of the isolated population express FLT3.

In various embodiments of the sixth aspect of the invention, the cells of the isolated population are hemangioblasts, mesenchymal stem cells, bone progenitor cells, hepatic progenitor cells, endothelial progenitor cells, hematopoietic progenitor cells, embryonal stem cells, brain progenitor cells, or dendritic progenitor cells. By "hemangioblast" is meant a cell that is a progenitor cell for both hemaopoietic and endothelial lineages. Preferably, the cells of the isolated population are hematopoietic progenitor cells. By a "mesenchymal stem cells" is meant the population of cells that is the progenitor for bone marrow stromal cells, including, without limitation, adipose tissue cells, cartilage-producing cells, muscle cells, and bone cells. Such cells of this aspect of the invention can be used, for example, for tissue repair.

Determination of what type of cells a progenitor cell of the invention will give rise to is made by the various progenitor cell assays described below. For example, if a progenitor cell is suspected of being an endothelial progenitor cell, the cell may be cultured in a methylcellulose progenitor cell assay in the presence of vascular endothelial growth factor. Should cells arising from such a culture have endothelial cell markers, the progenitor cell of the invention is a endothelial progenitor cell or perhaps a hemangioblast.

In certain embodiments of the sixth aspect of the invention, where the cells of the isolated population are hematopoietic progenitor cells, transplantation of the cell into an animal lacking a population of hematopoietic progenitor cells sufficient to enable survival of the animal reconstitutes the animal, wherein the transplanted animal survives. Determination of the ability of a hematopoietic progenitor cell to reconstitute an animal lacking a population of hematopoietic progenitor cells sufficient to enable survival of the animal may be made using the methods described below for the NOD-SCID mouse.

In certain embodiments, the hematopoietic progenitor cells are from a mouse or a human and the animal is a mouse. In some embodiments, the mouse is a severe combined immunodeficient (SCID) mouse (e.g., the NOD-SCID mouse described below) or a mouse that has been exposed to a sublethal dose of radiation and/or chemotherapy.

In certain embodiments of the sixth aspect of the invention, the hematopoietic progenitor cells are from a human and the animal is a human. In some embodiments, the human is a cancer patient receiving a treatment that depletes the patient's hematopoietic progenitor cells. In some embodiments, the treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In a seventh aspect, the invention provides a method for preserving progenitor cells ex vivo, comprising contacting a population of cells comprising at least one progenitor cell with an effective amount of a composition of a FRIL family member for an effective period of time, wherein the progenitor cell in the population are rendered quiescent. "FRIL family member" and "progenitor cell" are as described above for the first aspect of the invention.

In accordance with this aspect of the invention, the terms "effective amount" and "effective period of time" are used to denote known treatments at dosages and for periods of time effective to preserve progenitor cells. Where administered to a patient, preferably, such administration is systemic (e.g., by intravenous injection). Effective amounts and effective periods of time can be determined using the models and assays described herein. For example, the Examples below describe the preservation of progenitor cells that have SCID-reconstituting ability. In accordance with the invention, an effective amount may range from about 0.1 ng/mL to about 1 $\mu$g/mL of a FRIL family member, preferably about 1.0 ng/mL to to about 1.0 $\mu$g/mL, more preferably about 1.0 ng/mL to about 100 ng/mL, even more preferably about 10 ng/mL to about 50 ng/mL, and most preferably about 50 ng/mL of a FRIL family member in culture. In accordance with the invention, an effective period of time includes culturing the cells in the presence of a FRIL family member for between from about 2 hours to 5 days, more preferably from about 12 hours to about 3 days, and most preferably for about 24 hours.

In certain embodiments of the seventh aspect, the progenitor cells are from a human or from a domesticated animal. In certain embodiments, the population of cells is bone marrow cells.

In some embodiments, the non-progenitor cells in the population of cells differentiate or die. Thus, although the progenitor cells in the culture do not actually expand in number, they are enriched relative to the number of cells in the culture.

In certain embodiments of the seventh aspect, the population of cells is removed from a cancer patient prior to treatment of the cancer patient with a therapeutic treatment having a hematopoietic progenitor cell-depleting activity. In some embodiments, the therapeutic treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In an eighth aspect, the invention provides a method for preserving progenitor cells in vivo, comprising administering to a patient a therapeutically effective amount of a composition of a FRIL family member for a therapeutically effective period of time, wherein the progenitor cells in the patient are rendered quiescent. "FRIL family member" and "progenitor cell" are as described above for the first aspect of the invention. "Therapeutically effective amount" is as described for the third aspect of the invention.

By "therapeutically effective period of time" is meant treatment for a period of time effective to preserve progenitor cells. Where administered to a patient, preferably, such administration is systemic (e.g., by intravenous injection). Effective amounts and effective periods of time can be determined using the models and assays described herein. For example, the examples below describe the preservation of progenitor cells that have SCID-reconstituting ability. In accordance with the invention, a therapeutically effective period of time is injecting a therapeutically effective amount of a composition and/or pharmaceutical formulation of a FRIL family member between about 5 days before the patient receives treatment with a therapeutic treatment (e.g., a chemotherapeutic) having a progenitor cell-depleting activity to about 2 hours prior to treatment with the therapeutic treatment, wherein the therapeutically effective amount of a composition and/or pharmaceutical formulation of the FRIL family member is administered daily. In accordance with the invention, a preferred therapeutically effective period of time is injecting a patient (e.g., a cancer patient) with a therapeutically effective amount of a composition and/or pharmaceutical formulation of a FRIL family member between about 2 days before the patient receives treatment with a therapeutic treatment (e.g., a chemotherapeutic) having a progenitor cell-depleting activity to about 1 day prior to treatment with the therapeutic treatment, wherein the therapeutically effective amount of a composition and/or pharmaceutical formulation of a FRIL is administered daily. It will be understood that once the patient starts to receive treatment of a therapeutic treatment having a progenitor cell-depleting activity, the therapeutically effective amount of a composition and/or pharmaceutical formulation of a FRIL family member may be different from the therapeutically effective amount of the a composition and/or pharmaceutical formulation of a FRIL family member that the patient received prior to receiving treatment with the therapeutic treatment.

Preferably, the patient is a human or a domesticated animal. "Domesticated animal" is as described for the third aspect of the invention.

In certain embodiments of the eighth aspect of the invention, the patient is a cancer patient. In some embodiments, the effective amount of the composition of the FRIL family member is administered prior to the treatment of the patient with a therapeutic treatment having a hematopoietic progenitor cell-depleting activity. In some embodiments, the therapeutic treatment is a radiotherapeutic or a chemotherapeutic treatment, including, without limitation, cytarabine (Ara-C), doxorubicin (Dox), or 5-fluorouracil (5-FU), or a combination of a radiotherapeutic and a chemotherapeutic.

In a ninth aspect, the invention provides a method for identifying a progenitor cell, comprising contacting a candidate cell with a FRIL family member molecule, wherein binding of the candidate cell to the FRIL family member molecule identifies the candidate cell as a progenitor cell. "FRIL family member molecule" and "progenitor cell" are as described above for the first aspect of the invention.

In certain embodiments of the ninth aspect, the candidate cell is in a population of cells. In certain embodiments, the candidate cell is from a human.

In a tenth aspect, the invention provides a progenitor cell identified by a method comprising contacting a candidate cell with a FRIL family member molecule, wherein binding of the candidate cell to the FRIL family member molecule identifies the candidate cell as a progenitor cell. "FRIL family member" and "progenitor cell" are as described above for the first aspect of the invention.

In an eleventh aspect, the invention provides a method for identifying a composition of a member of the FRIL family of progenitor cell preservation factors, comprising contacting a candidate compound with a glycosylated extracellular domain of an FLT3 receptor, wherein the glycosylation pattern of the extracellular domain of the FLT3 receptor is the same as the glycosylation pattern of an extracellular domain of a normally glycosylated FLT3 receptor, wherein a candidate compound that binds the glycosylated extracellular domain of the FLT3 receptor is identified as a composition of a FRIL family member. "FRIL family member," "progenitor cell," and "normally glycosylated FLT3 receptor" are as described above for the first aspect of the invention.

In accordance with the eleventh aspect of the invention, the normally glycosylated extracellular domain of the FLT3 receptor may expressed on a cell surface (e.g., on the surface of an NIH 3T3 cell, as described in the examples below). Any normal cell may be transfected with a nucleic acid sequence encoding the extracellular domain of the FLT3 receptor (from, e.g., a human or a mouse) provided that the cell normally glycosylates the FLT3 receptor it expresses on its cell surface. It should be noted that the cell need not be transfected with a nucleic acid sequence encoding the entire FLT3 receptor. For example, the cell may be transfected with a nucleic acid molecule encoding a fusion protein comprising the intracellular domain of a non-FLT3 receptor (e.g., the Fms receptor) and the extracellular domain of the FLT3 receptor. A candidate compound according to this aspect of the invention is then incubated with the cell expressing the normally glycosylated extracellular domain of the FLT3 receptor, and binding of the candidate compound to the cell (as can be measured, as described below, by survival of the cell) identifies the candidate compound as a FRIL family member.

Alternatively, the normally glycosylated extracellular domain of the FLT3 receptor need not be expressed by a cell. Instead, the normally glycosylated extracellular domain of the FLT3 receptor may be detectably labeled or immobilized on a solid support (e.g., a magnetic bead). For example, the normally glycosylated extracellular domain of the FLT3 receptor can be bound to the surface of a 96 well microtiter plate. Compositions comprising different candidate compounds (or pools of such compounds) can be detectably labeled (e.g., with biotin), and added to the wells. After incubation for an amount of time required for binding of a positive control (e.g., a composition of a known FRIL family member) the plate is washed and detectably labeled avidin is added to each well. The plate can then be read on a standard microtiter plate reader to determine binding of a composition of a candidate compound to the plate-bound normally glycosylated extracellular domain of the FLT3 receptor, wherein binding (as measured by detection of the bound detectably labeled avidin) identifies the candidate compound in the composition as a FRIL family member.

In certain embodiments of the eleventh aspect, the candidate compound is a lectin. In certain embodiments, the lectin is synthetic. In certain embodiments, the lectin is from a legume.

In a twelfth aspect, the invention provides an essentially pure composition of a FRIL family member identified by the method comprising contacting a candidate compound with a glycosylated extracellular domain of an FLT3 receptor, wherein the glycosylation pattern of the extracellular domain of the FLT3 receptor is the same as the glycosylation pattern of an extracellular domain of a normally glycosylated FLT3 receptor, wherein a candidate compound that binds the glycosylated extracellular domain of the FLT3 receptor is identified as an essentially pure composition of a member of the FRIL family. "FRIL family member," "progenitor cell," and "normally glycosylated FLT3 receptor," and "essentially pure" are as described above for the first aspect of the invention.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein. Such equivalents are considered to be within the scope of this invention, and are covered by the following claims.

EXAMPLE 1

Purification and Cloning of a FRIL Family Member, Dl-FRIL Purification of Dl-FRIL from *Dolichos lab lab*

Seeds from the hyacinth beans (*Dolichos lab lab*) were purchased from Stokes Seeds (Buffalo, N.Y.) and grown in a greenhouse. Dry seeds were ground in a coffee mill and the powder was extracted in 5 volumes of 50 mM Tris/HCl containing 1 nM each of $MgCl_2$ and $CaCl_2$ for 4 hours at 4° C. Bean solids were pelleted by centrifugation at 10,000×g for 20 min. The pH of the supernatant was acidified to pH 4.0 with acetic acid, followed by a second centrifugation to clarify the supernatant, and finally the pH was readjusted to 8.0 with sodium hydroxide. This crude extract was stored at −20° C.

Single-step purification of the FRIL family member was achieved by binding to a mannose-Sepharose matrix (Sigma). The gel (i.e., matrix) was tumbled with the thawed crude extract for 4–12 hours at 4° C., carefully washed several times with 50 mM Tris/HCl containing 1 nM each of $MgCl_2$ and $CaCl_2$, and then eluted with 20 mM α-methyl α-D-mannoside. Because this FRIL family member was isolated from *Dolichos lab lab*, it is referred to herein as Dl-FRIL.

RNA Isolation and cDNA Synthesis of Dl-FRIL

Total RNA was prepared from mid-maturation *Dolichos lab lab* seeds stored at −70° C. following the procedure of Pawloski et al. *Mol. Plant Biol. Manual* 5:1-13, 1994). Poly $(A^+)$ RNA was obtained from this total RNA using the PolyATract mRNA Isolation System (Promega) according to the manufacturer's instructions. Avian myeloblastosis virus reverse transcriptase (Promega) was used to generate cDNA from 0.5 μg poly($A^+$)RNA, or from 3.0 μg of total RNA, using 1 μg of oligo(dT) in standard reaction conditions (Sambrook et al., *Molecular Cloning. A Laboratory Manual*, 2d ed., Cold Spring Harbor Laboratory, Cold Spring Harbor, 1989).

Polymerase Chain Reaction and cDNA Cloning of Dl-FRIL

Based on the amino acid sequence published by Gowda et al., *J. Biol. Chem.* 269:18789–18793, 1994, two degenerate oligonucleotide primers were designed using *Phaseolus* codon usage (Devereux et al., *Nucleic Acids Res.* 12:387–394, 1984):

MLA AA(AG)TT(TC)GA(TC)CC(AT)AATC)CA(AG)GA (AG)GA (SEQ ID NO:11)

MLZ TT(AT)CC(AG)TT(TC)TGCCA(AG)TCCCA (SEQ ID NO:12).

A 500+ bp product was amplified from cDNA prepared as described abpve, by 30 cycles of polymerase chain reaction (PCR), each cycle comprising 40 seconds at 94° C., 40 seconds at 50° C., 60 seconds at 72° C., followed by an extension step at 72° C. for 10 min. Reactions were performed in 50 μL containing 30 pmol of each primer, 0.2 mM deoxyribonucleotides, and 0.5 unit of AmpliTaq polymerase (Perkin Elmer, Norwalk, Conn.) in the corresponding buffer.

The 500 bp product obtained by PCR was cloned in the cloning vector, pCR2.1 (Invitrogen, Carlsbad, Calif.), and sequenced by sequenase dideoxy chain termination (United States Biochemicals) using the following primers:

GTACCGAGCTCGGAT (SEQ ID NO:13)

TCTAGATGCATGCTCGAG (SEQ ID NO:14).

This sequence was designated "Dl-FRILa," as relating to the gene encoding the protein of interest, designated "Dl-FRIL" as noted above.

Based on the sequence of the Dl-FRILa amplified product, a specific primer was prepared:

MLX GTTGGACGTCAATTCCGATGTG (SEQ ID NO:15).

A degenerate primer corresponding to the first five amino acids of the sequence published by Gowda et al., *J. Biol. Chem.* 269:18789–18793, 1994 was also prepared:

MLI GC(TC)CA(AG)TC(TC)CT(TC)TC(TC)TT (SEQ ID NO:16).

The MLX and MLI primers were used in combination to amplify a 480 bp product from cDNA prepared as described above, through 30 PCR cycles using the same conditions described above. This secondary amplified fragment was cloned in the pCR2.1 vector and sequenced as described above, and was designated "Dl-FRILb."

The 3' end of Dl-FRIL was obtained through rapid amplification of cDNA ends by polymerase chain reaction (RACE-PCR) (see, e.g., Frohman "RACE: Rapid amplification of cDNA ends," pp. 28–38 in *PCR Protocols: A Guide to Methods and Applications*, Innis M A, Gelfand D H, Sninsky J J, and White T J, eds., Academic Press, San Diego, 1990) using the 5'/3' RACEKIT (Boehringer Mannheim, Indianapolis, Ind.) according to the manufacturer's instructions. In the cDNA synthesis for the 3' RACE, an oligo(dT) anchor primer ("AP") supplied with the kit was used, at a concentration of 32.5 μM, using the standard conditions described earlier in this Example.

AP GACCACGCGTATCGATGTCGAC (SEQ ID NO:17).

Nested PCR amplifications were performed using the AP anchor primer in combination with a specific primer having the following sequence:

MLB AAGTTAGACAGTGCAGGAAAC (SEQ ID NO:18).

The amplification conditions were again 30 cycles of 40 seconds at 94° C., 40 seconds at 55° C., 60 seconds at 72° C. each, with an extension step at 72° C. for 10 min. A 900+ bp product was obtained, which was subcloned in pCR2.1 and sequenced as described above, and was designated "Dl-FRILc" (SEQ ID NO:1).

To obtain the full length cDNA clone, the anchor primer AP was used in combination with a specific primer corresponding to the first 5 amino acids encoded at the 5'-terminus:
MLII GCACAGTCATTGTCATTTAG (SEQ ID NO:19).

The full length cDNA was obtained through 30 cycles of PCR, each cycle comprising 60 seconds at 94° C., 60 seconds at 58° C., 90 seconds at 72° C., with an extension step at 72° C. for 10 min. The reaction was performed in 100 μL containing 30 pmol of each primer, 0.2 mM deoxyribonucleotide, 1.0 unit of Pfu polymerase (Stratagene, La Jolla, Calif.). The MLII and AP primers were designed to generate an EcoRI site at each end (3' and 5') of the polynucleotide sequence. The full length cDNA was ligated into the EcoRI site of the cloning vector pCR2.1, resulting in the final product "pCR2.1-DLA" illustrated schematically in FIG. 1.

The Nucleotide Sequence of Dl-FRIL

The Dl-FRILc clone was sequenced completely using the dideoxy chain termination method. The nucleotide sequence of the full-length cDNA was determined to be:

```
  1 GCACAGTCAT TGTCATTTAG TTTCACCAAG TTTGATCCTA ACCAAGAGGA (SEQ ID NO:1)
 51 TCTTATCTTC CAAGGTCATG CCACTTCTAC AAACAATGTC TTACAAGTCA
101 CCAAGTTAGA CAGTGCAGGA AACCCTGTGA GTTCTAGTGC GGGAAGAGTG
151 TTATATTCTG CACCATTGCG CCTTTGGGAA GACTCTGCGG TATTGACAAG
201 CTTTGACACC ATTATCAACT TTGAAATCTC AACACCTTAC ACTTCTCGTA
251 TAGCTGATGG CTTGGCCTTC TTCATTGCAC CACCTGACTC TGTCATCAGT
301 TATCATGGTG GTTTTCTTGG ACTCTTTCCC AACGCAAACA CTCTCAACAA
351 CTCTTCCACC TCTGAAAACC AAACCACCAC TAAGGCTGCA TCAAGCAACG
401 TTGTTGCTGT TGAATTTGAC ACCTATCTTA ATCCCGATTA TGGTGATCCA
451 AACTACATAC ACATCGGAAT TGACGTCAAC TCTATTAGAT CCAAGGTAAC
501 TGCTAAGTGG GACTGGCAAA ATGGGAAAAT AGCCACTGCA CACATTAGCT
551 ATAACTCTGT CTCTAAAAGA CTATCTGTTA CTAGTTATTA TGCTGGGAGT
601 AAACCTGCGA CTCTCTCCTA TGATATTGAG TTACATACAG TGCTTCCTGA
651 ATGGGTCAGA GTAGGGTTAT CTGCTTCAAC TGGACAAGAT AAAGAAAGAA
701 ATACCGTTCA CTCATGGTCT TTCACTTCAA GCTTGTGGAC CAATGTGGCG
751 AAGAAGGAGA ATGAAAACAA GTATATTACA AGAGGCGTTC TGTGATGATA
801 TATGTGTATC AATGATTTTC TATGTTATAA GCATGTAATG TGCGATGAGT
851 CAATAATCAC AAGTACAGTG TAGTACTTGT ATGTTGTTTG TGTAAGAGTC
901 AGTTTGCTTT TAATAATAAC AAGTGCAGTT AGTACTTGT
```

The Dl-FRIL nucleotide sequence enabled inference of the following derived amino acid sequence for the Dl-FRIL protein:

```
AQSLSFSFTK FDPNQEDLIF QGHATSTNNV LQVTKLDSAG NPVSSSAGRV (SEQ ID NO:2)

LYSAPLRLWE DSAVLTSFDT IINFEISTPY TSRIADGLAF FIAPPDSVIS

YHGGFLGLFP NANTLNNSST SENQTTTKAA SSNVVAVEFD TYLNPDYGDP

NYIHIGIDVN SIRSKVTAKW DWQNGKIATA HISYNSVSKR LSVTSYYAGS

KPATLSYDIE LHTVLPEWVR VGLSASTGQD KERNTVHSWS FTSSLWTNVA

KKENENKYIT RGVL
```

The naturally-occurring signal sequence from the FRIL family member isolated from *Dolichos lab lab* (i.e., Dl-FRIL) has the following sequence:

MASSNLLTLA LFLVLLTHAN SA (SEQ ID NO: 4)

This sequence is located directly N-terminal to the first amino acid of SEQ ID NO: 2. The nucleic acid sequence of the naturally-occurring Dl-FRIL protein is provided below.

```
   1 ATGGCTTCCT CCAACTTACT CACCCTAGCC CTCTTCCTTG TGCTTCTCAC  (SEQ ID NO:3)

51 CCACGCAAAC TCAGCCGCAC AGTCATTGTC ATTTAGTTTC ACCAAGTTTG

101 ATCCTAACCA AGAGGATCTT ATCTTCCAAG GTCATGCCAC TTCTACAAAC

151 AATGTCTTAC AAGTCACCAA GTTAGACAGT GCAGGAAACC CTGTGAGTTC

201 TAGTGCGGGA AGAGTGTTAT ATTCTGCACC ATTGCGCCTT TGGGAAGACT

251 CTGCGGTATT GACAAGCTTT GACACCATTA TCAACTTTGA AATCTCAACA

301 CCTTACACTT CTCGTATAGC TGATGGCTTG GCCTTCTTCA TTGCACCACC

351 TGACTCTGTC ATCAGTTATC ATGGTGGTTT TCTTGGACTC TTTCCCAACG

401 CAAACACTCT CAACAACTCT TCCACCTCTG AAAACCAAAC CACCACTAAG

451 GCTGCATCAA GCAACGTTGT TGCTGTTGAA TTTGACACCT ATCTTAATCC

501 CGATTATGGT GATCCAAACT ACATACACAT CGGAATTGAC GTCAACTCTA

551 TTAGATCCAA GGTAACTGCT AAGTGGGACT GGCAAAATGG GAAAATAGCC

601 ACTGCACACA TTAGCTATAA CTCTGTCTCT AAAAGACTAT CTGTTACTAG

651 TTATTATGCT GGGAGTAAAC CTGCGACTCT CTCCTATGAT ATTGAGTTAC

701 ATACAGTGCT TCCTGAATGG GTCAGAGTAG GGTTATCTGC TTCAACTGGA

751 CAAGATAAAG AAAGAAATAC CGTTCACTCA TGGTCTTTCA CTTCAAGCTT

801 GTGGACCAAT GTGGCGAAGA AGGAGAATGA AAACAAGTAT ATTACAAGAG

851 GCGTTCTGTG ATGATATATG TGTATCAATG ATTTTCTATG TTATAAGCAT

901 GTAATGTGCG ATGAGTCAAT AATCACAAGT ACAGTGTAGT ACTTGTATGT

951 TGTTTGTGTA AGAGTCAGTT TGCTTTTAAT AATAACAAGT GCAGTTAGTA

1001 GTTGT
```

A comparative illustration of the derived Dl-FRIL amino acid sequence with the reported amino acid sequence of the mannose lectin as determined by Gowda et al. (*J. Biol. Chem.* 269:18789–18793, 1994) is shown in FIG. 2. The single sequence derived for Dl-FRIL protein comprises domains that correspond directly and with substantial homology to the α subunit (SEQ ID NO:52) and β subunit (SEQ ID NO:50) of the protein described by Gowda et al., supra. When the β subunit of the Gowda et al. (supra) protein is assigned to the N-terminal domain and is followed linearly by the α subunit, the arrangement of the polypeptides shows homology to other legume lectins.

The derived Dl-FRIL amino acid sequence, however, comprises an additional eight amino acid residues (aa27–34) that does not occur in the amino acid sequence described Gowda et al., supra. Several other differences between the amino acid sequences of Dl-FRIL and the amino acid sequence described by Gowda et al., supra, are also readily discernible from FIG. 2.

Site-specific Mutagenesis

To establish functionality of homologs of the protein encoded by the Dl-FRIL cDNA, a mutation was made in the Dl-FRIL cDNA clone. The domains of the derived protein and the pea lectin that include the mutation site are shown below:

Dl-FRIL .YLNPDYG.DPNYIHIGIDV (SEQ ID NO:20)

Pea FY.NAAWDPSNRDRHIGIDV (SEQ ID NO:21).

It is known that the asparagine residue (the highlighted "N") in the pea lectin is involved in binding to its saccharide ligand. The corresponding asparagine in Dl-FRIL (position 141 of the amino acid sequence of SEQ ID NO: 2) was mutated to aspartic acid ("D"). This mutation was designated "N141D" for convenience.

To introduce the mutation, recombinant PCR was performed (see, e.g., Higuchi, R., *PCR Protocols: A Guide to Methods and Applications*, Innis M. A., Gelfand D. H., Sninsky J. J., and White T. J., eds., Academic Press, San Diego, 1990). Two PCR reactions were carried out separately on the full length cDNA using two primers that contain the same mutation and produce two products with an overlapping region:

MutI CCATAATCGGGATCAAGATAGGTG (SEQ ID NO:25)

MutII CACCTATCTTGATCCCGATTATGG (SEQ ID NO:26).

The primary PCR products were purified with the QIAquick PCR Purification kit (QIAGEN, Valencia, Calif.), according to the manufacturer's instructions. The overlapping primary products were then combined and amplified together in a single second reaction using flanking primers:

M1 Forw AACTCAGCCGCACAGTCATTGTCA (SEQ ID NO:27)

APEcoRI GAATTCGACCACGCGTATCGATGTCGAC (SEQ ID NO:28).

Both the primary and the secondary PCR reactions were performed in 100 μL containing 50 pmol of each primer, 0.4 mM deoxyribonucleotide and 1.0 unit Pfu polymerase (Stratagene) in the corresponding buffer. The primary PCR reaction amplified the two separate fragments in 30 cycles, each cycle comprising 40 seconds at 94° C., 40 seconds at 50° C., 60 seconds at 72° C., with an extension step at 72° C. for 10 min. The second PCR reaction amplified the recombinant fragment in 12 cycles using the same conditions described above.

Figure 3:
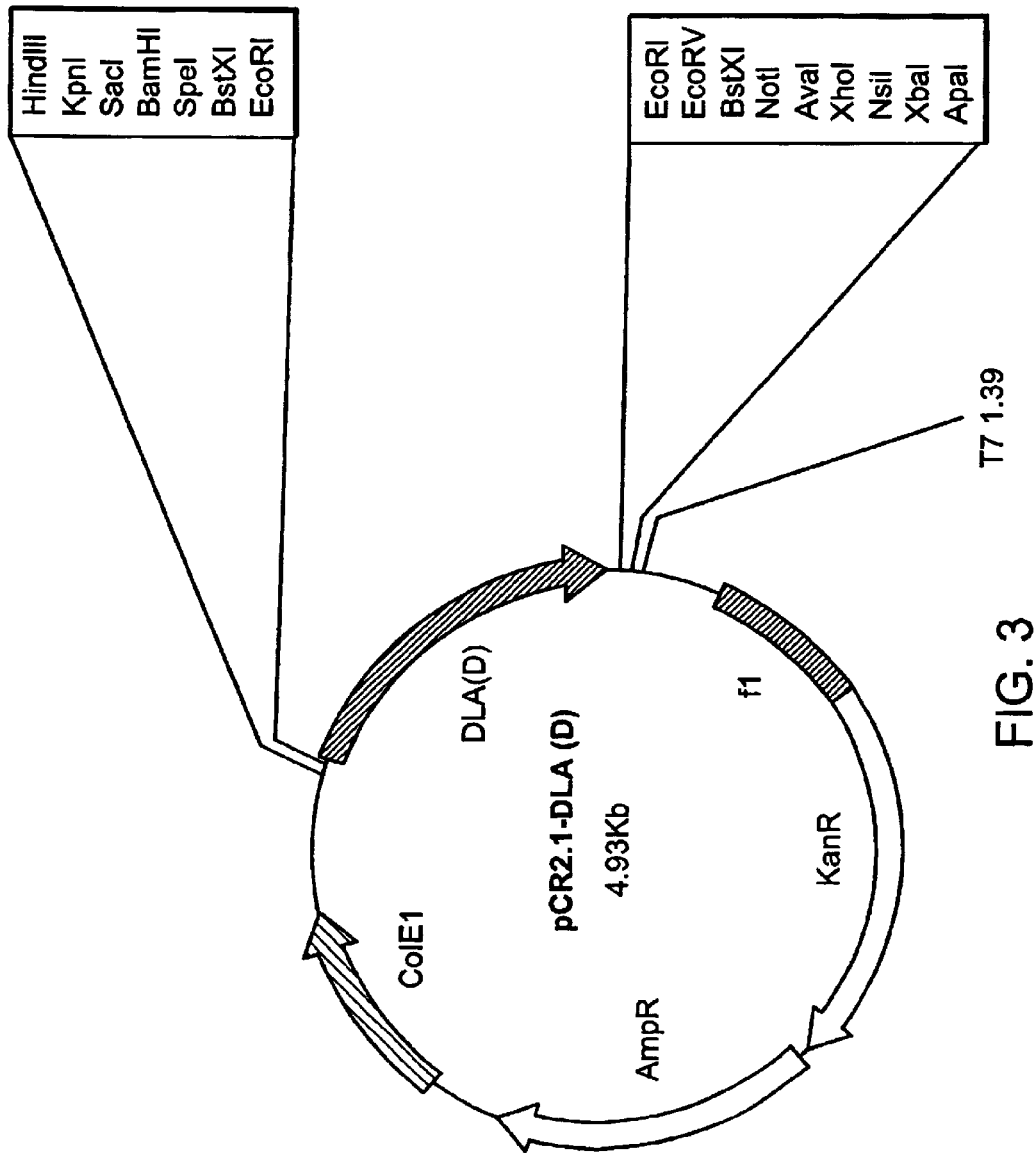
FIG. 3 is a map of a cloning vector pCR2.1-DLA(D) manufactured by ligating a mutated cDNA in the EcoRI site of the cloning vector pCR2.1.

The resulting full-length fragment contained the mutation. The recombinant mutated product was cloned in the EcoRI site of the cloning vector pCR2.1, as illustrated schematically in FIG. 3, and sequenced as described above. This plasmid is referred to as "pCR2.1-DLA(D)."

Construction of Dl-FRIL-expressing Plant Expression Vectors and *Nicotiana tabacum* Transformation Recombinant PCR was used to modify the 5' ends of both the wild-type and the mutant Dl-FRIL clones, to introduce a signal peptide for entry of the protein into the endoplasmic reticulum. Following the procedure of Higuchi, supra, the sequence encoding the signal peptide and the full-length cDNA clones were amplified in two separate primary PCR reactions. The signal peptide sequence was obtained from the amplification of the binary vector pTA4, harboring the complete sequence of the α-amylase inhibitor gene (Hoffman et al., *Nucleic Acids Res.* 10:7819–7828, 1982; Moreno et al., *Proc. Natl. Acad. Sci. USA* 86:7885–7889, 1989).

The following primers were used for amplification of the signal peptide sequence:

Sigforw GAATTCATGGCTTCCTCCAAC (SEQ ID NO:29)

Sigrev TGACTGTGCGGCTGAGTTTGCGTGGGTG (SEQ ID NO:30).

The primers M1Forw (SEQ ID NO:27) and APEcoRI (SEQ ID NO:28) used for amplification of the Dl-FRIL cDNA described above, were again used to amplify the Dl-FRIL cDNA.

The primers used for the secondary reactions were Sigforw and AP EcoRI, which were designed to generate EcoRI sites at the 5' and the 3' ends. Both the primary and the secondary PCR reactions were performed as discussed above for the site-directed mutagenesis.

Figure 4:
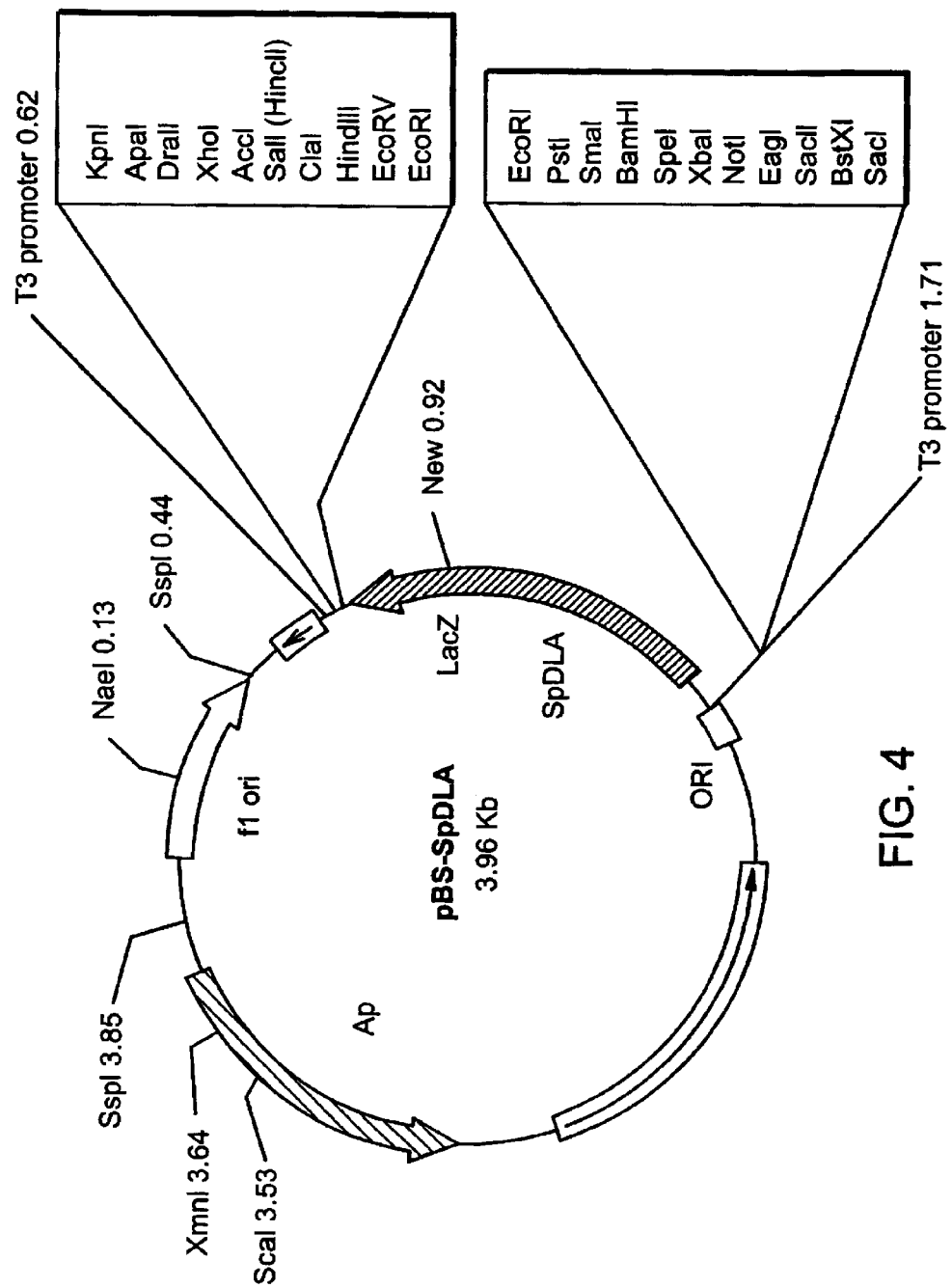
FIG. 4 is a map of a cloning vector pBS-SpDLA manufactured by ligating a recombinant fragment in the EcoRI site of the cloning vector pBluescript SK+.
Figure 5:
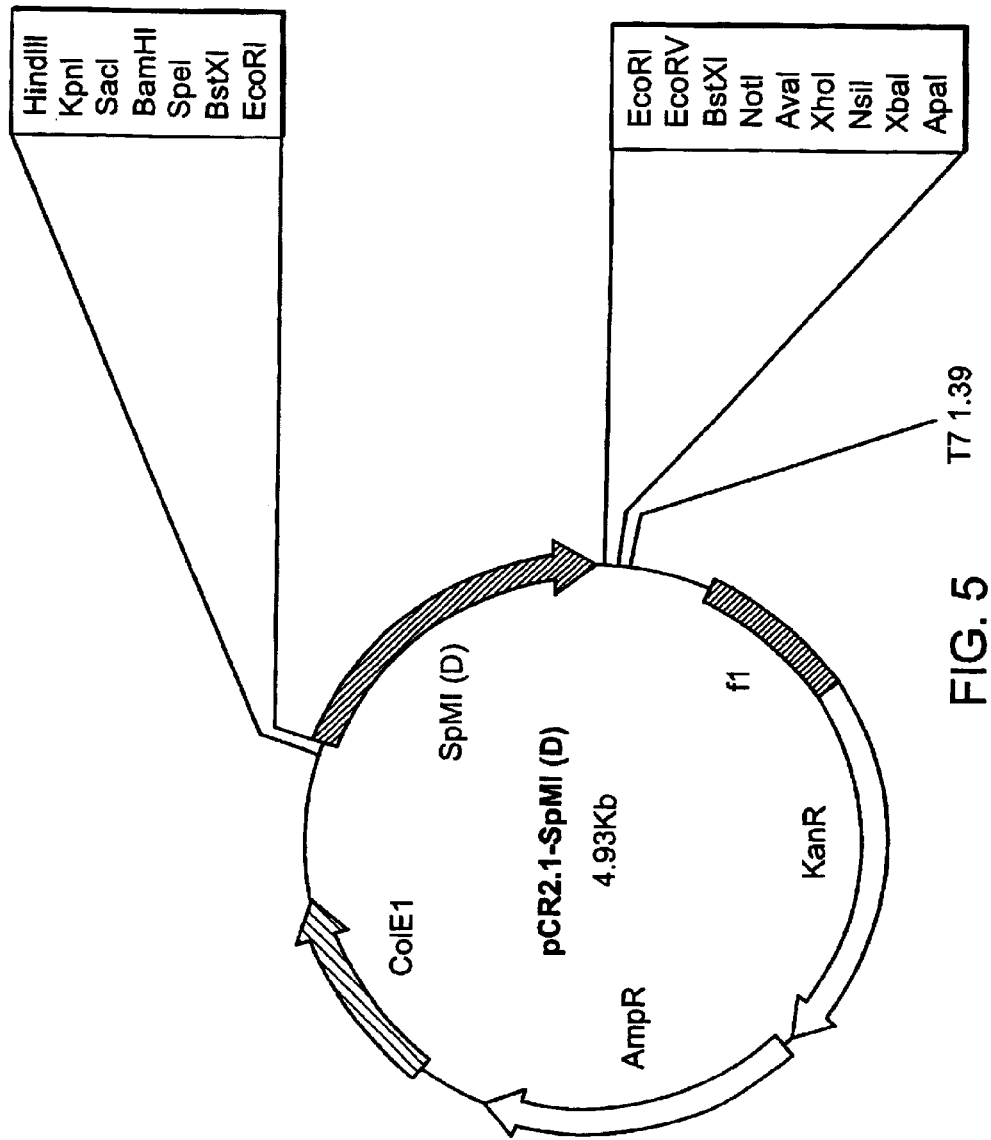
FIG. 5 is a map of a cloning vector pCR2.1-SpM1(D) manufactured by ligating a mutated recombinant clone in the EcoRI site of the cloning vector pCR2.1.
Figure 6:
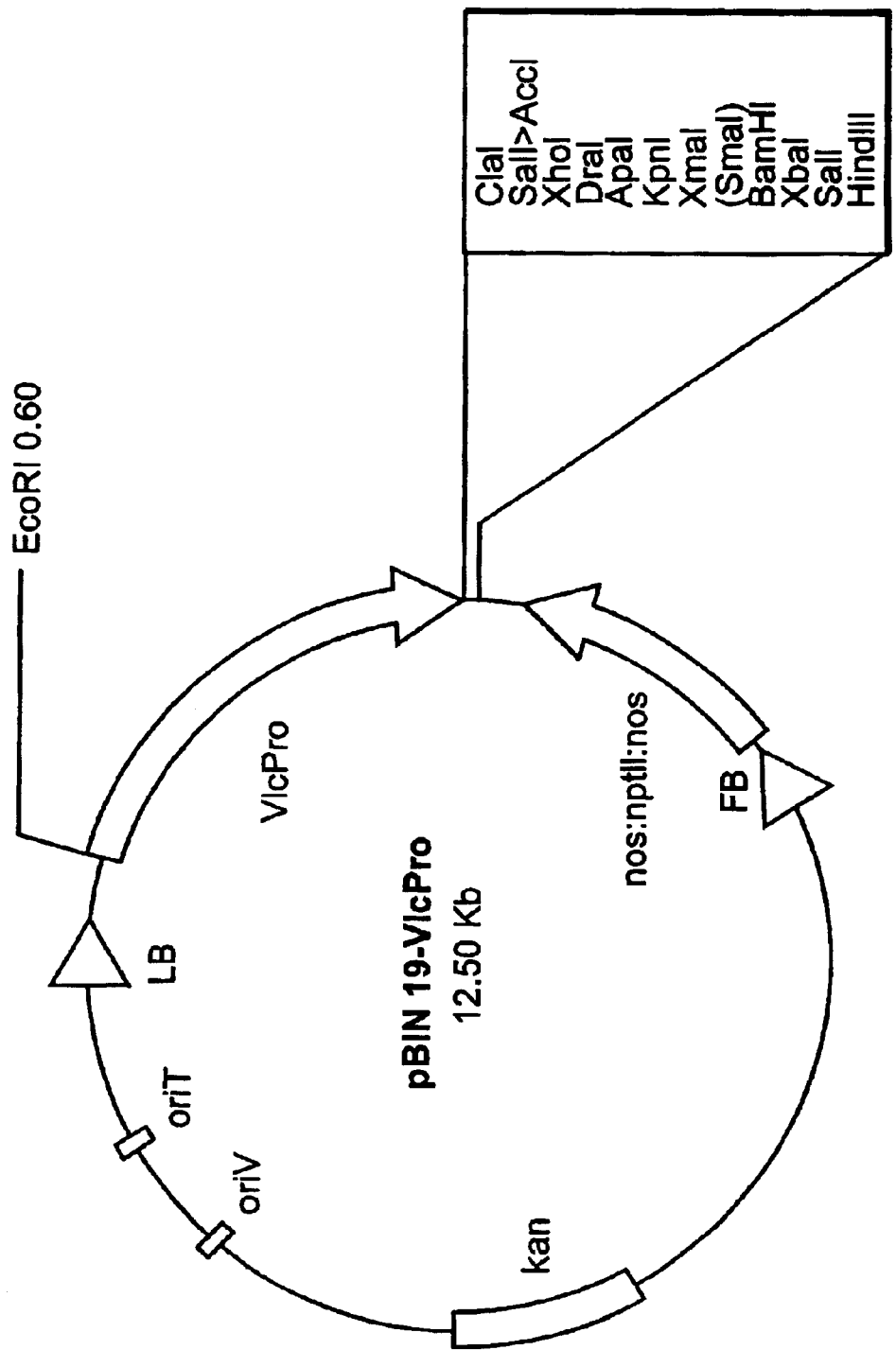
FIG. 6 is a map of a recombinant expression vector pBIN-VicPro manufactured by subcloning the vicilin promoter obtained from the pCW66 vector in the EcoRI/ClaI site of the plant binary vector pBIN19 for *Agrobacterium*-mediated transformation.
Figure 7:
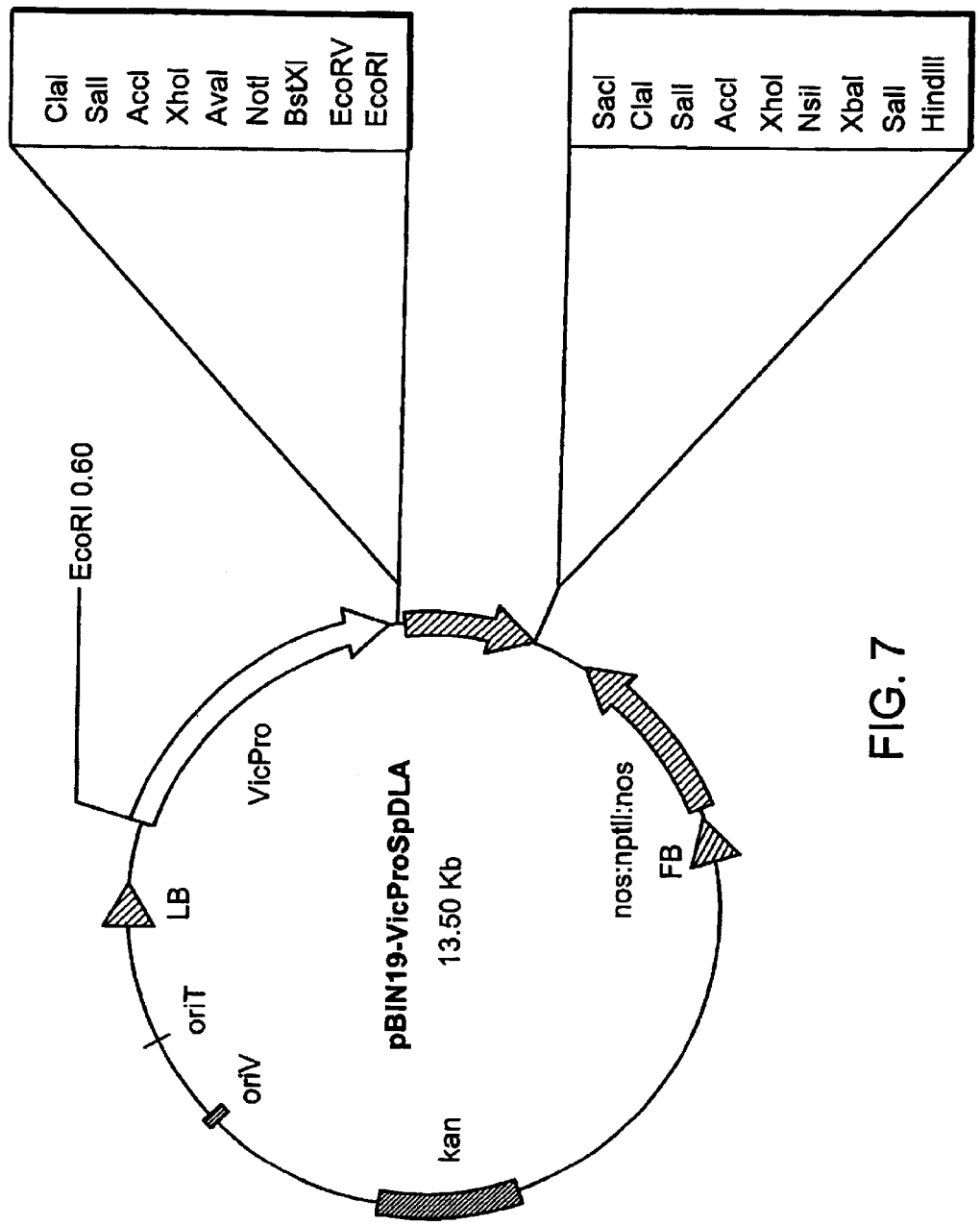
FIG. 7 is a map of a recombinant expression vector pBINVicPro-SpDLA manufactured by ligating a recombinant fragment in the EcoRI/SacI site of the pBINVicPro vector.
Figure 8:
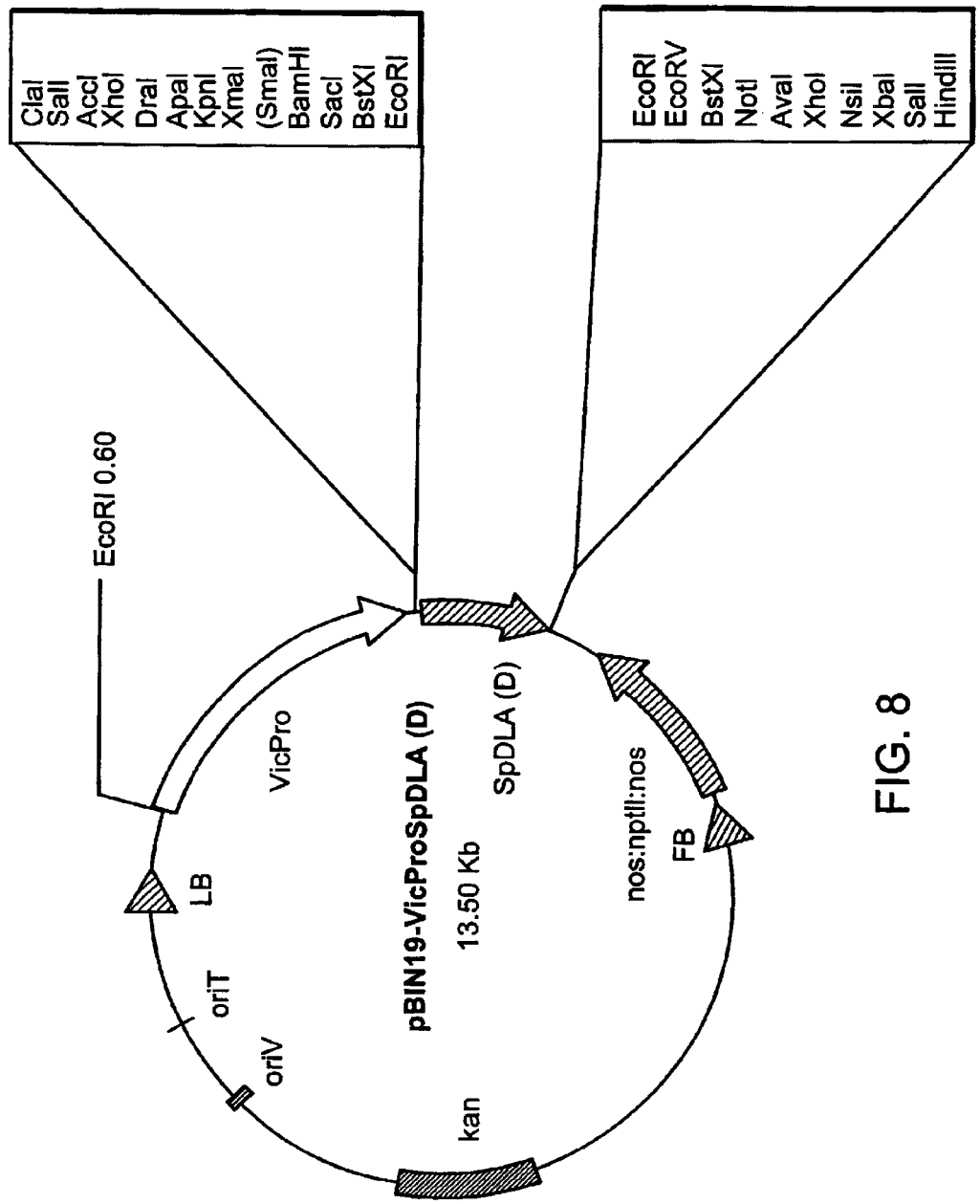
FIG. 8 is a map of a recombinant expression vector pBINVicPro-SpDLA(D) manufactured by ligating a mutated recombinant clone in the EcoRI site of the pBNVicPro vector.
Figure 9:
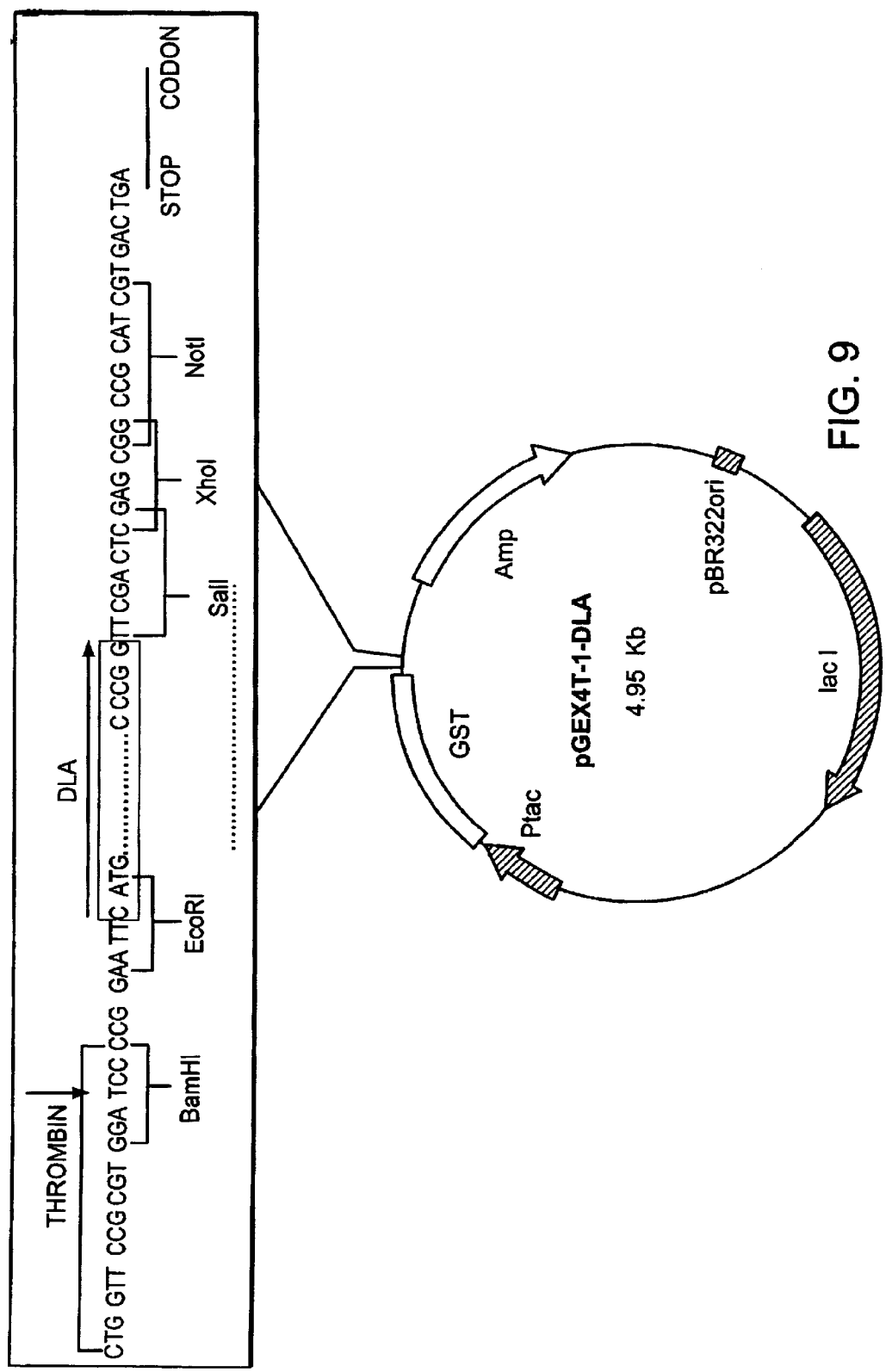
FIG. 9 is a map of a recombinant expression vector pGEX4T-1-DLA manufactured by ligating a wild-type cDNA clone in the EcoRI/SalI site of the *E. coli* expression vector pGEX4T-1 (insertion site as SEQ ID NO:53).
Figure 10:
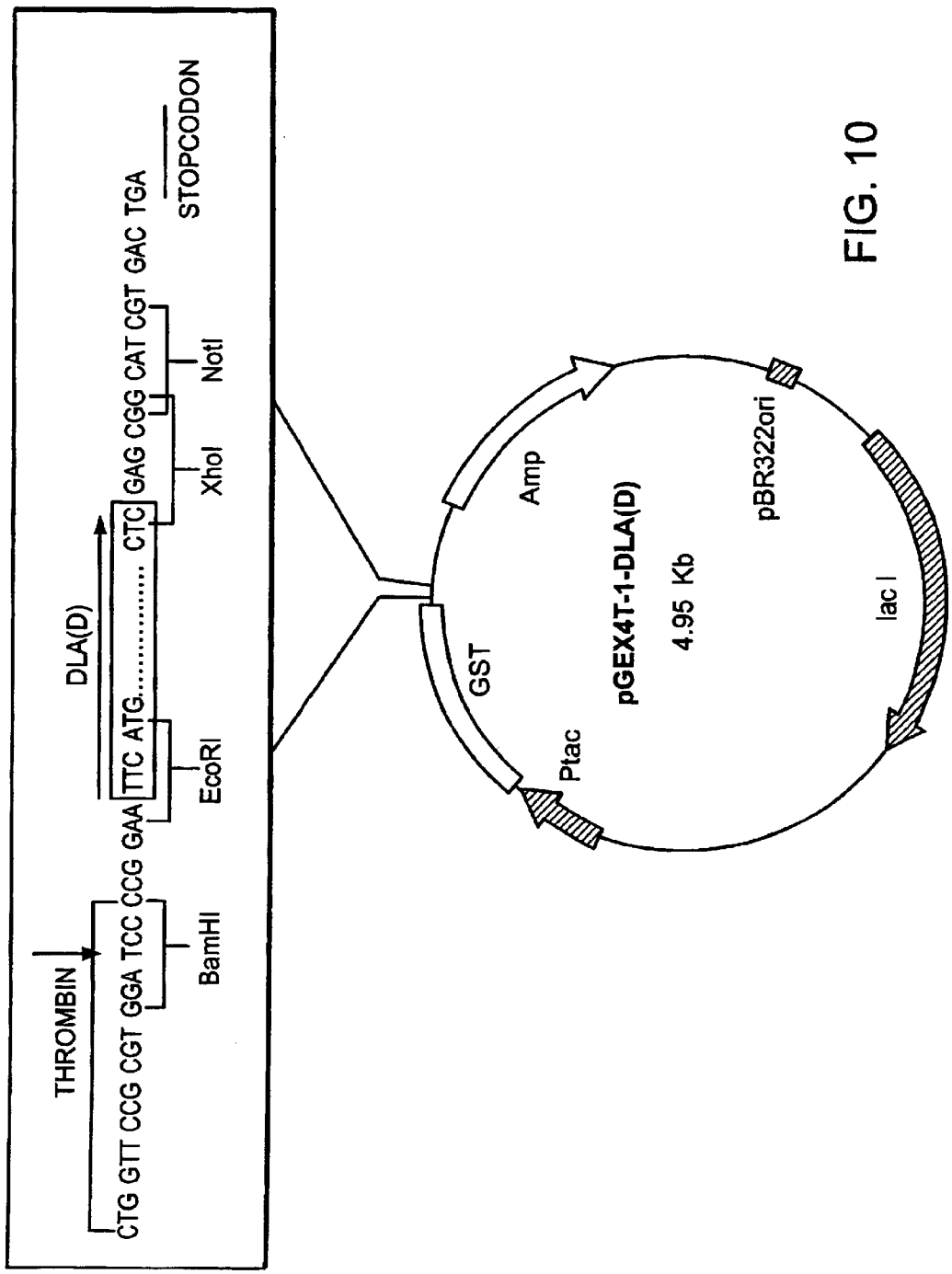
FIG. 10 is a map of a recombinant expression vector pGEX4T-1-DLA(D) manufactured by ligating a mutant cDNA clone in the EcoRI/XhoI site of the *E. coli* expression vector pGEX4T-1 (insertion site as SEQ ID NO:54).

The wild-type recombinant product SpDLA was cloned in the EcoRI site of the pBluescript SK+ cloning vector (Stratagene) to give the vector pBS-SpDLA, as shown in FIG. 4. The mutant SpDLA(D) was cloned in the same site of the cloning vector pCR2.1 to give the vector pCR2.1-SpM1, as shown in FIG. 5. The nucleotide sequence of each PCR product was determined as described above to verify the correct attachment of the signal peptide. The nucleotide sequence of SpDLA is defined by SEQ ID NO:22, and the derived amino acid sequence is defined by SEQ ID NO:23.

The sequences of SEQ ID NO: 22 and SEQ ID NO: 23 are as follows:

(xi) SEQUENCE DESCRIPTION: SEQ ID NO:22:

| | | | | | |
|---|---|---|---|---|---|
| ATGGCTTCCT | CCAACTTACT | CACCCTAGCC | CTCTTCCTTG | TGCTTCTCAC | CCACGCAAAC | 60 |
| TCAGCCGCAC | AGTCATTGTC | ATTTAGTTTC | ACCAAGTTTG | ATCCTAACCA | AGAGGATCTT | 120 |
| ATCTTCCAAG | GTCATGCCAC | TTCTACAAAC | AATGTCTTAC | AAGTCACCAA | GTTAGACAGT | 180 |
| GCAGGAAACC | CTGTGAGTTC | TAGTGCGGGA | AGACTCTTAT | ATTCTGCACC | ATTGCGCCTT | 240 |
| TGGGAAGACT | CTGCGGTATT | GACAAGCTTT | GACACCATTA | TCAACTTTGA | AATCTCAACA | 300 |
| CCTTACACTT | CTCGTATAGC | TGATGGCTTG | GCCTTCTTCA | TTGCACCACC | TGACTCTGTC | 360 |
| ATCAGTTATC | ATGGTGGTTT | TCTTGGACTC | TTTCCCAACG | CAAACACTCT | CAACAACTCT | 420 |
| TCCACCTCTG | AAAACCAAAC | CACCACTAAG | GCTGCATCAA | GCAACGTTGT | TGCTGTTGAA | 480 |
| TTTGACACCT | ATCTTAATCC | CGATTATGGT | GATCCAAACT | ACATACACAT | CGGAATTGAC | 540 |
| GTCAACTCTA | TTAGATCCAA | GGTAACTGCT | AAGTGGGACT | GGCAAAATGG | GAAAATAGCC | 600 |
| ACTGCACACA | TTAGCTATAA | CTCTGTCTCT | AAAAGACTAT | CTGTTACTAG | TTATTATGCT | 660 |
| GGGAGTAAAC | CTGCGACTCT | CTCCTATGAT | ATTGAGTTAC | ATACAGTGCT | TCCTGAATGG | 720 |
| GTCAGAGTAG | GGTTATCTGC | TTCAACTGGA | CAAGATAAAG | AAAGAAATAC | CGTTCACTCA | 780 |
| TGGTCTTTCA | CTTCAAGCTT | GTGGACCAAT | GTGGCGAAGA | AGGAGAATGA | AAACAAGTAT | 840 |
| ATTACAAGAG | GCGTTCTGTG | ATGATATATG | TGTATCAATG | ATTTTCTATG | TTATAAGCAT | 900 |
| GTAATGTGCG | ATGAGTCAAT | AATCACAAGT | ACAGTGTAGT | ACTTGTATGT | TGTTTGTGTA | 960 |
| AGAGTCAGTT | TGCTTTTAAT | AATAACAAGT | GCAGTTAGTA | CTTGT | | 1005 |

(xi) SEQUENCE DESCRIPTION: SEQ ID NO:23:

Met Ala Ser Ser Asn Leu Leu Thr Leu Ala Leu Phe Leu Val Leu Leu
                    5                  10                 15

Thr His Ala Asn Ser Ala Ala Gln Ser Leu Ser Phe Ser Phe Thr Lys
                  20                  25                30

-continued

```
Phe Asp Pro Asn Gln Glu Asp Leu Ile Phe Gln Gly His Ala Thr Ser
        35                  40                  45

Thr Asn Asn Val Leu Gln Val Thr Lys Leu Asp Ser Ala Gly Asn Pro
    50                  55                  60

Val Ser Ser Ser Ala Gly Arg Val Leu Tyr Ser Ala Pro Leu Arg Leu
65                  70                  75                  80

Trp Glu Asp Ser Ala Val Leu Thr Ser Phe Asp Thr Ile Ile Asn Phe
                85                  90                  95

Glu Ile Ser Thr Pro Tyr Thr Ser Arg Ile Ala Asp Gly Leu Ala Phe
            100                 105                 110

Phe Ile Ala Pro Pro Asp Ser Val Ile Ser Tyr His Gly Gly Phe Leu
        115                 120                 125

Gly Leu Phe Pro Asn Ala Asn Thr Leu Asn Asn Ser Ser Thr Ser Glu
        130                 135                 140

Asn Gln Thr Thr Thr Lys Ala Ala Ser Ser Asn Val Val Ala Val Glu
145                 150                 155                 160

Phe Asp Thr Tyr Leu Asn Pro Asp Tyr Gly Asp Pro Asn Tyr Ile His
                165                 170                 175

Ile Gly Ile Asp Val Asn Ser Ile Arg Ser Lys Val Thr Ala Lys Trp
            180                 185                 190

Asp Trp Gln Asn Gly Lys Ile Ala Thr Ala His Ile Ser Tyr Asn Ser
        195                 200                 205

Val Ser Lys Arg Leu Ser Val Thr Ser Tyr Tyr Ala Gly Ser Lys Pro
    210                 215                 220

Ala Thr Leu ser Tyr Asp Ile Glu Leu His Thr Val Leu Pro Glu Trp
225                 230                 235                 240

Val Arg Val Gly Leu Ser Ala Ser Thr Gly Gln Asp Lys Glu Arg Asn
            245                 250                 255

Thr Val His Ser Trp Ser Phe Thr Ser Ser Leu Trp Thr Asn Val Ala
            260                 265                 270

Lys Lys Glu Asn Glu Asn Lys Tyr Ile Thr Arg Val Leu
        275                 280                 285
```

A Plant Expression Vector Encoding Recombinant Dl-FRIL

A binary vector was constructed for seed-specific expression of Dl-FRIL. For seed expression, the vicilin promoter obtained from the pCW66 (Higgins et al., *Plant Mol. Biol.* 11:683–695, 1988) was cloned in EcoRI/KpnI sites of the plant expression vector pBIN19, to form pBNVicPro, as illustrated in FIG. 6. Downstream of the vicilin promoter, the SpDLA cDNA sequence was ligated into the EcoRI/SacI site, giving rise to the pBINVicPro-SpDLA, which is illustrated in FIG. 7. The mutated cDNA clone SpDLA(D) was ligated in EcoRI site of the pBINVicPro vector to yield pBINicPro-SpDLA(D), which is illustrated in FIG. 8. No additional termination sequences were added, relying instead on the stop codons and the polyadenylation site of the DLA and DLA(D) cDNA clones. Both vectors were transferred into *Agrobacterium tumefaciens* strain LBA4404 according to the freeze-thaw procedure reported by An et al., "Binary vectors," in *Plant Molecular Biology Manual*, Vol. A3, Gelvin S B, Schilperoort R A, and Verma D P S, eds., Kiuwer Academnic Publisher, Dordrecht, The Netherlands, pp. 1–19, 1988).

*Agrobacterium*-mediated transformation of *Nicotiana tabacum* leaf disks was carried out and assayed as described (Horsch et al., *Science* 227:1229–1231, 1985) using LBA4404 harboring the seed-specific expression vector pBNVicPro-SpDLA (FIG. 9). Kanamycin-resistant plants (resistance being conferred by transformation with the pBIN19-based vectors that carry the gene) were scored for their ability to form roots in two consecutive steps of propagation in Murashige-Skoog medium containing 3% of sucrose and kanamycin sulfate (Sigma, St. Louis, Mo.) at 100 mg/mL.

Recombinant Dl-FRIL fusion proteins were cleaved by the transformed plant cells in vivo. Thus, the transformed plant cells produced mature Dl-FRIL which, when purified, had a molecular mass of 60 kDa and comprised four subunits, two alpha subunits and two beta subunits (i.e., an $\alpha_2\beta_2$ heterodimer), where each subunit is about 15–18 kDa.

Expression of Recombinant Dl-FRIL in *E. coli*

The Dl-FRIL wild-type cDNA and mutant clones (without signal peptides), were ligated into the EcoRI/SalI and EcoRI/XhoI of the expression vector pGEX 4T-1 (Pharmacia Biotech, Uppsala, Sweden), to form the expression constructs pGEX-M1 and pGEX M1(D), respectively illustrated in FIGS. 9 and 10. The host *E. coli* strain, BL21(D3), was purchased from Novagen (Madison, Wis., and transformed with the above construct using the calcium chloride method (see Sambrook et al., supra; Gelvin and Schilperoort, *Plant Molecular Biology Manual*, Kluwer Academic Publishers, Dordrecht, The Netherlands, 1988; Altabella et al., *Plant Physiol* 93:805–810, 1990; and Pueyo et al., *Planta* 196:586–596, 1995). The induction of the tac promoter (Ptac) was achieved by adding IPTG (isopropyl-β-D-thiogalactopyranoside) (Sigma) at a 1.0 mM final concentration when the cells reached an optical density of 0.4–0.6 at 600 nm. The cultures were allowed to grow for 12 hours at 37° C. after the addition of IPTG. Control non-induced cultures were maintained under similar conditions. The cells were lysed by treatment with 4 mg/mL lysozyme in phosphate-buffered saline containing 1% TRITON® X-100.

Total cellular protein was extracted from transformed $E.$ $coli$ cells and analyzed on SDS-PAGE on a 15% gel using a standard procedure (Sambrook et al., supra). The cells from 1 mL of $E.$ $coli$ culture were suspended in the same volume of loading buffer (50 mM Tris HCl pH 6.8, 100 mM DTT, 2% SDS, 10% glycerol, 0.1% bromophenol blue) and vortexed. Following transfer to a nitrocellulose membrane, protein was stained with Coomassie Brilliant Blue R250. A representative separation is shown in FIG. 11, with the lanes identified in Table 1, below.

TABLE 1

Figure 11:
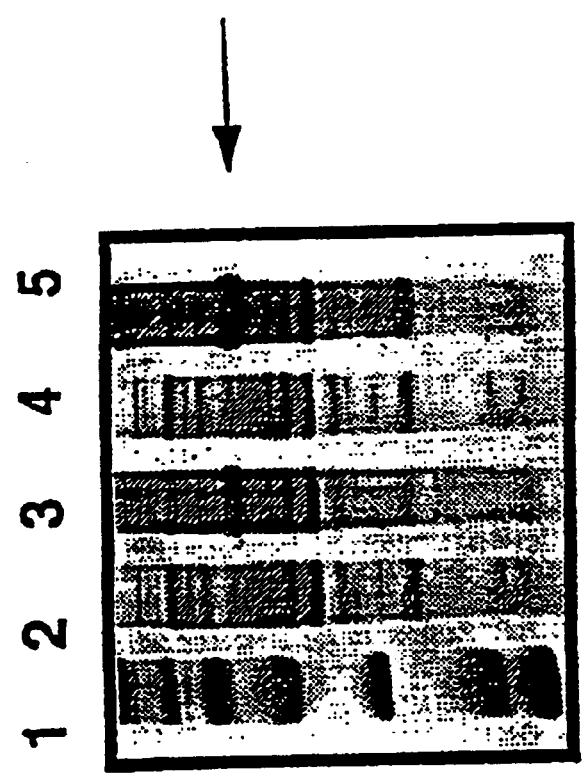
FIG. 11 is a representation of an electrophoretogram of a Southern blot of total protein extracts of *E. coli* cells transformed with the recombinant expression vectors pGEX4T-1-DLA and pGEX4T-1-DLA(D).

Key to FIG. 11

| Lane No. | Content |
|---|---|
| 1 | Molecular Mass Marker (Bio-Rad) |
| 2 | Total Protein Extract from Non-Induced BL21(D3) pGEX-M1 |
| 3 | Total Protein Extract from Induced BL21(D3) pGEX-M1 |
| 4 | Total Protein Extract from Non-Induced BL21(D3) pGEX-M1(D) |
| 5 | Total Protein Extract from Induced BL21(D3) pGEX-M1(D) |

The separation of proteins in FIG. 11 shows that the induced cells (lanes 3, 5) both produced an abundant polypeptide having a molecular mass of about 60 kDa (indicated by arrow). The non-induced cells failed to produce any significant amount of this protein (FIG. 11, lanes 2, 4).

Purification of Recombinant Dl-FRIL from Transformed $E.$ $coli$

Induced $E.$ $coli$ cells (200 mL) as described above were harvested after 12 hour induction at 37° C. by centrifugation at 5000 g for 10 min. The pellet was washed with 50 mM Tris-HCl pH 8.0,2 mM EDTA, and resuspended in 1/10 vol of 1% TRITON surfactant in TBS (20 mM Tris pH 7.5, 500 mM NaCl). The cells were lysed by adding 4 mg/mL of lysozyme and incubating at room temperature for 30–60 min. After centrifugation at 5000 g, the supernatant containing the total soluble proteins was discarded and the resulting pellet, comprising the inclusion bodies and containing the accumulated the recombinant fusion protein, was extracted with 8 M guanidine-HCl (Martson and Hartley, "Solubilization of Protein Aggregates" in $Guide$ $to$ $Protein$ $Purification$ vol. 182, eds. Deutscher, M. P., pp 266–267, 1993).

The recombinant fusion protein solubilized by guanidine-HCl was purified on GST-Sepharose beads (Pharmacia Biotech, Uppsala, Sweden) according the manufacturer's instructions and eluted in 1 mL of reduced glutathione (Sigma). Samples of the purified fusion proteins were cleaved with thrombin (Novagen) using 5 cleavage units/mL purified fusion protein.

For immunoblot analysis (Western blot), the purified proteins were separated by SDS-PAGE in general accordance with the method described above. The gel was equilibrated in transfer buffer (25 mM Tris pH 8.3, 192 mM Glycine, 20% MeOH) and blotted onto nitrocellulose (Bio-Rad, Hercules, Calif.) for 1 hour at 100 V using a Bio-Rad electrotransfer apparatus. Non-specific binding was blocked by incubating the blots for at least 1 hour in 1×TBS (20 mM Tris pH 7.5, 500 mM NaCl) containing 3% gelatin. Blotting was followed by incubation with a primary antibody (a polyclonal rabbit serum raised against the N-terminal peptide of the β-subunit of $Phaseolus$ $vulgaris$ FRIL (i.e., Pv-FRIL), 1:100 dilution, 3 hours; described below in Example 5), followed by incubation with a secondary antibody (goat anti-rabbit IgG conjugated to horseradish peroxidase at 1:1000 dilution for 1 hour). The blots were washed and the color developed with the color development reagent (Bio-Rad). A representative result is shown in FIG. 12, with the lanes identified in Table 2, below.

TABLE 2

Figure 12:
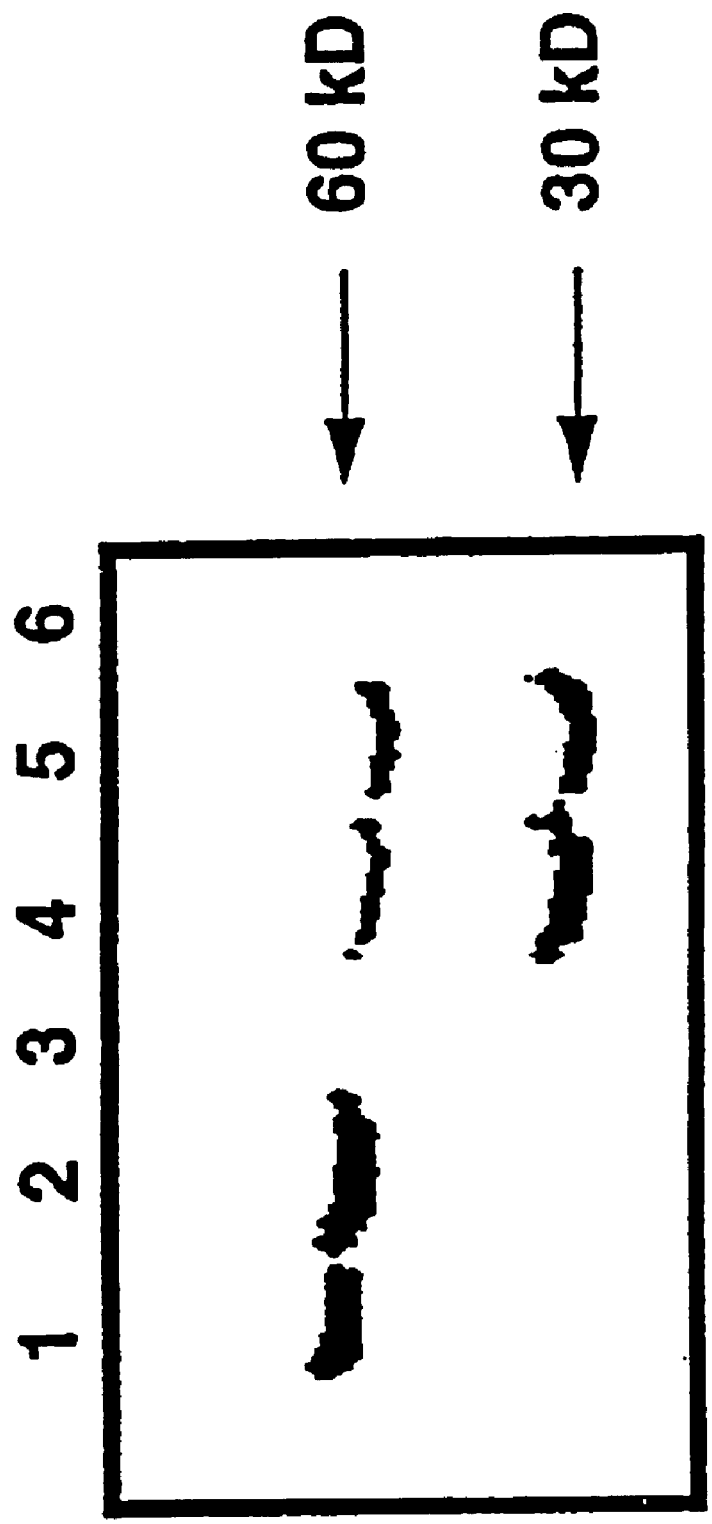
FIG. 12 is a representation of an electrophoretogram of a Western blot of purified GST-fusion proteins with and without cleavage by thrombin.

Key to FIG. 12

| Lane No. | Content |
|---|---|
| 1 | Purified Fusion Protein M1 |
| 2 | Purified Fusion Protein M1(D) |
| 3 | Control |
| 4 | Purified Fusion Protein M1 After Cleavage with Thrombin |
| 5 | Purified Fusion Protein M1(D) After Cleavage with Thrombin |
| 6 | Control |

The separation shown in FIG. 12 demonstrates that the two forms of fusion protein have similar molecular masses of about 60 kDa, and that thrombin cleaved both types of fusion protein to produce a new polypeptide of molecular mass 30 kDa.

EXAMPLE 2

Recombinant Dl-FRIL Specifically Stimulates Proliferation of 3T3 Cells Expressing the FLT3 Receptor Dl-FRIL interacts with the mammalian FLK2/FLT3 tyrosine kinase receptor. A specific and quantitative biological assay using NIH 3T3 fibroblasts transfected either with a chimeric receptor having the extracellular portion of the murine FLT3 receptor combined with the intracellular portion of the human Fms receptor (Dosil et al., $Mol.$ $Cell.$ $Biol.$ 13(10):6572–6585 1993) or with the full length human receptor (Small et al., $Proc.$ $Natl.$ $Acad.$ $Sci.$ $USA$ 91:459–463, 1994) can be used to evaluate lectin biological activity during purification. Serial two-fold dilutions of lectin samples across rows of a 96 well plate allowed for greater than a thousand-fold range to access FLT3 3T3 biological activity. Either the murine or human FLT3 ligand (FL) (Lyman et al., $Cell$ 75:1157–1167, 1993; Hannum et al., $Nature$ 368: 643–648, 1994) or the FRIL was found to rescue FLT3-transfected cells from death in this assay.

Specifically, 3T3 cells cultured in tissue culture plates (Becton Dickinson Labware, Lincoln Park, N.J.) were removed from the plates by washing cells twice in Hank's buffered saline solution (HBSS; Gibco Laboratories, Grand Island, N.Y.). Non-enzymatic cell dissociation buffer (Gibco) was added for 15 minutes at room temperature. The resulting cells were washed in medium. FLT3 3T3 cells were cultured at a final concentration of 3,000 cells per well in a volume of 100 μL of serum-defined medium containing 10 mg/mL rhIL1-α, 10% AIMV (Gibco, Grand Island, N.Y.) and 90% Dulbecco's modification of Eagle's medium (DMEM; Gibco) in 96 well plates. Under these assay conditions, cells die after two to four days of culture in a humidified incubator at 37° C. and 5% $CO_2$ unless exogenously added ligand rescues cells from death. Each 96 well plate contained wells of cells containing calf serum, which stimulates all 3T3 cells, as a positive control and wells of cells containing medium only as a negative control ("blank"). Full-length Fms-transfected 3T3 cells (biological response shown in Tessler et al., *J. Biol. Chem.*, 269:12456–12461, 1994) served as receptor-transfected control target cells, and parent 3T3 cells served as untransfected control cells. Proliferation and cell survival was quantitated by addition of XTT (2, 3-bis[Methoxy-4-nitro-5sulfophenyl]-2H-tetrazolium-5 carboxanilide inner salt) (Diagnostic Chemicals Ltd, Charlottetown, Prince Edward Island, Canada), which is a tetraformazan salt cleaved by actively respiring cells (Roehm et al., *J. Immunol. Methods* 142: 257–265, 1991). Proliferation and cell survival was quantitated spectrophotometrically using a Vmax kinetic plate reader (Molecular Devices Corp., Mountain View, Calif.), and recorded as either relative activity (units/mL) or as specific activity (units/mg). One unit of biological activity was defined as the reciprocal dilution at which half-maximal stimulation of cells is detected.

Figure 13A:
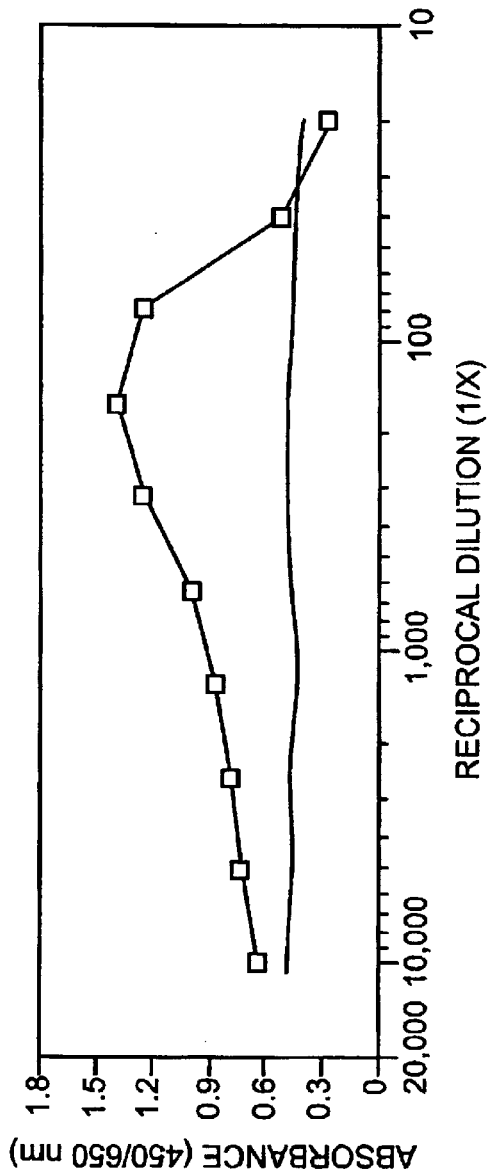
FIG. 13A is a representation of a graph showing that a crude extract of an *E. coli* culture containing expressed Dl-FRIL, a representative, non-limiting FRIL family member of the invention, specifically stimulates hFLT3 3T3 cells.
Figure 13B:
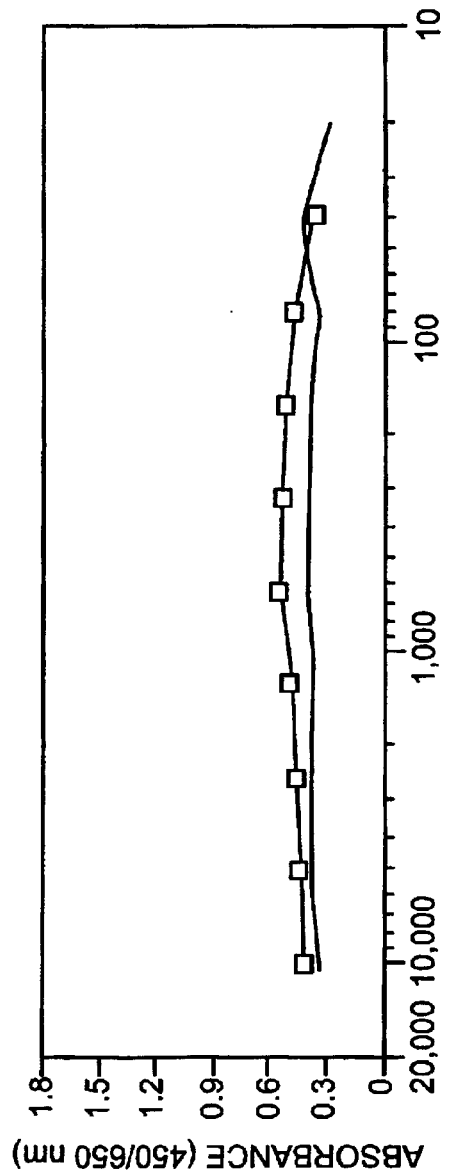
FIG. 13B is a graph showing that the same extract does not stimulate untransfected 3T3 cells.

The crude protein extract from the *E. coli* cultures described in Example 1, above, was tested to determine whether expressed recombinant Dl-FRIL possessed any capacity to stimulate FLT3 3T3 cells using this assay. The data from this experiment are summarized in FIGS. 13A and 13B. Specifically, FIG. 13A is a graph showing that the crude extract of the *E. coli* culture containing expressed Dl-FRIL specifically stimulates hFLT3 cells; FIG. 13B is a graph showing that the same extract does not stimulate untransfected 3T3 cells. In FIGS. 13A and 13B, medium control is represented by a solid line. The ordinate (absorbance) indicates cell viability measured by XTT at three days; the abscissa shows the reciprocal dilution of the extract sample. The apparent inhibition of proliferation observed at higher concentrations (FIG. 13A) is not understood, but may relate to toxic components in the crude *E. coli* extract or the consequences of dose-related preservation of the 3T3 fibroblasts.

EXAMPLE 3

Figure 14A:
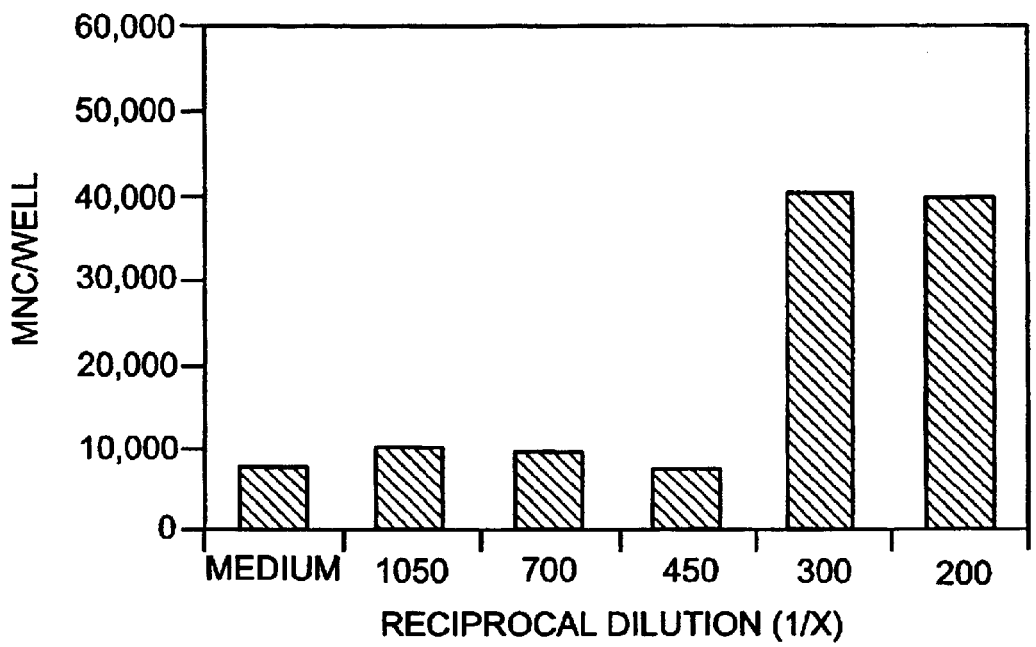
FIG. 14A is a representation of a histogram showing that purified Dl-FRIL, a representative, non-limiting FRIL family member of the invention, preserves cord blood mononuclear cells in a dose-responsive manner.
Figure 14B:
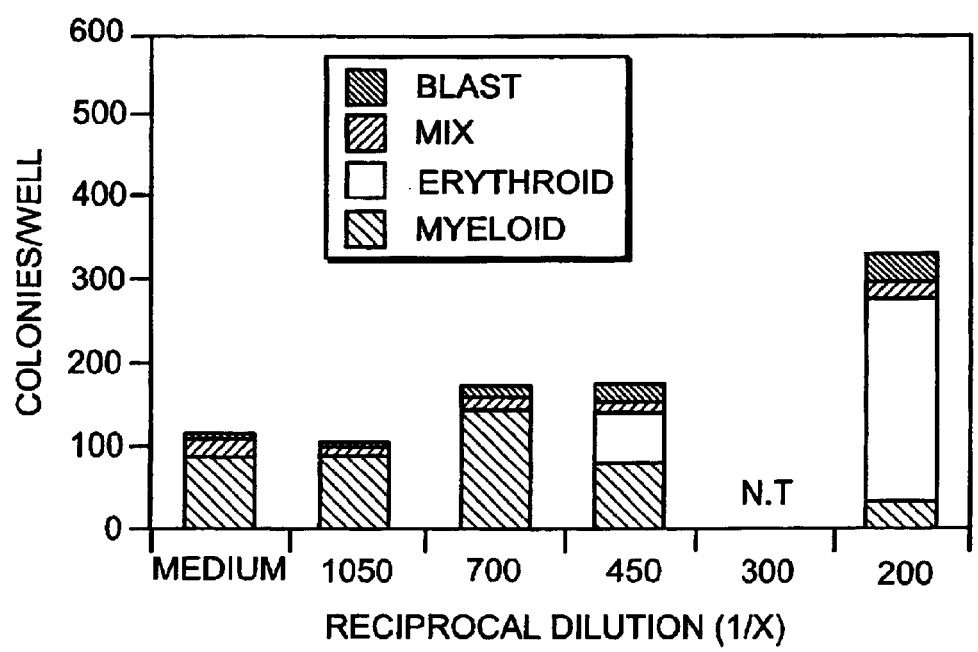
FIG. 14B is a representation of a histogram showing that purified Dl-FRIL, a representative, non-limiting FRIL family member of the invention, preserves hematopoietic progenitors in a dose-responsive manner.

Recombinant Dl-FRIL Preserves Mononuclear Cells and Progenitors in Liquid Culture The recombinant Dl-FRIL protein preserved functional progenitors for at least four weeks in liquid culture. FIGS. 14A and 14B, and Table 3 illustrate the results of experiments in which recombinant Dl-FRIL was shown to act in a dose-responsive manner to preserve human cord blood progenitors.

To do this, umbilical cord blood from healthy donors was collected in 100 units/ml of heparin. Cord blood mononuclear cells (CB mnc) were isolated within 4 hours of collection by separation using the density separation medium sold under the trademark of FICOLL-PAQUE® (Pharmacia Biotech, Piscataway, N.J.) following manufacturer's instruction and washed in X-VIVO 10 medium (BioWhittaker, Walkersville, Md.). CB mnc were then cultured in six well tissue culture plates (Corning Inc., Corning, N.Y.) at a concentration of 200,000 cells/mL in a volume of 4 mL of X-VIVO 10 (i.e., 800,000 cells total per well). Dl-FRIL and/or recombinant *E. coli* Flt3-L (recFL; BioSource International, Camarillo, Calif.) were added at a concentration of 40 ng/ml at the outset (with no addition as a control). Cultures were incubated in humidified chambers without medium changes for up to 29 days.

After incubation, the cultured CB mnc cells were harvested by washing in X-VIVO 10 (i.e., harvested cells were pelleted and resuspended in X-VIVO 10) to remove the Dl-FRIL and/or recFL, and then determining viable cell number by trypan blue (Sigma) exclusion. These results are shown in FIG. 14A The progenitor number and capacity of harvested cells were assessed by plating the washed cells in triplicate in fetal bovine serum-free, methylcellulose colony assay medium containing IL-2, granulocyte-macrophage CSF, and kit ligand (StemCell Technologies, Vancouver, BC, Canada). After two weeks, the resultant colonies from each of the triplicate wells were scored and the results are shown in FIG. 14B. Thus, FIGS. 14A and 14B show that recombinant Dl-FRIL preserved cord blood mononuclear cells and progenitors in a dose-responsive manner in liquid culture.

Table 3 shows the resulting colonies after 15, 21, or 29 days of incubation, demonstrating that Dl-FRIL, but not recFL, preserved progenitors in suspension culture.

TABLE 3

| Day | Medium | Myeloid* | Erythroid* | Mix* | Blast* |
|---|---|---|---|---|---|
| 15 | Dl-FRIL | 1,033 ± 12 | 67 ± 12 | 7 ± 12 | 0 |
|  | recFL | 40 ± 69 | 0 | 0 | 0 |
|  | Dl-FRIL + recFL | 933 ± 250 | 167 ± 95 | 0 | 0 |
|  | No Addition | 0 | 0 | 0 | 0 |
| 21 | Dl-FRIL | 387 ± 83 | 7 ± 12 | 0 | 167 ± 64 |
|  | recFL | 0 | 0 | 0 | 0 |
|  | Dl-FRIL + recFL | 473 ± 133 | 53 ± 42 | 0 | 300 ± 34 |
|  | No Addition | 0 | 0 | 0 | 0 |
| 29 | Dl-FRIL | 0 | 0 | 0 | 80 ± 72 |
|  | recFL | 0 | 0 | 0 | 0 |
|  | Dl-FRIL + recFL | 0 | 0 | 0 | 40 ± 20 |
|  | No Addition | 0 | 0 | 0 | 0 |

*Data reported as ± SD of the three values from the triplicate methylcellulose colony assay. The reported experiment is a representative of four experiments.

In FIGS. 14A and 14B and in Table 3, "blast" refers to colonies consisting of primitive, morphologically undifferentiated cells; "mix" refers to colonies consisting of myeloid and erythroid cells; "erythroid" refers to colonies consisting of erythroid cells; and "myeloid" refers to colonies consisting of myeloid cells. In FIGS. 14A and 14B, cell number (FIG. 14A) or colony number (FIG. 14B) is shown on the ordinate; the abscissa shows the reciprocal dilution of the sample.

As shown in Table 3, colonies derived from mature myeloid and erythroid progenitors formed from cells cultured for 15 days in either FRIL or FRIL plus recFL; 24-fold fewer mature colonies formed from cells cultured in recFL alone; and no colonies appeared if neither was present. After 21 days in culture, Table 3 shows that myeloid and erythroid colonies formed only from cells exposed to Dl-FRIL. The frequency of myeloid colonies in Dl-FRIL-only cultures (based on the initial number of CB mnc) decreased by 2.7 fold from 1 in 774 after 2 weeks in culture to 1 in 2,067 after 3 weeks; erythroid colonies decreased in frequency by 9.6 fold from 1 in 11,940 to1 in 114,287 (see Table 3).

Figure 15A:
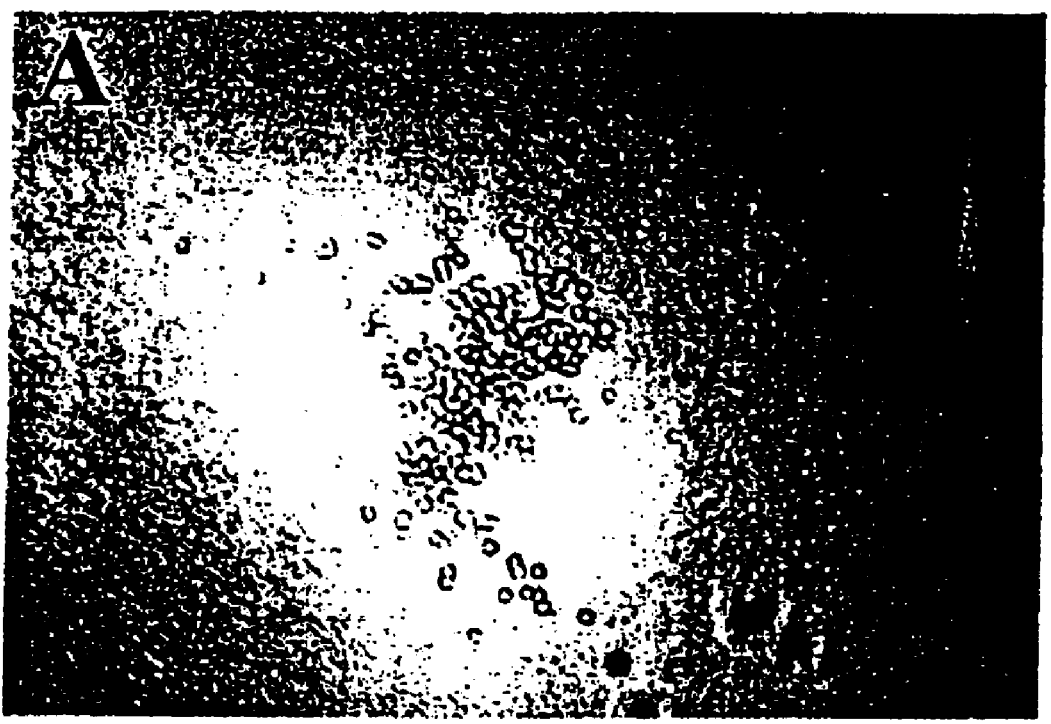
FIG. 15A is a representation of a photograph of colonies derived from human cord blood mononuclear cells cultured in 40 ng/mL Dl-FRIL, a representative, non-limiting FRIL family member of the invention, for 3 weeks, and then replated in methylcellulose colony assay medium.
Figure 15B:
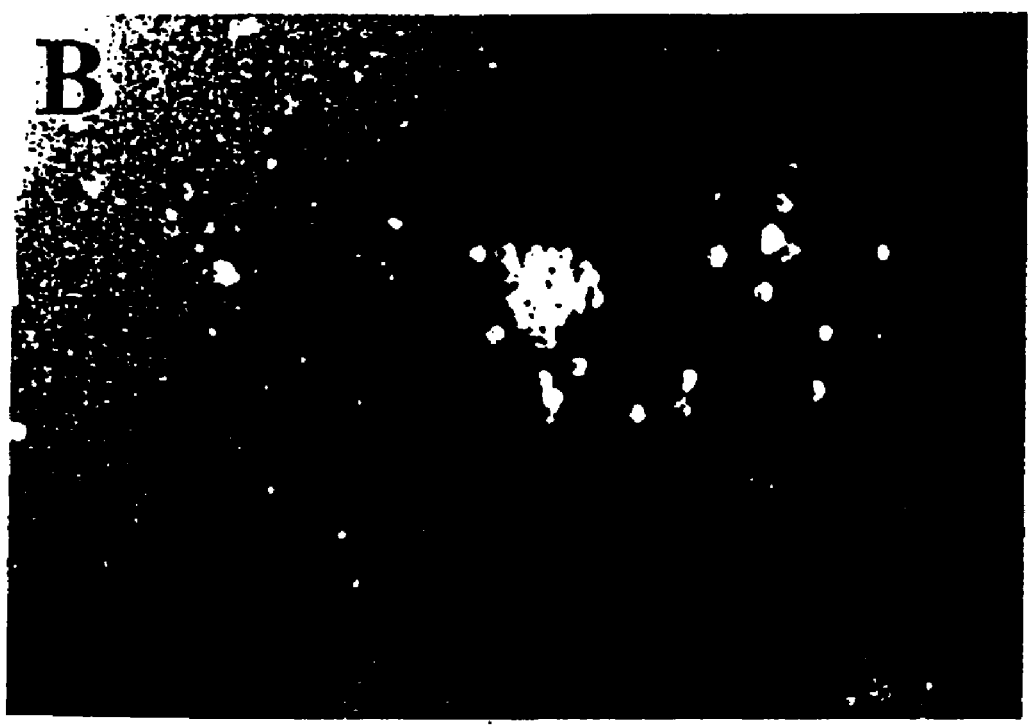
FIG. 15B is a representation of a photograph of colonies derived from human cord blood mononuclear cells cultured in 40 ng/mL Dl-FRIL, a representative, non-limiting FRIL family member of the invention, for 4 weeks, and then replated into methylcellulose colony assay medium.

The colonies from this assay were photographed at various time points. As shown in FIG. 15A, in addition to myeloid and erythroid colonies, day 21 cultures contained small colonies consisting of undifferentiated cells. FIG. 15B shows that only blast-like colonies were observed when the cells were cultured in Dl-FRIL for 29 days (see also Table 3).

Figure 16:
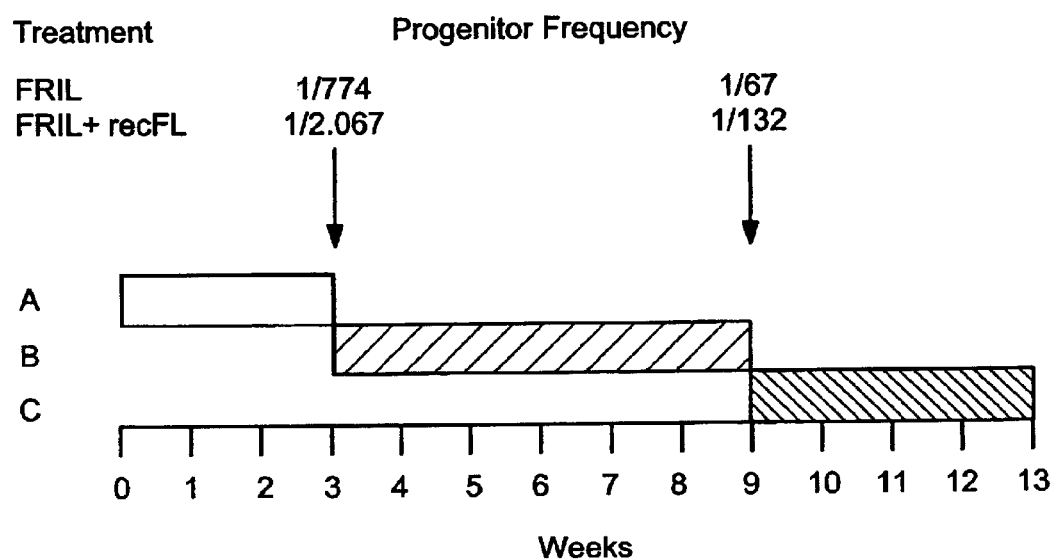
FIG. 16 is a schematic diagram showing the serial replating of progenitor cells cultured in Dl-FRIL, a representative, non-limiting FRIL family member of the invention, or Dl-FRIL+recFL (i.e., recombinant FLT3-Ligand). The human cord mononuclear cells were first cultured in suspension in 40 ng/mL Dl-FRIL of 40 ng/mL Dl-FRIL+40 ng/mL recFL (solid black box). The cells were then harvested and assessed for progenitor activity by being replated into methylcellulose colony assay medium for 6 weeks (middle striped box). Then the cells were harvested from the colony assay and again replated into methylcellulose colony assay medium for an additional 4 weeks (far right striped box). Progenitor frequencies were determined for cells after 3 weeks of suspension culture in Dl-FRIL or Dl-FRIL+recFL, and after an additional 6 weeks of methylcellulose culture (absent Dl-FRIL and/or recFL).
Figure 17:
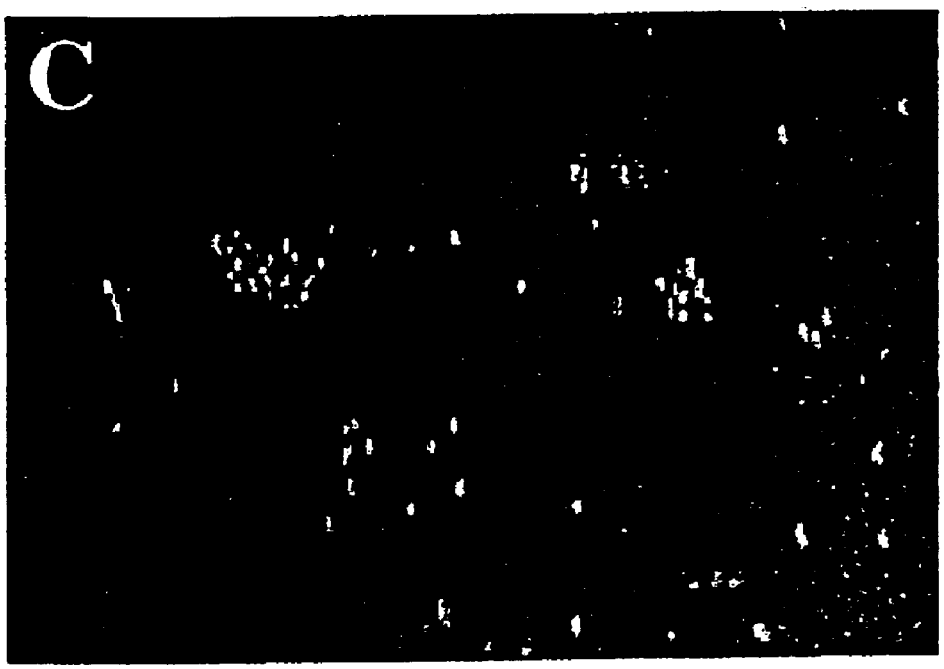
FIG. 17 is a representation of a photograph of colonies derived from human cord blood mononuclear cells initially cultured in 40 ng/mL Dl-FRIL, a representative, non-limiting FRIL family member of the invention, for 3 weeks, then replated into methylcellulose colony assay medium for 6 weeks, and then replated again into methylcellulose colony assay medium for an additional 4 weeks.

The progenitor capacity of the blast-like colonies was examined further for cells initially cultured for 3 weeks in either Dl-FRIL, recFL, no addition, or Dl-FRIL+recFL, and then without these regulators for an additional 6 weeks in a methylcellulose colony assay. No colonies were detected from the cells cultured for 21 days in either recFL alone or medium control. Viable cells were harvested from the cells initially cultured in Dl-FRIL alone and replated in an colony assay (in methylcellulose colony assay medium) for an additional 4 weeks. A schematic diagram of this experiment is shown in FIG. 16. As schematically diagramed in FIG. 16, the frequency of blast-like colonies cultured in Dl-FRIL alone decreased by 2.1 fold from day 21 to day 29, from 1 in 4,790 to 1 in 10,000, and 7.5 fold in Dl-FRIL+recFL cultures from 1 in 2,667 to 1 in 20,000 of the initial CB mnc cells cultures. Following the protocol schematically diagrammed in FIG. 16, small, diffuse, blast-like colonies were detected at a frequency of 1 in 67 (900 colonies/600,000 CB mnc) exclusively in dishes of cells initially cultured in Dl-FRIL alone, and at a frequency of 1 in 132 (990 colonies/131,000 CB mnc) for cells cultured in Dl-FRIL+recFL (see examplary colonies in FIG. 17).

EXAMPLE 4

Recombinant Dl-FRIL Acts Directly on Progenitor Cells

Figure 18:
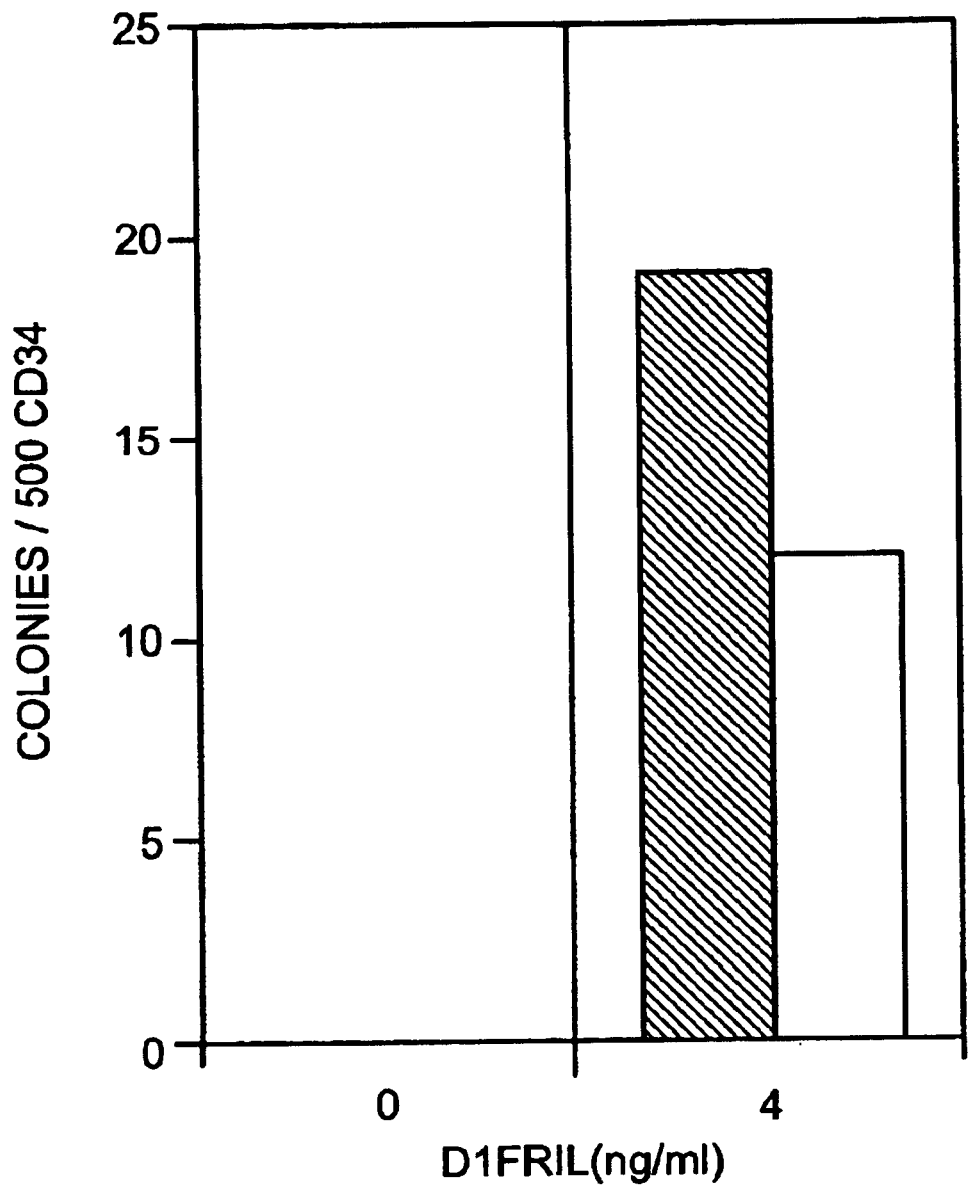
FIG. 18 is a representation of a bar graph showing that a representative, non-limiting FRIL family member of the invention, Dl-FRIL, encoded by a representative, non-limiting nucleic acid of the invention is sufficient to preserve progenitor cells ex vivo, whereas a cytokine cocktail fails to preserve such cells.

To assess whether recombinant Dl-FRIL acts directly or indirectly through accessory cells to preserve progenitor cells, cord blood mononuclear cells were first enriched for progenitors expressing the CD34 antigen by immunomagnetic bead isolation (Dynal Corp., Lake Success, N.Y.). Five hundred CD34$^+$ cells were placed into wells containing 100 $\mu$L of serum-free medium (BIT9500, StemCell Technologies, Vancouver, BC, Canada) either in the presence of recFL (PeproTech, Princeton, N.J.) or a cytokine cocktail of recombinant human interleukin 3 (rhIL3)+ recombinant human interleukin 6 (rhIL6)+recombinant human interleukin 11 (rhIL11)+rhTpo Thrombopoietin+FL (FLT3-Ligand) (BioSource International, Camarillo, Calif.) in 96-well plates and cultured for four weeks without medium changes. The numbers of functional progenitors from these cultures were assessed by plating cells in complete serum-free methylcellulose colony assay medium (StemCell Technologies). After two weeks, the resultant colonies were scored and the results are shown in FIG. 18 (solid bars=recombinant Dl-FRIL; open bars=cytokine cocktail). Clearly, progenitors were preserved only in the recombinant Dl-FRIL-containing cultures (FIG. 18). Thus, purified recombinant Dl-FRIL acts directly on primitive hematopoietic progenitors.

EXAMPLE 5

Identification and Cloning of Pv-FRIL, a Second FRIL Family Member FRIL Activity in PHA-LCM Media A biological screening assay to search for novel stimulators of the Flt3 receptor was developed using NIH 3T3 cells transfected with expression vectors containing cDNA of murine and human Flt3 and the related Fms receptor. The mFlt3/Fms 3T3 cell line is a 3T3 cell line transfected with nucleic acid encoding a fusion protein consisting of the murine extracellular domain of the Flt3 receptor fused to the transmembrane and intracellular domains of the human Fms (provided by Dr. Ihor Lemischka, Princeton University, Princeton, N.J.). The Stk 3T3 cell line is a 3T3 cell line transfected with the full-length human Flt3 receptor (provided by Dr. Donald Small, Johns Hopkins University, Baltimore, Md.). The human FMS 3T3 cell line is a 3T3 cell line transfected with the full-length human Fms receptor (provided by Dr. Charles Sherr, Saint Jude Children's Research Hospital, Memphis, Tenn. Parent 3T3 cells were purchased from American Type Culture Collection ("ATCC"; Manassas, Va.). Receptor-transfected cells contained Neo resistance genes and were maintained in medium containing 750 g/ml of G418 (Life Technologies, Rockville, Md.).

To create factor-dependence for receptor-transfected 3T3 cells, growth conditions were compromised to permit only ligands to rescue cells from death. To do this, 3T3 cell lines were assayed in 96 well plates (Becton Dickinson Labware, Lincoln Park, N.J.) containing 3,000 cells in 100 $\mu$L of serum-free medium consisting of 10% AIMV (Life Technologies) and 90% DMEM. In each experiment, samples were serially diluted two-fold across rows starting at a 1:10 dilution. Viable cells were quantitated after 3–5 days by XTT (2,3-bis[Methoxy-4-nitro-5sulfophenyl]-2H-tetrazolium-5 carboxanilide inner salt) (Sigma, St. Louis, Mo.) (Roehm et al., supra). Relative activity (units/ml) and specific activity (units/mg) are defined as the reciprocal dilution at which half-maximal stimulation of cells was detected.

Figure 19A:
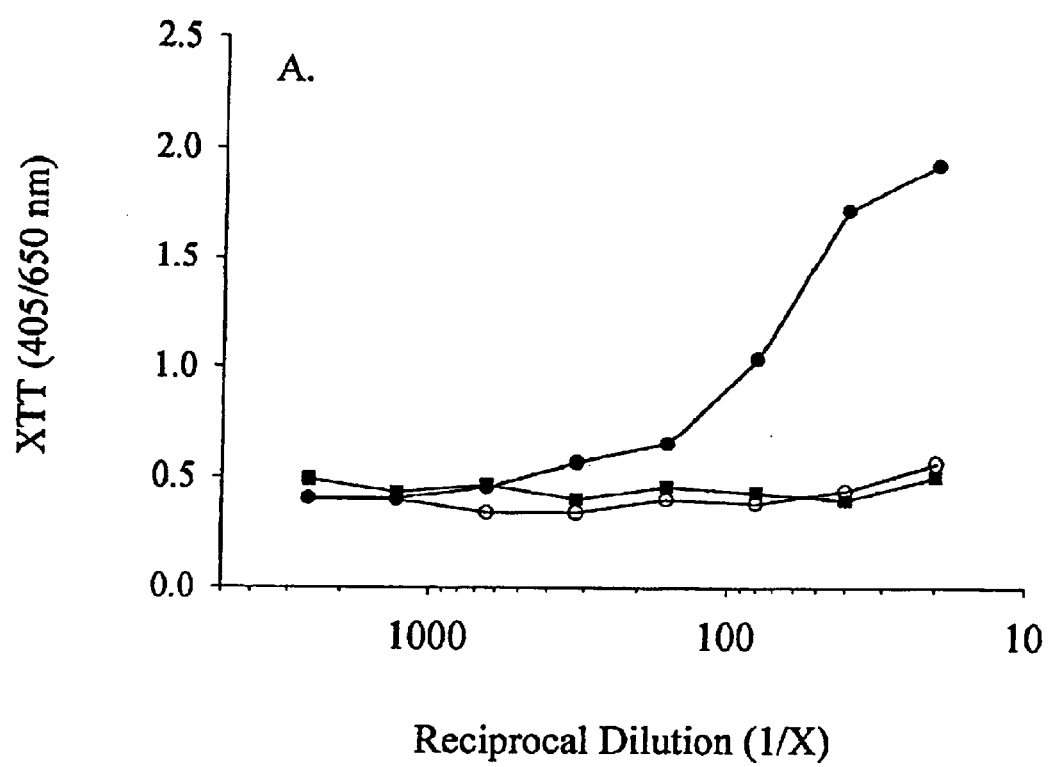
FIGS. 19A and 19B are representations of line graphs showing the biological specificity of receptor-transfected 3T3 cells.

The FMS 3T3 cells (transfected with cDNA encoding the human Fms tyrosine kinase receptor) and its ligand, human M-CSF, served as a model system. Recombinant human M-CSF stock of 1 $\mu$g/mL was serially diluted (where the first dilution, 1:20, was 50 ng/mL) was used to stimulate Fms3T3 cells. As shown in FIG. 19A, Fms 3T3 cells responded to M-CSF in a dose-responsive manner. Neither the mFlt3/Fms 3T3 cells nor the parent untransfected 3T3 cells responded to M-CSF (FIG. 19A).

Various sources of conditioned medium were screened for the presence of Flt3 3T3 stimulatory activity. The most potent source was conditioned medium harvested from human peripheral blood cells activated to secrete high levels and a broad range of cytokines by the mitogenic legume lectin, phytohemagglutinin (PHA), which is derived from impure red kidney bean extracts. This source, commonly called PHA leukocyte-conditioned medium (PHA-LCM), has been used as a standard positive control in hematopoietic colony assays for over two decades (Sharon and Lis, *Science* 246: 227, 1989). To make PHA-LCM, leukopherized blood from normal volunteers was purchased from North American Biologicals Inc., Miami, Fla. Mononuclear cells were isolated by separation using the density separation medium sold under the trademark of FICOLL-PAQUE®, washed in AIMV, and cultured at a concentration of 2×10$^6$ cells/ml in AIMV containing a 1% volume of crude red kidney bean extract containing PHA from Life Technologies (catalog number 10576-015) in either T150 flasks (Becton Dickinson Labware, Lincoln Park, N.J.) or roller bottles (Becton Dickinson Labware) for one week. Cells and debris were removed by centrifugation and conditioned medium was stored at −20° C.

Figure 19B:
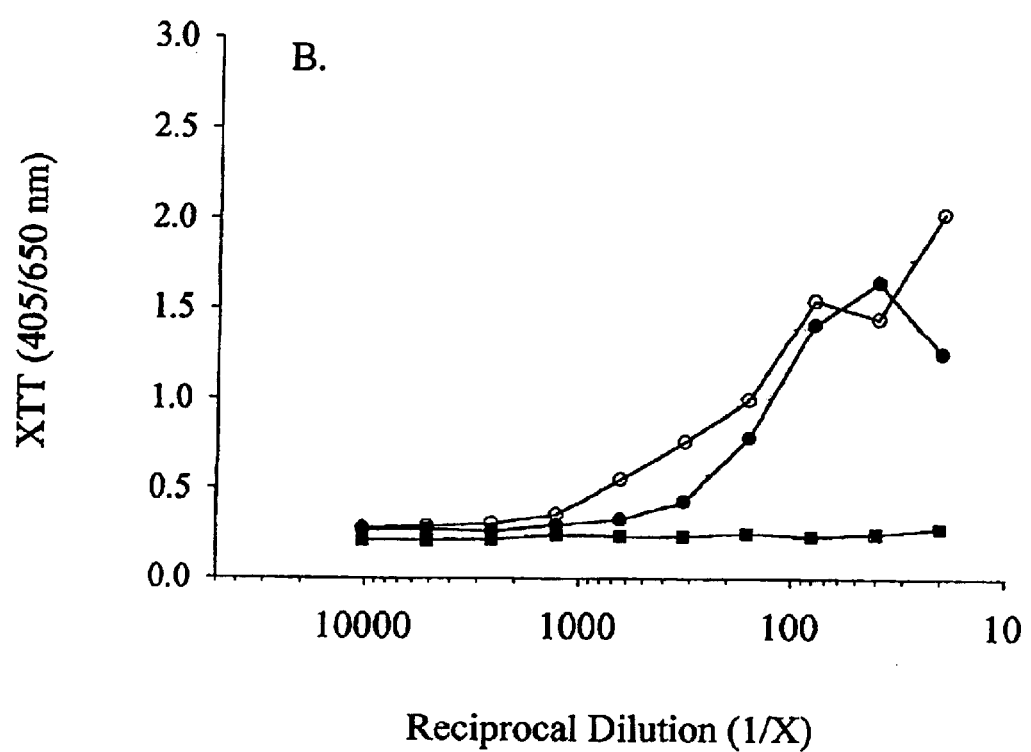

PHA-LCM induced proliferation of mFlt3/Fms 3T3 cells and Stk 3T3 (expressing the human Flt3 receptor) in an indistinguishable manner at approximately 200 units/mL (FIG. 19B). Untransfected 3T3 cells did not respond to PHA-LCM (FIG. 19B) and Fms 3T3 cells responded weakly (data not shown).

Purification of Pv-FRIL from PHA-stimulated Leukocyte Conditioned Media

Each batch of PHA-LCM was generated in serum-free medium with cells from individual normal donors. To start purification, the PHA-LCM with Flt3 3T3 activity was pooled in 30 liter lots with approximately $10^7$ Flt3 3T3 units. Twenty-five liters of PHA-LCM was diafiltered into 50 mM Tris-HCl, pH 7.6, 50 mM NaCl and then concentrated to 2–2.5 liters by tangential flow ultrafiltration on a 10 kDa molecular weight cutoff membrane (Pellicon, Millipore, Bedford, Mass.). A Blue-sepharose FF (Pharmacia Biotech) column (10 cm×15 cm) was equilibrated with 50 mM Tris-HCl, pH 7.4,50 mM NaCl. To remove the human serum albumin, concentrated PHA-LCM was applied to the column at 25 ml/min by pump and the flow through was collected. The flow-through fraction from Blue-sepharose was subjected to anion exchange chromatography by being applied to a Q-sepharose FF (Pharmacia Biotech) column (5 cm×5 cm) equilibrated with 10 mM Tris-HCl, pH 7.6. The column was washed with equilibration buffer and then eluted at 12 ml/min with a continuous gradient of 0–0.7 M NaCl in 10 mM Tris. Fractions were collected (6 ml/fraction) and an aliquot of each fraction was tested for Flt3 3T3 activity (i.e., an ability to stimulate mFlt3/fms 3T3 cells and/or Stk 3T3 cells) in 96 well plates.

After validation that a fraction had Flt3 3T3 activity, a phenyl-sepharose HP (Pharmacia Biotech) column (1.6 cm×10 cm) was equilibrated with 20 mM phosphate, pH 7, 1.5 M $NH_4SO_4$. The pooled sample from Q-sepharose was adjusted to 1.5 M $NH_4SO_4$ and applied to the phenyl-sepharose column. The column was washed with equilibration buffer and eluted at 1 ml/min with a gradient of 1.5–0.1 M $NH_4SO_4$ in 20 mM phosphate, pH 7. Fractions (1 ml) were collected and tested for Flt3 3T3 activity. Fractions with Flt3 3T3 activity were polled and dialyzed against 50 mM Tris-HCl, pH 7.2, 100 mM NaCl and concentrated by vacuum centrifugation.

A Superdex 75 (Pharmacia Biotech) column (1.6 cm×60 cm) was equilibrated with 50 mM Tris-HCl, pH 7.4, 100 mM NaCl. The pooled sample from phenyl-sepharose was applied to the Superdex 75 column and eluted at 0.6 ml/min. Fractions (1.8 ml) were collected and tested for Flt3 3T3 activity. The active fractions were dialyzed against Tris-HCl, pH 7.2 and concentrated by vacuum centrifugation.

A C4 reverse-phase column (4.6 mm×100 mm, Vydac, Hesperia, Calif.) was equilibrated with 0.1% trifluoroacetic acid (TFA) in HPLC grade $H_2O$. Pooled and concentrated sample from Superdex 75 chromatography was applied to the C4 column and the column was eluted with a gradient of 10–55% acetonitrile, 0.1% TFA over 70 min at 0.5 ml/min. Fractions of 0.5 mL were collected and evaporated by vacuum centrifugation.

Analysis by ELISA for cytokines (IL1-α, IL1-β, IL2, IL3, IL4, IL6, GM CSF, G-CSF and SCF) during purification of Pv-FRIL were performed using kits purchased from R&D Systems (Minneapolis, Minn.).

Pv-FRIL Specific Rabbit Anti-serum

Throughout purification of Pv-FRIL a New Zealand White rabbit (HRP, Denver, Pa.) was immunized with crude PHA-LCM, boosted with increasingly purified samples containing Flt3 3T3 activity, and finally immunized with a peptide corresponding to Pv-FRIL (AQSLSF[N, C, S]FTKFDLD; SEQ ID NO:31), referred to as the AQS-peptide. Samples were glutaraldehyde conjugated to keyhole limpet hemocyanin (KLH, Sigma). The rabbit was immunized with KLH-AQS peptide-containing samples using either Complete Freund's Adjuvant (Sigma) or Hunter's Titermax (Vaxcel, Inc., Norcross, Ga.). Antiserum demonstrated a 1:5,000 titer to the AQS peptide in an ELISA (data not shown). Since the antiserum contained reactivities to other proteins, further enrichment for AQS peptide-specific antibodies was achieved by either depletion of cross-reactive antibodies or by affinity purification using a AQS peptide covalently linked to an agarose support (AminoLink coupling gel, Pierce).

An anti-AQS affinity column was prepared either by purifying IgG from high titer rabbit antiserum by protein A affinity chromatography (ImmunoPure kit, Pierce) or antibody isolated from the AQS peptide column and then covalently linking antibody to an activated agarose support (AminoLink coupling gel, Pierce).

Activity of Purified Pv-FRIL

To relate the observations of Pv-FRIL's activity on receptor-transfected 3T3 cells to Flt3 receptor-expressing hematopoietic progenitors, a suspension culture of human cord blood cells enriched for $Flt3^+$ progenitors by CD34 immunomagnetic bead selection was adapted to a 96 well plate format. To do this, umbilical cord blood from healthy donors was collected in 100 units/ml of heparin (Fujisawa Healthcare, Deerfield, Ill.). Mononuclear cells were isolated by FICOLL-PAQUE® (Pharmacia Biotech, Piscataway, N.J.), washed in HBSS, and resuspended in serum-defined medium, either AIMV or XVIVO-10 (BioWhittaker, Walkersville, Md.). Mononuclear cells were enriched for $Flt3^+$ progenitors by CD34 immunomagnetic bead selection (Dynal Corporation, Lake Success, N.Y.). $CD34^+$ cells were cultured in 6 well plates (Becton Dickinson Labware) in at a concentration of $10^5$ cells in 1 mL of DMEM containing 10 ng/mL recombinant human IL3 (BioSource International, Camarillo, Calif.) and 10% fetal calf serum. The number of refractive cells present in culture wells was scored microscopically.

Figures 20A, 20B, 20C, 20D:
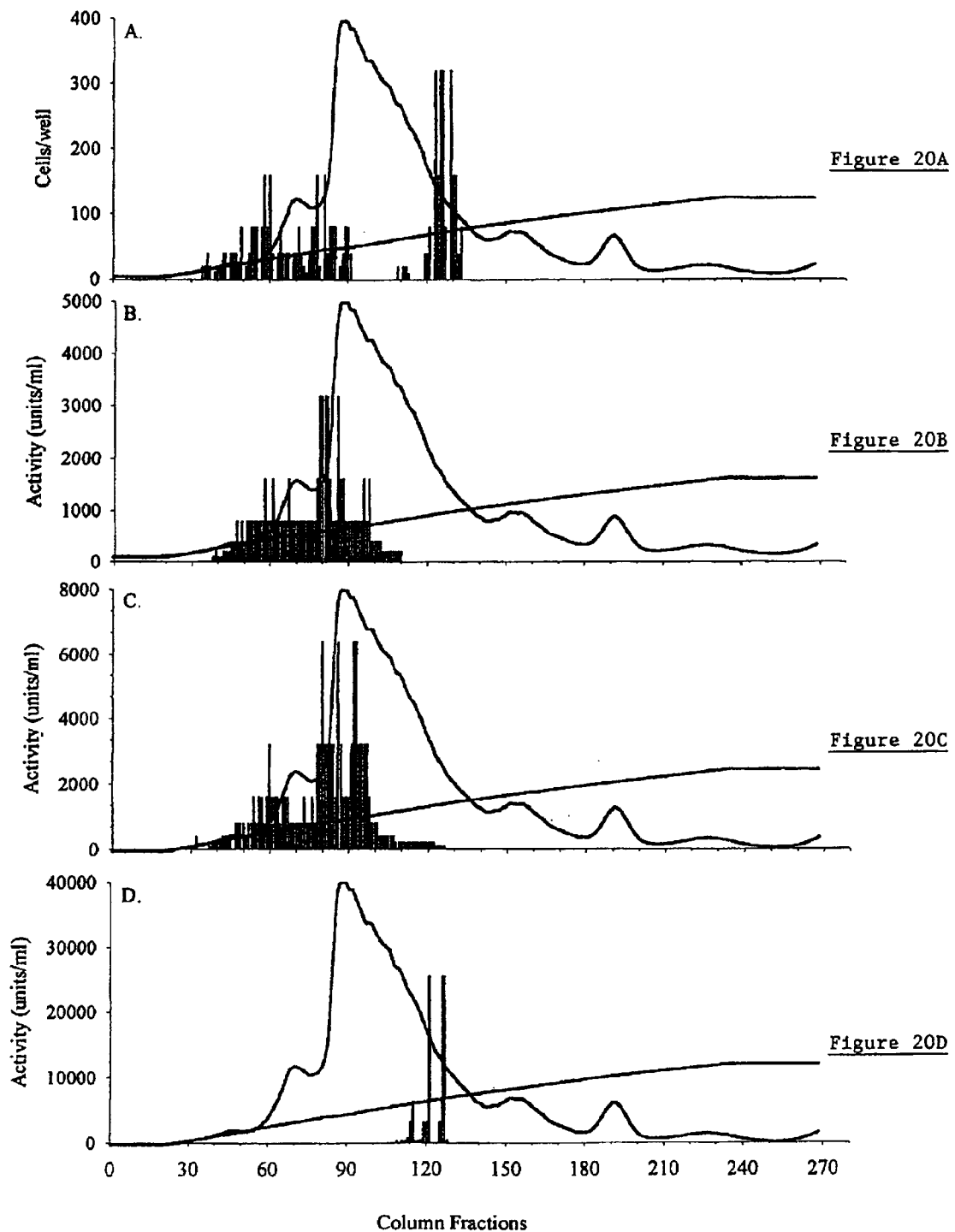
FIGS. 20A–20D are representations of the detected biological activities of PHA-LCM fractionated by anion exchange chromatography.

Culture medium always contained IL-3 since early-acting cytokines require additional co-factor(s) for survival and proliferation. FIG. 20A shows that cord blood cells responded to column fractions in two regions of the material eluted from an anion exchange column. The first region of activity corresponded with Flt3 3T3 stimulatory activity (FIGS. 20B and 20C); the second associated with an activity detected with Fms 3T3 cells (FIG. 20D); no response was detected in untransfected 3T3 cells (data not shown). The active material, corresponding to Flt3 3T3 activity (peak one in FIG. 20A), was further characterized and purified on different chromatographic matrices including a cation exchange resin, heparin sepharose, hydroxyappatite, ConA-sepharose, phenyl sepharose, and gel filtration (Superdex 75) (data not shown).

Figure 21A:
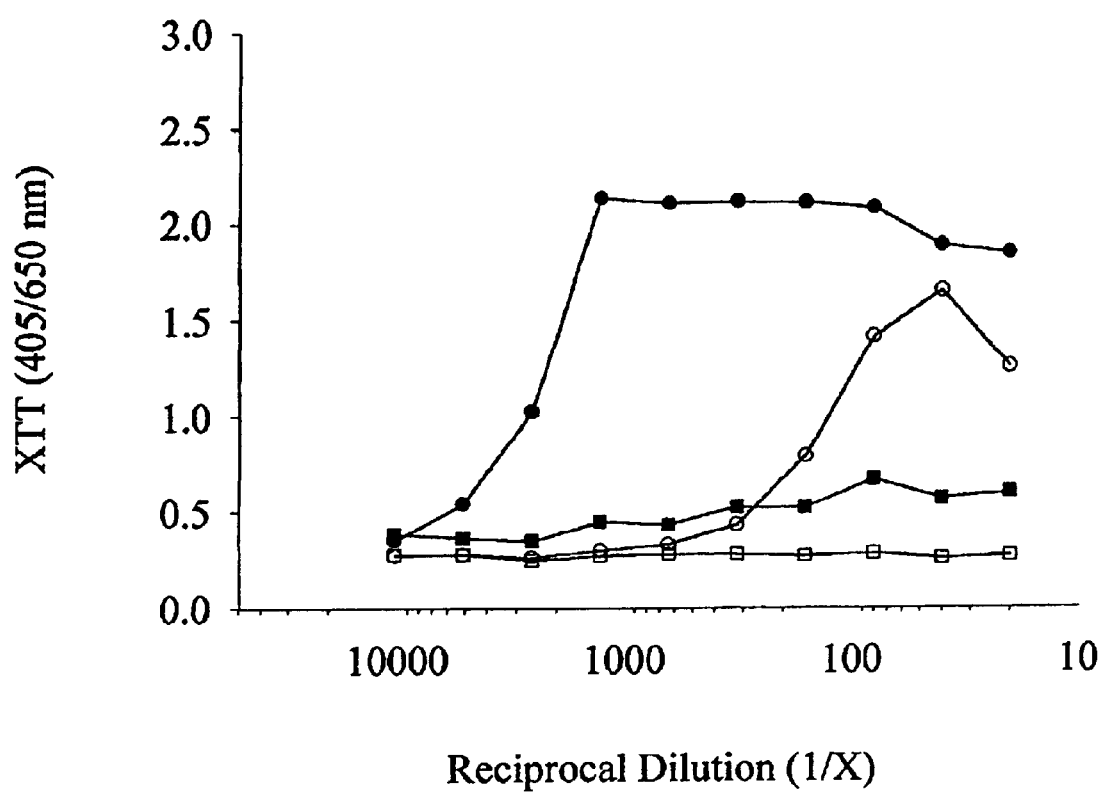
FIGS. 21A and 21B are representations of line graphs showing the co-factors required in the Flt3 3T3 assay during purification of Pv-FRIL, a representative, non-limiting FRIL family member of the invention.
Figure 21B:
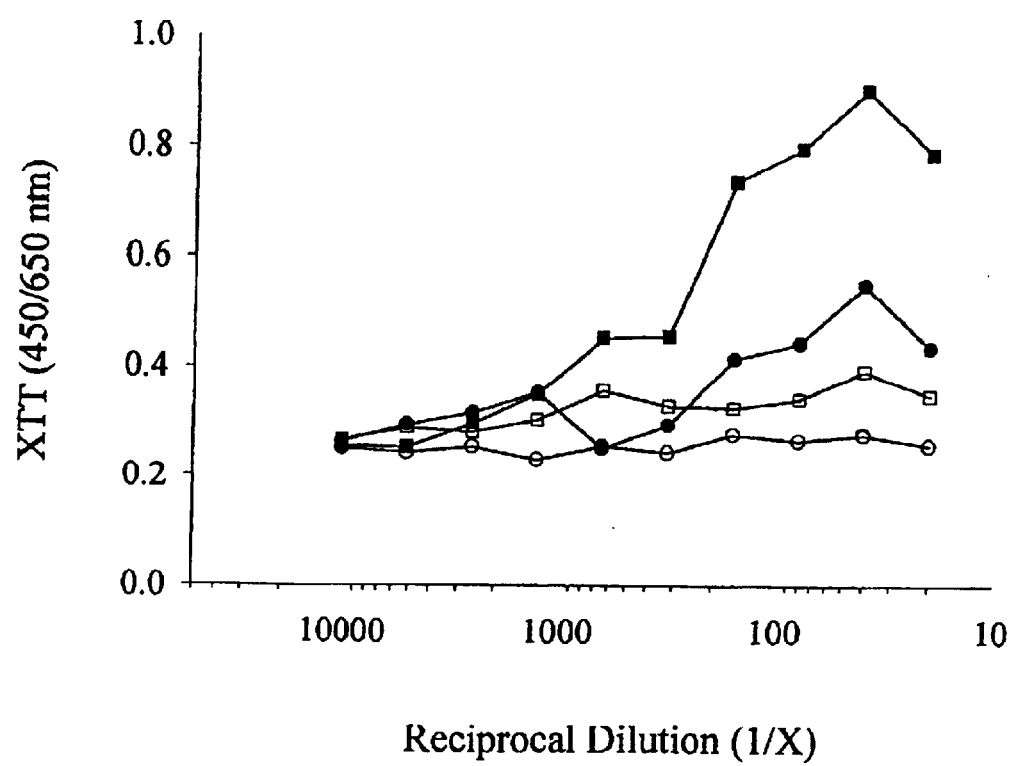

The further purified Pv-FRIL was used in the Flt3 3T3 assay described above. Plateau stimulation of Flt3 3T3 cells decreased with sequential purification steps (see FIG. 21A), suggesting removal of essential co-factor(s). Addition of suboptimal levels of crude PHA-LCM to Pv-FRIL obtained in the later stages of purification, restored activity of this partially purified Pv-FRIL to maximal plateau levels (FIG. 21B).

Analysis by ELISA for cytokines that act on hematopoietic progenitors (interleukin 1-α (IL1-α), interleukin 1-β (IL1-β), interleukin 2 (IL2), interleukin 3 (IL3), interleukin 4 (IL4), interleukin 6 (IL6), granulocyte-macrophage colony stimulating factor (GM-CSF), G-CSF (granulocyte colony stimulating factor), and stem cell factor (SCF)) in fractions containing Pv-FRIL purified to near homogeneity revealed that IL1-α had remained with Pv-FRIL through every step of purification (data not shown).

Flt3 3T3 activity was depleted but not eliminated either by adding neutralizing antibodies to IL1 or by removing IL1 by antibody affinity chromatography (data not shown). However, at the levels (<1 ng/mL) found in fractions containing purified Pv-FRIL, exogenous recombinant hIL1-α by itself had no stimulatory activity (data not shown). This observation suggested the possibility that IL1-α may act as a necessary co-factor to obtain maximal stimulation by Pv-FRIL. In subsequent experiments when testing purified Pv-FRIL, the co-factor requirement was met by the addition of either IL1-α or PHA-LCM added at a concentration that did not stimulate Flt3 3T3 cells by itself.

Using this modified Flt3 3T3 assay with the addition of sub-stimulatory amounts of either IL1-α or PHA-LCM, the active protein was purified to near homogeneity in three independent experiments. Table 4 summarizes the results of one such experiment in which a 1% recovery was accompanied by an 80,000-fold purification and resulted in a fraction with a specific activity of 244,500 units/mg.

TABLE 4

| Purification Step | Total Protein (mg) | Total Activity (units) | Specific Activity (u/mg) | Fold Purification | Recovery (%) |
|---|---|---|---|---|---|
| PHA-LCM | 231,774 | 7,500,000 | 3 | 1 | 100 |
| Blue Sepharose FF | 1,294 | 2,600,000 | | 670 | 35 |
| Q-Sepharose FF | 347 | 1,400,000 | 4,035 | 1,345 | 19 |
| Phenyl-Sepharose HP | 14 | 1,200,000 | 85,714 | 28,571 | 16 |
| Superdex 75 | 0.12 | 29,340 | 244,500 | 81,500 | 1 |

Pv-FRIL was purified by its ability to stimulate Flt3-expressing 3T3 cells using four different chromatographic media. This resulted in a 80,000-fold purification with a 1% yield.

Purified Pv-FRIL

SDS-PAGE showed the purified material to contain a limited number of polypeptides and the molecular size of the active material was determined by eluting the protein from SDS-PAGE gel slices run under non-reducing conditions and assaying the activity of the eluted material. Flt3 3T3 activity was always found in a gel slice that contained 14–22 kDa polypeptides and sometimes in a gel slice containing 32–43 kDa polypeptides (data not shown).

The polypeptide(s) in the active fraction corresponding to the 14–22 kDa range were subjected to aminoterminal sequencing by Edman degradation. To do this, an 18 kDa species from C4 reverse-phase chromatography was resolved by SDS-PAGE, electroblotted onto polyvinylidene difluoride (PVDF) membrane (Immobilon-P, Millipore) and stained with Ponceau S (Bio-Rad Laboratories, Inc., Hercules, Calif.). The 18 kDa band was cut from the PVDF membrane and N-terminal sequence was determined by automated Edman degradation on an ABI model 477A protein sequencer (PE Applied Biosystems, Foster, Calif.). The derived peptide sequences were compared against the SwissProt protein sequence database.

In each of three experiments, the sequence AQSLSFXFT-KDALD (SEQ ID NO:32) was obtained from a polypeptide of 18 kDa (where X is an unknown amino acid). For the material at the dye front (14 kDa and below) the aminoterminal sequence of TDSRVVAVEFDXFP (SEQ ID NO:33) was found twice. The amino terminus of a smooth muscle protein (SM22-α) was found twice and the amino terminus of myoglobin identified once. Since the sequence starting with AQS was the only sequence identified in each experiment, this polypeptide was concluded to be responsible for Flt3 3T3 activity.

Figure 22A:
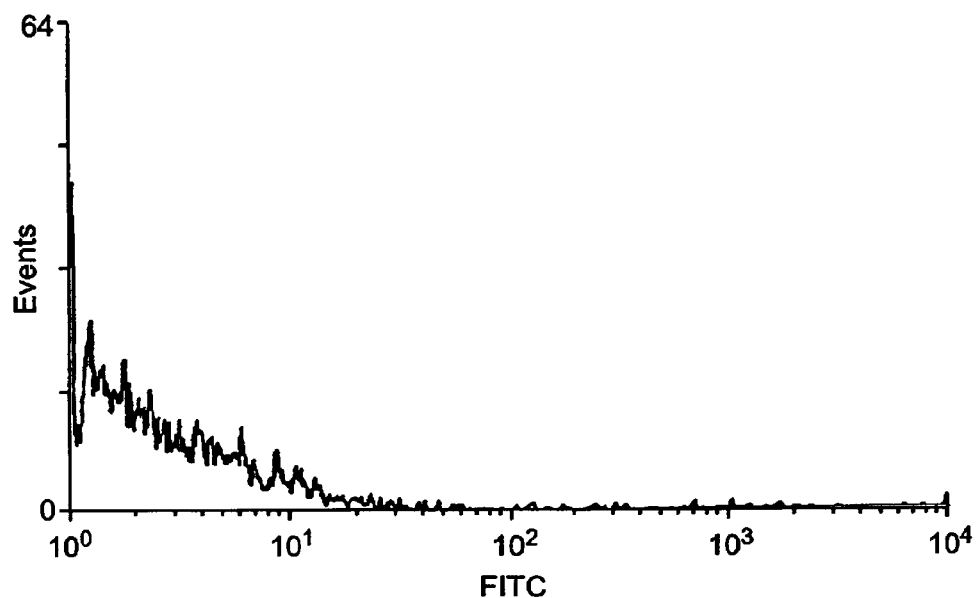
FIGS. 22A–22D are representations of a series of flow cytometry histograms showing the re-analysis of CD34 expression of cord blood CD34$^+$ cells after two weeks in suspension culture with pooled AQS affinity column fractions. CD34 expression was re-analyzed by flow cytometry on pooled AQS affinity column fractions 1–5 (FIG. 22A), fractions 6–10 (FIG. 22B), fractions 11–15 (FIG. 22C), and fractions 16–20 (FIG. 22D). Fluorescence intensity on the abcissa and frequency of events on the ordinate in FIGS. 22A–22D.
Figure 22B:
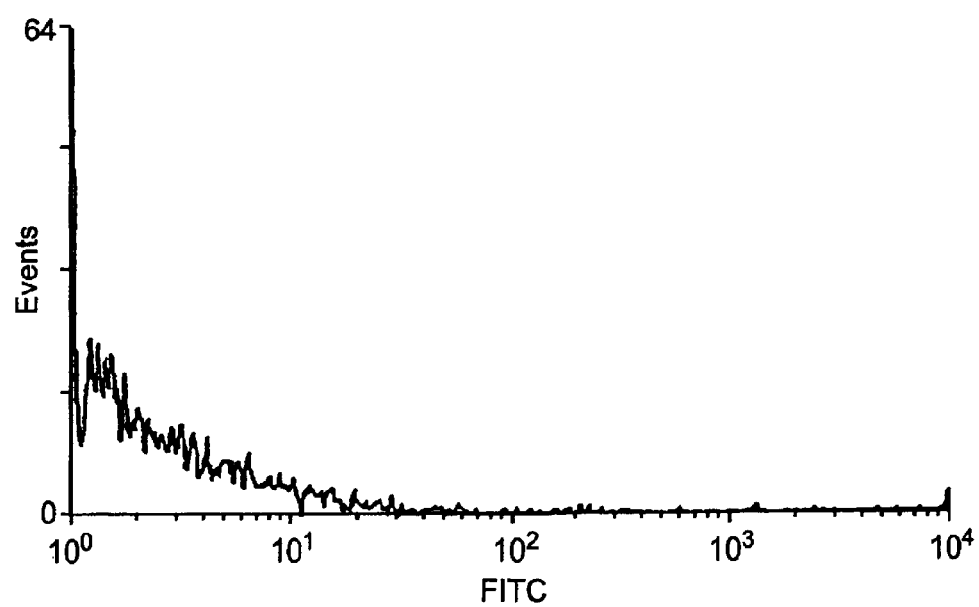
Figure 22C:
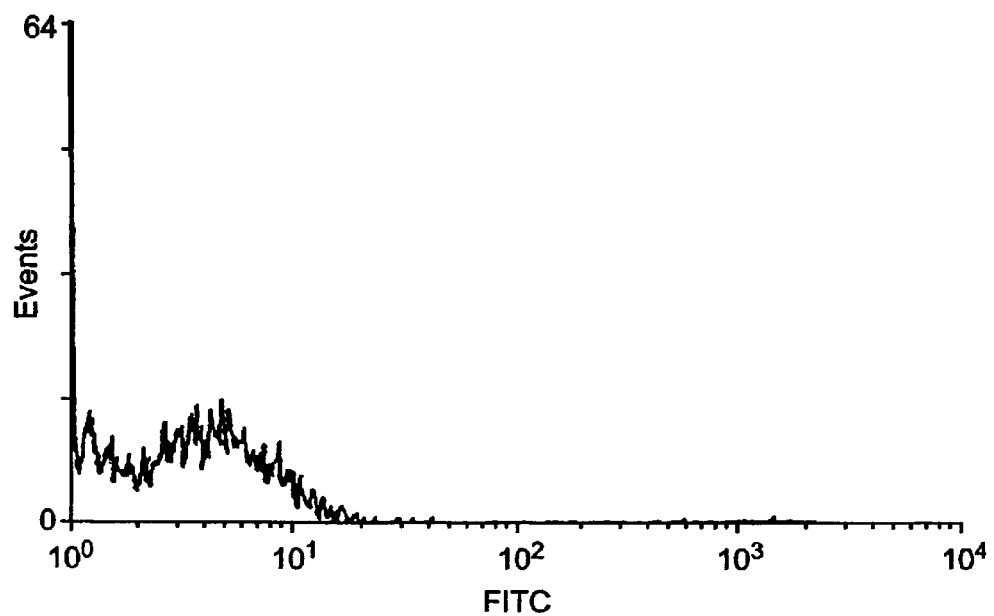
Figure 22D:
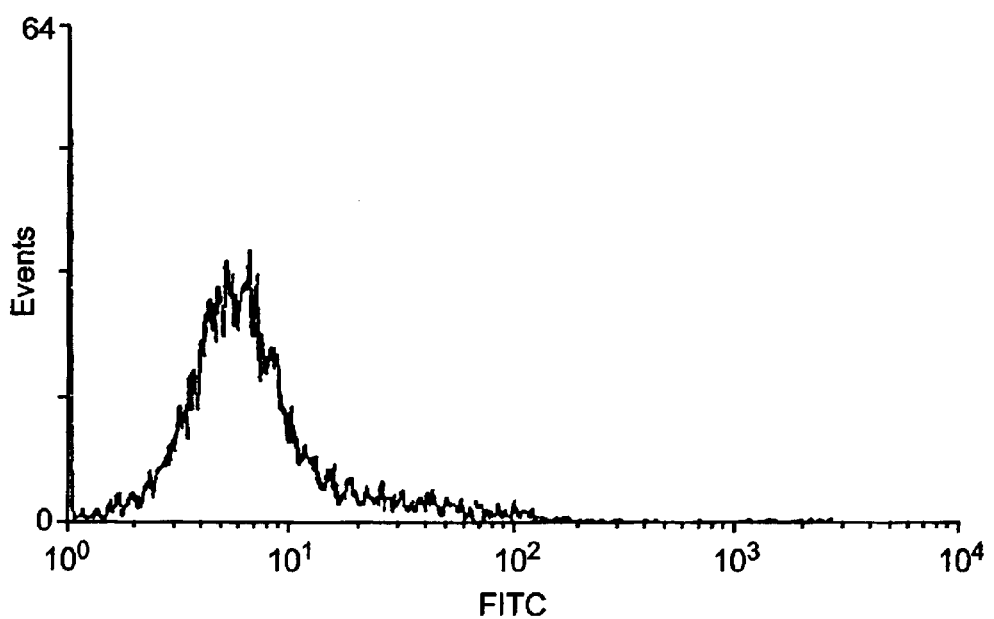

Further purification of Pv-FRIL was obtained by immunoaffinity chromatography using a rabbit antiserum described above that was generated against a synthetic peptide of 13 amino acids corresponding to the N-terminus obtained for the 18 kDa polypeptide (referred to as anti-AQS). Crude PHA-LCM was applied to a rabbit anti-AQS affinity column, and after washing, bound protein was eluted under acidic conditions. Four pools of fractions were assayed for activity in the two different assay systems. The Flt3 3T3 cells responded weakly (<100 u/mL) to the pooled fractions (data not shown). FIGS. 22A–22D shows results of an experiment where the pooled fractions were assayed on cord blood cells in the presence of IL3. After two weeks of suspension culture, the number of viable cells and status of CD34 expression was evaluated. A representative of three AQS affinity chromatography experiments is shown in FIGS. 22A–22D. Cell cultures supplemented with the two early column fraction pools contained approximately four-fold more cells (426,000 cells and 466,250 cells, respectively) than at the 100,000 cells seeded and no appreciable CD34 staining (FIGS. 22A and 22B). The increase in cell number and loss of CD34 expression is attributed to the expected consequences of IL3-induced proliferation and differentiation. In contrast, cell cultures treated with the late-eluting fraction pool (FIG. 22D) contained less than 10,000 cells, or a tenth of input cells, and a uniform population of cells expressing CD34. The late-eluting AQS affinity pool did not show the potent effects of IL3 (high cell numbers and exhausted medium); instead the persistence of viable cells expression CD34 after two weeks in suspension culture suggested that the active component might preserve CD34$^+$Flt3$^+$ progenitors.

Pv-FRIL is Derived from Phaseolus vulgaris

Because PHA is derived form red kidney bean extract and because a FRIL family member, Dl-FRIL, was isolated from another legume, namely Dolichos lab lab, mannose-binding lectins were isolated from red kidney bean (Phaseolus vulgaris) extract using standard methods, such as the procedure of Rudiger, H., Isolation of Plant Lectins, H.-J. Gabius and S. Gabius, eds., pp. 31–46, Berlin, 1993). The kidney bean mannose-binding lectin consisted of polypeptides with molecular weights of 18 kDa and 15 kDa, and the aminotermini of these two polypeptides started with AQSLSFXFKFDPN (SEQ ID NO:34) and TDSRV-VAVEDF (SEQ ID NO:35), respectively (where X is an unknown amino acid).

Figure 23:
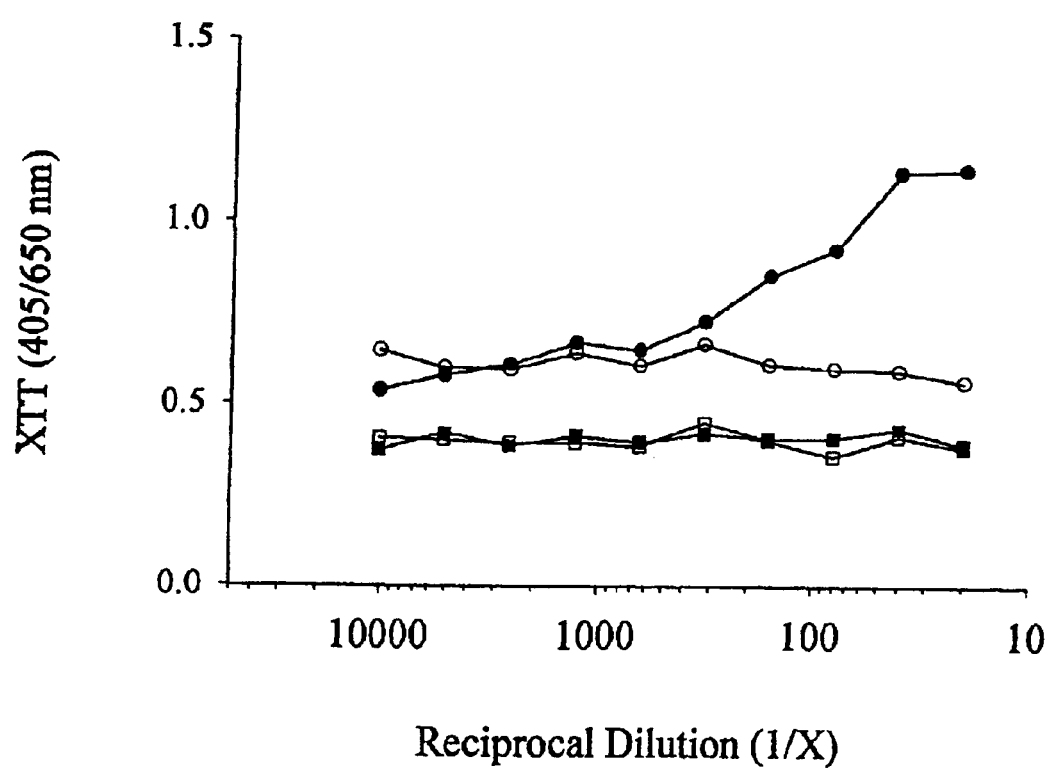
FIG. 23 is a representation of a line graph showing the IL1-dependent response of mFlt3/Fms 3T3 cells to FRIL isolated from commercial red kidney bean extract. mFlt3/Fms 3T3 cells respond to FRIL in the presence of rhIL1 (solid circles) but not the absence of IL1 (solid squares). Corresponding medium only controls are shown with open symbols.

Pv-FRIL isolated from Phaseolus vulgaris was tested for activity in the Flt3 3T3 cell assay. As shown in FIG. 23, Flt3 3T3 cells responded in a dose dependent manner to Pv-FRIL, while parent untransfected 3T3 cells did not.

Purification of Pv-FRIL from Phaseolus vulgaris

Dry seeds from the red and white kidney beans (Phaseolus vulgaris) were purchased from W. Atlee Burpee & Company, Warminster, Pa. Lectins were eluted using a standard protocol. Briefly, beans were pulverized in a home coffee grinder and added to buffer of 50 mM Tris/HCl, pH. 8.0, 1 nM each of MgCl$_2$ and CaCl$_2$ for 4 hours at 4° C. with constant mixing. Bean solids were pelleted by centrifugation at 10,000×g for 20 min. The pH of the supernatant was modified to pH 4.0 with acetic acid and constant mixing to remove contaminating storage proteins, followed by centrifugation to clarify the supernatant, and finally the pH was readjusted to 8.0 with sodium hydroxide before storing at −20° C.

Specific binding of Pv-FRIL to mannose enabled a single-step purification of the lectin from the supernatant of the bean extract. 50 μL extracts of either red or white kidney beans were incubated in a conical tube with 1 mL of mannose covalently bound to agarose beans (Sigma) at 4° C. with constant mixing for 4 hours to overnight. Beans were washed gently by centrifugation (300 g, 5 min) in lectin binding buffer. Mannose binding protein was eluted from the mannose beans after washing by incubation either with 200 mM α-methyl mannoside (Sigma) or 100 mM glycine, pH 2.8.

DNA Isolation and PCR amplification of Pv-FRIL-Encoding Nucleic Acid

Total genomic DNA was isolated from young *Phaseolus vulgaris* shoots according to the procedure of Dellaporta ("Plant DNA miniprep and microprep: Versions 2.1–2.3,". Freeling, M. and V. Walbot (Ed.). *The Maize Handbook*. *XXVI*+759p. Springer-Verlag New York, Inc.: New York, N.Y., USA; Berlin, Germany.), and stored at −20° C. Based on the determined N-terminal amino acid sequences of Pv-FRIL, four degenerate oligonucleotides (PVbeta1, PVbeta2, PValfa1, PValfa2) were designed using *Phaseolus vulgaris* codon usage. The sequences of the primers is as follows:

PVBeta1: TTY ACY AAR TTY GAY YTN GA (SEQ ID NO:36)
PVBeta2: ATY TTY CAR GGW GAY GC (SEQ ID NO:37)
PVAlfa1: TTR ACR TCR ATW CCR ATR TG (SEQ ID NO:38)
PVAffa2: TAR TTW GGR TCR ATR TTR GCR TT (SEQ ID NO:39).

Two sequential polymerase chain reactions (PCR) were performed. In the first reaction, 10 ng of bean genomic DNA was amplified by 30 cycles of PCR, each cycle comprising 40 seconds at 94° C., 40 seconds at 50° C., 60 seconds at 72° C., and an extension step at 72° C. for 10 min. The reactions were performed in 50 μl containing 30 pmol of each primer, PVbeta 1 and PValfa1, 0.2 mM deoxyribonucleotides and 0.5 unit of Ampli-Taq polymerase (Perkin Elmer) in the corresponding buffer. One microliter of the PCR product was amplified by 30 PCR cycles using the same conditions as described above. The reaction was performed in 50 μL containing 30 pmol of the two primers, PVbeta 2 and PV alfa2, using 0.2 mM deoxyribonucleotides and 0.5 unit of Ampli-Taq polymerase (Perkin Elmer) in the corresponding buffer. The 460 bp fragment obtained was cloned in a T/A plasmid, pCR2.1 (Invitrogen) and sequenced by sequenase dideoxy chain termination (United States Biochemicals).

RNA Isolation and cDNA synthesis of Pv-FRIL-encoding Nucleic Acid

Total RNA was prepared from mid-maturation *Phaseolus vulgaris* seeds stored at −70° C. following the procedure reported by Pawloski et al. (*Mol. Plant Biol. Manual* 5: 1–13, 1994). The 5'/3' RACEKIT (Boehringer Mannheim) was used to generate cDNA from 5.0 μg total RNA used according to the manufacturer's instructions. In the cDNA synthesis for the 3' RACE, the oligo(dT) anchor primer was at the concentration of 32.5 μM, in the standard conditions. For the 5' RACE, a specific primer (SPV1) was used at the concentration of 32.5 μM. The cDNA purification and the subsequent tailing reaction was performed according to the manufacturer's instructions.

Polymerase Chain Reaction and cDNA Cloning of Pv-FRIL-encoding Nucleic Acid

The 3' end of Pv-FRIL was obtained through rapid amplification of cDNA ends by polymerase chain reaction (RACE-PCR) using the 5'/3' RACEKIT (Boehringer Mannheim) used according to the manufacturer's instructions. Nested PCR amplifications were performed using the PCR-Anchor primer with the specific primers (PV3 and PV4) in two successive amplification reactions. The sequences of these primers is as follows:

PV3: CAA TGT CTT ACA ACT CAC TAA G (SEQ ID NO:40)
PV4: AGT GTG GGA AGA GTG TTA TTC (SEQ ID NO:41).

The amplification conditions were 30 cycles of 40 seconds at 94° C., 40 seconds at 55° C., 60 seconds at 72° C. each and an extension step at 72° C. for 10 min. The reactions were performed in 50 μL containing 30 pmol of each primer, PV3 and PCR-Anchor primer in the first, and PV4 and PCR-Anchor primer in the second, 0.2 mM deoxyribonucleotides and 0.5 units of Ampli-Taq polymerase (Perkin Elmer) in the corresponding buffer. The 831 bp product obtained was sub-cloned in pCR2.1 and sequenced as above reported.

For the 5'RACE, again nested PCR reactions were performed using in combination with the Anchor Primer the specific primers SPV2 and SPV3.

The sequences of these primers is as follows:
SPV2: ACC AAA GCT TTG GTT TTC AGA (SEQ ID NO:42)
SPV3: TCT GAA AAC GTT TGA GTA GAG (SEQ ID NO:43).

The amplification conditions for both reactions were 30 cycles of 40 seconds at 94° C., 40 seconds at 50° C., 60 seconds at 72° C. each and an extension step at 72° C for 10 min. The reactions were performed in 50 μL containing 30 pmol of each primer, SPV2 and PCR-Anchor primer in the first, and SPV3 and PCR-Anchor primer in the second, 0.2 mM deoxyribonucleotides and 0.5 unit of Ampli-Taq polymerase (Perkin Elmer) in the corresponding buffer.

To obtain the full-length cDNA clone, recombinant PCR was performed (Higuchi R., supra). Two PCR reactions were carried out separately, one on the 5' fragment and the other on the 3' RACE product using primers with an overlapping region. The overlapping primary products were subsequently re-amplified using the flanking primers resulting in a full-length fragment.

The primary PCR products were purified with the QIAquick PCR Purification kit (QIAGEN) used according to the manufacturer's instructions, and amplified together in a single second reaction. For the second PCR reaction, the primers PVEcoRI and the APEcoRI were used. The sequences of these primers is as follows:

PVEcoRI TAC ATG AAT TCG CTC AGT CAT TAT CTT TTA AC (SEQ ID NO:44)
APEcoRI: GAA TTC GAC CAC GCG TAT CGA TGT CGAC (SEQ ID NO:28).

Figure 24A:
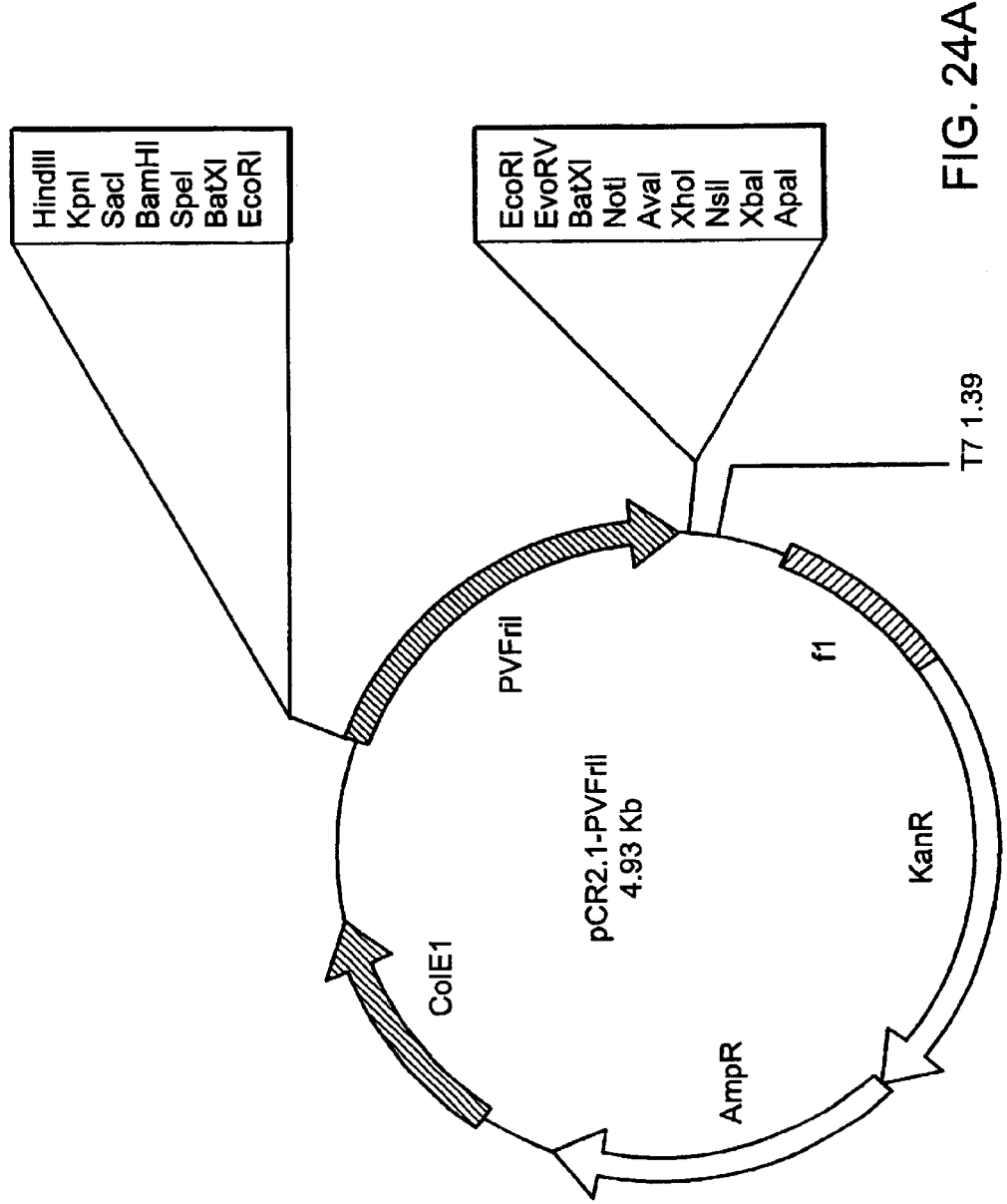
FIG. 24A is a map of a cloning vector pCR2.1-Pv-FRIL manufactured by ligating a cDNA according to the invention in the EcoRI site of the cloning vector pCR2.1.
Figure 25:
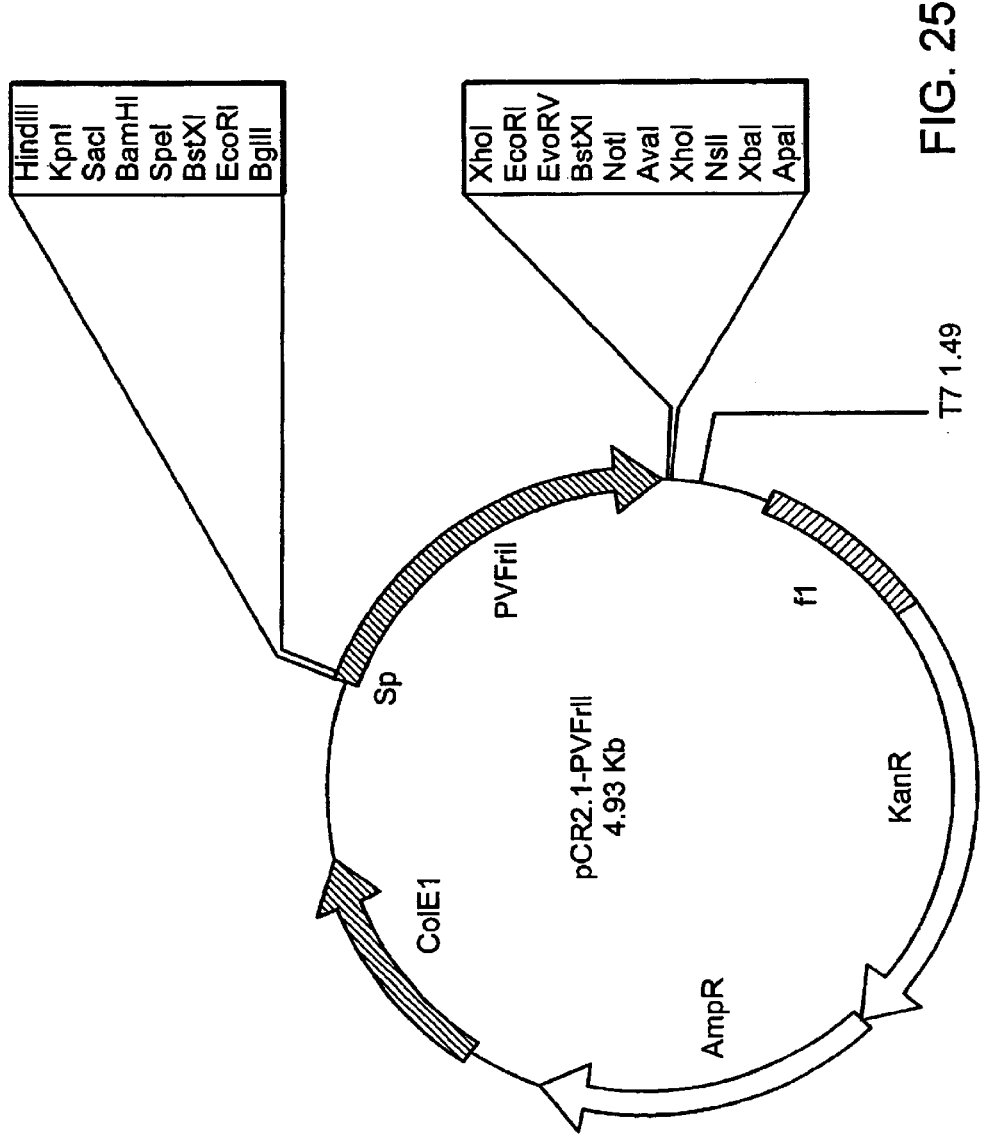
FIG. 25 is a map of a cloning vector pCR2.1-SpPv-FRIL manufactured by ligating a cDNA according to the invention in the Xhol site of the cloning vector pCR2.1.
Figure 26:
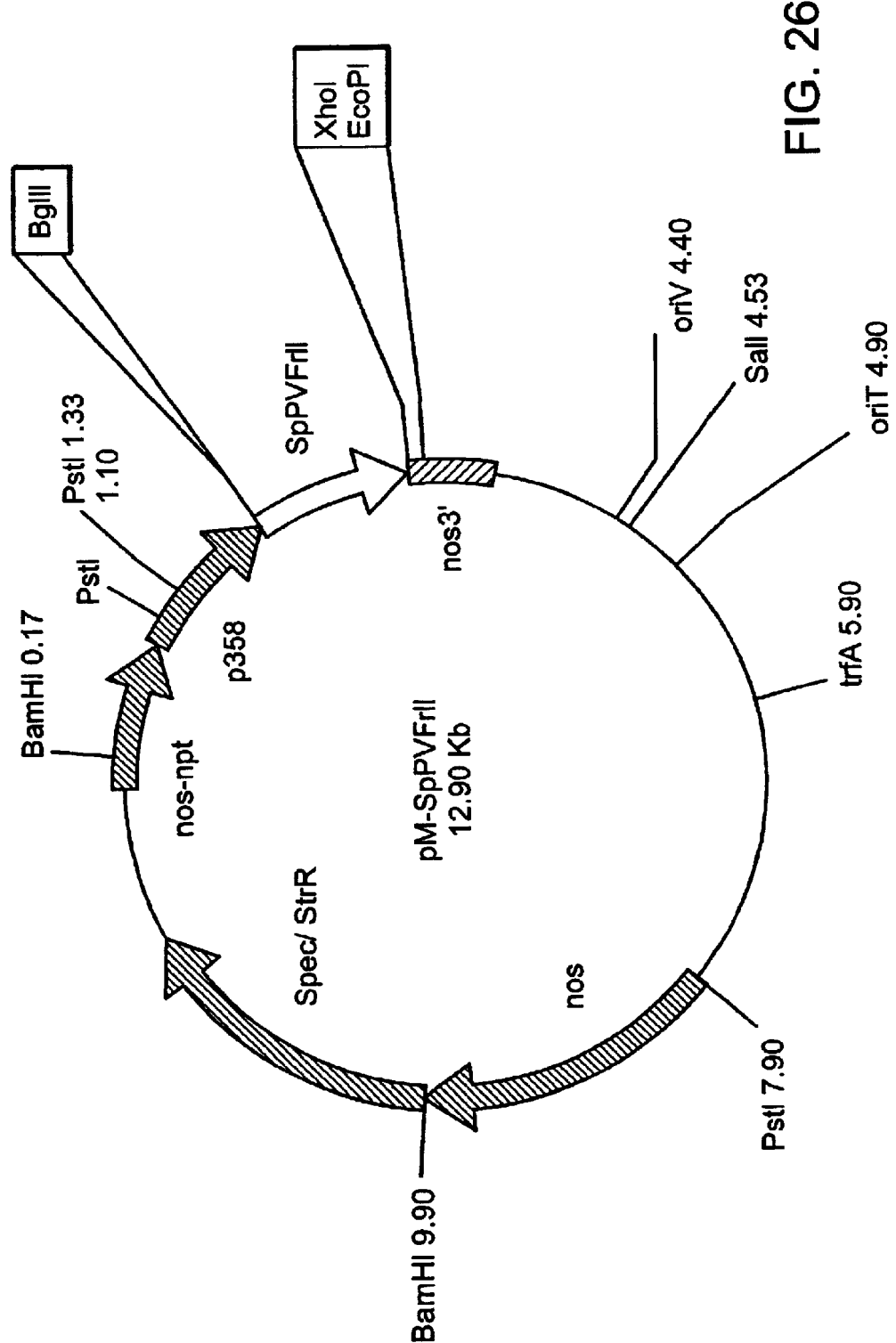
FIG. 26 is a map of a cloning vector pM-SpPv-FRIL manufactured by ligating a cDNA according to the invention in the BglII/Xhol sites of the cloning vector SpPv-FRIL.

Both primary and secondary PCR reactions were performed in 100 μL containing 50 pmol of each primer, 0.4 mM deoxyribonucleotide and 1.0 unit Pfu polymerase (Stratagene) in the corresponding buffer. The primary PCR reaction amplified the two separate fragments by 30 cycles, each cycle comprising 40 seconds at 94° C., 40 seconds at 50° C., 60 seconds at 72° C. and an extension step at 72° C. for 10 min. The second PCR reaction amplified the recombinant fragment in 12 cycles using the same conditions reported above. The full-length product was cloned in the EcoRI site of the cloning vector pCR2.1 (FIG. 24A) and sequenced as noted above. This plasmid is referred to as pCR2.1-Pv-FRIL.

The nucleic acid sequence of the Pv-FRIL cDNA is as follows:

```
  1 GCTCAGTCAT TATCTTTTAA CTTTACCAAG TTTGATCTTG ACCAAAAAGA (SEQ ID NO:5)

51 TCTTATCTTC CAAGGTGATG CCACTTCTAC AAACAATGTC TTACAACTCA

101 CTAAGTTAGA CAGTGGAGGA AACCCTGTGG GTGCTAGTGT GGGAAGAGTG

151 TTATTCTCTG CACCATTTCA TCTTTGGGAA AACTCTATGG CAGTGTCAAG

201 CTTTGAAACT AATCTCACCA TTCAAATCTC AACACCTCAC CCTTATTATG

251 CAGCTGATGG CTTTGCCTTC TTCCTTGCAC CACATGACAC TGTCATCCCT

301 CCAAATTCTT GGGGCAAATT CCTTGGACTC TACTCAAACG TTTTCAGAAA

351 CTCCCCCACC TCTGAAAACC AAAGCTTTGG TGATGTCAAT ACTGACTCAA

401 GAGTTGTTGC TGTCGAATTT GACACCTTCC CTAATGCCAA TATTGATCCA

451 AATTACAGAC ACATTGGAAT CGATGTGAAC TCTATTAAGT CCAAGGAAAC

501 TGCTAGGTGG GAGTGGCAAA ATGGGAAAAC GGCCACTGCA CGCATCAGCT

551 ATAACTCTGC CTCTAAAAAA TCAACTGTTA CTACGTTTTA TCCTGGGATG

601 GAAGTTGTGG CTCTCTCCCA TGATGTTGAC TTACATGCAG AGCTTCCTGA

651 ATGGGTTAGA GTAGGGTTAT CTGCTTCAAC TGGAGAGGAG AAACAAAAAA

701 ATACCATTAT CTCATGGTCT TTCACTTCAA GCTTGAAGAA CAACGAGGTG

751 AAGGAGCCGA AAGAAGACAT GTATATTGCA AACGTTGTGC GATCATATAC

801 ATGGATCAAT GACGTTCTAT CTTATATAAG CAATAAATAA ATGTATGATG

851 CACTCAATAA TAATCACAAG TACGTACGGT GTAGTACTTG TATGTTGTTT

901 ATGAAAAAAA AAAA
```

The amino acid sequence of Pv-FRIL is as follows:

```
AQSLSFNFTKFDLDQKDLIFQGDATSTNNVLQLTKLDSGGNPVGASVGRVLFSAPFHLWENSMAV   (SEQ ID NO:6)

SSFETNLTIQISTPHPYYAADGFAFFLAPHDTVIPPNSWGKFLGLYSNVFRNSPTSENQSFGDVN

TDSRVVAVEFDTFPNANIDPNYRHIGIDVNSIKSKETARWEWQNGKTATARISYNSASKKSTVTT

FYPGMEVVALSHDVDLHAELPEWVRVGLSASTGEEKQKNTIISWSFTSSLKNNEVKEPKEDMYIA

NVVRSYTWINDVLSYISNK*MYDALNNNHKYVRCSTCMLFMKKK
```

The amino acid sequence of Pv-FRIL was compared to the amino acid sequences of Dl-FRIL and of the PHA-E lectin. This comparison is shown on FIG. 24B.

Pv-FRIL-Encoding Plant Expression Vectors and *Nicotiana tabacum* Transformation Recombinant PCR was used to introduce a signal peptide for entry of Pv-FRIL into the end reported of An et al., supra. *Agrobacterium*-mediated transformation of *Nicotiana tabacum* leaf disks was carried out as described by Horsh et al. (*Science* 227: 1229–1231, 1985) using C58 harboring the expression vector pM-SpPv-FRIL. Kanamycin resistant plants were scored for their ability to form roots in two consecutive steps of propagation in Murashige-Skoog medium containing 3% sucrose and kanamycin sulfate (Sigma) at 100 mg/L.

Tobacco plants transformed with this construct were grown in a growth room under controlled conditions. The leaves (20 grams) of young plants were harvested and frozen in liquid nitrogen and powdered in a mortar with a pestle. The powder was stirred in a buffer mixture consisting of 1× phosphate buffered saline containing 1 mM $CaCl_2$ with a cocktail of protease inhibitors (PMSF, Pepstatin and Leupeptin). This slurry was centrifuged at 2000 rpm and the supernatant was centrifuged at 40,000 rpm in a Beckman ultracentrifuge. The clear supernatant was tumbled with 1 ml of ovalbumin-Sepharose for 3 hours. The beads were washed with the same buffer and tumbled overnight with 200 mM trehalose in 1/10 phosphate buffered saline containing the cocktail of protease inhibitors. Coomassie blue stained gel showed this preparation to be pure Pv-FRIL. An immunoblot showed the presence of both alpha and beta subunits, thus, the single polypeptide chain encoding both subunits was cleaved by the transformed cells in vivo. Binding to the ovalbumin-sepharose and release by trehalose shows that the product of the transgene is an active lectin.

EXAMPLE 6

Dl-FRIL Supports Prolonged ex vivo Maintenance of Quiescent Human CD34+,CD38−/SCID-Repopulating Cells To further characterize the progenitor cell preservation activity of Dl-FRIL, a functional in vivo assay for primitive human hematopoietic cells was used to determine the cells' ability to home to and repopulate the marrow of sublethally irradiated C.B-17 and NOD/LtSz mice homozygous for the severe combined immunodeficiency Prkdc $^{scid}$ mutation (Lapidot et al., *Science* 255:1137, 1992; Larochelle et al., *Nat. Med.* 2:1329–1337, 1996). To do this, the following methods were used:

Preparation of Human Cells

Human umbilical cord blood (CB) samples were obtained from full term deliveries. The blood samples were diluted 1:1 in phosphate-buffered-saline (PBS) without $Mg^{+2}/Ca^{+2}$, supplemented with 10% fetal bovine serum (FBS). Low density mononuclear cells were collected after standard separation on Ficoll-Paque (Pharmacia Biotech, Uppsala, Sweden), and washed in RPMI with 10% FBS. Some samples were frozen in 10% DMSO, while the others were used fresh. Enrichment of CD34+ cells was performed with mini MACS separation kit (Miltenyi Biotec, Bergisch Gladbach, Germany) according to the manufacturer's instructions. The purity of the enriched CD34+ cells was 60–80% using one column. CD34+CD38$^{-/low}$ cells were purified by FACS sorting (FACStar+, Becton Dickinson, San Jose, Calif.) after staining CD34+ enriched cells with mAb anti human CD34-FITC (Becton Dickinson) and anti human CD38 PE (Coulter, Miami Fla. USA) (Purity >99%).

Mice

Eight week old NOD/LtSz-Prkdc$^{scid}$/Prkdc$^{scid}$ (NOD-SCID) mice and NOD/SCID β2 microglobulin knockout mice, hereafter termed NOD/SCID B2M$^{null}$ (Christianson et al., *J. Immunol.* 158:3578–3586, 1997), bred and maintained under defined flora conditions in sterile micro isolator cages, were irradiated with a sublethal dose of 375 cGy at 67cGy/min. from a cobalt ($^{60}$Co) source prior to transplantation.

Human cells were injected into the tail vein of irradiated mice in 0.5 mL of RPMI with 10% FBS. In some experiments (as indicated) non engrafting irradiated (1500 cGy) CD34− cells served as carrier cells, and were cotransplanted with cultured cells at a final concentration of $0.5 \times 10^6$ cells/mouse. Mice were sacrificed 1 month post transplantation, and bone marrow (BM) cells were flushed from the 8 bones of each mouse (femurs, tibias, humeri, and pelvis).

Ex vivo Cultures Human CD34+ enriched cells were cultured in 24 well plates ($2–4 \times 10^5$ cells in 0.5 mL), containing RPMI supplemented with 10% FBS+1% BSA. Ex vivo cultures contained the following cytokine combination: Stem cell factor (SCF)—100 ng/mL and Flt3 ligand (Flt3-L)—100 ng/mL (R&D Systems Inc. Minneapolis, Minn., USA), rhIL-6–50 ng/mL and sIL6R—1280 ng/mL, (InterPharm Laboratories, Ares-Serono Group, Ness Ziona, Israel) or Dl-FRIL—10 ng/mL (ImClone Systems Inc., NY, USA). In some experiments where indicated, the growth factor cocktail included 300 ng/mL SCF, 300 ng/mL Flt3-L, 50 ng/mL G-CSF, 10 ng/mL IL-3 (R&D Systems), and 10 ng/mL IL-6. The cultures were incubated at 37° C. in a humidified atmosphere containing 5% $CO_2$. After 3, 6, 10 and 13 days, the cells were collected, counted, analyzed by FACS, seeded in to semisolid cultures and transplanted into NOD-SCID mice. For CD56+NK cell development, BM cells from engrafted mice were cultured with 100 ng/mL of SCF and IL-15 (R&D) for 10–14 days.

Preparation of Dl-FRIL

Dl-FRIL was isolated from the seeds of hyacinth beans (*Dolichos lab lab*) using the protocol described above in Example 1.

CFU Assay.

Semisolid cultures were performed in order to detect the levels of human progenitors in ex vivo cultures, and in the marrow of transplanted mice. The cells were plated ($4 \times 10^3$ cells/mL) in 0.9% methylcellulose (Sigma, St. Louis, Mo., USA), 30% FBS, $5 \times 10^{-5}$M 2ME, 50 ng/mL SCF, 5 ng/mL IL-3, 5 ng/mL GM-CSF (R&D), and 2 u/mL Erythropoietin (Ortho Bio Tech, Don Mills, ON, Canada). Human cells from the BM of engrafted mice were plated ($2 \times 10^5$ cells/mL) in 15% FBS+15% human plasma, selective for human colonies only. The cultures were incubated at 37° C. in a humidified atmosphere containing 5% $CO_2$ and scored 14 days later with an inverted microscope for myeloid, erythroid, and mixed colonies by morphologic criteria.

Cell Cycle Analysis.

Cells were analyzed for their DNA content by staining with propidium iodide (Sigma). The cells were cultured in ex vivo cultures as described, for 3, 6, 10, and 13 days as indicated. At each time point, the cells were collected, resuspended to a final concentration of $0.1–1 \times 10^6$ cells/mL, and incubated with 0.1% Triton X 100 (Sigma) for 20 minutes on ice. 50 mg/mL propidium iodide (PI) were added before analysis. Flow cytometeric analyses were performed using FACSort (Becton Dickinson, San Jose, Calif.).

Flow Cytometry Analyses.

Human and mouse Fc receptors on BM cells from transplanted mice were blocked by using human plasma (1:50) and anti mouse Fc receptor blockers (anti mouse CD16/CD32 mAb, Pharmingen, San Diego, Calif., USA). Isotype control mAb were used in order to exclude false positive cells (Coulter, Miami Fla. USA). The purity of enriched subpopulations after magnetic bead separation, were analyzed by two color staining, using anti-human CD34 FITC (Becton Dickinson, San Jose, Calif., USA) and anti-human CD38 PE (Coulter). The levels of human cells and lymphoid lineages in the marrow of engrafted mice were detected by double staining with anti-human CD45 FITC (Immuno Quality Products, Groningen, The Netherlands) together with anti-human CD19 PE (Coulter) for detection of pre B cells, or with anti-human CD56 PE (Coulter) for detection of NK cells. Cells were washed with PBS supplemented with 1% FBS and 0.02% azide, suspended to a volume of $0.1–1\times10^6$ cells/mL, stained with direct-labeled mAb and incubated for 25 minutes on ice. After staining, cells were washed once in the same buffer and analyzed on a FACSort (Becton Dickinson). Analysis was performed using CELLquest software (Becton Dickinson).

Human Cell Engraftment Analysis.

The levels of human cell engraftment were determined by both flow cytometry for analysis of human myeloid $CD45^+$ and lymphoid $CD45^+CD19^+$ pre B cells and quantification of human DNA as previously described (Lapidot et al., *Science* 255:1137, 1992; Larochelle et al., *Nat. Med.* 2:1329–1337, 1996; Peled et al., *Science* 283:845–848, 1999). Briefly, high molecular weight DNA was obtained from the BM of transplanted mice by phenol/chloroform extraction. DNA (5 g) was digested with EcoRI, subjected to electrophoresis on 0.6% agarose gel, blotted onto a nylon membrane, and hybridized with a human chromosome 17-specific α-satellite probe (p17H8) labeled with $^{32}P$ (Lapidot et al., supra). The intensity of the bands in the samples were compared to artificial human/mouse DNA mixtures (0%, 0.1%, 1%, and 10% human DNA) to quantify the human DNA (lanes to the right of lane 4 in FIG. 31). Multiple exposures of the autoradiographs were taken to ensure sensitivity down to 0.01% human DNA. A transplanted mouse was scored positive when both human myeloid and lymphoid cells and human DNA were detected in its BM.

From these experiments, the following results were obtained:

Dl-FRIL maintains but does not expand CB $CD34^+$ Progenitors in Suspension Culture As shown above, Dl-FRIL by itself preserves immature CB progenitor cells up to a month in suspension culture without medium changes (see, e.g., FIGS. 14A and 14B, and Table 3). To compare Dl-FRIL's progenitor-preserving properties to a combination of cytokines (SCF, Flt3-L, IL-6, and sIL6-R) shown to maintain CB progenitor cells in suspension culture (Sui et al., *Proc. Natl. Acad. Sci. USA* 92:2859, 1995; Ebihara et al., *Blood* 90:4363–4368, 1997), enriched CB $CD34^+$ cells were cultured with either Dl-FRIL or cytokines for 3, 6, 10, or 13 days in medium containing 10% FBS and 1% BSA in RPMI. Fresh media and Dl-FRIL and/or cytokines were added on day 6. Cells harvested at each time point were counted and assayed for clonogenic progenitor cells by plating (i.e., seeding) in semisolid media.

As shown in FIG. 27A, the total number of cells in Dl-FRIL cultures gradually declined over time from $2\times10^5$ cells initially seeded to $1.26\times10^5$ cells at day 13, in contrast to the expected 14.3-fold increase to $2.8\times10^6$ cells in cytokine cultures at day 13. Similarly, as shown in FIG. 27B, the levels of progenitor cells in Dl-FRIL cultures also remained relatively constant until day 10, after which they declined to 9% of the starting population (from $24.7\times10^3$ colonies on day 0 to $2.3\times10^3$ colonies on day 13). Progenitor levels increased in cytokine cultures by 10-fold from the outset to day 13 of culture (FIG. 27B).

Figure 28A:
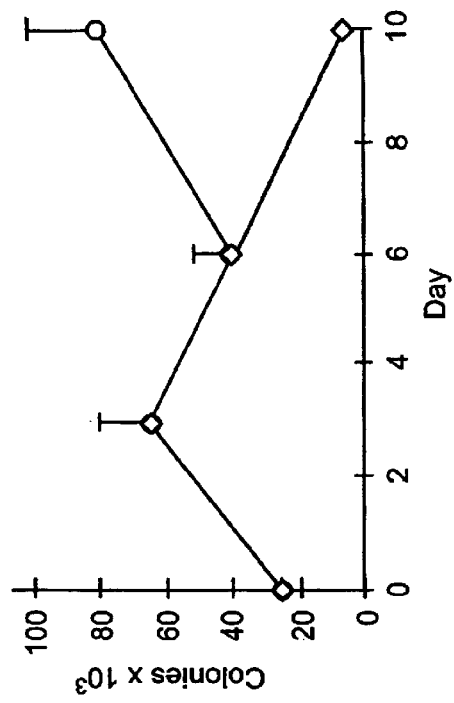
FIGS. 28A–28D are representations of line and bar graphs showing the total cell numbers and progenitor levels first in the presence of Dl-FRIL, a representative, non-limiting FRIL family member of the invention, and second in presence of cytokines.
Figure 28B:
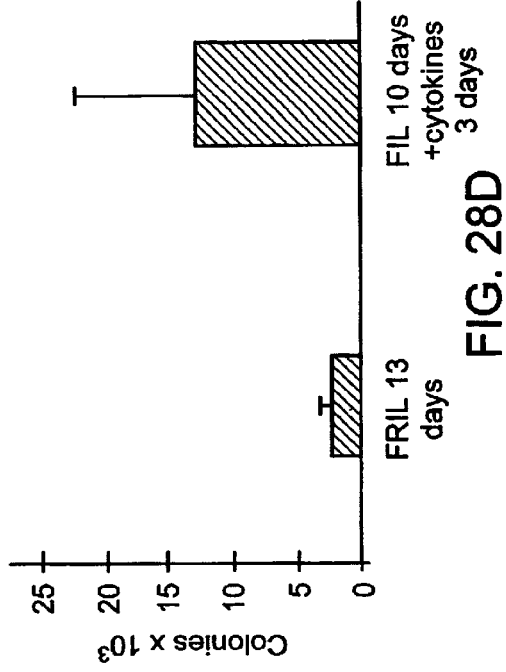

Dl-FRIL maintains the expansion capacity of $CD34^+$ Progenitors up to 2 Weeks in ex vivo Culture To characterize the expansion capacity of Dl-FRIL-preserved progenitor cells in suspension culture, $CD34^+$ cells cultured for 6 days with Dl-FRIL were washed and exposed to cytokines (without Dl-FRIL) for an additional 4 days. Total cell counts and clonogenic progenitor assays were performed and the results were compared to cells cultured for 10 days with Dl-FRIL. Fresh media and Dl-FRIL were added on day 6. Interestingly, the Dl-FRIL-cultured cells proliferated in response to cytokine stimulation, resulting in a 3.4-fold increase in cell numbers (FIG. 28A) and 13-fold increase in progenitor levels (FIG. 28B).

Further experiments tested Dl-FRIL's ability to preserve cytokine-responsive $CD34^+$ progenitor cells cultured with either Dl-FRIL for 10 days followed by 3 days of cytokine stimulation or only with Dl-FRIL for the entire 13 days. Fresh media and Dl-FRIL were added on day 6. A 2.9-fold increase in total cell numbers (FIG. 28C) and a 5.5-fold increase in progenitor levels (FIG. 28D) were observed for cells cultured with Dl-FRIL for 10 days followed by an additional 3 days of cytokine stimulation compared to cultures with Dl-FRIL alone for 13 days. These results provide evidence that Dl-FRIL alone maintains the proliferative capacity of human progenitor cells up to 13 days in suspension culture and that subsequent stimulation of cells cultured for 10 days with Dl-FRIL still respond to the proliferative signals of the cytokines.

Dl-FRIL Maintains SCID Repopulating Stem Cells (SRC) in ex vivo Cultures

At each time point during culture, the human CB $CD34^+$ cells were collected and the content of each well was assayed for progenitor levels (described above) and $2\times10^5$ of the remaining cells were transplanted into one mouse. One month later, mice were sacrificed and their bone marrows were harvested and assayed for the presence of human myeloid and lymphoid cells. Before assaying, human DNA levels in the bone marrow of individual transplanted mice was quantitated by Southern blotting analysis. A representative Southern blot analysis showing the detection of a 0%, 0.1%, 1%, and 10% human DNA per murine DNA is provided in FIG. 29E.

Figure 28C:
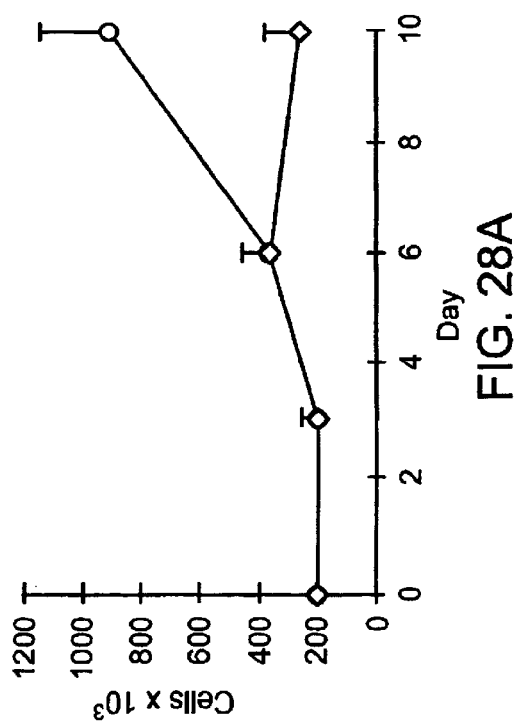
Figure 28D:
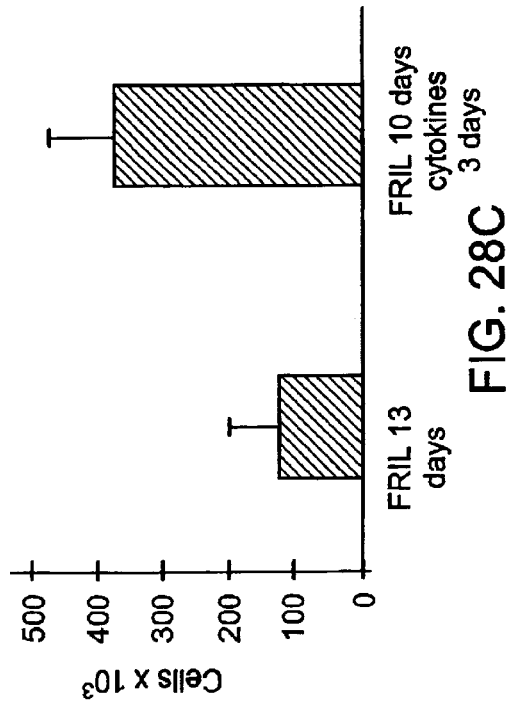

FIGS. 29A–29D show representative Southern blot analyses of the BM of mice transplanted with ex vivo cultured cells. FIG. 29A is a representative Southern blot showing human DNA in the marrow of mice transplanted with cells cultured with FRIL for 6 days (lane 1), FRIL for 10 days (lane 2), or with FRIL for 6 days followed by 4 days with cytokine stimulation (lane 3). In a typical experiment, the levels of engraftment by cells cultured with Dl-FRIL for 10 days decreased by approximately 10-fold from cells cultured with Dl-FRIL for 6 days (FIG. 29A, lanes 1 and 2). However, when cells cultured with Dl-FRIL for 6 days were subsequently stimulated with cytokines for 4 days, there was an approximate 10-fold increase in the level of engraftment (FIG. 29A, lane 3) compared to Dl-FRIL alone for 10 days (lane 2). Similar results were obtained when cells from other donors were transplanted as shown in FIG. 29B, lanes 3–4 (cells cultured with Dl-FRIL for 6 days followed by 4 days of cytokine stimulation) compared to lanes 1–2 (cells cultured with Dl-FRIL alone for 10 days) prior to transplantation. Dl-FRIL cultures could be prolonged even to 13 days, as shown in FIGS. 28C–28D, prior to transplantation into mice. A modest increase in the levels of engraftment was seen comparing the marrow of mice transplanted with the original cells, which were not cultured with Dl-FRIL, prior to seeding (FIG. 29C, lane 1) with cells cultured with Dl-FRIL for 13 days (FIG. 29C, lane 2). FIG. 28D shows the results of another experiment, where the difference between engraftment levels obtained by cells cultured with Dl-FRIL for 10 days (lane 1) or with Dl-FRIL for 6 days followed by 4 days of cytokine stimulation (lane 2) are minor. Nevertheless, a 10-fold increase was observed for cells cultured either with Dl-FRIL for 13 days (FIG. 29D, lane 3) or with Dl-FRIL for 10 days followed by 3 days of cytokine stimulation (FIG. 29D, lane 4) when compared to cells cultured for 10 days (FIG. 29D, lanes 1 and 2).

Figure 30:
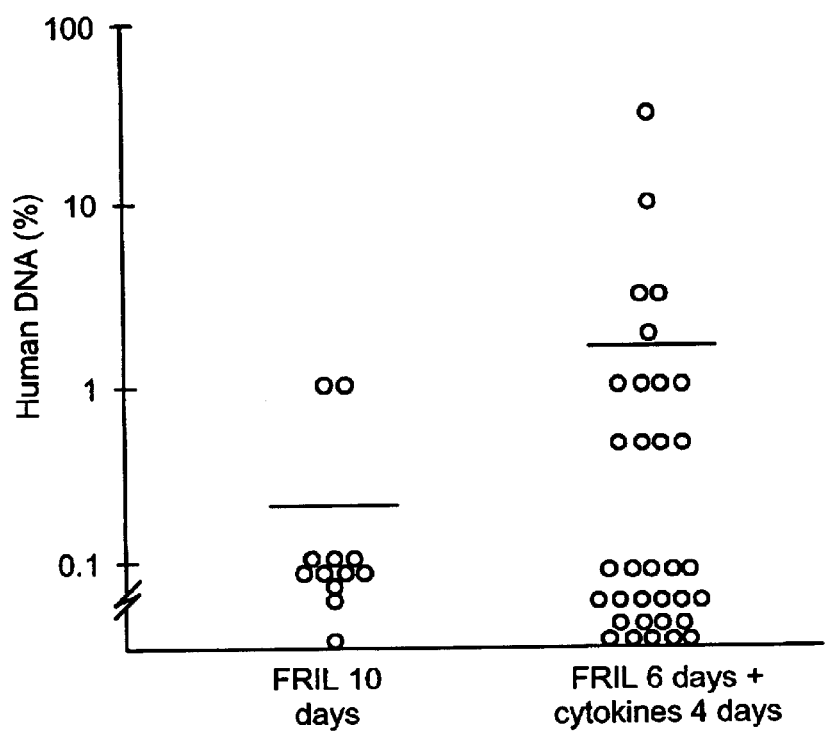
FIG. 30 is a representation of a survival chart summarizing the levels of human cell engraftment in the marrow of mice transplanted with $CD34^+$ cells cultured in either Dl-FRIL, a representative, non-limiting FRIL family member of the invention, for ten days (left panel), or in the presence of Dl-FRIL for 6 days followed by culture in the presence of cytokines for four days.

Levels of human engraftment in the marrow of mice transplanted with $CD34^+$ cells cultured with either Dl-FRIL for 10 days (n=12) or Dl-FRIL for 6 days (n=33) followed by cytokine stimulation for 4 days are summarized in FIG. 30. Cells cultured with Dl-FRIL followed by cytokines, engrafted at levels 7.4-fold greater than cells cultured with Dl-FRIL alone for 10 days (FIG. 30, p=0.05).

To test the effect of Dl-FRIL on CB populations highly enriched for primitive human SRC, $CD34^+$ cells isolated by immunomagnetic beads were further sorted by flow cytometry based on the absence of CD38 expression. $CD34^+ CD38^{-/low}$ cells (99% purity) cultured with either Dl-FRIL alone or Dl-FRIL followed by cytokines showed patterns of engraftment in NOD/SCID $B2M^{null}$ mice (Christianson et al., supra), similar to those observed for $CD34^+$ cells. These mice have been used successfully for secondary human stem cell transplantation (Peled et al., supra), have less innate immunity due to lack of NK activity and thus require fewer (10 fold) human cells for engraftment compared to NOD/SCID mice.

Figure 31:
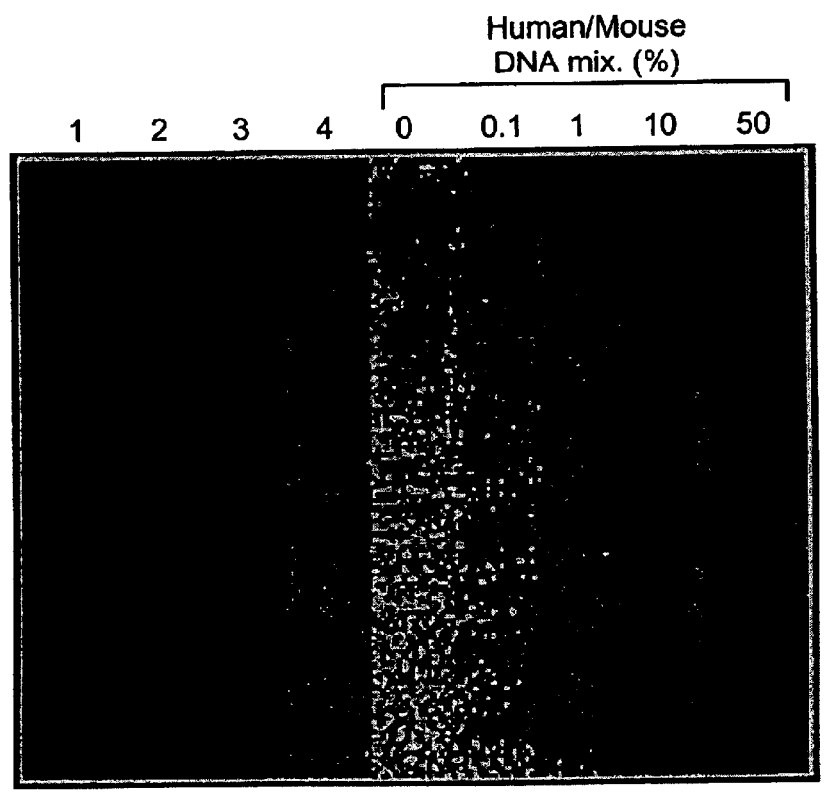
FIG. 31 is a representation of a representative Southern blotting analysis showing the levels of human cell engraftment in the BM of NOD/SCID $B2M^{null}$ transplanted with $CD34^+CD38^{-/low}$ cells cultured in the presence of Dl-FRIL, a representative, non-limiting FRIL family member of the invention. Sorted cells ($2\times10^5$ initial cells/treatment) were cultured in the presence of Dl-FRIL for 6 days followed by additional 4 days exposure to cytokines, or with Dl-FRIL alone for 10 days. After 10 days, $3.6\times10^5$ cells harvested from cytokine culture were divided and transplanted into 3 mice (lanes 1–3), while $3.5\times10^4$ cells harvested from Dl-FRIL alone culture were transplanted to one mouse (lane 4). DNA was harvested from the bone marrow of transplanted mice and subjected to Southern blotting analysis with radiolabeled human chromosome 17-specific α-satellite probe (p17H8). A representative experiment out of 4 is shown.

FIG. 31 is a representative Southern blot (1 out of 4 experiments) showing the relative level of engraftment of cells that were cultured with Dl-FRIL for 10 days (lane 4) compared to 6 days with Dl-FRIL followed by 4 days cytokine stimulation (lanes 1–3) prior to transplantation into mice. High molecular weight DNA was obtained from the BM of transplanted mice and subjected to Southern blotting analysis for the presence of human DNA.

Figure 32:
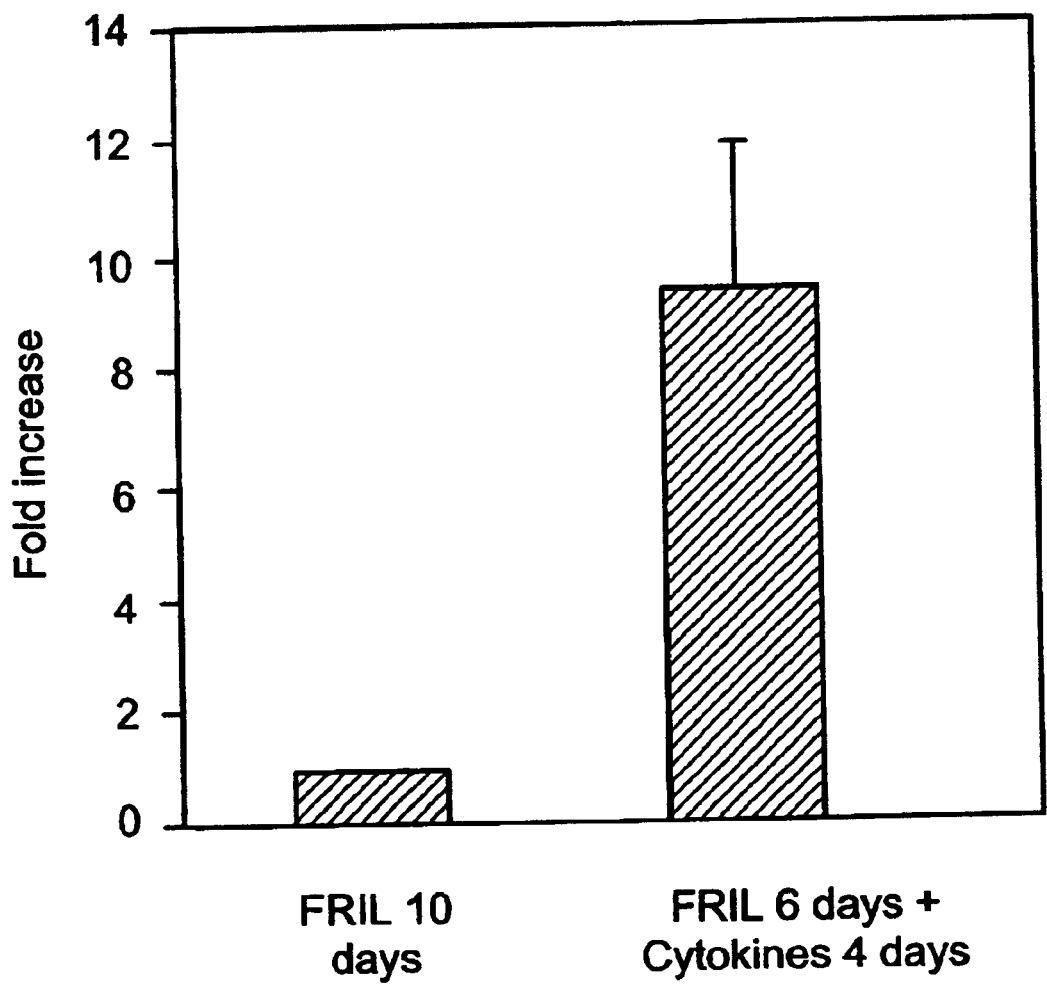
FIG. 32 is a representation of a bar graph showing the average fold increase of engraftment levels obtained with $CD34^+CD38^{-/low}$ cells that were cultured with Dl-FRIL, a representative, non-limiting FRIL family member of the invention, for 6 days and with cytokines for 4 days (right bar), as compared to 10 days with Dl-FRIL alone (left bar). Data represent mean±SE from 4 experiments.

Based on these results, an increased level of engraftment in cells exposed to cytokines after Dl-FRIL was expected. Consequently, the same initial cell dose transplanted into one mouse in lane 4 was divided into 3 mice in lanes 1–3, indicating an expansion of Dl-FRIL cultured SRC when they were subsequently exposed to cytokine stimulation. The level of engraftment in mice transplanted with cells that were treated with Dl-FRIL followed by cytokines (FIG. 31, lanes 1–3) was about 10-fold higher compared to the mouse transplanted with cells cultured with Dl-FRIL alone (FIG. 31, lane 4). Since the initial dose of cells for the Dl-FRIL+ cytokines sample was split into three mice, a 30-fold increase in the level of engraftment is observed for $CD34^+ CD38^{-/low}$ cells stimulated by cytokines after Dl-FRIL compared to the culture with Dl-FRIL alone. In addition, this result represents about a 3-fold greater level of expansion of SRC for $CD34^+CD38^{-/low}$ cells than for total $CD34^+$ cells. FIG. 32 summarizes the fold increase observed in the engraftment levels of $CD34^+CD38^{-/low}$ cells cultured with Dl-FRIL alone compared to cells subsequently stimulated with cytokines in 6 experiments (3 experiments with NOD/SCID $B2M^{null}$ mice and 3 experiments with NOD/SCID mice, gave similar results). These data indicated a 30-fold expansion of SRC for $CD34^+CD38^{-/low}$ cells and a 3-fold greater level than that of total $CD34^+$ cells in the corresponding experiments.

Further studies have demonstrated that Dl-FRIL preserves long-term repopulating stem cells. Bone marrows harvested from NOD/SCID mice that were initially transplanted with CD34+ cord blood cells cultured in Dl-FRIL were transplanted into a second set of sublethaly irradiated NOD/SCID mouse recipients. After one month, bone marrows from the second set of recipients were analyzed for the presence of human hematopoiesis, as determined using the assays described above. Multilineage engraftment was observed in the second set sublethaly irradiated NOD/SCID mouse recipients. This observed persistence of repopulating cells in this serial transplantation study indicated the presence of long-term repopulating stem cells.

Dl-FRIL Preserves SRC Potential of Multilineage Differentiation in the Murine BM Southern blot analysis detected and quantified the levels of human DNA in the marrow of transplanted mice without specifically indicating the differentiation status of human cells recovered from the murine BM. Since SCID repopulating stem cells (SRC) are defined by multilineage differentiation of myeloid and lymphoid cells in NOD/SCID mice, the in vivo differentiation processes of Dl-FRIL-cultured CB $CD34^+$ cells in the murine BM were further studied. To do this, $CD34^+$ or sorted $CD34^+CD38^{-/low}$ cells were cultured either with FRIL for 10 days or with FRIL for 6 days followed by cytokine stimulation for 4 days prior to transplantation. BM of transplanted mice was collected 1 month later and the cells were either seeded in semisolid media selective for human colonies (results shown in FIG. 33A) or were analyzed for lineage specific markers by flow cytometry (results shown in FIGS. 33B–33F).

Figure 33A:
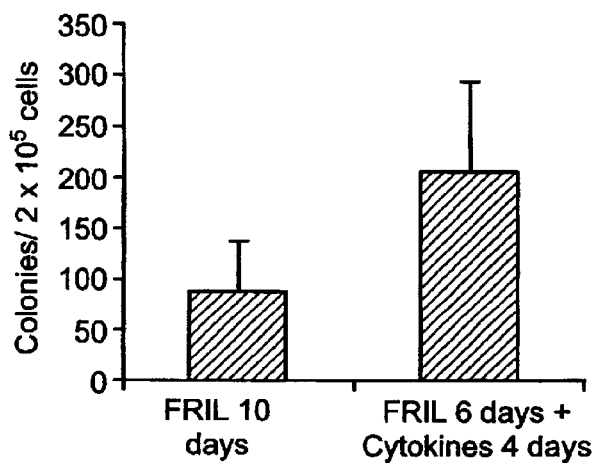
FIGS. 33A–33F are representations of a bar graph (FIG. 33A) and representative flow cytometry histograms (FIG. 33B–33F) showing the multilineage differentiation of SRC cultured with Dl-FRIL, a representative, non-limiting FRIL family member of the invention, in the BM of transplanted mice.
Figure 33B:
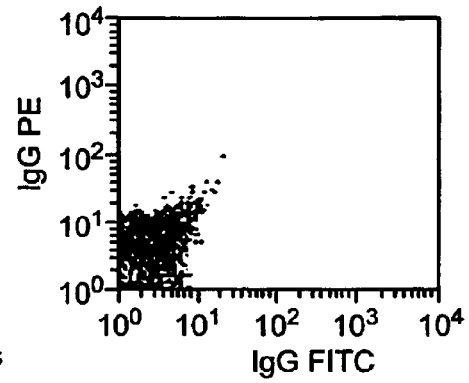
Figure 33C:
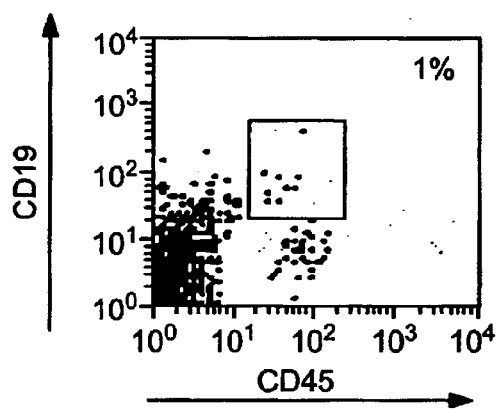
Figure 33D:
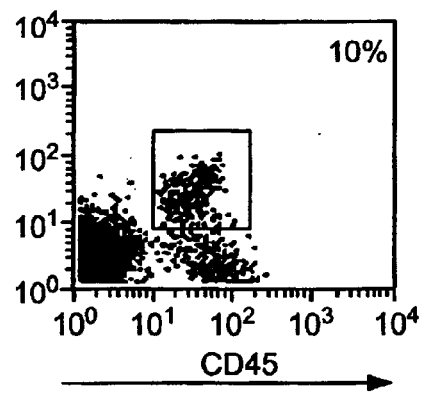

The progenitor capacity of human CB $CD34^+$ cells cultured for 10 days with Dl-FRIL and harvested one month after transplantation into NOD/SCID mice was evaluated in semi solid-colony assays that selectively promoted growth of human progenitors. FIG. 33A shows that the levels of human progenitors in the bone marrow of transplanted mice increased 2.3-fold when SRC were stimulated with cytokines for 4 days after 6 days of Dl-FRIL incubation compared to Dl-FRIL alone for 10 days prior to transplantation Moreover, both myeloid and erythroid colonies formed in the colony assays (data not shown) as well as human B cell differentiation that was determined by flow cytometry (FIGS. 33C and 33D), indicating that incubation with Dl-FRIL maintained the multilineage differentiation potential of SRC. A representative flow cytometry analysis demonstrated the presence of human $CD45^+CD19^+$ pre-B cells in the marrow of mice transplanted with either $CD34^+$ cells (FIG. 33C) or $CD34^+CD38^{-/low}$ cells (FIG. 33D) cultured with Dl-FRIL for 10 days (1% or 10% $CD19^+$ cells, respectively).

Figure 33E:
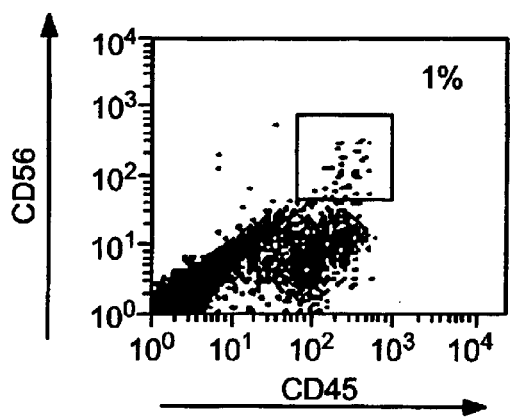
Figure 33F:
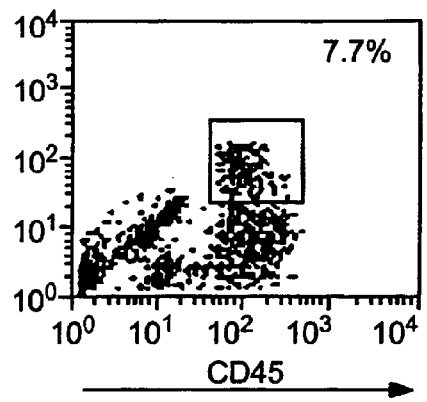

To determine whether human lymphoid precursors in the marrow of transplanted mice have the potential to differentiate in addition to myeloid cells also into lymphoid NK cells, cells from transplanted murine bone marrow were also cultured with SCF and IL-15 for 10 days. Cells harvested from cultures were analyzed for human NK cells by flow cytometry using the human-specific monoclonal antibodies to CD45 and the NK cell antigen, CD56. Cells from mice transplanted with $CD34^+$ or $CD34^+CD38^{-/low}$ cells are shown (1% or 7.7% of $CD56^+$ cells; FIGS. 33E and 33F, respectively).

Ex vivo Preservation of Early Progenitors with Dl-FRIL Compared to Flt3 Ligand

Dl-FRIL was identified by its ability to stimulate proliferation of NIH 3T3 cells transfected with Flt3 and not by untransfected cells or cells transfected with the related Fms tyrosine kinase receptor (Moore et al., *Blood* 90 supp. 1:308, 1997). Although Dl-FRIL and Flt3-L both stimulate proliferation of Flt3 3T3 cells, they exert different activities on CB progenitor cells. Flt3-L induces quiescent primitive cells into cycle (Lyman and Jacobsen, *Blood* 91:1101–11345, 1998). In contrast, Dl-FRIL by itself maintains progenitors in serum-defined medium from 15–29 days in culture without medium changes (Colucci et al., *Proc. Natl. Acad. Sci. USA* 96(2):646–650, 1999). The abilities of Dl-FRIL or Flt3-L to maintain CB CD34$^+$ progenitors in suspension cultures consisting of 10% FBS and 1% BSA in RPMI for 10 days were compared in the presence and absence of cytokines. The cells were then were seeded for CFU assay.

Figure 34A:
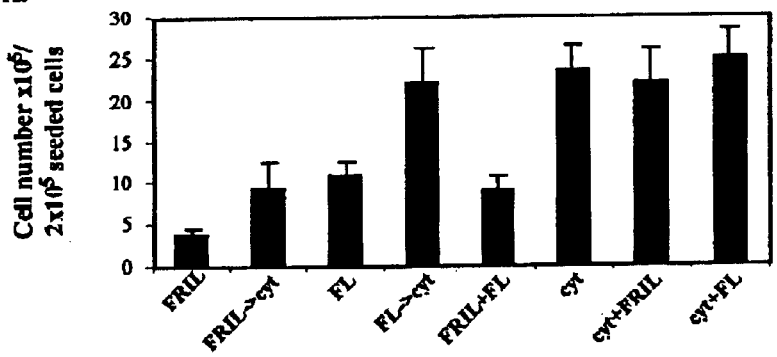
FIGS. 34A–34B are representations of bar graphs showing the growth effect of Dl-FRIL, a representative, non-limiting FRIL family member of the invention, on $CD34^+$ cells and progenitors compared to Flt3 ligand and cytokine combinations. (+) indicates co-culture of factors for the entire 10 days while (−>) indicates substitution of the first factor after 6 days with cytokines, as indicated under the x axis.

As shown in FIG. 34A, the number of total cells harvested after 10 days of suspension culture in Dl-FRIL increased minimally by 1.9-fold, whereas cells cultured in either Flt3-L alone or in combination with Dl-FRIL increased by 4.5-fold and 5.4-fold, respectively (p<0.05). Cultures containing CB CD34$^+$ cells with cytokines, either alone or with Dl-FRIL and Flt3-L, led to 10.9–12.5 fold increase in cell numbers; however cells cultured with Dl-FRIL alone followed by cytokines, increased only by 4.6-fold (FIG. 34A, p<0.05).

Figure 34B:
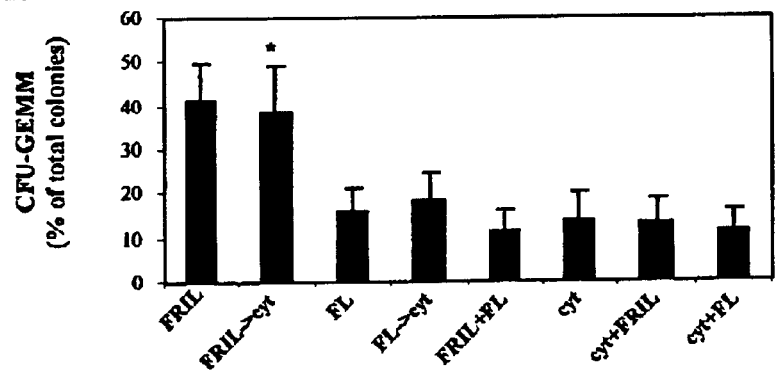

Interestingly, cells cultured with Dl-FRIL alone or followed by cytokines, selectively maintained a higher number and proportion of the primitive granulocyte-erythroid-macrophage-megakaryocyte colony forming-units (CFU-GEMM) compared to other treatments (FIG. 34B, p<0.05). About 40% of the progenitor cells maintained by Dl-FRIL were CFU-GEMM, a relative 2.6- to 3.7-fold increase with Dl-FRIL cultures compared to other combinations (FIG. 34B, p<0.05). In contrast to Flt3-L, exposure of cells first cultured with Dl-FRIL to cytokines, maintained the high percentage of CFU-GEMM, 18.2% versus 38.6%, respectively (FIG. 34B p<0.05). These results demonstrate that Dl-FRIL and Flt3-L may act differently on primitive progenitor cells in culture.

Figure 35A:
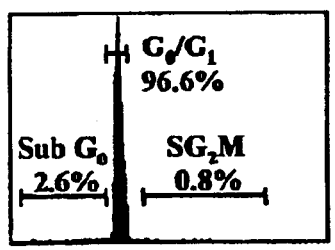
FIGS. 35A–35G are representatives of flow cytometry histograms showing the cell cycle analyses of $CD34^+$ cells cultured with Dl-FRIL, a representative, non-limiting FRIL family member of the invention, or various cytokines, or with combinations thereof. DNA content was determined by flow cytometry with propidium iodide staining. Enriched $CD34^+$ cells were cultured for 3 days with no treatment (FIG. 35A), Dl-FRIL (FIG. 35B), Flt3-L (FIG. 35C), Dl-FRIL+Flt3-L (FIG. 35D), SCF+G-CSF+IL-3+IL-6 (SG36) (FIG. 35E), SG36+Dl-FRIL (FIG. 35F), and SG36+Flt3-L (FIG. 35G).
Figure 35B:
Figure 35C:
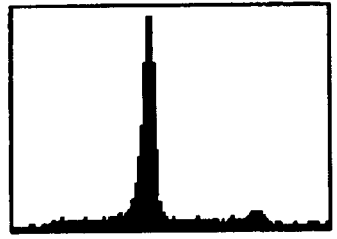
Figure 35D:
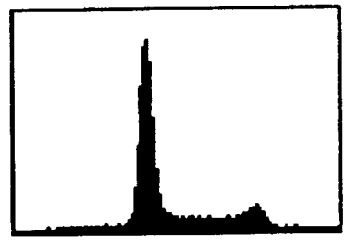
Figure 35E:
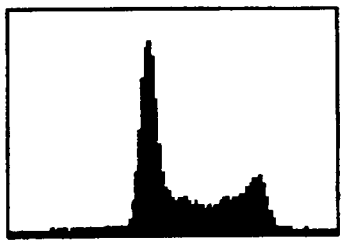
Figure 35F:
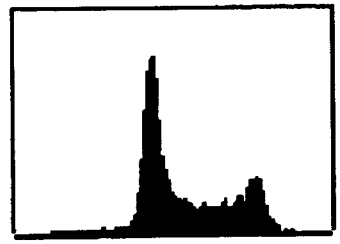
Figure 35G:
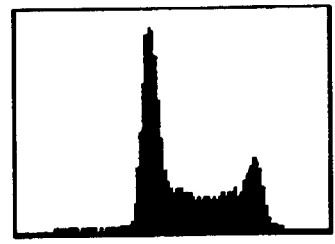

Dl-FRIL Maintains Higher Levels of CD34$^+$ Cells in $G_0/G_1$ Phase of Cell Cycle Compared to Cytokine Treated Cells In vivo, immature CD34$^+$ cells are predominantly quiescent, non-cycling cells (Young et al., *Blood* 87:545, 1996; Movassagh et al., *Stem Cells* 15:214–222, 1997; Ladd et al., *Blood* 90:658–668, 1997). Since Dl-FRIL maintains relatively constant levels of progenitor cells over two weeks in suspension culture that can subsequently respond to cytokine stimulation (see FIG. 27), the cell cycle status of CD34$^+$ cells incubated with Dl-FRIL was investigated and compared to cultures with cytokine stimulation. DNA content of CB CD34$^+$ cells was analyzed by flow cytometry immediately after isolation of cells. A mean value of 96.6% of cells were observed in the $G_0/G_1$ phase of cell cycle (FIG. 35A).

The cell cycle status of CB CD34$^+$ cells was analyzed in 5 indepent experiments with cells cultured for 3–13 days with either Dl-FRIL or a cytokine combination (SCF, Flt3-L, G-CSF, IL-3, IL-6) (Bhatia et al., *J. Exp. Med.* 186:619–624, 1997; Conneally et al., *Proc. Natl. Acad. Sci. USA* 94:9836–9841, 1997). The percentage of cycling cells in $SG_2M$ phase in both cultures decreased by half from day 3 to day 13, from 17.7% to 9.1% for Dl-FRIL and from 50.9% to 23.2% for cytokines (Table 1) (3.4% of cells initially seeded were in $SG_2M$).

TABLE 5

Percentage and numbers of cycling CD34$^+$ cells (in $SG_2M$ phase) cultured with Dl-FRIL or cytokines for 3, 6, 10 or 13 days

| Days in culture | Dl-FRIL (%) | Cytokines (%) | Dl-FRIL (cells × 10$^3$) | Cytokines (cells × 10$^3$) | Fold increase induced by cytokines |
|---|---|---|---|---|---|
| day 3 | 17.7 ± 1.9 | 50.8 ± 1.4 | 35 | 212 | 6 |
| day 6 | 20 ± 2 | 26 | 43.6 | 389.5 | 9 |
| day 10 | 10 ± 1.9 | 29.7 ± 1 | 26.4 | 553 | 21 |
| day 13 | 9.1 ± 4.1 | 23.14 | 11.4 | 664.6 | 60 |

CD34$^+$ cells were cultured (2 × 10$^5$ cells/0.5 ml) with Dl-FRIL or SCF + Flt3 ligand + IL-3 + G-CSF + IL-6. Cell cycle analysis was performed with propidium iodide staining. Cell numbers were calculated by multiplying percent of cycling cells by total cell numbers. Data represents mean ± SE values, from 5 experiments.

More dramatically, the number of cells in $SG_2M$ phase during culture differed from the 6.8×10$^3$ cells in $SG_2M$ phase initially seeded. The average number of cycling cells in Dl-FRIL cultures remained relatively constant from 35×10$^3$ cells at day 3 and 43.6×10$^3$ cells at day 6 to a reduced level of 26.4×10$^3$ cells at day 10 and 11.4×10$^3$ cells at day 13. This pattern of cells in cycle explains the low levels of total cell numbers and progenitor cells (see FIG. 27). In contrast, the expected number of cycling cells in cytokine cultures increased dramatically. The average number of cells in $SG_2M$ phase in cytokine cultures increased by 31-fold to 212×10$^3$ cells at day 3, by 57-fold to 389.5×10$^3$ cells at day 6, by 81-fold to 553×10$^3$ cells at day 10, and by 97.7-fold to 664.6×10$^3$ cycling cells at day 13, compared to 6.8×10$^3$ cells in $SG_2M$ seeded in culture (Table 1). Taken together, these results support the notion that Dl-FRIL preserves more immature progenitor cells in a quiescent state up to 2 weeks in culture compared to cytokine treated cultures.

To test whether Dl-FRIL acts in a dominant manner to prevent cytokines from inducing the quiescent progenitor population into $SG_2M$ phase, the cell cycle status of cells cultured with either Dl-FRIL or Flt3-L, in the presence and absence of cytokines was analyzed, after 3 days of suspension culture as indicated in FIGS. 35A–35G and Table 6. FIGS. 35A–35G show representative cell cycle histograms of CD34$^+$ cells cultured with no addition (FIG. 35A), Dl-FRIL alone (FIG. 35B) or various cytokines or combinations thereof (FIGS. 35C–35G) for 3 days, and the mean percentage of cells in each cell cycle phase is summarized in Table 6.

TABLE 6

Cell cycle status of CD34 + cells, ex vivo cultured for 3 days

| Culture conditions | Sub $G_0/G_1$ | $G_0/G_1$ | $SG_2M$ |
|---|---|---|---|
| Dl-FRIL | 9.4 ± 2.8 | 72.9 ± 2.8 | 17.7 ± 1.9 |
| Flt3-L | 9.4 ± 3.3 | 68.4 ± 2.1* | 22.2 ± 5.4* |
| Dl-FRIL + Flt3-L | 8.6 ± 3.9 | 67.1 ± 1.8* | 24.3 ± 5.65* |
| Cytokines | 2.6 ± 1.7 | 46.5 ± 4.5* | 50.9 ± 1.4* |
| Cytokines + Dl-FRIL | 2.5 ± 0.6 | 47.5 ± 2.2* | 50.0 ± 2.7* |
| Cytokines + Flt3-L | 2.1 ± 0.5 | 47.7 ± 2.4* | 50.2 ± 2.9* |

Data shown is mean percentage ± SE, from 4 independent experiments.
p values = (vs. Dl-FRIL):
*p < 0.05.

As was also shown in Table 5, Dl-FRIL maintains a significantly higher percentage of quiescent cells and lower percentage of cycling cells (FIG. 35B and Table 6) compared to stimulation with cytokines (FIGS. 35C–35G and Table 6).

Cultures with Flt3-L alone led to a modest, although significant, decrease percentage of cells in $G_0/G_1$, ($p<0.05$) and to a corresponding increase in $SG_2M$ phase, compared to cells cultured with Dl-FRIL alone (Table 6). Cultures containing Dl-FRIL and Flt3-L together slightly increased the percentage of cells in $SG_2M$ phase, from 17.7% (with Dl-FRIL alone) to 24.3% ($p<0.05$, Table 6). As shown in Table 5, exposure of CB CD34$^+$ cells to cytokines for 3 days induced a substantially greater proportion of cells into $SG_2M$ phase compared to culture with Dl-FRIL alone ($p<0.05$). The percentage of cells undergoing apoptosis, as determined by sub$G_0/G_1$ population, when cultured in Dl-FRIL was slightly higher than under cytokine conditions. Neither Dl-FRIL nor Flt3-L, under these culture conditions, effected cytokine induction into $SG_2M$ phase of the mostly quiescent CD34$^+$ cell population (Table 6).

EXAMPLE 7

Dl-FRIL Preserves CB Progenitors in a Dormant State in the Presence of Potent Stimulators Dl-FRIL was purified from *Dolichos lab lab* as described above in Example 1. Dl-FRIL was assayed over a 5-log dose range (10 ng/mL-1,000 ng/mL) on human CB MNC cultured in serum-defined medium containing agar-leukocyte conditioned medium, a potent source of a broad range of stimulators. The number of viable MNC and progenitors were evaluated after 5 days in culture. Results from 1 of 3 representative experiments are shown in Table 7 below. The number of viable MNC at the end of culture was reduced by 1.7- to 5-fold in cultures containing 10-1,000 ng/ml of Dl-FRIL. The frequencies of myeloid and erythroid progenitors in these cultures increased from 1.4- to 2.4-fold over the same dose range.

TABLE 7

| Dl-FRIL | MNC | Progenitor frequency (Colonies/10$^{-5}$ MNC) | |
| --- | --- | --- | --- |
| (ng/ml) | (×10$^{-4}$) | Myeloid | Erythroid |
| 1,000 | 20 | 90 +/− 85 | 150 +/− 42 |
| 100 | 55 | 44 +/− 15 | 85 +/− 12 |
| 10 | 70 | 77 +/− 12 | 103 +/− 6 |
| 1 | 120 | 16 +/− 2 | 38 +/− 7 |
| 0.1 | 115 | 21 +/− 7 | 50 +/− 7 |
| 0 | 120 | 38 +/− 7 | 63 +/− 32 |

Culture of CB MNC in Dl-FRIL results in fewer MNC and a greater frequency of progenitors. 4 × 10$^6$ CB MNC were cultured in 2 mL of AIMV (Life Technologies) containing Agar-SCM (StemCell Technologies) and varying concentrations of Dl-FRIL. Cultures were harvested after 5 days and the number of viable MNC and progenitors were assessed. The colony data shown were normalized as the frequency of progenitors per 10$^5$ MNC.

A reduction in cell number and a corresponding increase in the frequency of progenitors in cultures containing Dl-FRIL in the presence of potent stimulators are consistent with our hypothesis that Dl-FRIL can prevent cytokine-induced proliferation and differentiation of progenitors. Table 8 below shows the relative decrease of MNC in Dl-FRIL-containing cultures compared to controls and the relative increase in progenitor frequency of progenitors. The total number of progenitors was reduced as expected (progenitors are at varying stages of differentiation - no direct correlation between progenitor number and MNC would be expected).

TABLE 8

| Dl-FRIL | Fold DECREASE | Fold INCREASE Progenitor frequency | |
| --- | --- | --- | --- |
| (ng/ml) | MNC | Myeloid | Erythroid |
| 1,000 | 5.0 | 2.4 | 2.4 |
| 100 | 2.0 | 1.2 | 1.4 |
| 10 | 1.7 | 2.1 | 1.6 |
| 1 | 1.0 | 0.4 | 0.6 |
| 0.1 | 1.0 | 0.6 | 0.8 |
| 0 | 1.0 | 1.0 | 1.0 |

Reduction in MNC correlates with the relative increase in frequency of progenitors. The relative reduction in MNC of Dl-FRIL cultures is consistent with increased progenitor frequency in corresponding samples.

EXAMPLE 8

Dl-FRIL Protects CB MNC from the Toxicity of Chemotherapy Drugs

Figure 36B:
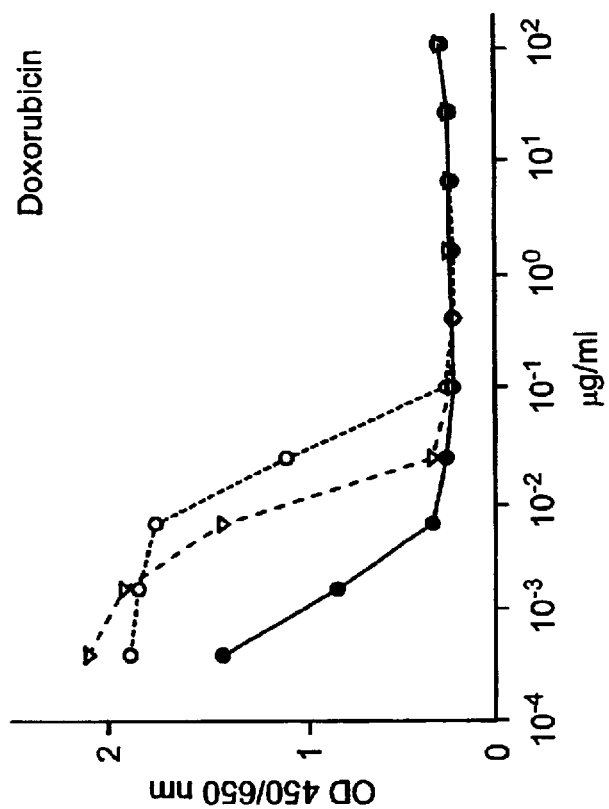
FIGS. 36A–36C are representations of line graphs showing the dose response of CB mnc chemotherapeutic agents in the presence and absence of Dl-FRIL, a representative, non-limiting FRIL family member of the invention. Chemotherapy agents were assayed over a 5-log dose range on CB MNC ($2\times10^5$ cells/0.1 mL) in AIMV (Life Technologies) containing Agar-SCM (StemCell Technologies). Viable cells were determined after 5 days of culture by XTT. Solid squares indicate chemotherapy drug with no Dl-FRIL; solid triangles indicate cultures containing Dl-FRIL at 10 ng/ml in all wells; and open circles indicate Dl-FRIL in all wells at 100 ng/ml.
Figure 36A:
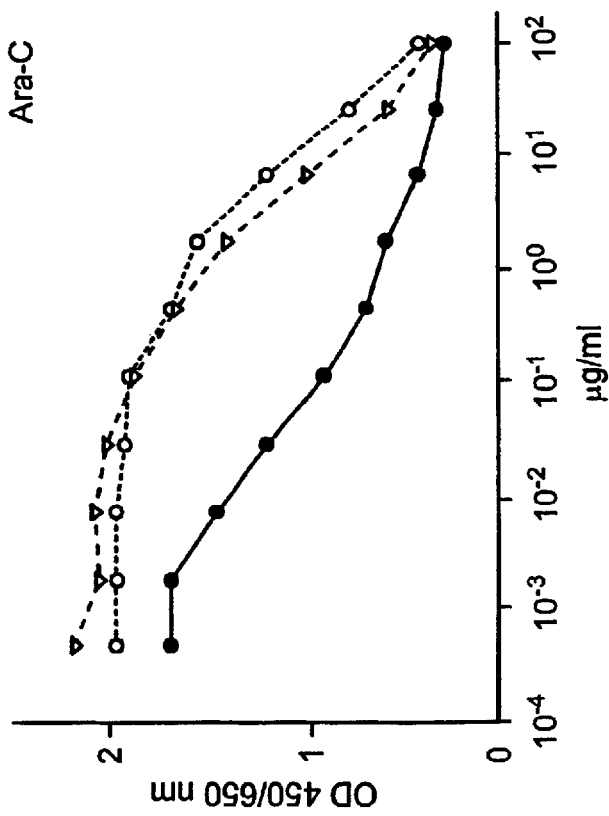
Figure 36C:
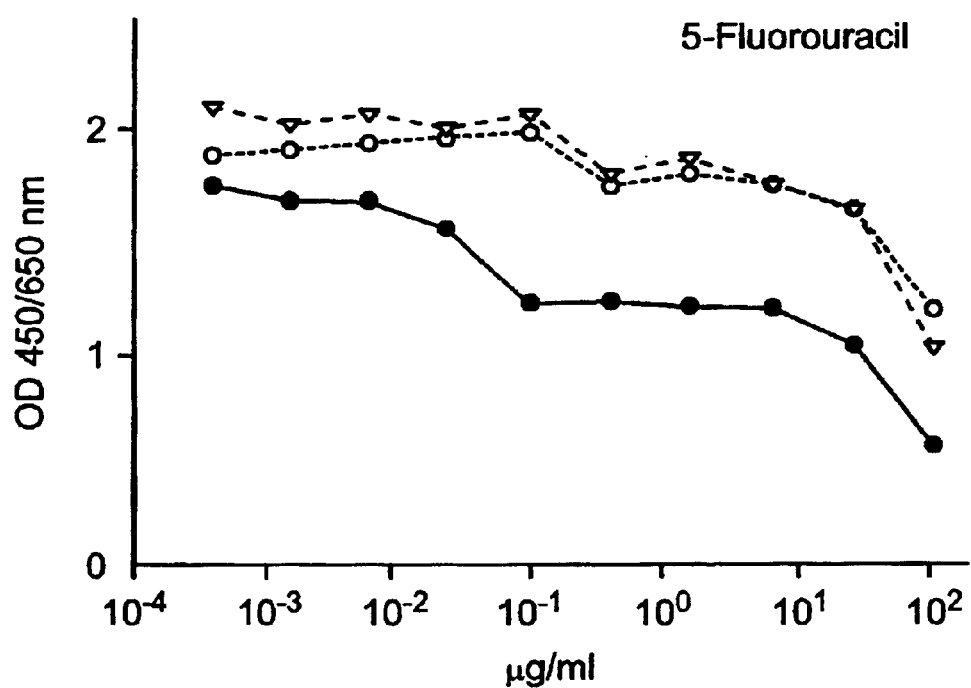

Experiments showing that Dl-FRIL can prevent proliferation and differentiation of CB progenitors in cultures containing potent stimulators indicated that Dl-FRIL protects progenitors from the toxicity of cell cycle-active chemotherapy drugs. The culture system described above was adapted to a 96 well plate format and the widely used chemotherapeutics, cytarabine (Ara-C) (FIG. 36A), doxorubicin (Dox) (FIG. 36B), and 5-fluorouracil (5-FU) (FIG. 36C) over a 5-log dose range were assayed on CB MNC cultured in the presence and absence of Dl-FRIL (see FIGS. 36A–36C). Dl-FRIL was purified from *Dolichos lab lab* as described above in Example 1. Cultures containing Dl-FRIL (either at 10 ng/ml or 100 ng/ml) resulted in a 2–3 log dose shift of CB MNC to Ara-C (FIG. 36A and Dox (FIG. 36B). As shown in FIG. 36C, the presence of Dl-FRIL in 5-FU cultures increased viability over a large dose range. Differences between the dose shift of Ara-C and Dox by Dl-FRIL compared to 5-FU may be explained by recent reports demonstrating that 5-FU acts via an RNA mechanism rather than as a DNA-specific drug (Bunz et al., *J. Clin. Invest.* 104:263–269, 1999).

EXAMPLE 9

Mice Tolerate High Levels of Dl-FRIL

The in vivo toxicity of Dl-FRIL was determined in mice. Initially, Dl-FRIL was administered intravenously to mice over a 3-log dose range of 0.006–1 mg/kg (0.32–20 µg/mouse). Dl-FRIL was well tolerated and these mice have subsequently received 2 monthly challenges of Dl-FRIL without any observable short- or long-term adverse effects.

Protocols to test chemoprotective properties of cytokines in mice typically involve daily pre-treatment (bolus or continuous delivery) regimens of 4–10 days before starting chemotherapy. Using this framework as a starting point, Dl-FRIL was injected at 5 mg/kg (100 µg/mouse) intravenously daily for 4 days. No gross adverse effects have been observed in over 150 mice treated with this dose regimen. Dl-FRIL was purified from *Dolichos lab lab* as described above in Example 1.

The upper limits of Dl-FRIL toxicity were next explored by injecting a single bolus intraperitoneal injection of Dl-FRIL (to accommodate 1 mL volume) at 500 mg/kg and monitored the survival of mice for 48 hours. Of the four BALB/c mice receiving this treatment (2 males and 2 females, aged 5 months), only 1 mouse (a male) survived 48 hours. The surviving mouse's weight decreased by approximately 15% in the first 2 days and returned to normal by day 4. The surviving mouse's blood counts were in the normal range 3 days after injection of FRIL. The results demonstrate that even a very large dose of Dl-FRIL is not completely toxic.

Additional dose range finding studies are performed to determine toxicity in mice receiving high doses of Dl-FRIL administered by various routes (intravenous, intraperitoneal, subcutaneous, and oral).

EXAMPLE 10

In vivo Modulation of Progenitors by Dl-FRIL in Mice

Using the initial planned dose regimen of Dl-FRIL (5 mg/kg×4 days) for testing chemoprotection, hematopoietic parameters were examined in mice 3, 5, and 7 days after completing Dl-FRIL treatment. Dl-FRIL was purified from *Dolichos lab lab* as described above in Example 1. Weight-matched BALB/c mice (females, aged 8 weeks) were injected intravenously with either 0.2 ml of Dl-FRIL (500 mg/ml) or 0.2 ml of HBSS daily for 4 days. Two mice from each group were evaluated at 3 days, 5 days, and 7 days after completing Dl-FRIL treatment. Blood was collected in heparinized tubes by eye bleeds prior to sacrificing mice by $CO_2$. Two femurs and a spleen were harvested from each mouse and the samples were processed within 1 hour. Progenitors wee accessed using standard hematopoietic colony assays (StemCell Technologies). The results from this study are shown below in Table 9.

TABLE 9

Hematopoietic parameters 3, 5, and 7 days after Dl-FRIL treatment (5 mg/kg × 4 days)

| | Cellularities | | | |
|---|---|---|---|---|
| Days | RBC | WBC | BM | Spleen |
| 3 | 0.58 | 0.34 | 0.59 | 1.01 |
| 5 | 1.26 | 0.98 | 0.75 | 0.72 |
| 7 | 0.95 | 0.82 | 0.91 | 1.12 |

| | CFU-C | | CFU-E | | BFU-E + Mix | |
|---|---|---|---|---|---|---|
| Days | Freq. | Total | Freq | Total | Freq | Total |
| Bone marrow progenitors | | | | | | |
| 3 | 1.85 | 1.10 | 1.63 | 1.01 | 1.61 | 1.01 |
| 5 | 1.17 | 0.87 | 0.86 | 0.63 | 1.03 | 0.80 |
| 7 | 1.81 | 1.69 | 0.61 | 0.57 | 2.59 | 2.47 |
| Spleen progenitors | | | | | | |
| 3 | — | — | 2.83 | 3.35 | — | — |
| 5 | 2.41 | 1.68 | 0.95 | 0.63 | 2.12 | 1.42 |
| 7 | — | — | 1.74 | 1.78 | — | — |

Dl-FRIL data are reported as relative to control values.

As shown in Table 9, the peripheral blood counts (red blood cell (RBC) and white blood cell (WBC)) of Dl-FRIL-treated mice were found to be reduced by 1.7- and 2.9-fold, respectively, at 3 days, and returned to normal by day 5. Bone marrow (BM) cellularity was also reduced by 2.5-fold at day 3, and returned to normal after 7 days. The spleen cellularity was lower at day 5 but normal at day 3 and day 7.

As shown in Table 9, the frequency of progenitors was slightly increased in bone marrow, by 1.6- to 1.85-fold at day 3, but the total number of progenitors in the bone marrow remained unchanged. In the spleen, a compensatory organ during hematopoiesis stress, a 2.83-fold higher frequency and 3.35-fold higher number of erythroid progenitors were observed in the spleen at day 3 (see Table 9). The frequencies and total number of progenitors in the bone marrow appeared normal at day 5 but fewer mature erythroid progenitors (CFU-E) and more primitive progenitors (BFU-E/mix) were observed at day 7. A similar reduction in CFU-E was observed in spleens at day 5; otherwise, the frequencies and total numbers of progenitors increased from days 3–7.

EXAMPLE 11

Dl-FRIL Protects Mice from 5-FU Induced Death in the Critical First Week

A dose regimen was established to determine whether FRIL protects mice from death resulting from hematopoietic toxicity of Ara-C and Dox. This murine 5-FU chemoprotection model is based on studies showing that a single dose of 5-FU (150 mg/kg) resulted in >90% reduction of bone marrow cellularity but had limited cytotoxic effect on stem cells (Lerner and Harrison, *Exp. Hematol.* 18:114–118, 1990). This finding was consistent with the understanding that stem cells reside in the bone marrow in predominantly a quiescent state. Bone marrow cellularity in these mice was restored after 2 weeks by the recruitment of the dormant progenitors and responsive stem cells that escaped toxicity of 5-FU. Administration of a second dose of 5-FU (also at 150 mg/kg) 3-7 days after the initial dose killed those stem cells and progenitors recruited into S-phase in response to the first treatment of 5-FU (Lerner and Harrison, supra).

de Haan et al. (*Blood* 87:4581–4588., 1996) applied this model to test whether prophylactic treatment of mice with hematopoietic regulators, pegylated SCF+IL11, could expand the stem cell and primitive progenitor compartments and better protect mice from death by 5-FU induced hematopoietic toxicity. These experiments demonstrated that although SCF+IL11 pretreatment could accelerate hematopoietic recovery after it was underway by 4 days - 5 days when compared to controls (from approximately 11 days to 7 days for 40% survival, the SCF+IL11 cytokine pretreatment strategy did not rescue mice from death when the second dose of 5-FU was administered in the critical first week when stem cells are ablated (de Haan et al. (supra).

In this study described below, the pretreatment dose regimen for Dl-FRIL described above (5 mg/kg×4 days) was selected based on the requirement of treating animals with cytokines for several days prior to starting chemotherapy and because Dl-FRIL-treated mice easily tolerated doses (5 mg/kg) that were 10- to 100-fold greater than that used for cytokines. Since FRIL and cytokines act on progenitors in the same concentration range (ng/ml), this pretreatment dose regimen was used to test whether Dl-FRIL can protect mice from 5-FU administered at 2 intervals in the first week: 5-FU (150 mg/kg) was injected at day 0 and then a second dose (also at 150 mg/kg) was injected either on day 3 (d0/3 dose interval) or day 5 (d0/5 dose interval). No survival on the day 3 interval was observed by de Haan et al. (supra) at day 3.

Dl-FRIL was purified from *Dolichos lab lab* as described above in Example 1.

Weight-matched BALB/c mice (10 mice/group) were injected intravenously with either with 0.2 mL of Dl-FRIL (500 mg/mL) or 0.2 mL of HBSS daily for 4 days. Two hours after the final treatment of Dl-FRIL, mice were injected intraperitoneally with 5-FU (150 mg/kg). Groups of mice received a second dose of 5-FU (150 mg/kg) at either day 3 or day 5. No mice died from a single dose of 5-FU.

As shown in Table 10, Dl-FRIL pretreatment improved survival of mice in two separate experiments.

TABLE 10

| | | 5-FU Dose Interval | | | |
| | | D0/3 | | D0/5 | |
| Exp. | Mice | FRIL | HBSS | FRIL | HBSS |
| --- | --- | --- | --- | --- | --- |
| 1 | Males, 16 wk | 3/10 | 0/10 | N.T. | N.T. |
| 2 | Females, 8 wk | 0/10 | 0/10 | 4/10 | 1/10 |

Improved survival of mice pretreated with FRIL (5 mg/kg × 4 days) prior to undergoing 5-FU dose intervals of d0/3 and d0/5.

In the first experiment, 3 of 10 mice survived a d0/3 dose interval of 5-FU compared to no mice in the HBSS pretreatment control. In the second experiment, 4 of 10 mice pretreated with Dl-FRIL survived a d0/5 dose interval of 5-FU compared to 1 of 10 for HBSS pretreated mice.

EXAMPLE 12

Optimization of the Dose Regiment of a FRIL Family Member to Protect Mice from 5-FU Induced Death FRIL family members are relatively abundant in legumes. For example, Dl-FRIL accounts for approximately 0.02% of the mass of hyacinth beans.

Figure 37:
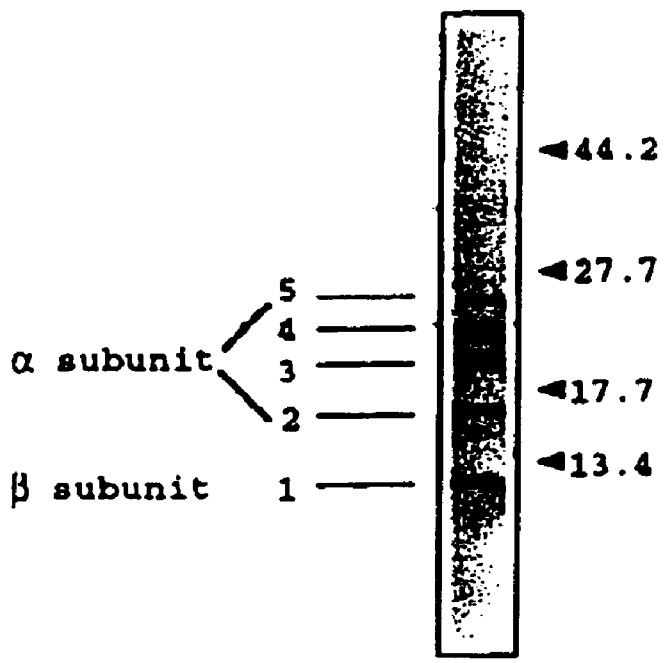
FIG. 37 is a representation of a photograph of purified Dl-FRIL, a representative, non-limiting FRIL family member of the invention, resolved by SDS-PAGE analysis. Five discrete bands appeared which corresponded to the α and β subunits, each of which was subjected to amino-terminal sequencing. The amino acid sequences of the five bands are as indicated.

Dl-FRIL is purified by carbohydrate affinity chromatography as described in Example 1, and is evaluated for purity by SDS-PAGE (5 discrete bands are visualized on an overloaded gel; see FIG. 37); is analyzed for mass and composition by amino acid analysis; and is assayed in the cord blood progenitor assay described above.

The murine 5-FU chemoprotection model (Lerner and Harrison, supra; de Haan, supra) is used to empirically derive the optimal dose regimen of Dl-FRIL to protect mice from death. Dl-FRIL is administered intravenously to mice over a 3-log dose range (5–5,000 mg/kg) under various regimens that include Dl-FRIL treatment prior to chemotherapy (daily from 3 days to 2 hour before initiation of chemotherapy) and during chemotherapy.

The mice used in these studies are BALB/c female mice, 8–10 weeks at outset of experiments (Jackson Laboratory, Bar Harbor, Me.), weight matched each for experiment, where there are 10 mice per group. Organs from mice receiving a dose of 5,000 mg/kg of FRIL (with no 5-FU treatment) are collected for toxicity studies The five doses of Dl-FRIL are 0, 5, 50, 500, and 5,000 μg/kg. The four dose regimens of Dl-FRIL will be -2 hour; -1 day and -2 hour; -2 day, -1 day, and -2 hour; -3 day, -2 day, -1 day, and -2 hour prior to 5-FLU treatment. The two maintenance regimens are either daily×7 day (-2 hour to day 7) or every other day (days 0, 2, 4, 6). Thus, one group of mice will receive a dose of Dl-FRIL daily for 7 days; while the second group will receive a dose of Dl-FRIL every other day for 7 days.

The 5-FU dose intervals of 150 mg/kg are at dose intervals of d0/3, d0/5, and d0/7.

EXAMPLE 13

A FRIL Family Member has Chemoprotective Properties with Widely used Cell Cycle-active Chemotherapeutics After establishing the optimal dose regimen of a FRIL family member, the FRIL family member's ability to protect mice from death by cytarabine (Ara-C) and doxorubicin.

Initial dose regimens of cytarabine (Ara-C) and doxorubicin are as follows: Doxorubicin - 14 mg/kg as single bolus i.p. injection (Grzegorzewski et al., *J. Exp. Med.* 180:1047–1057, 1994); Ara-C-300 mg/kg at time as an i.p. injection at 0 and 12 hours (Paukovits et al., *Blood* 77:1313–1319, 1991). Further studies are based on targeted clinical indication.

EXAMPLE 14

Characterization of the Hematopoietic Status of Mice during Optimal Dose Regimen of a FRIL Family Member to Protect Mice from 5-FU Induced Death Peripheral blood counts and the status of hematopoietic progenitors (frequency, total number, and cycling status) are characterized in mice during and after receiving the optimal dose regimen of a FRIL family member.

To do this, mice injected with a dose regimen of a FRIL family member with no 5-FU treatment are evaluated daily during and for one week after treatment with the FRIL family member. The mice are evaluated for the following hematopoietic parameters: WBC and RBC counts; bone marrow and spleen cellularities; and progenitor status, which includes hematopoietic colony assays (StemCell Technologies). The progenitors assayed are myeloid (CFU-C), erythroid (CFU-E), and primitive, multipotential (BFU-E/Mix). The frequencies and total numbers are determined, as well as the cycling status of these cells, as measured by $^3$H-thymidine suicide assay (Moore et al., *Exp. Hematol.* 14:222–229, 1986).

EXAMPLE 15

Analysis of Pharmacology and Toxicology of FRIL in Mice

The clearance of a FRIL family member from the circulation and its accumulation in the body is determined by preliminary pharmacokinetics.

For these studies, $^{125}$I-FRIL is injected into mice (dosage of FRIL based on optimization results). Clearance of FRIL from the blood is evaluated at the following timepoints after injection: 5 min., 15 min., 30 min., 1 hour, 2 hours, 4 hours, 8 hours, 12 hours, 36 hours, 48 hours. Two mice are evaluated at each timepoint. Following this study, the animals are sacrificed and the organs collected and evaluated.

Dose-range finding experiments determine the maximal tolerated dose of a FRIL family member by various routes of administration (intravenous, intraperitoneal, subcutaneous, and oral). To do this dose range finding study, four routes at four doses are used. The routes of administration are intravenous, intraperitoneal, subcutaneous, oral. The highest dose of a FRIL family member is 1 g/kg. The dosage of the FRIL family member is reduced by 2-fold until mice survive. Survival is measured at 48 hours after treatment. Other clinical observations are made, including behavorial, lethargy, vocalization, diarrhea. CBC analyses are made. The animals are evaluated for any necropsy (i.e., gross lesions). Following this study, the animals are sacrificed and the organs collected and evaluated.

Acute dose toxicity studies allow identify target organs that may develop lesions after exposure to a FRIL family member. For these acute dose toxicity studies, a dose is selected, and a FRIL family member is injected daily for 7 days. Acute toxicity is evaluated at 7 days, and recovery from acute toxicity is evaluated at 21 days. Blood chemistries, target organs, bone marrow and blood, and other health indicator are evaluated.

Hypersensitivity studies in guinea pigs are performed to test for any adverse immunologic reactions. To do this, fifteen guinea pigs (5 FRIL, 5 DNCB positive control, 5 saline negative control) are used. A FRIL family member is intradermally injected at 0.1 mL. Daily clinical observations at site for redness and edema are compared to the DNCB positive control. The FRIL guinea pigs are challenged at at 2 weeks with 0.05 mL of the FRIL family member, and daily clinical observations are made.

A determination of development of mouse anti-FRIL family member antibodies in mice receiving treatment with a FRIL family member is made to determine the extent and nature of the body's response to a FRIL family member. To do this, a FRIL family member is attached to Dynal's tosylactivated magnetic beads. The FRIL family member-coated beads are incubated with plasma (pooled or individual) from a mouse who has received treatment with the FRIL family member. Using rabbit and rat antiserum to FRIL used as positive control, the presence of FRIL family member-specific antibodies is evaluated by SDS-PAGE and Western blot analysis (horseradish peroxidase or chemiluminesce). Lastly, a determination is made as to whether sugar blocks antibody binding ($\alpha$-D-mannopyranoside and negative control).

EXAMPLE 16

Purification of Progenitor Cells using Dl-FRIL-Coated Magnetic Beads

Using magnetic beads coated with a non-limiting FRIL family member, Dl-FRIL, a population of progenitor cells was isolated and characterized. To do this, the following methods were used.

Preparation of FRIL-beads for Cell Isolation

Dl-FRIL was purified from *Dolichos lab lab* seeds as described in Example 1. Dl-FRIL can be immobilized on magnetic beads (M-280 Dynabeads Tosylactivated, Lake Success, N.Y.) via amino- and sulfhydryl-groups of the lectin according to the manufacturer's directions. Dl-FRIL can also immobilized on magnetic beads by a biotin-strepavidin interaction.

In this example, Dl-FRIL was immobilized on magnetic beads by a biotin-strepavidin interaction. Biotinylation of Dl-FRIL via primary amine-groups (EZ-Link Sulfo-NHS-LC-LC-Biotin, Pierce Chemical Company, Rockford, Ill.) was carried out according to the manufacturer's directions. Biotinylated Dl-FRIL was incubated with strepavidin-labeled magnetic beads (Dynal or Miltenyi Biotec, Auburn, Calif.) according to the manufacturer's directions.

Preparation of Cells

Human cord blood (CB), peripheral blood, and bone marrow, collected in sterile receptacles containing anticoagulant (e.g., heparin, EDTA), was processed to isolate mononuclear cells (mnc) within six hours of collection by density centrifugation on Ficoll-Paque PLUS (Pharmacia Biotech, Piscataway, N.J.) according to the manufacturer's directions. Mononuclear cells harvested at the interface of plasma and Ficoll-Paque were washed and resuspended in serum-defined medium (e.g., XVIVO-10, Biowhittaker, Walkerville, Md. or AIM-V, Life Technologies, Rockville, Md.).

Dl-FRIL-bead Cell Isolation

Dl-FRIL-coated beads specifically bound a minor mnc population found in CB, peripheral blood, and bone marrow. A ten-fold excess of Dl-FRIL-beads was incubated with the cells. For CB, where Dl-FRIL-beads captured approximately 1% of mnc, the ratio of beads to cells was 1:10, or 10-fold greater number of beads for every target cell. The ratio for other FLT3-expressing cell populations, was hematopoietic and non-hematopoietic, was experimentally determined by serial exposure of cells to fresh Dl-FRIL-beads.

Dl-FRIL-beads were washed twice in serum-defined medium prior to use. An aliquot of Dl-FRIL-beads was added to 10 mL of serum-defined medium in a 15 mL conical centrifuge tube (Falcon, Becton-Dickinson, Lincoln, N.J.), mixed, and placed in a magnet (Dynal or Miltenyi Biotec, depending on source of magnetic beads) for ten minutes. Medium was aspirated with a 10 mL pipette without disturbing beads bound to walls of centrifuge tube by the magnet charge from the magnet. After washing, 0.5 mL of serum-defined medium was added to the tubes to wash the beads from the walls to the bottom of the conical tube. Medium was added to beads in a small volume (<2 mL) and the centrifuge tube was tumbled on a rocker in a cold room (i.e., at approximately 4° C.) for one hour. After incubation, serum-defined medium was added to a final volume of 10 mL and the tube was placed in the magnet for ten minutes. Medium was removed by aspiration without disturbing cells bound to Dl-FRIL-beads on the walls of the centrifuge tube via the magnetic charge. Cells were washed a second time by removing the conical tube from the magnet, adding 10 mL of serum-defined medium, mixing cells, and placing the conical tube back onto the magnet. Following aspiration of the medium, the final volume was adjusted to 2 mL.

Detachment of Dl-FRIL Beads from Cells

For some applications, detachment of Dl-FRIL-beads from cells is preferred. About half of Dl-FRIL-beads detached from CB mnc after overnight incubation on a rocker in the cold room. Although binding studies have demonstrated that excess mannose and $\alpha$-methyl $\alpha$-D-mannoside prevent Dl-FRIL from binding to Flt3, neither sugar released tightly bound Dl-FRIL-beads from CB mnc. To remove Dl-FRIL-beads from this subpopulation of cells, the cells were incubated in 100 mM trehalose (Sigma, St. Louis, Mo.) for one hour on a rocker in the cold room.

It should be noted that since Miltenyi beads are very small (approximately 50 nm) as compared to Dynal beads (approximately 10 $\mu$m), when Miltenyi beads were used to purify Dl-FRIL-binding progenitor cells, the beads were allowed to remain attached to the purified progenitor cells.

Receptor Tyrosine Kinase Gene Expression

Receptor tyrosine kinase gene expression was characterized by RT-PCR.

Using these methods, the following results were obtained:

Functional Properties of Dl-FRIL Bead-selected CB mnc

The progenitor capacity of Dl-FRIL-selected CB mnc was tested in a methylcellulose colony assay under conditions to promote proliferation and differentiation along either the hematopoietic or endothelial lineages (as described above. Table 11 shows the number of hematopoietic colonies (myeloid, erythroid, and mix) and endothelial colonies (other) that formed after culture of unselected cells (CB mnc), Dl-FRIL-selected cells (Dl-FRIL$^+$) and CB mnc that did not bind to Dl-FRIL-beads (Dl-FRIL$^-$).

TABLE 11

Response of Dl-FRIL-selected cells to hematopoietic and endothelial stimuli

| Stimulator | Myeloid | Erythroid | Mix | Other | Total |
|---|---|---|---|---|---|
| +CSFs | | | | | |
| CB mnc | 1 | 3 | 2 | 0 | 6 |
| Dl-FRIL$^+$ | 14 | 10 | 4 | 0 | 28 |
| Dl-FRIL$^-$ | 1 | 1 | 2 | 0 | 4 |
| +VEGF | | | | | |
| CB mnc | 0 | 0 | 0 | 2 | 2 |
| Dl-FRIL$^+$ | 0 | 0 | 0 | 19 | 19 |
| Dl-FRIL$^-$ | 0 | 0 | 0 | 5 | 5 |

Cord blood mononuclear cells were isolated by Ficoll-Paque, bead selected, and plated in MethoCult□, StemCell Technologies, Vancouver, BC, Canada).

As shown in Table 11, Dl-FRIL-selection increased the number of hematopoietic colonies (stimulated with colony stimulating factors (CSFs) by 14-fold for myeloid colonies, 3.3- to 10-fold for erythroid colonies (CB mnc and Dl-FRIL– cells, respectively), and by 2-fold for mixed colonies. Similar levels of Dl-FRIL-bead enrichment was observed for endothelial colonies (stimulated with vascular endothelial growth factor (VEGF)): 9.5-fold over CB mnc and 3.8-fold for Dl-FRIL$^-$ cells.

Cell Surface Phenotypic Properties of Dl-FRIL Bead-selected CB mnc

The cell surface phenotypic properties of Dl-FRIL bead-selected CB mnc was characterized by flow cytometry. Table 12 shows the phenotypes (by percentage of cells expressing the indicated cell surface phenotype marker) of the three CB cell populations: (1) cells not selected by Dl-FRIL-beads (Dl-FRIL$^-$); (2) cells that detached from Dl-FRIL-beads after overnight incubation in the coldroom on a rocker (Dl-FRIL$^+$); and (3) cells that retained Dl-FRIL-beads after overnight incubation (Dl-FRIL$^{++}$). The two Dl-FRIL-binding cell populations were analyzed separately to see whether tightness of binding (avidity) related to type of cells selected. Isotype control levels were set at 2%; all values of 2% represent no reactivity with test antibody.

TABLE 12

Flow cytometric analysis of Dl-FRIL-selected CB mnc

| Antigen | Cell Type | Dl-FRIL$^-$ (%) | Dl-FRIL$^+$ (%) | Dl-FRIL$^{++}$ (%) |
|---|---|---|---|---|
| CD3 | Mature T | 26 | 35 | 6 |
| CD11b | Mac-1, CR3 | 19 | 35 | 67 |
| CD11c | LeuCAMc | 10 | 22 | 32 |
| CD13 | Pan myeloid, CFU-GM | 5 | <2 | <2 |
| CD19 | Pan B | 4 | 5 | 12 |
| CD32 | Low affinity IgG Fcγ-R | 5 | 19 | 26 |
| CD33 | Myeloid progenitors | 3 | 2 | 8 |
| CD34 | Pan progenitors | <2 | <2 | <2 |
| CD38 | Activated T | 88 | 96 | 93 |
| CD42a | Platelet gpIX | 5 | 2 | 7 |
| CD69 | Early activation ag (EA-1) | 6 | 8 | 14 |
| CDw90 | Thy-1, progenitor subset | 8 | 14 | 13 |
| CD117 | c-kit, progenitors | 4 | 2 | 2 |

As shown in Table 12, Dl-FRIL-beads did not capture CB mnc that express CD34, the hallmark marker of hematopoietic stem cells and progenitors. This observation was unexpected because Dl-FRIL-selected cells enrich for progenitors (see Table 11). Although CB CD34$^+$ cells uniformly express FLT3, only 70% of Flt3$^+$ CB mnc also express CD34 (Rappold et al., Blood 90:111–125, 1997). Consequently, 30% of CB mnc expressed the phenotype of CD34$^-$Flt3$^+$. Dl-FRIL-beads appeared to capture this latter population of cells.

Cells expressing dendritic cell (DC) markers, CD11b and CD11c, were enriched approximately 2-fold in the Dl-FRIL$^+$ cell population and over 3-fold in the Dl-FRIL$^{++}$ cell population (Table 12). This observation is consistent with reports that Flt3 is involved in dendritic cell proliferation and maturation in mice (Pulendran et al., J. Immunol. 159:2222–2231, 1997) and humans (Miller et al., Blood 93:96–106., 1999). The rare hematopoietic dendritic cell population is useful in inducing tumor regression and for the treatment of AIDS.

Differences of the cell surface phenotypes were observed between Dl-FRIL$^+$ and Dl-FRIL$^{++}$ CB cells (see Table 11). The percentage of CD3 T cells decreased from 35% for Dl-FRIL$^+$ cells to 6% for Dl-FRIL$^{++}$ cells. Conversely, the percentage of CD11b$^+$ cells and CD11c$^+$ cells increased from 35% to 67% and from 22% to 32% for Dl-FRIL$^+$ and Dl-FRIL$^{++}$ cell populations, respectively.

Cells that retained Dl-FRIL-beads after overnight incubation on a rocker in the cold room (Dl-FRIL$^{++}$ cells) were observed as single cells or as clumps of bead-bound cells. These clumps could not be disrupted either by mechanical means or by elution with competing sugars, mannose or mannose derivatives (data not shown). From studies to characterize the carbohydrate-binding properties of Dl-FRIL, α,α-trehalose demonstrated a 3.6-fold greater potency than mannose and a 1.6- to 2.1-fold greater potency than α-methyl α-D-mannoside derivatives that were tested (Mo et al., Glycobiology 9:173–179, 1999). Incubation of clumped Dl-FRIL-bead bound cells with 100 mM Trehalose effectively disrupted the clumped cells and removed most of the Dl-FRIL-beads from cells.

Two populations of trehalose-disrupted Dl-FRIL$^{++}$ cells were analyzed by flow cytometry: cells that no longer bound beads (Dl-FRIL$^{++}$) and cells that still retained beads following incubation with trehalose (Dl-FRIL$^{+++}$). The results of one experiment are shown in Table 13.

TABLE 13

Flow cytometric analysis of Dl-FRIL-selected CB mnc after exposure to trehalose

| Antigen | Cell Type | Dl-FRIL$^{++}$ (%) | Dl-FRIL$^{+++}$ (%) |
|---|---|---|---|
| CD3 | Mature T | 6 | 3 |
| CD11b | Mac-1, CR3 | 52 | 76 |
| CD11c | LeuCAMc | 16 | 43 |
| CD13 | Pan myeloid, CFU-GM | 72 | 46 |
| CD19 | Pan B | 5 | 9 |
| CD32 | Low affinity IgG Fc-γ | 43 | 19 |
| CD33 | Myeloid progenitors | 56 | 15 |
| CD34 | Pan progenitors | 2 | 2 |
| CD117 | c-kit, progenitors | 2 | 12 |
| CD135 | Flt3, progenitors | 2 | 5 |

The difference in cell surface phenotypes between Dl-FRIL$^{++}$ cells and Dl-FRIL$^{+++}$ cells in Table 13 was greater than those observed for Dl-FRIL$^+$ cells and Dl-FRIL$^{++}$ cells in Table 12. In Table 13, the percentage of CD3, CD13, CD32, and CD33 cells decreased by 1.6 to 3.7-fold in Dl-FRIL$^{+++}$ cells compared to Dl-FRIL$^{++}$ cells. Conversely, the percentage of CD11b, CD11c, CD19, CD117, and CD135 cells increased by 1.5- to 6-fold in Dl-FRIL$^{+++}$ cells compared to Dl-FRIL$^{++}$ cells. Again no CD34 was observed in either cell population.

The increase in percentage of cells that express CD117 and CD135, two tyrosine kinase receptors central to hematopoietic stem cell and progenitor function (Lyman and Jacobson, *Blood* 91:1101–1134, 1998), suggested that avidity of Dl-FRIL-bead binding of cells might correspond to the primitive status of the cells. The studies described herein which characterize the carbohydrate binding properties of Dl-FRIL supported this notion. Dl-FRIL has neither an extending carbohydrate combining-binding site nor a hydrophobic binding site adjacent to it (Mo et al., *Glycobiology* 9:173–179, 1999). Dl-FRIL binds most tightly to a trimannoysl structure that is the basis for N-linked glycosylation in mammals. Consequently, Dl-FRIL may bind cells that have undergone less processing of glycosylation, which is consistent with more primitive cells. This property of Dl-FRIL-binding may provide a unique method to isolate primitive cells not currently possible by antibodies to CD34. Thus, Dl-FRIL binds the normally glycosylated FLT3 receptor more tightly than the FLT3-Ligand binds to normally glycosylated FLT3. Dl-FRIL binds normally glycosylated FLT3 receptor more tightly than the typical antibody binds its specific ligand.

Receptor Tyrosine Kinase Gene Expression in Dl-FRIL-selected CB Cells

The number of cell surface receptors and markers increases as pluripotent hematopoietic stem cells proliferate and differentiate. The number of functional receptors on the most primitive cells is probably less than ten. The levels of detection for flow cytometry are probably in the range of several hundred cell surface molecules. Consequently, analysis of primitive cell populations cannot be analyzed by flow cytometry.

The presence or absence of functional tyrosine kinase receptors on primitive cells was further characterized by RT-PCR Expression of Flt3, Kit, Fms, Flk1, Flt1, and Flt4 mRNA was determined for CB mnc, CD34-selected cells, and Dl-FRIL-selected cells. For CB mnc, the PCR products for the receptors were either faint or not detectable. The pattern of gene expression for cells selected by CD34-beads or Dl-FRIL-beads was the same; all tyrosine kinase receptors showed stronger PCR signals. These data suggest that receptors associated with stem cells (Flt3 and Kit) and primitive endothelial cells (Flk1, Flt1, and Flt4) are also detected in Dl-FRIL selected cells.

EXAMPLE 17

Use of Beads Coated with a FRIL Family Member to Isolate CD34$^-$ Primitive Stem Cells A rare human stem cell population with the phenotype of CD34$^-$CD38$^-$Lin$^-$ has been identified by its ability to establish multilineage engraftment in NOD/SCID mice (Bhatia et al., *Nat. Med.* 4:1038–1045, 1998). These repopulating cells give rise to stem cells that express the hallmark CD34 marker. Isolating CD34$^-$CD38$^-$Lin$^-$ cells is labor-intensive methods of negative selection that includes the use of immunomagnetic beads and flow cytometry to deplete cells that express CD34, CD38, and lineage markers. Rapid, efficient, positive selection of CD34$^-$CD38$^-$Lin$^-$ cells would be preferable for clinical uses. However, the absence of the highly expressed CD34 marker and low number of functional receptors on this rare population of cells will prevent use of antibodies for cell isolation.

FRIL attached to magnetic beads are used in a unique method to isolate the rare CD34$^-$CD38$^-$Lin$^-$ cell population by binding primitive cells that express this phenotype. Isolation of CD34$^-$CD38$^-$Lin$^-$ is achieved by a single-step cell isolation. However, since FRIL-beads also recognize cells that express CD11b, CD11c, and CD38, optimal isolation of CD34$^-$CD38$^-$Lin$^-$ cells is improved by first negatively selecting unwanted cells by immunomagnetic beads that bind to CD11b, CD11c, and/or CD38.

EXAMPLE 18

Use of Beads Coated with a FRIL Family Member to Isolate Normal Stem Cells from Patients with Leukemia A majority of leukemias express the phenotype of CD34$^+$Flt3$^+$ (Carow et al., *Blood* 87:1089–1096, 1996). Consequently, methods that rely on CD34 expression cannot distinguish normal stem cells and progenitors from leukemic cells in the bone marrow and peripheral blood of patients.

FRIL does not interact with two cell leukemic lines tested with the CD34$^+$Flt3$^+$ phenotype (KG1-A and ML-1). FRIL neither effects growth of these leukemic cell lines nor do FRIL-beads capture appreciable numbers of cells (data not shown). Since FRIL-beads select normal progenitors with the phenotype of CD34$^-$Flt3$^+$, FRIL-beads provide a unique method that distinguishes between normal and leukemic cells.

A FRIL family member attached to magnetic beads is used to isolate normal hematopoietic stem cells and progenitors from the bone marrow and peripheral blood of leukemia patients. This is accomplished using a method similar to leukopheresis, where blood is passed through a device that retains cells of interest. In this example, FRIL-beads binds CD34$^-$Flt3$^+$ normal cells. Since FRIL also interacts with Flt3-expressing CD11b and CD11c cells, prior exposure and removal of the cells that immunomagnetic beads that bind to CD11b and/or CD11c (i.e., negative selection) may permit enrichment of primitive cells.

EXAMPLE 19

Use of FRIL-beads to Isolate Dendritic Progenitors and Mature Cells from Normal Individuals Dendritic cells (DC) are immune cells that capture antigens and initiate T cell-mediated immune responses (Banchereau and Steinman, *Nature* 392:245–252, 1998). DC act as first lines of defense in the skin, gut, and lymphoid organs. Antigens on DC can activate naive and quiescent T cells and small numbers of DC pulsed with lose dosages of antigens stimulate strong T cell responses. Under certain circumstances, DC also induce T cell tolerance. Consequently, the unique properties of DC has generated significant interest to use these cells to treat cancer and AIDS. DC are derived from CD34$^+$ progenitors in the bone marrow of humans. The cytokines GM-CSF, TNF-$\alpha$, and Flt3 ligand (FL) influence DC development (Banchereau and Steinman, supra; Pulendran et al., *J. Immunol.* 159:2222–2231, 1997). Injection of FLT3-Ligand in mice dramatically increases the number of DC (Pulendran et al., supra). FRIL interacts with the Flt3 receptor on DC, and FRIL-beads capture cells with the dendritic phenotype of CD11b and CD11c. Selecting dendritic cells with FRIL-beads from human bone marrow, peripheral blood, or cord blood allows the efficient and effective isolation of DC for clinical use.

EXAMPLE 20

Use of FRIL-beads to Isolate Endothelial Stem Cells and Progenitors

Endothelial stem cells and progenitors give rise to cells that form blood vessels in a process called angiogenesis.

During strokes and heart attacks, new blood vessels are needed to repair damage. Activation of endothelial stem cells and progenitors to produce more mature cells is mediated by the cytokines that activate the Flk1/KDR, Flt1, and Flt4 tyrosine kinase receptors. Flt3 is expressed on very primitive endothelial progenitors. FRIL-beads are used to capture a population of cells from cord blood that express all of these receptors.

EXAMPLE 21

Use of FRIL Family Members and Non-FRIL Family Member Lectins to Alter Signal Transduction and Other Cellular Pathways Drags designed to alter signal transduction pathways need to specifically distinguish target cells. FRIL is used as a targeting vehicle to deliver small molecules to Flt3-expressing cells such as stem cells, progenitors, and dendritic cells. FRIL has several advantages for drug delivery: 1) FRIL is specific for Flt3; 2) FRIL is stable in the cytoplasm; 3) FRIL is capable of undergoing conjugation with small molecules; 4) FRIL can be delivered in dose-responsive manner; and 5) FRIL provides specificity for overlapping pathways of signal transduction.

Other legume- or bulb-derived lectins can also deliver small molecule drugs to specific cell populations. For example, the lectins PHA and ConA both bind to CD3-T cell receptor complex and the FC-gamma receptor (CD32) (Leca et al. *Scand. J. Immunol.* 23:539–544, 1986); UDA binds the Vβ domain of the T cell receptor (Galelli et al., *J. Immunol.* 151:1821–1831, 1993).

Standard methods of conjugation are used to attach small molecules, oligos, or enzymes to plant lectins.

EXAMPLE 22

Purification and Cloning of YamFRIL from *Sphenostylis stenocarpa*

Dry seeds of Yam bean (*Sphenostylis stenocarpa*) were ground in a coffee mill and the powder was extracted with 5 volumes of 10 mM Na Acetate buffer, pH 5.2, containing 1 mM $CaCl_2$ for 1 hour at 4° C. After centrifugation, the clear supernatant was neutralized with Tris-HCl pH 8.0.

YamFril purification was achieved through and absorption on a ovalbumin gel affinity column (Sigma) and was eluted with 200 mM trehalose.

The resulting protein was fractionated into 2 polypeptides that were submitted to N-terminal amino acid sequences.

```
Beta band:     AQSVSFTFTKFDSDQ    (SEQ ID NO:9)

Alpha band:    AASNNVVAVEFDTXPN   (SEQ ID NO:10)
```

Reverse-transcriptase PCR was performed on total RNA obtained from International Institute of Tropical Agriculture (Ibadan, Oyo State, Nigeria), using degenerate primers based on the alpha and beta N-terminus sequences (i.e., SEQ ID NO: 10 and SEQ ID NO: 9, respectively).

3' RACE PCR was performed on total and polyA+RNA using gene specific primers with an Anchor Primer.

Partial cDNA clones were obtained and the following sequences deduced.

```
YamFril: partial mRNA sequence

ACGAAGTTCGACAGCGACCAAAAGGATCTTATGTTCCAAGGTCATACCATTTCTAGCAGC  (SEQ ID NO:7)

AATGTCATACAACTCACCAAGTTAGACAGTAATGGAAACCCTGTGAGTACCAGTGTGGGA

AGAGTGTTATACTCTGCACCATTGCGCCTTTGGGAAAGCTCTACAGTAGTGTCAACCTTT

GAGACCACTTTCACCTTTCAAATCTCAACACCTTACACTAGTCCTCCTGGTGATGGGCTC

GCCTTCTTCCTTGCACCATATGACACTGTCATCCCTCCAAATTCTGCTGGCAATCTTCTT

GGACTCTTTCCTAACTTAAATGCTTTAAGAAACTCCACCACCAGTAAAGAAACCACTATT

GATGTCAATGCTGCATCTAACAACGTTGTTGCCGTTGAATTTGACACCTACCCTAACGAC

AATATTGGTGATCCAAGATACAAACACATTGGAATCGATGTCAACTCTATCAGGTCCAAG

GCAACTGTTGCGTGGGACTGGCAAAATGGGAAAACAGCCACTGCACACATCAGCTATAAC

TCTGCCTCTAAAAGACTATCTGTTACTACTTTTTATCCTGGGGGTAAAGCTGTGAGTCTT

TCCCATGACGTTGAGCTCACTCAAGTGCTTCCTCAATGGATTAGAGTAGGGTTCTCTGCT

TCAACAGGATTAGAGAAA

YamFril: deduced amino acid sequence

AQSVSFTFTKFDSDQKDLMFQGHTISSSNVIQLTKLDSNGNPVSTSVGRVLYSAPLRLWE  (SEQ ID NO:8)

SSTVVSTFETTFTFQISTPYTSPPGDGLAFFLAPYDTVIPPNSAGNLLGLFPNLNALRNS

TTSKETTIDVNAASNNVVAVEFDTYPNDNIGDPRYKHIGIDVNSIRSKATVAWDWQNGKT

ATAHISYNSASKRLSVTTFYPGGKAVSLSHDVELTQVLPQWIRVGFSASTGLEK

What is claimed is:

1. A pharmaceutical formulation comprising:
   (a) a pharmaceutically acceptable carrier; and
   (b) a protein that:
      (1) binds to a normally glycosylated FLT3 receptor;
      (2) has at least 95% amino acid sequence identity to an amino acid sequence selected from the group consisting of SEQ ID NO: 2, SEQ ID NO: 6, and SEQ ID NO:8; and
      (3) preserves hematopoietic progenitor cells.

2. A pharmaceutical formulation comprising:
   (a) a pharmaceutically acceptable carrier; and
   (b) an effective amount of a protein that:
      (1) binds to a normally glycosylated FLT3 receptor;
      (2) has at least 95% amino acid sequence identity to an amino acid sequence selected from the group consisting of SEQ ID NO: 2, SEQ ID NO: 6, and SEQ ID NO: 8; and
      (3) reduces a progenitor cell depleting activity in a subject undergoing a therapeutic treatment having progenitor cell depleting activity.

3. The pharmaceutical formulation of claim 2, wherein said subject is a human undergoing treatment for cancer.

4. The pharmaceutical formulation of claim 2, wherein said therapeutic treatment is selected from the group consisting of radiotherapy, chemotherapy, or a combination of radiotherapy and chemotherapy.

5. The pharmaceutical formulation of claim 4, wherein said chemotherapy comprises administration of a chemotherapeutic selected from the group consisting of cytarabine, doxorubicin, and 5-fluorouracil.

6. The pharmaceutical formulation of claim 1 or 2, wherein said pharmaceutical formulation is suitable for parenteral administration.

7. The pharmaceutical formulation of claim 6, wherein said parenteral administration is selected from the group consisting of intravenous, intra-arterial, subcutaneous, intramuscular, intraperitoneal and intra-marrow administration.

8. The pharmaceutical formulation of claim 1 or 2, wherein said protein comprises the amino add sequence of SEQ ID NO: 2.

9. The pharmaceutical formulation of claim 1 or 2, wherein said protein comprises the amino acid sequence of SEQ ID NO:6.

10. The pharmaceutical formulation of claim 1 or 2, wherein said protein comprises the amino acid sequence of SEQ ID NO: 8.

11. The pharmaceutically formulation of claim 1 or 2, wherein said protein comprises an amino acid sequence having 95% amino acid sequence identity to the amino acid sequence identity to the amino acid sequence set forth in SEQ ID NO: 2.

12. The pharmaceutical formulation of claim 1 or 2, wherein said protein comprises an amino acid sequence having 95% amino acid sequence identity to the amino acid sequence set fr 13. The pharmaceutical formulation of claim 1 or 2, wherein said protein comprises an amino acid sequence having 95%; amino acid sewquence identity to the amino acid sequence set forth in SEQ ID NO: 8.

* * * * *

UNITED STATES PATENT AND TRADEMARK OFFICE
CERTIFICATE OF CORRECTION

PATENT NO. : 6,991,794 B1
DATED : January 31, 2006
INVENTOR(S) : Colucci et al.

It is certified that error appears in the above-identified patent and that said Letters Patent is hereby corrected as shown below:

Column 112,
Line 24, replace "amino add" with -- amino acid --.
Line 32, replace "pharmaceutically" with -- pharmaceutical --.
Line 35, replace "sequence identity to the amino acid sequence set forth" with
-- sequence set forth --.
Line 40, replace "sequence set fr" with -- sequence set forth in SEQ ID NO: 6 --.
Line 43, replace "95%; amino acid sewquence" with -- 95% amino acid sequence --.

Signed and Sealed this

Second Day of May, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,991,794 B1 |
| APPLICATION NO. | : 09/476485 |
| DATED | : January 31, 2006 |
| INVENTOR(S) | : Colucci et al. |

It is certified that error appears in the above-identified patent and that said Letters Patent is hereby corrected as shown below:

Claim 11, column 112, line 34: replace "having 95% amino acid" with -- having at least 95% amino acid --

Claim 12, column 112, line 39: replace "having 95% amino acid" with -- having at least 95% amino acid --

Claim 13, column 112, line 43: replace "having 95% amino acid" with -- having at least 95% amino acid --

Signed and Sealed this

Eighteenth Day of July, 2006

JON W. DUDAS
*Director of the United States Patent and Trademark Office*

```

SEQUENCE LISTING

<160> NUMBER OF SEQ ID NOS: 57

<210> SEQ ID NO 1
<211> LENGTH: 939
<212> TYPE: DNA
<213> ORGANISM: Artificial Sequence
<220> FEATURE:
<223> OTHER INFORMATION: D1-FRIL.

<400> SEQUENCE: 1

```
gcacagtcat tgtcatttag tttcaccaag tttgatccta accaagagga tcttatcttc      60
caaggtcatg ccacttctac aaacaatgtc ttacaagtca ccaagttaga cagtgcagga     120
aaccctgtga gttctagtgc gggaagagtg ttatattctg caccattgcg cctttgggaa     180
gactctgcgg tattgacaag ctttgacacc attatcaact ttgaaatctc aacaccttac     240
acttctcgta tagctgatgg cttggccttc ttcattgcac cacctgactc tgtcatcagt     300
tatcatggtg gttttcttgg actctttccc aacgcaaaca ctctcaacaa ctcttccacc     360
tctgaaaacc aaaccaccac taaggctgca tcaagcaacg ttgttgctgt tgaatttgac     420
acctatctta atcccgatta tggtgatcca aactacatac acatcggaat tgacgtcaac     480
tctattagat ccaaggtaac tgctaagtgg gactggcaaa atgggaaaat agccactgca     540
cacattagct ataactctgt ctctaaaaga ctatctgtta ctagttatta tgctgggagt     600
aaacctgcga ctctctccta tgatattgag ttacatacag tgcttcctga atgggtcaga     660
gtagggttat ctgcttcaac tggacaagat aaagaaagaa ataccgttca ctcatggtct     720
ttcacttcaa gcttgtggac caatgtggcg aagaaggaga atgaaaacaa gtatattaca     780
agaggcgttc tgtgatgata tatgtgtatc aatgattttc tatgttataa gcatgtaatg     840
tgcgatgagt caataatcac aagtacagtg tagtacttgt atgttgtttg tgtaagagtc     900
agtttgcttt taataataac aagtgcagtt agtacttgt                             939
```

<210> SEQ ID NO 2
<211> LENGTH: 264
<212> TYPE: PRT
<213> ORGANISM: Artificial Sequence
<220> FEATURE:
<223> OTHER INFORMATION: D1-FRIL.

<400> SEQUENCE: 2

```
Ala Gly Ser Leu Ser Phe Ser Phe Thr Lys Phe Asp Pro Asn Gln Glu
1               5                   10                  15

Asp Leu Ile Phe Gln Gly His Ala Thr Ser Thr Asn Asn Val Leu Gln
            20                  25                  30

Val Thr Lys Leu Asp Ser Ala Gly Asn Pro Val Ser Ser Ser Ala Gly
        35                  40                  45

Arg Val Leu Tyr Ser Ala Pro Leu Arg Leu Trp Glu Asp Ser Ala Val
    50                  55                  60

Leu Thr Ser Phe Asp Thr Ile Ile Asn Phe Glu Ile Ser Thr Pro Tyr
65                  70                  75                  80

Thr Ser Arg Ile Ala Asp Gly Leu Ala Phe Phe Ile Ala Pro Pro Asp
                85                  90                  95

Ser Val Ile Ser Tyr His Gly Gly Phe Leu Gly Leu Phe Pro Asn Ala
            100                 105                 110

Asn Thr Leu Asn Asn Ser Ser Thr Ser Glu Asn Gln Thr Thr Thr Lys
        115                 120                 125
```

```
Ala Ala Ser Ser Asn Val Val Ala Val Glu Phe Asp Thr Tyr Leu Asn
            130                 135                 140

Pro Asp Tyr Gly Asp Pro Asn Tyr Ile His Ile Gly Ile Asp Val Asn
145                 150                 155                 160

Ser Ile Arg Ser Lys Val Thr Ala Lys Trp Asp Trp Gln Asn Gly Lys
                165                 170                 175

Ile Ala Thr Ala His Ile Ser Tyr Asn Ser Val Ser Lys Arg Leu Ser
            180                 185                 190

Val Thr Ser Tyr Tyr Ala Gly Ser Lys Pro Ala Thr Leu Ser Tyr Asp
                195                 200                 205

Ile Glu Leu His Thr Val Leu Pro Glu Trp Val Arg Val Gly Leu Ser
    210                 215                 220

Ala Ser Thr Gly Gln Asp Lys Glu Arg Asn Thr Val His Ser Trp Ser
225                 230                 235                 240

Phe Thr Ser Ser Leu Trp Thr Asn Val Ala Lys Lys Glu Asn Glu Asn
                245                 250                 255

Lys Tyr Ile Thr Arg Gly Val Leu
            260

<210> SEQ ID NO 3
<211> LENGTH: 1005
<212> TYPE: DNA
<213> ORGANISM: Artificial Sequence
<220> FEATURE:
<223> OTHER INFORMATION: Nucleic acid sequence of the naturally-occurring D1-FRIL protein.

<400> SEQUENCE: 3
atggcttcct ccaacttact caccctagcc ctcttccttg tgcttctcac ccacgcaaac     60
tcagccgcac agtcattgtc atttagtttc accaagtttg atcctaacca agaggatctt    120
atcttccaag gtcatgccac ttctacaaac aatgtcttac aagtcaccaa gttagacagt    180
gcaggaaacc ctgtgagttc tagtgcggga agagtgttat attctgcacc attgcgcctt    240
tgggaagact ctgcggtatt gacaagcttt gacaccatta tcaactttga atctcaaca    300 ccttacactt ctcgtatagc tgatggcttg gccttcttca ttgcaccacc tgactctgtc    360
atcagttatc atggtggttt tcttggactc tttcccaacg caaacactct caacaactct    420
tccacctctg aaaaccaaac caccactaag gctgcatcaa gcaacgttgt tgctgttgaa    480
tttgacacct atcttaatcc cgattatggt gatccaaact acatacacat cggaattgac    540
gtcaactcta ttagatccaa ggtaactgct aagtgggact ggcaaaatgg gaaaatagcc    600
actgcacaca ttagctataa ctctgtctct aaaagactat ctgttactag ttattatgct    660
gggagtaaac ctgcgactct ctcctatgat attgagttac atacagtgct tcctgaatgg    720
gtcagagtag ggttatctgc ttcaactgga caagataaag aaagaaatac cgttcactca    780
tggtctttca cttcaagctt gtggaccaat gtggcgaaga aggagaatga aaacaagtat    840
attacaagag gcgttctgtg atgatatatg tgtatcaatg attttctatg ttataagcat    900
gtaatgtgcg atgagtcaat aatcacaagt acagtgtagt acttgtatgt tgtttgtgta    960
agagtcagtt tgcttttaat aataacaagt gcagttagta cttgt                  1005

<210> SEQ ID NO 4
<211> LENGTH: 22
<212> TYPE: PRT
<213> ORGANISM: Artificial Sequence
<220> FEATURE:
<223> OTHER INFORMATION: Signal sequence from the FRIL family isolated from
      Dolichos lab lab
```

<400> SEQUENCE: 4

Met Ala Ser Ser Asn Leu Leu Thr Leu Ala Leu Phe Leu Val Leu Leu
1               5                   10                  15

Thr His Ala Asn Ser Ala
            20

<210> SEQ ID NO 5
<211> LENGTH: 914
<212> TYPE: DNA
<213> ORGANISM: Artificial Sequence
<220> FEATURE:
<223> OTHER INFORMATION: Pv-FRIL.

<400> SEQUENCE: 5

| gctcagtcat tatctttttaa ctttaccaag tttgatcttg accaaaaaga tcttatcttc | 60 |
| caaggtgatg ccacttctac aaacaatgtc ttacaactca ctaagttaga cagtggagga | 120 |
| aaccctgtgg gtgctagtgt gggaagagtg ttattctctg caccatttca tctttgggaa | 180 |
| aactctatgg cagtgtcaag cttgaaact aatctcacca ttcaaatctc aacacctcac | 240 |
| ccttattatg cagctgatgg cttgccttc ttccttgcac cacatgacac tgtcatccct | 300 |
| ccaaattctt ggggcaaatt ccttggactc tactcaaacg ttttcagaaa ctcccccacc | 360 |
| tctgaaaacc aaagctttgg tgatgtcaat actgactcaa gagttgttgc tgtcgaattt | 420 |
| gacaccttcc ctaatgccaa tattgatcca aattacagac acattggaat cgatgtgaac | 480 |
| tctattaagt ccaaggaaac tgctaggtgg gagtggcaaa atgggaaaac ggccactgca | 540 |
| cgcatcagct ataactctgc ctctaaaaaa tcaactgtta ctacgtttta tcctgggatg | 600 |
| gaagttgtgg ctctctccca tgatgttgac ttacatgcag agcttcctga atgggttaga | 660 |
| gtagggttat ctgcttcaac tggagaggag aaacaaaaaa ataccattat ctcatggtct | 720 |
| ttcacttcaa gcttgaagaa caacgaggtg aaggagccga agaagacat gtatattgca | 780 |
| aacgttgtgc gatcatatac atggatcaat gacgttctat cttatataag caataaataa | 840 |
| atgtatgatg cactcaataa taatcacaag tacgtacggt gtagtacttg tatgttgttt | 900 |
| atgaaaaaaa aaaa | 914 |

<210> SEQ ID NO 6
<211> LENGTH: 303
<212> TYPE: PRT
<213> ORGANISM: Artificial Sequence
<220> FEATURE:
<223> OTHER INFORMATION: Pv-FRIL.

<400> SEQUENCE: 6

Ala Gln Ser Leu Ser Phe Asn Phe Thr Lys Phe Asp Leu Asp Gln Lys
1               5                   10                  15

Asp Leu Ile Phe Gln Gly Asp Ala Thr Ser Thr Asn Asn Val Leu Gln
            20                  25                  30

Leu Thr Lys Leu Asp Ser Gly Gly Asn Pro Val Gly Ala Ser Val Gly
        35                  40                  45

Arg Val Leu Phe Ser Ala Pro Phe His Leu Trp Glu Asn Ser Met Ala
    50                  55                  60

Val Ser Ser Phe Glu Thr Asn Leu Thr Ile Gln Ile Ser Thr Pro His
65                  70                  75                  80

Pro Tyr Tyr Ala Ala Asp Gly Phe Ala Phe Leu Ala Pro His Asp
                85                  90                  95

```
Thr Val Ile Pro Pro Asn Ser Trp Gly Lys Phe Leu Gly Leu Tyr Ser
            100                 105                 110
Asn Val Phe Arg Asn Ser Pro Thr Ser Glu Asn Gln Ser Phe Gly Asp
        115                 120                 125
Val Asn Thr Asp Ser Arg Val Val Ala Val Glu Phe Asp Thr Phe Pro
    130                 135                 140
Asn Ala Asn Ile Asp Pro Asn Tyr Arg His Ile Gly Ile Asp Val Asn
145                 150                 155                 160
Ser Ile Lys Ser Lys Glu Thr Ala Arg Trp Glu Trp Gln Asn Gly Lys
                165                 170                 175
Thr Ala Thr Ala Arg Ile Ser Tyr Asn Ser Ala Ser Lys Lys Ser Thr
            180                 185                 190
Val Thr Thr Phe Tyr Pro Gly Met Glu Val Val Ala Leu Ser His Asp
        195                 200                 205
Val Asp Leu His Ala Glu Leu Pro Glu Trp Val Arg Val Gly Leu Ser
    210                 215                 220
Ala Ser Thr Gly Glu Glu Lys Gln Lys Asn Thr Ile Ile Ser Trp Ser
225                 230                 235                 240
Phe Thr Ser Ser Leu Lys Asn Asn Glu Val Lys Glu Pro Lys Glu Asp
                245                 250                 255
Met Tyr Ile Ala Asn Val Val Arg Ser Tyr Thr Trp Ile Asn Asp Val
            260                 265                 270
Leu Ser Tyr Ile Ser Asn Lys Met Tyr Asp Ala Leu Asn Asn Asn His
        275                 280                 285
Lys Tyr Val Arg Cys Ser Thr Cys Met Leu Phe Met Lys Lys Lys
    290                 295                 300

<210> SEQ ID NO 7
<211> LENGTH: 678
<212> TYPE: DNA
<213> ORGANISM: Artificial Sequence
<220> FEATURE:
<223> OTHER INFORMATION: YamFri1 partial mRNA sequence.

<400> SEQUENCE: 7
acgaagttcg acagcgacca aaaggatctt atgttccaag gtcataccat ttctagcagc     60
aatgtcatac aactccaccaa gttagacagt aatggaaaacc ctgtgagtac cagtgtggga    120
agagtgttat actctgcacc attgcgcctt tgggaaagct ctacagtagt gtcaacctt     180
gagaccactt tcacctttca aatctcaaca ccttacacta gtcctcctgg tgatgggctc    240
gccttcttcc ttgcaccata tgacactgtc atccctccaa attctgctgg caatcttctt    300
ggactctttc ctaacttaaa tgctttaaga aactccacca ccagtaaaga aaccactatt    360
gatgtcaatg ctgcatctaa caacgttgtt gccgttgaat ttgacaccta ccctaacgac    420
aatattggtg atccaagata caaacacatt ggaatcgatg tcaactctat caggtccaag    480
gcaactgttg cgtgggactg gcaaaatggg aaaacagcca ctgcacacat cagctataac    540
tctgcctcta aaagactatc tgttactact ttttatcctg ggggtaaagc tgtgagtctt    600
tcccatgacg ttgagctcac tcaagtgctt cctcaatgga ttagagtagg gttctctgct    660
tcaacaggat tagagaaa                                                  678

<210> SEQ ID NO 8
<211> LENGTH: 234
<212> TYPE: PRT
<213> ORGANISM: Artificial Sequence
```

```
<220> FEATURE:
<223> OTHER INFORMATION: YamFril deduced amino acid squence.

<400> SEQUENCE: 8

Ala Gln Ser Val Ser Phe Thr Phe Thr Lys Phe Asp Ser Asp Gln Lys
1               5                   10                  15

Asp Leu Met Phe Gln Gly His Thr Ile Ser Ser Asn Val Ile Gln
            20                  25                  30

Leu Thr Lys Leu Asp Ser Asn Gly Asn Pro Val Ser Thr Ser Val Gly
        35                  40                  45

Arg Val Leu Tyr Ser Ala Pro Leu Arg Leu Trp Glu Ser Ser Thr Val
    50                  55                  60

Val Ser Thr Phe Glu Thr Thr Phe Thr Phe Gln Ile Ser Thr Pro Tyr
65                  70                  75                  80

Thr Ser Pro Pro Gly Asp Gly Leu Ala Phe Phe Leu Ala Pro Tyr Asp
                85                  90                  95

Thr Val Ile Pro Pro Asn Ser Ala Gly Asn Leu Leu Gly Leu Phe Pro
            100                 105                 110

Asn Leu Asn Ala Leu Arg Asn Ser Thr Thr Ser Lys Glu Thr Thr Ile
        115                 120                 125

Asp Val Asn Ala Ala Ser Asn Asn Val Val Ala Val Glu Phe Asp Thr
    130                 135                 140

Tyr Pro Asn Asp Asn Ile Gly Asp Pro Tyr Arg Lys His Ile Gly Ile
145                 150                 155                 160

Asp Val Asn Ser Ile Arg Ser Lys Ala Thr Val Ala Trp Asp Trp Gln
                165                 170                 175

Asn Gly Lys Thr Ala Thr Ala His Ile Ser Tyr Asn Ser Ala Ser Lys
            180                 185                 190

Arg Leu Ser Val Thr Thr Phe Tyr Pro Gly Gly Lys Ala Val Ser Leu
        195                 200                 205

Ser His Asp Val Glu Leu Thr Gln Val Leu Pro Gln Trp Ile Arg Val
    210                 215                 220

Gly Phe Ser Ala Ser Thr Gly Leu Glu Lys
225                 230

<210> SEQ ID NO 9
<211> LENGTH: 15
<212> TYPE: PRT
<213> ORGANISM: Artificial Sequence
<220> FEATURE:
<223> OTHER INFORMATION: Beta band polypeptide.

<400> SEQUENCE: 9

Ala Gln Ser Val Ser Phe Thr Phe Thr Lys Phe Asp Ser Asp Gln
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Alpha band polypeptide.
<220> FEATURE:
<221> NAME/KEY: PEPTIDE
<222> LOCATION: (14)..(14)
<223> OTHER INFORMATION: Amino acid 14 is Xaa wherein Xaa = any amino acid.

<400> SEQUENCE: 10

Ala Ala Ser Asn Asn Val Val Ala Val Glu Phe Asp Thr Xaa Pro Asn
1               5                   10                  15
```

```
<210> SEQ ID NO 11
<211> LENGTH: 23
<212> TYPE: DNA
<213> ORGANISM: Artificial Sequence
<220> FEATURE:
<223> OTHER INFORMATION: MLA degenerate oligonucleotide primer.
<220> FEATURE:
<221> NAME/KEY: misc_feature
<222> LOCATION: (3)..(21)
<223> OTHER INFORMATION: Nucleotides 3, 18 and 21 are n wherein n = a or g.
<220> FEATURE:
<221> NAME/KEY: misc_feature
<222> LOCATION: (6)..(15)
<223> OTHER INFORMATION: Nucleotides 6, 9, and 15 are n wherein n = t or c.
<220> FEATURE:
<221> NAME/KEY: misc_feature
<222> LOCATION: (12)..(12)
<223> OTHER INFORMATION: Nucleotide 12 is n wherein n = a or t.

<400> SEQUENCE: 11
aanttnganc cnaancanga nga                                            23

<210> SEQ ID NO 12
<211> LENGTH: 20
<212> TYPE: DNA
<213> ORGANISM: Artificial Sequence
<220> FEATURE:
<223> OTHER INFORMATION: MLZ degenerate oligonucleotide primer.
<220> FEATURE:
<221> NAME/KEY: misc_feature
<222> LOCATION: (3)..(3)
<223> OTHER INFORMATION: Nucleotide 3 is n wherein n = a or t.
<220> FEATURE:
<221> NAME/KEY: misc_feature
<222> LOCATION: (6)..(15)
<223> OTHER INFORMATION: Nucleotides 6 and 15 are n wherein n = a or g.
<220> FEATURE:
<221> NAME/KEY: misc_feature
<222> LOCATION: (9)..(9)
<223> OTHER INFORMATION: Nucleotide 9 is n wherein n = t or c.

<400> SEQUENCE: 12
ttnccnttnt gccantccca                                                20

<210> SEQ ID NO 13
<211> LENGTH: 15
<212> TYPE: DNA
<213> ORGANISM: Artificial Sequence
<220> FEATURE:
<223> OTHER INFORMATION: primer.

<400> SEQUENCE: 13
gtaccgagct cggat                                                     15

<210> SEQ ID NO 14
<211> LENGTH: 18
<212> TYPE: DNA
<213> ORGANISM: Artificial Sequence
<220> FEATURE:
<223> OTHER INFORMATION: primer.

<400> SEQUENCE: 14
tctagatgca tgctcgag                                                  18

<210> SEQ ID NO 15
<211> LENGTH: 22
<212> TYPE: DNA
<213> ORGANISM: Artificial Sequence
<220> FEATURE:
<223> OTHER INFORMATION: MLX primer.
```

-continued

```
<400> SEQUENCE: 15
gttggacgtc aattccgatg tg                                              22

<210> SEQ ID NO 16
<211> LENGTH: 17
<212> TYPE: DNA
<213> ORGANISM: Artificial Sequence
<220> FEATURE:
<223> OTHER INFORMATION: MLI degenerate primer.
<220> FEATURE:
<221> NAME/KEY: misc_feature
<222> LOCATION: (3)..(15)
<223> OTHER INFORMATION: Nucleotides 3, 9, 12 and 15 are n wherein n = t or c.
<220> FEATURE:
<221> NAME/KEY: misc_feature
<222> LOCATION: (6)..(6)
<223> OTHER INFORMATION: Nucleotide 6 is n wherein n = a or g.

<400> SEQUENCE: 16
gcncantcnc tntcntt                                                    17

<210> SEQ ID NO 17
<211> LENGTH: 22
<212> TYPE: DNA
<213> ORGANISM: Artificial Sequence
<220> FEATURE:
<223> OTHER INFORMATION: Oligo(dT) anchor primer.

<400> SEQUENCE: 17
gaccacgcgt atcgatgtcg ac                                              22

<210> SEQ ID NO 18
<211> LENGTH: 21
<212> TYPE: DNA
<213> ORGANISM: Artificial Sequence
<220> FEATURE:
<223> OTHER INFORMATION: MLB primer.

<400> SEQUENCE: 18
aagttagaca gtgcaggaaa c                                               21

<210> SEQ ID NO 19
<211> LENGTH: 20
<212> TYPE: DNA
<213> ORGANISM: Artificial Sequence
<220> FEATURE:
<223> OTHER INFORMATION: MLII primer.

<400> SEQUENCE: 19
gcacagtcat tgtcatttag                                                 20

<210> SEQ ID NO 20
<211> LENGTH: 18
<212> TYPE: PRT
<213> ORGANISM: Artificial Sequence
<220> FEATURE:
<223> OTHER INFORMATION: D1-FRIL.

<400> SEQUENCE: 20

Tyr Leu Asn Pro Asp Tyr Gly Asp Pro Asn Tyr Ile His Ile Gly Ile
1               5                  10                  15

Asp Val
```

-continued

```
<210> SEQ ID NO 21
<211> LENGTH: 19
<212> TYPE: PRT
<213> ORGANISM: Artificial Sequence
<220> FEATURE:
<223> OTHER INFORMATION: Pea.

<400> SEQUENCE: 21

Phe Tyr Asn Ala Ala Trp Asp Pro Ser Asn Arg Asp Arg His Ile Gly
1               5                   10                  15

Ile Asp Val

<210> SEQ ID NO 22
<211> LENGTH: 1005
<212> TYPE: DNA
<213> ORGANISM: Artificial Sequence
<220> FEATURE:
<223> OTHER INFORMATION: SpDLA.

<400> SEQUENCE: 22
atggcttcct ccaacttact caccctagcc ctcttccttg tgcttctcac ccacgcaaac      60
tcagccgcac agtcattgtc atttagtttc accaagtttg atcctaacca agaggatctt     120
atcttccaag gtcatgccac ttctacaaac aatgtcttac aagtcaccaa gttagacagt     180
gcaggaaacc ctgtgagttc tagtgcggga agagtgttat attctgcacc attgcgcctt     240
tgggaagact ctgcggtatt gacaagcttt gacaccatta tcaactttga aatctcaaca     300
ccttacactt tcgtatagc tgatggcttg gccttcttca ttgcaccacc tgactctgtc      360
atcagttatc atggtggttt tcttggactc tttcccaacg caaacactct caacaactct     420
tccacctctg aaaaccaaac caccactaag gctgcatcaa gcaacgttgt tgctgttgaa     480
tttgacacct atcttaatcc cgattatggt gatccaaact acatacacat cggaattgac     540
gtcaactcta ttagatccaa ggtaactgct aagtgggact ggcaaaatgg gaaaatagcc     600
actgcacaca ttagctataa ctctgtctct aaaagactat ctgttactag ttattatgct     660
gggagtaaac ctgcgactct ctcctatgat attgagttac atacagtgct tcctgaatgg     720
gtcagagtag ggttatctgc ttcaactgga caagataaag aaagaaatac cgttcactca     780
tggtctttca cttcaagctt gtggaccaat gtggcgaaga aggagaatga aaacaagtat     840
attacaagag gcgttctgtg atgatatatg tgtatcaatg attttctatg ttataagcat     900
gtaatgtgcg atgagtcaat aatcacaagt acagtgtagt acttgtatgt tgtttgtgta     960
agagtcagtt tgcttttaat aataacaagt gcagttagta cttgt                   1005

<210> SEQ ID NO 23
<211> LENGTH: 286
<212> TYPE: PRT
<213> ORGANISM: Artificial Sequence
<220> FEATURE:
<223> OTHER INFORMATION: SpDLA.

<400> SEQUENCE: 23

Met Ala Ser Ser Asn Leu Leu Thr Leu Ala Leu Phe Leu Val Leu Leu
1               5                   10                  15

Thr His Ala Asn Ser Ala Ala Gln Ser Leu Ser Phe Ser Phe Thr Lys
            20                  25                  30

Phe Asp Pro Asn Gln Glu Asp Leu Ile Phe Gln Gly His Ala Thr Ser
        35                  40                  45

Thr Asn Asn Val Leu Gln Val Thr Lys Leu Asp Ser Ala Gly Asn Pro
    50                  55                  60
```

```
Val Ser Ser Ser Ala Gly Arg Val Leu Tyr Ser Ala Pro Leu Arg Leu
 65                  70                  75                  80

Trp Glu Asp Ser Ala Val Leu Thr Ser Phe Asp Thr Ile Ile Asn Phe
                 85                  90                  95

Glu Ile Ser Thr Pro Tyr Thr Ser Arg Ile Ala Asp Gly Leu Ala Phe
             100                 105                 110

Phe Ile Ala Pro Pro Asp Ser Val Ile Ser Tyr His Gly Gly Phe Leu
         115                 120                 125

Gly Leu Phe Pro Asn Ala Asn Thr Leu Asn Asn Ser Ser Thr Ser Glu
     130                 135                 140

Asn Gln Thr Thr Thr Lys Ala Ala Ser Ser Asn Val Val Ala Val Glu
145                 150                 155                 160

Phe Asp Thr Tyr Leu Asn Pro Asp Tyr Gly Asp Pro Asn Tyr Ile His
                165                 170                 175

Ile Gly Ile Asp Val Asn Ser Ile Arg Ser Lys Val Thr Ala Lys Trp
            180                 185                 190

Asp Trp Gln Asn Gly Lys Ile Ala Thr Ala His Ile Ser Tyr Asn Ser
        195                 200                 205

Val Ser Lys Arg Leu Ser Val Thr Ser Tyr Tyr Ala Gly Ser Lys Pro
    210                 215                 220

Ala Thr Leu Ser Tyr Asp Ile Glu Leu His Thr Val Leu Pro Glu Trp
225                 230                 235                 240

Val Arg Val Gly Leu Ser Ala Ser Thr Gly Gln Asp Lys Glu Arg Asn
                245                 250                 255

Thr Val His Ser Trp Ser Phe Thr Ser Ser Leu Trp Thr Asn Val Ala
            260                 265                 270

Lys Lys Glu Asn Glu Asn Lys Tyr Ile Thr Arg Gly Val Leu
        275                 280                 285

<210> SEQ ID NO 24
<211> LENGTH: 8
<212> TYPE: PRT
<213> ORGANISM: Dolichos lablab
<220> FEATURE:
<221> NAME/KEY: PEPTIDE
<222> LOCATION: (7)..(7)
<223> OTHER INFORMATION: Amino acid 7 is Xaa wherein Xaa = any amino acid.

<400> SEQUENCE: 24

Thr Asn Asn Val Leu Gln Xaa Thr
1               5

<210> SEQ ID NO 25
<211> LENGTH: 24
<212> TYPE: DNA
<213> ORGANISM: Artificial Sequence
<220> FEATURE:
<223> OTHER INFORMATION: MutI primer.

<400> SEQUENCE: 25
ccataatcgg gatcaagata ggtg                                          24

<210> SEQ ID NO 26
<211> LENGTH: 24
<212> TYPE: DNA
<213> ORGANISM: Artificial Sequence
<220> FEATURE:
<223> OTHER INFORMATION: MutII primer.
```

-continued

```
<400> SEQUENCE: 26
cacctatctt gatcccgatt atgg                                          24

<210> SEQ ID NO 27
<211> LENGTH: 24
<212> TYPE: DNA
<213> ORGANISM: Artificial Sequence
<220> FEATURE:
<223> OTHER INFORMATION: M1 Forw primer.

<400> SEQUENCE: 27
aactcagccg cacagtcatt gtca                                          24

<210> SEQ ID NO 28
<211> LENGTH: 28
<212> TYPE: DNA
<213> ORGANISM: Artificial Sequence
<220> FEATURE:
<223> OTHER INFORMATION: APEcoRI primer.

<400> SEQUENCE: 28
gaattcgacc acgcgtatcg atgtcgac                                      28

<210> SEQ ID NO 29
<211> LENGTH: 21
<212> TYPE: DNA
<213> ORGANISM: Artificial Sequence
<220> FEATURE:
<223> OTHER INFORMATION: Sigforw primer.

<400> SEQUENCE: 29
gaattcatgg cttcctccaa c                                             21

<210> SEQ ID NO 30
<211> LENGTH: 28
<212> TYPE: DNA
<213> ORGANISM: Artificial Sequence
<220> FEATURE:
<223> OTHER INFORMATION: Sigrev primer.

<400> SEQUENCE: 30
tgactgtgcg gctgagtttg cgtgggtg                                      28

<210> SEQ ID NO 31
<211> LENGTH: 14
<212> TYPE: PRT
<213> ORGANISM: Artificial Sequence
<220> FEATURE:
<223> OTHER INFORMATION: Peptide corresponding to Pv-FRIL.
<220> FEATURE:
<221> NAME/KEY: PEPTIDE
<222> LOCATION: (7)..(7)
<223> OTHER INFORMATION: Amino acid 7 is Xaa wherein Xaa = Asn, Cys or Ser.

<400> SEQUENCE: 31

Ala Gln Ser Leu Ser Phe Xaa Phe Thr Lys Phe Asp Leu Asp
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Polypeptide of 18 kDa.
```

```
<220> FEATURE:
<221> NAME/KEY: PEPTIDE
<222> LOCATION: (7)..(7)
<223> OTHER INFORMATION: Amino acid 7 is Xaa wherein Xaa = unknown amino acid.

<400> SEQUENCE: 32

Ala Gln Ser Leu Ser Phe Xaa Phe Thr Lys Asp Ala Leu Asp
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Aminoterminal sequence.
<220> FEATURE:
<221> NAME/KEY: PEPTIDE
<222> LOCATION: (12)..(12)
<223> OTHER INFORMATION: Amino acid 12 is Xaa wherein Xaa = unknown amino acid.

<400> SEQUENCE: 33

Thr Asp Ser Arg Val Val Ala Val Glu Phe Asp Xaa Phe Pro
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Aminoterminal polypeptide.
<220> FEATURE:
<221> NAME/KEY: PEPTIDE
<222> LOCATION: (7)..(7)
<223> OTHER INFORMATION: Amino acid 7 is Xaa wherein Xaa = unknown amino acid.

<400> SEQUENCE: 34

Ala Gln Ser Leu Ser Phe Xaa Phe Lys Phe Asp Pro Asn
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Aminoterminal polypeptide.

<400> SEQUENCE: 35

Thr Asp Ser Arg Val Val Ala Val Glu Asp Phe
1               5                   10

<210> SEQ ID NO 36
<211> LENGTH: 20
<212> TYPE: DNA
<213> ORGANISM: Artificial Sequence
<220> FEATURE:
<223> OTHER INFORMATION: Degenerate oligonucleotide PVBeta1.
<220> FEATURE:
<221> NAME/KEY: misc_feature
<222> LOCATION: (18)..(18)
<223> OTHER INFORMATION: Nucleotide 18 is n wherein n = any nucleotide.

<400> SEQUENCE: 36
ttyacyaart tygayytnga                                                  20

<210> SEQ ID NO 37
<211> LENGTH: 17
<212> TYPE: DNA
<213> ORGANISM: Artificial Sequence
```

```
<220> FEATURE:
<223> OTHER INFORMATION: Degenerate oligonucleotide PVBeta2.

<400> SEQUENCE: 37
atyttycarg gwgaygc                                                  17

<210> SEQ ID NO 38
<211> LENGTH: 20
<212> TYPE: DNA
<213> ORGANISM: Artificial Sequence
<220> FEATURE:
<223> OTHER INFORMATION: Degenerate oligonucleotide PVAlfa1.

<400> SEQUENCE: 38
ttracrtcra twccratrtg                                               20

<210> SEQ ID NO 39
<211> LENGTH: 23
<212> TYPE: DNA
<213> ORGANISM: Artificial Sequence
<220> FEATURE:
<223> OTHER INFORMATION: Degenerate oligonucleotide PVAlfa2.

<400> SEQUENCE: 39
tarttwggrt cratrttrgc rtt                                           23

<210> SEQ ID NO 40
<211> LENGTH: 22
<212> TYPE: DNA
<213> ORGANISM: Artificial Sequence
<220> FEATURE:
<223> OTHER INFORMATION: PV3 PCR-Anchor primer.

<400> SEQUENCE: 40
caatgtctta caactcacta ag                                            22

<210> SEQ ID NO 41
<211> LENGTH: 21
<212> TYPE: DNA
<213> ORGANISM: Artificial Sequence
<220> FEATURE:
<223> OTHER INFORMATION: PV4 PCR-Anchor primer.

<400> SEQUENCE: 41
agtgtgggaa gagtgttatt c                                             21

<210> SEQ ID NO 42
<211> LENGTH: 21
<212> TYPE: DNA
<213> ORGANISM: Artificial Sequence
<220> FEATURE:
<223> OTHER INFORMATION: SPV2 Anchor primer.

<400> SEQUENCE: 42
accaaagctt tggttttcag a                                             21

<210> SEQ ID NO 43
<211> LENGTH: 21
<212> TYPE: DNA
<213> ORGANISM: Artificial Sequence
<220> FEATURE:
<223> OTHER INFORMATION: SPV3 Anchor primer.

<400> SEQUENCE: 43
tctgaaaacg tttgagtaga g                                             21
```

```
<210> SEQ ID NO 44
<211> LENGTH: 32
<212> TYPE: DNA
<213> ORGANISM: Artificial Sequence
<220> FEATURE:
<223> OTHER INFORMATION: PVEcoRI primer.

<400> SEQUENCE: 44
tacatgaatt cgctcagtca ttatctttta ac                              32

<210> SEQ ID NO 45
<211> LENGTH: 21
<212> TYPE: DNA
<213> ORGANISM: Artificial Sequence
<220> FEATURE:
<223> OTHER INFORMATION: Sigfor BglII primer.

<400> SEQUENCE: 45
agatctatgg cttcctccaa c                                          21

<210> SEQ ID NO 46
<211> LENGTH: 32
<212> TYPE: DNA
<213> ORGANISM: Artificial Sequence
<220> FEATURE:
<223> OTHER INFORMATION: Sigrev primer.

<400> SEQUENCE: 46
aaagataatg actgagcggc tgagtttgcg tg                              32

<210> SEQ ID NO 47
<211> LENGTH: 32
<212> TYPE: DNA
<213> ORGANISM: Artificial Sequence
<220> FEATURE:
<223> OTHER INFORMATION: SpM1forw primer.

<400> SEQUENCE: 47
cacgcaaact cagccgctca gtcattatct tt                              32

<210> SEQ ID NO 48
<211> LENGTH: 27
<212> TYPE: DNA
<213> ORGANISM: Artificial Sequence
<220> FEATURE:
<223> OTHER INFORMATION: APXhoI primer.

<400> SEQUENCE: 48
ctcgaggacc acgcgtatcg atgtcga                                    27

<210> SEQ ID NO 49
<211> LENGTH: 106
<212> TYPE: PRT
<213> ORGANISM: Artificial Sequence
<220> FEATURE:
<223> OTHER INFORMATION: Beta-subunit of the mannose lectin of Gowda et al.

<400> SEQUENCE: 49

Ala Gln Ser Leu Ser Phe Ser Ser Phe Thr Lys Phe Asp Pro Asn Gln
1               5                   10                  15

Glu Asp Le

```
Leu Arg Leu Trp Glu Asp Ser Ala Val Leu Thr Ser Phe Asp Pro Thr
    50                  55                  60

Ile Tyr Ile Phe Thr Asn Tyr Thr Ser Arg Ile Ala Asp Gly Leu Ala
65                  70                  75                  80

Phe Ile Ala Pro Pro Asp Ser Val Ile Ser Tyr His Gly Gly Phe Leu
                85                  90                  95

Gly Leu Phe Pro Asn Ala Ala Glu Ser Gly
                100                 105

<210> SEQ ID NO 50
<211> LENGTH: 123
<212> TYPE: PRT
<213> ORGANISM: Artificial Sequence
<220> FEATURE:
<223> OTHER INFORMATION: Beta-subunit of D1-FRIL.

<400> SEQUENCE: 50

Ala Gln Ser Leu Ser Phe Ser Phe Thr Lys Phe Asp Pro Asn Gln Glu
1               5                   10                  15

Asp Leu Ile Phe Gln Gly His Ala Thr Ser Thr Asn Asn Val Leu Gln
                20                  25                  30

Val Thr Lys Leu Asp Ser Ala Gly Asn Pro Val Ser Ser Ser Ala Gly
            35                  40                  45

Arg Val Leu Tyr Ser Ala Pro Leu Arg Leu Trp Glu Asp Ser Ala Val
    50                  55                  60

Leu Thr Ser Phe Asp Thr Ile Ile Asn Phe Glu Ile Ser Thr Pro Tyr
65                  70                  75                  80

Thr Ser Arg Ile Ala Asp Gly Leu Ala Phe Phe Ile Ala Pro Pro Asp
                85                  90                  95

Ser Val Ile Ser Tyr His Gly Gly Phe Leu Gly Leu Phe Pro Asn Ala
                100                 105                 110

Asn Thr Leu Asn Asn Ser Ser Thr Ser Glu Asn
            115                 120

<210> SEQ ID NO 51
<211> LENGTH: 132
<212> TYPE: PRT
<213> ORGANISM: Artificial Sequence
<220> FEATURE:
<223> OTHER INFORMATION: Alpha-subunit of the mannose lectin of Gowda et al.

<400> SEQUENCE: 51

Ile Ala Glu Ser Asn Val Val Ala Val Glu Phe Asp Thr Asp Tyr Leu
1               5                   10                  15

Asn Pro Asp Tyr Gly Asp Pro Asn Tyr Ile His Ile Gly Ile Asp Val
                20                  25                  30

Asn Ser Ile Arg Ser Lys Val Thr Ala Ser Trp Asp Trp Gln Asn Gly
            35                  40                  45

Lys Ile Ala Thr Ala His Ile Ser Tyr Asn Ser Val Ser Lys Arg Leu
    50                  55                  60

Ser Val Thr Thr Tyr Tyr Pro Gly Arg Gly Lys Pro Ala Thr Ser Tyr
65                  70                  75                  80

Asp Ile Glu Leu His Thr Val Leu Pro Glu Trp Val Arg Val Gly Leu
                85                  90                  95

Ser Ala Ser Thr Gly Gln Asn Ile Glu Arg Asn Thr Val His Ser Trp
                100                 105                 110
```

```
Ser Phe Thr Ser Ser Leu Trp Thr Asn Val Ala Lys Val Gly Val Ala
        115                 120                 125

Ser Ile Ser Gly
    130
```

<210> SEQ ID NO 52
<211> LENGTH: 147
<212> TYPE: PRT
<213> ORGANISM: Artificial Sequence
<220> FEATURE:
<223> OTHER INFORMATION: Alpha-subunit of D1-FRIL.

<400> SEQUENCE: 52

```
Gln Thr Thr Thr Lys Ala Ala Ser Ser Asn Val Val Ala Val Glu Phe
1               5                   10                  15

Asp Thr Tyr Leu Asn Pro Asp Tyr Gly Asp Pro Asn Tyr Ile His Ile
            20                  25                  30

Gly Ile Asp Val Asn Ser Ile Arg Ser Lys Val Thr Ala Lys Trp Asp
        35                  40                  45

Trp Gln Asn Gly Lys Ile Ala Thr Ala His Ile Ser Tyr Asn Ser Val
    50                  55                  60

Ser Lys Arg Leu Ser Val Thr Ser Tyr Tyr Ala Gly Ser Lys Pro Ala
65                  70                  75                  80

Thr Leu Ser Tyr Asp Ile Glu Leu His Thr Val Leu Pro Glu Trp Val
                85                  90                  95

Arg Val Gly Leu Ser Ala Ser Thr Gly Gln Asp Lys Glu Arg Asn Thr
            100                 105                 110

Val His Ser Trp Ser Phe Thr Ser Ser Leu Trp Thr Asn Val Ala Lys
        115                 120                 125

Lys Glu Asn Glu Asn Lys Tyr Ile Thr Arg Gly Val Leu Tyr Met Cys
    130                 135                 140

Ile Asn Asp
145
```

<210> SEQ ID NO 53
<211> LENGTH: 64
<212> TYPE: DNA
<213> ORGANISM: Artificial Sequence
<220> FEATURE:
<223> OTHER INFORMATION: Recombinant expression vector.

<400> SEQUENCE: 53

```
ctggttccgc gtggatcccc ggaattcatg cccggttcga ctcgagcggc cgcatcgtga    60
ctga                                                                 64
```

<210> SEQ ID NO 54
<211> LENGTH: 54
<212> TYPE: DNA
<213> ORGANISM: Artificial Sequence
<220> FEATURE:
<223> OTHER INFORMATION: Recombinant expression vector.

<400> SEQUENCE: 54

```
ctggttccgc gtggatcccc ggaattcatg ctcgagcggc cgcatcgtga ctga          54
```

<210> SEQ ID NO 55
<211> LENGTH: 237
<212> TYPE: PRT
<213> ORGANISM: Artificial Sequence
<220> FEATURE:
<223> OTHER INFORMATION: DLL.

-continued

```
<400> SEQUENCE: 55

Ala Gln Ser Leu Ser Phe Ser Phe Thr Lys Phe Asp Pro Asn Gln Glu
1               5                   10                  15

Asp Leu Ile Phe Gln Gly Thr Ala Thr Ser Lys Leu Asp Ser Ala Gly
            20                  25                  30

Asn Pro Val Ser Ser Ser Ala Gly Arg Val Leu Tyr Ser Ala Pro Leu
        35                  40                  45

Arg Leu Trp Glu Asp Ser Ala Val Leu Thr Ser Phe Asp Pro Thr Ile
    50                  55                  60

Tyr Ile Phe Thr Asn Tyr Thr Ser Arg Ile Ala Asp Gly Leu Ala Phe
65                  70                  75                  80

Ile Ala Pro Pro Asp Ser Val Ile Ser Tyr His Gly Gly Phe Leu Gly
                85                  90                  95

Leu Phe Pro Asn Ala Ala Glu Ser Gly Ile Ala Glu Ser Asn Val Val
            100                 105                 110

Ala Val Glu Phe Asp Thr Asp Tyr Leu Asn Pro Asp Tyr Gly Asp Pro
        115                 120                 125

Asn Tyr Ile His Ile Gly Ile Asp Val Asn Ser Ile Arg Ser Lys Val
130                 135                 140

Thr Ala Ser Trp Asp Trp Gln Asn Gly Lys Ile Ala Thr Ala His Ile
145                 150                 155                 160

Ser Tyr Asn Ser Val Ser Lys Arg Leu Ser Val Thr Thr Tyr Tyr Pro
                165                 170                 175

Gly Arg Gly Lys Pro Ala Thr Ser Tyr Asp Leu Glu Leu His Thr Val
            180                 185                 190

Leu Pro Glu Trp Val Arg Val Gly Leu Ser Ala Ser Thr Gly Gln Asn
        195                 200                 205

Ile Glu Arg Asn Thr Val His Ser Trp Ser Phe Thr Ser Ser Leu Trp
    210                 215                 220

Thr Asn Val Ala Lys Val Gly Val Ala Ser Ile Ser Gly
225                 230                 235

<210> SEQ ID NO 56
<211> LENGTH: 279
<212> TYPE: PRT
<213> ORGANISM: Artificial Sequence
<220> FEATURE:
<223> OTHER INFORMATION: PvFRIL.

<400> SEQUENCE: 56

Ala Gln Ser Leu Ser Phe Asn Phe Thr Lys Phe Asp Leu Asp Gln Lys
1               5                   10                  15

Asp Leu Ile Phe Gln Gly Asp Ala Thr Ser Thr Asn Asn Val Leu Gln
            20                  25                  30

Leu Thr Lys Leu Asp Ser Gly Gly Asn Pro Val Gly Ala Ser Val Gly
        35                  40                  45

Arg Val Leu Phe Ser Ala Pro Phe His Leu Trp Glu Asn Ser Met Ala
    50                  55                  60

Val Ser Ser Phe Glu Thr Asn Leu Thr Ile Gln Ile Ser Thr Pro His
65                  70                  75                  80

Pro Tyr Tyr Ala Ala Asp Gly Phe Ala Phe Leu Ala Pro His Asp
                85                  90                  95

Thr Val Ile Pro Pro Asn Ser Trp Gly Lys Phe Leu Gly Leu Tyr Ser
            100                 105                 110
```

```
Asn Val Phe Arg Asn Ser Pro Thr Ser Glu Asn Gln Ser Phe Gly Asp
            115                 120                 125

Val Asn Thr Asp Ser Arg Val Val Ala Val Glu Phe Asp Thr Phe Pro
            130                 135                 140

Asn Ala Asn Ile Asp Pro Asn Tyr Arg His Ile Gly Ile Asp Val Asn
145                 150                 155                 160

Ser Ile Lys Ser Lys Glu Thr Ala Arg Trp Glu Trp Gln Asn Gly Lys
            165                 170                 175

Thr Ala Thr Ala Arg Ile Ser Tyr Asn Ser Ala Ser Lys Lys Ser Thr
            180                 185                 190

Val Thr Thr Phe Tyr Pro Gly Met Glu Val Val Ala Leu Ser His Asp
            195                 200                 205

Val Asp Leu His Ala Glu Leu Pro Glu Trp Val Arg Val Gly Leu Ser
            210                 215                 220

Ala Ser Thr Gly Glu Glu Lys Gln Lys Asn Thr Ile Ile Ser Trp Ser
225                 230                 235                 240

Phe Thr Ser Ser Leu Lys Asn Asn Glu Val Lys Glu Pro Lys Glu Asp
            245                 250                 255

Met Tyr Ile Ala Asn Val Val Arg Ser Tyr Thr Trp Ile Asn Asp Val
            260                 265                 270

Leu Ser Tyr Ile Ser Asn Lys
            275

<210> SEQ ID NO 57
<211> LENGTH: 254
<212> TYPE: PRT
<213> ORGANISM: Artificial Sequence
<220> FEATURE:
<223> OTHER INFORMATION: PHA-E.

<400> SEQUENCE: 57

Ala Ser Gln Thr Ser Phe Ser Phe Gln Arg Phe Asn Glu Thr Asn Leu
1               5                   10                  15

Ile Leu Gln Arg Asp Ala Thr Val Ser Ser Lys Gly Gln Leu Arg Leu
            20                  25                  30

Thr Asn Val Asn Asp Asn Gly Glu Pro Thr Leu Ser Ser Leu Gly Arg
            35                  40                  45

Ala Phe Tyr Ser Ala Pro Ile Gln Ile Trp Asp Asn Thr Thr Gly Ala
    50                  55                  60

Val Ala Ala Ser Pro Thr Ser Phe Thr Phe Asn Ile Asp Val Pro Asn
65                  70                  75                  80

Asn Ser Gly Pro Ala Asp Gly Leu Ala Phe Val Leu Leu Pro Val Gly
            85                  90                  95

Ser Gln Pro Lys Asp Lys Gly Gly Leu Leu Gly Leu Phe Asn Asn Tyr
            100                 105                 110

Lys Tyr Asp Ser Asn Ala His Thr Val Ala Val Glu Phe Asp Thr Leu
            115                 120                 125

Tyr Asn Val His Trp Asp Pro Lys Pro Arg His Ile Gly Ile Asp Val
            130                 135                 140

Asn Ser Ile Lys Ser Ile Lys Thr Thr Thr Trp Asp Phe Val Lys Gly
145                 150                 155                 160

Glu Asn Ala Glu Val Leu Ile Thr Tyr Asp Ser Ser Thr Lys Leu Leu
            165                 170                 175

Val Ala Ser Leu Val Tyr Pro Ser Leu Lys Thr Ser Phe Ile Val Ser
            180                 185                 190
```

-continued

```
Asp Thr Val Asp Leu Lys Ser Val Leu Pro Glu Trp Val Ile Val Gly
        195                 200                 205

Phe Thr Ala Thr Thr Gly Ile Thr Lys Gly Asn Val Glu Thr Asn Asp
        210                 215                 220

Ile Leu Ser Trp Ser Phe Ala Ser Lys Leu Ser Asp Gly Thr Thr Ser
225                 230                 235                 240

Glu Ala Leu Asn Leu Ala Asn Phe Ala Leu Asn Gln Ile Leu
                245                 250
```